United States Patent
Ledeboer et al.

(10) Patent No.: US 8,937,064 B2
(45) Date of Patent: Jan. 20, 2015

(54) PYRAZOLO[1,5-A]PYRIMIDINES USEFUL AS JAK2 INHIBITORS

(75) Inventors: Mark Ledeboer, Acton, MA (US); Valerie Marone, Somerville, MA (US); Michelle Stewart, Brookline, MA (US); David Messersmith, Somerville, MA (US); John Duffy, Northborough, MA (US); Gabriel Martinez Botella, Wayland, MA (US); Jon Come, Cambridge, MA (US); Huai Gao, Arlington, MA (US); Albert Pierce, Cambridge, MA (US); Francesco Salituro, Marlborough, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 12/817,785

(22) Filed: Jun. 17, 2010

(65) Prior Publication Data

US 2011/0118255 A1 May 19, 2011

Related U.S. Application Data

(63) Continuation of application No. PCT/US2008/008736, filed on Dec. 18, 2008.

(60) Provisional application No. 61/014,824, filed on Dec. 19, 2007.

(51) Int. Cl.
*A61K 31/535* (2006.01)
*C07D 415/00* (2006.01)
*C07D 487/00* (2006.01)
*A01N 43/90* (2006.01)
*C07D 487/04* (2006.01)

(52) U.S. Cl.
CPC .................................... *C07D 487/04* (2013.01)
USPC ...................... 514/233.2; 514/259.3; 544/117; 544/281

(58) Field of Classification Search
None
See application file for complete search history.

(56) References Cited

U.S. PATENT DOCUMENTS

| | | | |
|---|---|---|---|
| 7,226,919 B2 | 6/2007 | Ledeboer et al. | |
| 7,491,730 B2 | 2/2009 | Forster et al. | |
| 7,528,138 B2 * | 5/2009 | Knegtel et al. | 514/259.3 |
| 7,872,129 B2 | 1/2011 | Forster et al. | |
| 8,242,272 B2 | 8/2012 | Jimenez et al. | |
| 8,518,953 B2 | 8/2013 | Pierce et al. | |
| 8,598,361 B2 | 12/2013 | Jimenez et al. | |
| 2006/0135537 A1 * | 6/2006 | Knegtel et al. | 514/259.3 |
| 2007/0117805 A1 | 5/2007 | Dow et al. | |

FOREIGN PATENT DOCUMENTS

| | | |
|---|---|---|
| WO | 98/08847 A1 | 3/1998 |
| WO | 98/54093 A1 | 12/1998 |
| WO | 00/53605 A1 | 9/2000 |
| WO | 02/066481 A1 | 8/2002 |
| WO | 2004/013140 A1 | 2/2004 |
| WO | 2004/052315 A2 | 6/2004 |
| WO | 2004/058749 A1 | 7/2004 |
| WO | 2006/044958 A1 | 4/2006 |
| WO | 2006/052913 A1 | 5/2006 |
| WO | 2007/017678 A1 | 2/2007 |
| WO | 2008/078100 A2 | 7/2008 |
| WO | 2008/112651 A2 | 9/2008 |
| WO | 2009/018415 A1 | 2/2009 |

OTHER PUBLICATIONS

Williams et al. (Foye's Principles of Medicinal Chemistry, 5th edition, pp. 50 and 59-61, 2002).*
Elnagdi, M.H. and Erian, A.W., "Synthesis of Substituted Azaindenes: Synthesis of New Pyrazolo-[1,5-a]pyrimidine Derivatives", Bull Chem Soc Jpn, 63, pp. 1854-1856 (1990).
Ho, Y.W., "Studies on the Synthesis of New 3-(3,5-Diamino-1-substituted-pyrazol-4-yl)azo-thieno[2,3-13]pyridines and 3-(2-Amino-5,7-disubstituted-pyrazolo[1,5-a]pyrimidine-3-yl)azo-thieno[2,3-b]pyridines", J Chin Chem Soc (Taipei), 46 (6), pp. 955-962 (1999).
International Preliminary Report on Patentability / Written Opinion, PCT/US2008/087362, dated Jun. 22, 2010.
International Search Report, PCT/US2008/087362, dated Jul. 9, 2009.
Ledeboer, M.W., et al., "2-Aminopyrazolo[1,5-a]pyrimidines as potent and selective inhibitors of JAK2", Bioorg Med Chem Lett, 19(23), pp. 6529-6533 (2009).
Levine, R.L. and Gilliland, D.G., "Myeloproliferative disorders", Blood, 112(6), pp. 2190-2198 (2008).

(Continued)

*Primary Examiner* — Anna Pagonakis
(74) *Attorney, Agent, or Firm* — Booyong S. Lim

(57) ABSTRACT

The present invention relates to compounds of formula (I) useful as selective inhibitors of JAK2 kinase. The invention also provides pharmaceutical acceptable compositions comprising said compounds and methods of using the compositions in the treatment of various diseases, conditions or disorders. The invention also provides processes for preparing the compounds of the invention.

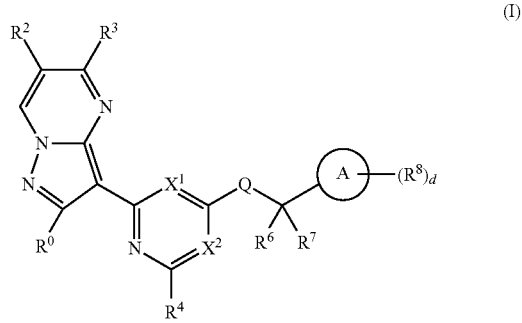

(I)

2 Claims, No Drawings

(56) References Cited

OTHER PUBLICATIONS

Clark, M.P., et al., "Development of new pyrrolopyrimidine-based inhibitors of Janus kinase 3 (JAK3)", Bioorg Med Chem Lett, 17(5), pp. 1250-1253 (2007).

Chen, J.J., et al., "Development of pyrimidine-based inhibitors of Janus tyrosine kinase 3", Bioorg Med Chem Lett, 16 (21), pp. 5633-5638 (2006).

McPherson, A., et al., Abstracts of Papers, 233rd ACS National Meeting, Chicago, IL, United States, Mar. 25-29, 2007 (2007), AN 2007:295553 CAPLUS.

Cao, J., et al., Abstracts of Papers, 233rd ACS National Meeting, Chicago, IL, United States, Mar. 25-29, 2007 (2007), AN 2007:295552 CAPLUS.

* cited by examiner

PYRAZOLO[1,5-A]PYRIMIDINES USEFUL AS JAK2 INHIBITORS

CROSS-REFERENCE TO RELATED APPLICATIONS

The present application claims the benefit of U.S. Provisional Patent Application Ser. No. 61/014,824, filed on Dec. 19, 2007. The entire contents of the above-mentioned application are incorporated herein by reference.

TECHNICAL FIELD OF THE INVENTION

The present invention relates to compounds useful as selective inhibitors of Janus kinases (JAK), in particular JAK2. The invention also provides pharmaceutically acceptable compositions comprising the compounds of the invention and methods of using the compositions in the treatment of various disorders.

BACKGROUND OF THE INVENTION

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK2 is a well validated target with strong potential in the treatment of myeloproliferative disorders (MPDs), which include polycythemia vera (PV), essential thrombocythemia, chronic idiopathic myelofibrosis, myeloid metaplasia with myelofibrosis, chronic myeloid leukemia, chronic myelomonocytic leukemia, chronic eosinophilic leukemia, hypereosinophilic syndrome and systematic mast cell disease. The strongest evidence for the link between JAK2 and MPDs is the prevalence of the V617F mutation in PV patients. The treatment of PV patients is currently considered non-optimal. A combination of phlebotomy and non-specific hematopoietic suppression with hydroxy urea is the current standard of care for PV patients. Other agents used to treat PV such as anagrelide and interferon-alpha, also require careful monitoring and elicit multiple side effects such as risk of leukemic progression, headache and gastrointestinal discomfort.

JAK3 has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematological malignancies such as leukemias and lymphomas.

Accordingly, there is a great need to develop compounds useful as inhibitors of protein kinases. In particular, it would be desirable to develop compounds that are useful as selective inhibitors of JAK2 for the treatment of myeloproliferative and other related proliferative disorders. In particular, selectivity against JAK3 would provide an adequate safety margin with respect to undesired immune suppression specifically mediated by JAK3.

SUMMARY OF THE INVENTION

It has now been found that compounds of this invention, and pharmaceutically acceptable compositions thereof, are effective as selective inhibitors of protein kinases, particularly JAK2. These compounds have the general formula I:

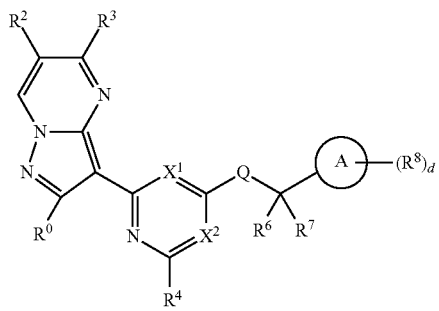

or a pharmaceutically acceptable salt thereof, wherein Ring A, $R^0$, $R^2$, $R^3$, $R^4$, $R^6$, $R^7$, $R^8$, Q, $X^1$ and $X^2$ are as defined herein.

These compounds, and pharmaceutically acceptable compositions thereof, are useful for treating or lessening the severity of a variety of myeloproliferative disorders, which include polycythemia vera, essential thrombocythemia, chronic idiopathic myelofibrosis, myeloid metaplasia with myelofibrosis, chronic myeloid leukemia, chronic myelomonocytic leukemia, chronic eosinophilic leukemia, hypereosinophilic syndrome and systematic mast cell disease.

The compounds and compositions provided by this invention are also useful for the study of JAK kinases in biological and pathological phenomena; the study of intracellular signal transduction pathways mediated by such kinases; and the comparative evaluation of new kinase inhibitors.

DETAILED DESCRIPTION OF THE INVENTION

Definitions and General Terminology

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry", Thomas Sorrell, University Science Books, Sausalito: 1999, and "March's Advanced Organic Chemistry", 5th Ed., Smith, M. B. and March, J., eds. John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

As described herein, when the term "optionally substituted" precedes a list, said term refers to all of the subsequent substitutable groups in that list. If a substituent radical or structure is not identified or defined as "optionally substituted", the substituent radical or structure is unsubstituted. For example, if X is halogen; optionally substituted $C_{1-3}$alkyl or phenyl; X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-3}$alkyl or phenyl wherein X is optionally substituted by $J^X$, then both $C_{1-3}$alkyl and phenyl may be optionally substituted by $J^X$. As is apparent to one having ordinary skill in the art, groups such as H, halogen, $NO_2$, CN, $NH_2$, OH, or $OCF_3$ would not be included because they are not substitutable groups.

Combinations of substituents envisioned by this invention are preferably those that result in the formation of stable or chemically feasible compounds. The term "stable", as used herein, refers to compounds that are not substantially altered when subjected to conditions to allow for their production, detection, and, preferably, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and, in yet other embodiments, aliphatic groups contain 1-4 aliphatic carbon atoms. Suitable aliphatic groups include, but are not limited to, linear or branched, substituted or unsubstituted alkyl, alkenyl, or alkynyl groups. Further examples of aliphatic groups include methyl, ethyl, propyl, butyl, isopropyl, isobutyl, vinyl, and sec-butyl.

The term "cycloaliphatic" (or "carbocycle" or "cycloalkyl") refers to a hydrocarbon that is completely saturated or that contains one or more units of unsaturation, but which is not aromatic, that has a single point of attachment to the rest of the molecule. Unless otherwise specified, the term "cycloaliphatic" refers to a monocyclic $C_3$-$C_8$ hydrocarbon or bicyclic $C_8$-$C_{12}$ hydrocarbon, wherein any individual ring in said bicyclic ring system has 3-7 members. Suitable cycloaliphatic groups include, but are not limited to, cycloalkyl, cycloalkenyl, and cycloalkynyl. Further examples of aliphatic groups include cyclopropyl, cyclobutyl, cyclopentyl, cyclopentenyl, cyclohexyl, cyclohexenyl, cycloheptyl, and cycloheptenyl.

The term "heterocycle", "heterocyclyl" or "heterocyclic" as used herein refers to a monocyclic, bicyclic, or tricyclic ring system in which one or more ring members are an independently selected heteroatom and that is completely saturated or that contains one or more units of unsaturation, but which is not aromatic, that has a single point of attachment to the rest of the molecule. In some embodiments, the "heterocycle", "heterocyclyl" or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydroimidazol-2-one.

The term "heteroatom" means one or more of oxygen, sulfur, nitrogen, phosphorus, or silicon, including any oxidized form of nitrogen, sulfur, phosphorus, or silicon, the quaternized form of any basic nitrogen, or a substitutable nitrogen of a heterocyclic ring, for example N (as in 3,4-dihydro-2H-pyrrolyl), NH (as in pyrrolidinyl) or $NR^+$ (as in N-substituted pyrrolidinyl).

The term "unsaturated", as used herein, means that a moiety has one or more units of unsaturation.

The term "aryl" used alone or as part of a larger moiety as in "aralkyl", "aralkoxy", or "aryloxyalkyl", refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring". Examples of aryl rings would include phenyl, naphthyl, and anthracene.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, wherein each ring in the system contains 3 to 7 ring members and that has a single point of attachment to the rest of the molecule. The term "heteroaryl" may be used interchangeably with the term "heteroaryl ring" or the term "heteroaromatic".

Further examples of heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

In some embodiments, an aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from those listed in the definitions of $R^3$, $R^4$ and $R^8$ below. Other suitable substituents include: halogen; —$R^o$; —$OR^o$; —$SR^o$; 1,2-methylenedioxy; 1,2-ethylenedioxy; phenyl (Ph) optionally substituted with $R^o$; —O(Ph) optionally substituted with $R^o$; —$(CH_2)_{1-2}$(Ph), optionally substituted with R°; —CH=CH(Ph), optionally substituted with R°; —NO₂; —CN; —N(R°)₂; —NR°C(O)R°; —NR°C(S)R°; —NR°C(O)N(R°)₂; —NR°C(S)N(R°)₂; —NR°CO₂R°; —NR°NR°C(O)R°; —NR°NR°C(O)N(R°)₂; —NR°NR°CO₂R°; —C(O)C(O)R°; —C(O)CH₂C(O)R°; —CO₂R°; —C(O)R°; —C(S)R°; —C(O)N(R°)₂; —C(S)N(R°)₂; —OC(O)N(R°)₂; —OC(O)R°; —C(O)N(OR°)R°; —C(NOR°)R°; —S(O)₂R°; —S(O)₃R°; —SO₂N(R°)₂; —S(O)R°; —NR°SO₂N(R°)₂; —NR°SO₂R°; —N(OR°)R°; —C(=NH)—N(R°)₂; or —(CH₂)₀₋₂NHC(O)R°; wherein each independent occurrence of R° is selected from hydrogen, optionally substituted $C_{1-6}$ aliphatic, an unsubstituted 5-6 membered heteroaryl or heterocyclic ring, phenyl, —O(Ph), or —CH₂(Ph), or, two independent occurrences of R°, on the same substituent or different substituents, taken together with the atom(s) to which each R° group is bound, form a 5-8-membered heterocyclyl, aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group of R° are selected from NH₂, NH($C_{1-4}$aliphatic), N($C_{1-4}$aliphatic)₂, halogen, $C_{1-4}$aliphatic, OH, O($C_{1-4}$aliphatic), NO₂, CN, CO₂H, CO₂($C_{1-4}$aliphatic), O(halo$C_{1-4}$ aliphatic), or halo$C_{1-4}$aliphatic, CHO, N(CO)($C_{1-4}$aliphatic), C(O)N($C_{1-4}$aliphatic), wherein each of the foregoing $C_{1-4}$aliphatic groups of R° is unsubstituted.

In some embodiments, an aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)₂, =NNHC(O)R*, =NNHCO₂(alkyl), =NNHSO₂(alkyl), or =NR*, where each R* is independently selected from hydrogen or an optionally substituted $C_{1-6}$ aliphatic. Optional substituents on the aliphatic group of R* are selected from NH₂, NH($C_{1-4}$ aliphatic), N($C_{1-4}$ aliphatic)₂, halogen, $C_{1-4}$ aliphatic, OH, O($C_{1-4}$ aliphatic), NO₂, CN, CO₂H, CO₂($C_{1-4}$ aliphatic), O(halo $C_{1-4}$ aliphatic), or halo($C_{1-4}$ aliphatic), wherein each of the foregoing $C_{1-4}$aliphatic groups of R* is unsubstituted.

In some embodiments, optional substituents on the nitrogen of a non-aromatic heterocyclic ring include —R⁺, —N(R⁺)₂, —C(O)R⁺, —CO₂R⁺, —C(O)C(O)R⁺, —C(O)CH₂C(O)R⁺, —SO₂R⁺, —SO₂N(R⁺)₂, —C(=S)N(R⁺)₂, —C(=NH)—N(R⁺)₂, or —NR⁺SO₂R⁺; wherein R⁺ is hydrogen, an optionally substituted $C_{1-6}$ aliphatic, optionally substituted phenyl, optionally substituted —O(Ph), optionally substituted —CH₂(Ph), optionally substituted —(CH₂)₁₋₂(Ph); optionally substituted —CH=CH(Ph); or an unsubstituted 5-6 membered heteroaryl or heterocyclic ring having one to four heteroatoms independently selected from oxygen, nitrogen, or sulfur, or, two independent occurrences of R⁺, on the same substituent or different substituents, taken together with the atom(s) to which each R⁺ group is bound, form a 5-8-membered heterocyclyl, aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group or the phenyl ring of R⁺ are selected from NH₂, NH($C_{1-4}$ aliphatic), N($C_{1-4}$ aliphatic)₂, halogen, $C_{1-4}$ aliphatic, OH, O($C_{1-4}$ aliphatic), NO₂, CN, CO₂H, CO₂($C_{1-4}$ aliphatic), O(halo $C_{1-4}$ aliphatic), or halo ($C_{1-4}$ aliphatic), wherein each of the foregoing $C_{1-4}$aliphatic groups of R⁺ is unsubstituted.

As detailed above, in some embodiments, two independent occurrences of R° (or R⁺, or any other variable similarly defined herein), may be taken together with the atom(s) to which each variable is bound to form a 5-8-membered heterocyclyl, aryl, or heteroaryl ring or a 3-8-membered cycloalkyl ring. Exemplary rings that are formed when two independent occurrences of R° (or R⁺, or any other variable similarly defined herein) are taken together with the atom(s) to which each variable is bound include, but are not limited to the following: a) two independent occurrences of R° (or R⁺, or any other variable similarly defined herein) that are bound to the same atom and are taken together with that atom to form a ring, for example, N(R°)₂, where both occurrences of R° are taken together with the nitrogen atom to form a piperidin-1-yl, piperazin-1-yl, or morpholin-4-yl group; and b) two independent occurrences of R° (or R⁺, or any other variable similarly defined herein) that are bound to different atoms and are taken together with both of those atoms to form a ring, for example where a phenyl group is substituted with two occurrences of OR°

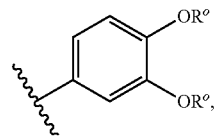

these two occurrences of R° are taken together with the oxygen atoms to which they are bound to form a fused 6-membered oxygen containing ring:

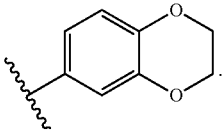 [SMILES: *c1ccc2c(c1)OCCO2]

It will be appreciated that a variety of other rings can be formed when two independent occurrences of R° (or R⁺, or any other variable similarly defined herein) are taken together with the atom(s) to which each variable is bound and that the examples detailed above are not intended to be limiting.

In some embodiments, an alkyl or aliphatic chain can be optionally interrupted with another atom or group. This means that a methylene unit of the alkyl or aliphatic chain is optionally replaced with said other atom or group. Examples of such atoms or groups would include, but are not limited to, —NR—, —O—, —S—, —CO₂—, —OC(O)—, —C(O)CO—, —C(O)—, —C(O)NR—, —C(=N—CN), —NRCO—, —NRC(O)O—, —SO₂NR—, —NRSO₂—, —NRC(O)NR—, —OC(O)NR—, —NRSO₂NR—, —SO—, or —SO₂—, wherein R is defined herein. Unless otherwise specified, the optional replacements form a chemically stable compound. Optional interruptions can occur both within the chain and at either end of the chain; i.e. both at the point of attachment and/or also at the terminal end. Two optional replacements can also be adjacent to each other within a chain so long as it results in a chemically stable compound. Unless otherwise specified, if the replacement or interruption occurs at the terminal end, the replacement atom is bound to an H on the terminal end. For example, if —CH₂CH₂CH₃ were optionally interrupted with —O—, the resulting compound could be —OCH₂CH₃, —CH₂OCH₃, or —CH₂CH₂OH.

As described herein, a bond drawn from a substituent to the center of one ring within a multiple-ring system (as shown below), represents substitution of the substituent at any substitutable position in any of the rings within the multiple ring system. For example, Structure a represents possible substitution in any of the positions shown in Structure b.

Structure a

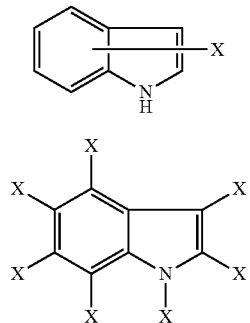

Structure b

This also applies to multiple ring systems fused to optional ring systems (which would be represented by dotted lines). For example, in Structure c, X is an optional substituent both for ring A and ring B.

Structure c

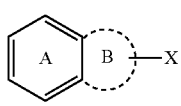

If, however, two rings in a multiple ring system each have different substituents drawn from the center of each ring, then, unless otherwise specified, each substituent only represents substitution on the ring to which it is attached. For example, in Structure d, Y is an optionally substituent for ring A only, and X is an optional substituent for ring B only.

Structure d

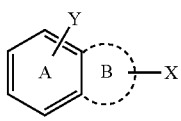

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C-$ or $^{14}C$-enriched carbon are within the scope of this invention. Such compounds are useful, for example, as analytical tools or probes in biological assays.

Description of Compounds of the Invention

The present invention relates to a compound of formula I:

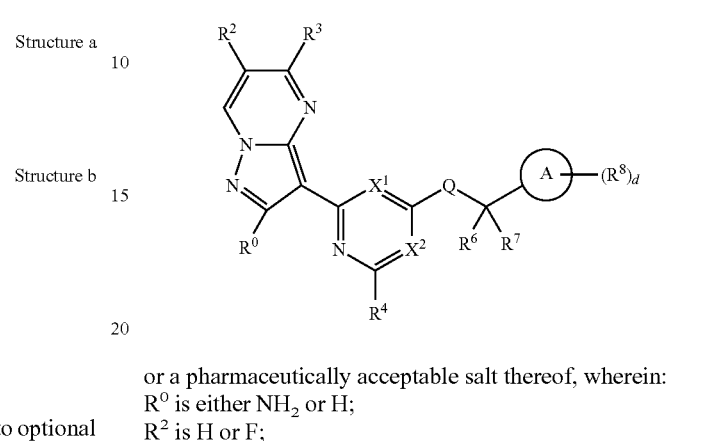

I or a pharmaceutically acceptable salt thereof, wherein:
$R^0$ is either $NH_2$ or H;
$R^2$ is H or F;
$R^3$ is H, halogen, CN, $R^1$, $OR^1$, $SR^1$, $N(R^1)_2$, $C(O)R^1$, $C(O)N(R^1)_2$, $NR^1C(O)R^1$, $C(O)OR^1$, $OC(O)R^1$, $C(O)COR^1$, $NC(=N-CN)NR^1$, $NR^1C(O)OR^1$, $SO_2NR^1$, $NR^1SO_2R^1$, $NR^1C(O)N(R^1)_2$, $OC(O)N(R^1)_2$, $NR^1SO_2N(R^1)_2$, $SOR^1$, or $SO_2R^1$;
each $R^1$ is independently selected from H, $C_{1-6}$ aliphatic or a 3-6 membered cycloaliphatic, wherein $R^1$ is optionally substituted with 1-4 occurrences of $J^{R1}$;
each $J^{R1}$ is independently selected from halogen, $OCH_2CH_3$, $OCH_3$, OH, $NO_2$, $NH_2$, $SCH_2CH_3$, $SCH_3$, $NHCH_2CH_3$, $NHCH_3$, $N(CH_2CH_3)_2$, $N(CH_3)_2$, CN, or unsubstituted $C_{1-4}$aliphatic, or wherein two $J^{R1}$, together with the carbon to which they are attached, form a cyclopropyl ring or a C=O group;
$R^4$ is $-(U)_m-Y$;
U is a $C_{1-6}$ aliphatic, wherein up to two methylene units are optionally and independently replaced by $G^U$ and wherein U is optionally substituted with 1-6 $J^U$;
$G^U$ is $-NH-$, $-NR^9-$, $-O-$, $-S-$, $-CO_2-$, $-OC(O)-$, $-C(O)CO-$, $-C(O)-$, $-C(O)NH-$, $-C(O)NR^9-$, $-NC(=N-CN)N-$, $-NHCO-$, $-NR^9CO-$, $-NHC(O)O-$, $-NR^9C(O)O-$, $-SO_2NH-$, $-SO_2NR^9-$, $-NHSO_2-$, $-NR^9SO_2-$, $-NHC(O)NH-$, $-NR^9C(O)NH-$, $-NHC(O)NR^9-$, $-NR^9C(O)NR^9-$, $-OC(O)NH-$, $-OC(O)NR^9-$, $-NHSO_2NH-$, $-NR^9SO_2NH-$, $-NHSO_2NR^9-$, $-NR^9SO_2NR^9-$, $-SO-$, $-SO_2-$, $-CO(NR^9)CO-$, or $C=NOR^9$;
$R^9$ is $C_{1-6}$ aliphatic or a $C_{3-10}$ cycloaliphatic; or two $R^9$ groups, together with the atom to which they are attached, optionally form a 3-7 membered cycloaliphatic or heterocyclyl, wherein said aliphatic, cycloaliphatic or heterocyclyl is optionally substituted with R", $-OR"$, $-SR"$, $-NO_2$, $-CF_3$, $-CN$, $-CO_2R"$, $-COR"$, OCOR", CONHR", NHCOOR" or NHCOR";
R" is H or an unsubstituted $C_{1-6}$ aliphatic;
m is 0 or 1;
Y is H, halogen, CN, $NO_2$ or a group selected from a $C_{1-6}$ aliphatic, a $C_{3-10}$ cycloaliphatic, a $C_{5-10}$ aryl, a 5-10 membered heteroaryl, or a 3-10 membered heterocyclyl, wherein said group is optionally substituted with 1-8 occurrences of $J^Y$;

each $J^U$ is independently selected from halogen, L, -($L_n$)-R', -($L_n$)-N(R')$_2$, -($L_n$)-SR', -($L_n$)-OR', -($L_n$)-($C_{3-10}$ cycloaliphatic), -($L_n$)-($C_{6-10}$ aryl), -($L_n$)-(5-10 membered heteroaryl), -($L_n$)-(5-10 membered heterocyclyl), oxo, $C_{1-4}$haloalkoxy, $C_{1-4}$haloalkyl, -($L_n$)-NO$_2$, -($L_n$)-CN, -($L_n$)-OH, -($L_n$)-CF$_3$, —CO$_2$R', —CO$_2$H, —COR', —COH, —OC(O)R', —C(O)NHR', C(O)N(R')$_2$, —NHC(O)R', or NR'C(O)R'; or two $J^U$ groups, on the same substituent or different substituents, together with the atom(s) to which each $J^U$ group is bound, form a 5-7 membered saturated, unsaturated, or partially saturated ring;

each $J^Y$ is independently selected from halogen, L, -($L_n$)-R', -($L_n$)-N(R')$_2$, -($L_n$)-SR', -($L_n$)-OR', -($L_n$)-($C_{3-10}$ cycloaliphatic), -($L_n$)-($C_{6-10}$ aryl), -($L_n$)-(5-10 membered heteroaryl), -($L_n$)-(5-10 membered heterocyclyl), oxo, $C_{1-4}$haloalkoxy, $C_{1-4}$haloalkyl, -($L_n$)-NO$_2$, -($L_n$)-CN, -($L_n$)-OH, -($L_n$)-CF$_3$, —CO$_2$R', —CO$_2$H, —COR', —COH, —OC(O)R', —C(O)NHR', C(O)N(R')$_2$, NHC(O)OH, NR'C(O)OH, NHC(O)H, NR'C(O)H, NHC(O)OR', NR'C(O)OR', NHC(O)R' or NR'C(O)R'; or two $J^Y$ groups, on the same substituent or different substituents, together with the atom(s) to which each $J^Y$ group is bound, form a 5-7 membered saturated, unsaturated, or partially saturated ring;

each L is independently a $C_{1-6}$ aliphatic wherein up to three methylene units are replaced by —NH—, —NR$^L$—, —O—, —S—, —CO$_2$—, —OC(O)—, —C(O)CO—, —C(O)—, —C(O)NH—, —C(O)NR$^L$—, —NC(=N—CN)N—, —NHCO—, —NR$^L$CO—, —NHC(O)O—, —NR$^L$C(O)O—, —SO$_2$NH—, —SO$_2$NR$^L$—, —NHSO$_2$—, —NR$^L$SO$_2$—, —NHC(O)NH—, —NR$^L$C(O)NH—, —NHC(O)NR$^L$—, —NR$^L$C(O)NR$^L$—, —OC(O)NH—, —OC(O)NR$^L$—, —NHSO$_2$NH—, —NR$^L$SO$_2$NH—, —NHSO$_2$NR$^L$—, —NR$^L$SO$_2$NR$^L$—, —SO—, or —SO$_2$—;

each n is independently 0 or 1;

each R' is independently H or $C_{1-6}$ aliphatic; or two R' groups, together with the atom to which they are attached, optionally form a 3-6 membered cycloaliphatic or heterocyclyl, wherein said aliphatic, cycloaliphatic or heterocyclyl is optionally substituted with R*, —OR*, —SR*, —NO$_2$, —CF$_3$, —CN, —CO$_2$R*, —COR*, OCOR*, NHCOR*, wherein R* is H or $C_{1-6}$ aliphatic;

$R^L$ is selected from $C_{1-6}$ aliphatic, $C_{3-10}$ cycloaliphatic, $C_{6-10}$ aryl, 5-10 membered heteroaryl, or 5-10 membered heterocyclyl; or two $R^L$ groups, on the same substituent or different substituents, together with the atom(s) to which each $R^L$ group is bound, form a 3-8 membered heterocyclyl;

$X^1$ is N or CH or CF;

$X^2$ is N or CR$^{10}$;

$R^{10}$ is -(T)$_b$-R$^{11}$, wherein R$^{10}$ is optionally substituted with 1-8 occurrences of $J^{R10}$;

or $R^4$ and $R^{10}$, together with the atoms to which each of $R^4$ and $R^{10}$ are bound, form a 3-8 membered carbocyclic ring, a 5-8 membered heterocyclic ring, or a 5-6 membered aryl or heteroaryl ring, wherein said ring is optionally substituted with 1-4 $J^Z$;

T is a $C_{1-6}$ aliphatic, wherein up to two methylene units are optionally and independently replaced by $G^T$ and wherein T is optionally substituted with 1-4 $J^T$;

$G^T$ is —NH—, —NR$^9$—, —O—, —S—, —CO$_2$—, —OC(O)—, —C(O)CO—, —C(O)—, —C(O)NH—, —C(O)NR$^9$—, —NC(=N—CN)N—, —NHCO—, —NR$^9$CO—, —NHC(O)O—, —NR$^9$C(O)O—, —SO$_2$NH—, —SO$_2$NR$^9$—, —NHSO$_2$—, —NR$^9$SO$_2$—, —NHC(O)NH—, —NR$^9$C(O)NH—, —NHC(O)NR$^9$—, —NR$^9$C(O)NR$^9$, —OC(O)NH—, —OC(O)NR$^9$—, —NHSO$_2$NH—, —NR$^9$SO$_2$NH—, —NHSO$_2$NR$^9$—, —NR$^9$SO$_2$NR$^9$—, —SO—, or —SO$_2$—;

b is 0 or 1;

$R^{11}$ is H, halogen, CN, NO$_2$, or a group selected from a $C_{1-6}$ aliphatic, a $C_{3-10}$ cycloaliphatic, a $C_{6-10}$ aryl, a 5-10 membered heteroaryl, or a 5-10 membered heterocyclyl, wherein said group is optionally substituted with 1-8 occurrences of $J^{R11}$;

each $J^T$ is independently selected from halogen, L, -($L_n$)-R', -($L_n$)-N(R')$_2$, -($L_n$)-SR', -($L_n$)-OR', -($L_n$)-($C_{3-10}$ cycloaliphatic), -($L_n$)-($C_{6-10}$ aryl), -($L_n$)-(5-10 membered heteroaryl), -($L_n$)-(5-10 membered heterocyclyl), oxo, $C_{1-4}$haloalkoxy, $C_{1-4}$haloalkyl, -($L_n$)-NO$_2$, -($L_n$)-CN, -($L_n$)-OH, -($L_n$)-CF$_3$, —CO$_2$R', —CO$_2$H, —COR', —COH, —OC(O)R', —C(O)NHR', C(O)N(R')$_2$, NHC(O)OH, NR'C(O)OH, NHC(O)H, NR'C(O)H, NHC(O)OR', NR'C(O)OR', NHC(O)R' or NR'C(O)R'; or two $J^T$ groups, on the same substituent or different substituents, together with the atom(s) to which each $J^T$ group is bound, form a 5-7 membered saturated, unsaturated, or partially saturated ring;

each $J^{R10}$ is independently selected from halogen, L, -($L_n$)-R', -($L_n$)-N(R')$_2$, -($L_n$)-SR', -($L_n$)-OR', -($L_n$)-($C_{3-10}$ cycloaliphatic), -($L_n$)-($C_{6-10}$ aryl), -($L_n$)-(5-10 membered heteroaryl), -($L_n$)-(5-10 membered heterocyclyl), oxo, $C_{1-4}$haloalkoxy, $C_{1-4}$haloalkyl, -($L_n$)-NO$_2$, -($L_n$)-CN, -($L_n$)-OH, -($L_n$)-CF$_3$, —CO$_2$R', —CO$_2$H, —COR', —COH, —OC(O)R', —C(O)NHR', C(O)N(R')$_2$, NHC(O)OH, NR'C(O)OH, NHC(O)H, NR'C(O)H, NHC(O)OR', NR'C(O)OR', NHC(O)R' or NR'C(O)R'; or two $J^{R11}$ groups, on the same substituent or different substituents, together with the atom(s) to which each $J^{R11}$ group is bound, form a 5-7 membered saturated, unsaturated, or partially saturated ring;

each $J^{R11}$ is independently selected from halogen, L, -($L_n$)-R', -($L_n$)-N(R')$_2$, -($L_n$)-SR', -($L_n$)-OR', -($L_n$)-($C_{3-10}$ cycloaliphatic), -($L_n$)-($C_{6-10}$ aryl), -($L_n$)-(5-10 membered heteroaryl), -($L_n$)-(5-10 membered heterocyclyl), oxo, $C_{1-4}$haloalkoxy, $C_{1-4}$haloalkyl, -($L_n$)-NO$_2$, -($L_n$)-CN, -($L_n$)-OH, -($L_n$)-CF$_3$, —CO$_2$R', —CO$_2$H, —COR', —COH, —OC(O)R', —C(O)NHR', C(O)N(R')$_2$, NHC(O)OH, NR'C(O)OH, NHC(O)H, NR'C(O)H, NHC(O)OR', NR'C(O)OR', NHC(O)R' or NR'C(O)R'; or two $J^{R11}$ groups, on the same substituent or different substituents, together with the atom(s) to which each $J^{R11}$ group is bound, form a 5-7 membered saturated, unsaturated, or partially saturated ring;

Q is —O—, —S—, —S(O)—, —S(O)$_2$— or —N(R$^5$)—, —C(O)— or —C(F$_2$)—;

$R^5$ is H, CF$_3$, $C_{1-4}$ aliphatic, cyclopropyl, OCH$_3$, C(O)NH$_2$, C(O)CH$_3$;

or $R^5$ and $R^{10}$, together with the atoms to which each of $R^5$ and $R^{10}$ are bound, along with any intervening atoms, form a 5-7 membered heterocyclic ring, or a 5-6 membered heteroaryl ring, wherein said ring is optionally substituted with 1-4 $J^Z$;

$R^6$ is —(V)$_q$—Z;

V is a $C_{1-2}$ aliphatic, wherein up to one methylene unit is optionally and independently replaced by $G^V$ and wherein V is optionally substituted with 1-3 $J^V$;

$G^V$ is —NH—, —NR$^{13}$—, —O—, —S—, —CO$_2$—, —OC(O)—, —C(O)CO—, —C(O)—, —C(O)NH—, —C(O)NR$^{13}$—, —NC(=N—CN)N—, —NHCO—, —NR$^{13}$CO—, —NHC(O)O—, —NR$^{13}$C(O)O—, —SO$_2$NH—, —SO$_2$NR$^{13}$—, —NHSO$_2$—, —NR$^{13}$SO$_2$—, —NHC(O)NH—, —NR$^{13}$C(O)NH—, —NHC(O)NR$^{13}$—, —NR$^{13}$C(O)NR$^{13}$—, —OC(O)NH—,

—OC(O)NR$^{13}$—, —NHSO$_2$NH—, —NR$^{13}$SO$_2$NH—, —NHSO$_2$NR$^{13}$—, —NR$^{13}$SO$_2$NR$^{13}$—, —SO—, or —SO$_2$—;

R$^{13}$ is a C$_{1-4}$ aliphatic, wherein said aliphatic is optionally substituted with halogen, —OH, —SH, —NO$_2$, —CF$_3$, —CN, —CO$_2$H, —COH, OCOH, CONH$_2$, or NHCOH or NHCOOH;

q is 0 or 1;

Z is H, halogen, CN, NO$_2$, or a group selected from a C$_{1-6}$ aliphatic, a C$_{3-6}$ cycloaliphatic, phenyl, a 5-6 membered heteroaryl, or a 3-6 membered heterocyclyl, wherein said group is optionally substituted with 1-4 J$^Y$;

each J$^Y$ is independently selected from unsubstituted C$_{1-4}$ aliphatic, halogen, —OR$^{27}$, —SR$^{27}$, —NO$_2$, N(R$^{27}$)$_2$, —CF$_3$, —CN, —CO$_2$R$^{27}$, —COR$^{27}$, OCOR$^{27}$, CON (R$^{27}$)$_2$, or NR$^{27}$COR$^{27}$ or NR$^{27}$COOR$^{27}$;

R$^{27}$ is H or an unsubstituted C$_{1-4}$ aliphatic;

Or two R$^{27}$, together with the atom to which they are bound can form a heterocyclyl optionally substituted with up to four F;

each J$^Z$ is independently selected from unsubstituted C$_{1-4}$ aliphatic, halogen, —OR$^{27}$, —SR$^{27}$, —NO$_2$, N(R$^{27}$)$_2$, —CF$_3$, —CN, —CO$_2$R$^{27}$, —COR$^{27}$, OCOR$^{27}$, CON (R$^{27}$)$_2$, or NR$^{27}$COR$^{27}$ or NR$^{27}$COOR$^{27}$; or two J$^Z$ groups, on the same substituent or different substituents, together with the atom(s) to which each J$^Z$ group is bound, form a 5-7 membered saturated, unsaturated, or partially saturated ring;

or R$^5$ and R$^6$, together with the atoms to which each of R$^5$ and R$^6$ are bound, form a 3-7 membered heterocyclic ring, or a 5 membered heteroaryl ring, wherein said ring is optionally substituted with 1-4 J$^Z$;

or R$^6$ and R$^7$, together with the atom to which R$^6$ and R$^7$ are bound, form a 3-5 membered carbocyclic or heterocyclic ring, wherein said ring is optionally substituted with 1-4 J$^Z$ or they together form a carbonyl group;

or R$^6$ and R$^8$, together with the atoms to which each of R$^6$ and R$^8$ are bound, along with any intervening atoms, form a 4-7 membered carbocyclic ring, a 4-7 membered heterocyclic ring, or a 5-6 membered aryl or heteroaryl ring, wherein said ring is optionally substituted with 1-4 J$^Z$;

or R$^5$ and R$^8$, together with the atoms to which each of R$^5$ and R$^8$ are bound, along with any intervening atoms form a 4-7 membered heterocyclic ring, or a 5-6 membered heteroaryl ring, wherein said ring is optionally substituted with 1-4 J$^Z$;

R$^7$ is H or a C$_{1-2}$ alkyl optionally substituted with 1-3 occurrences of J$^{R7}$;

each J$^{R7}$ is independently selected from F, CH$_3$, OH, OCH$_3$, C(O)OH, C(O)OCH$_3$, CONH$_2$, CONHCH$_3$, CON(CH$_3$)$_2$, or CN;

Ring A is phenyl or a 5-6 membered monocyclic heteroaryl or a 9-10 bicyclic heteroaryl, having 1-4 heteroatoms selected from nitrogen, oxygen, or sulfur;

R$^8$ is halogen, CN, NO$_2$, R, OR, SR, N(R)$_2$, C(O)R, C(O)N (R)$_2$, NRC(O)R, C(O)OR, OC(O)R, C(O)COR, NC(=N—CN)NR, NRC(O)OR, SO$_2$NR, NRSO$_2$R, NRC (O)N(R)$_2$, OC(O)N(R)$_2$, NRSO$_2$N(R)$_2$, SOR, or SO$_2$R;

each R is independently selected from H or C$_{1-4}$ aliphatic, wherein R is optionally substituted with 1-4 occurrences of a group selected from F, OCH$_2$CH$_3$, OCH$_3$, OH, NO$_2$, NH$_2$, SCH$_2$CH$_3$, SCH$_3$, NHCH$_2$CH$_3$, NHCH$_3$, N(CH$_2$CH$_3$)$_2$, N(CH$_3$)$_2$, CN, or unsubstituted C$_{1-4}$aliphatic and d is 0, 1, 2, 3 or 4.

In one embodiment, R$^2$ is H.

In one embodiment, R$^3$ is H, halogen, R$^1$, OR$^1$, SR$^1$, CN or N(R$^1$)$_2$, wherein R$^1$ is optionally substituted with 1-4 occurrences of J$^{R1}$. In a further embodiment, R$^1$ is H or C$_{1-3}$ aliphatic.

In another embodiment, R$^3$ is selected from H, F, Cl, CN, CH$_3$, —CH$_2$CH$_3$, —CH$_2$CH$_2$CH$_3$, CH(CH$_3$)$_2$, cyclopropyl, OCH$_3$, OCH$_2$CH$_3$, SCH$_3$ or SCH$_2$CH$_3$, wherein said group is optionally substituted with 1-6 occurrences of F.

In yet another embodiment, both R$^2$ and R$^3$ are H.

In another embodiment, R$^4$ is H, CN, NH$_2$, C$_{1-4}$ aliphatic, C$_{3-6}$ cycloalkyl, 5-6 membered heterocyclyl, O(C$_{1-6}$ aliphatic), S(C$_{1-6}$ aliphatic), NH(C$_{1-6}$ aliphatic), O(5-10 membered heterocyclyl), S(5-10 membered heterocyclyl), NH(5-10 membered heterocyclyl), 5-6 membered heteroaryl or phenyl, N—SO$_2$(C$_{1-6}$ aliphatic)$_2$ or N(CO)(C$_{1-6}$ aliphatic) and wherein said group is optionally substituted with 1-4 J$^Y$.

In one embodiment, Q is —N(R$^5$)—. In a further embodiment, R$^5$ is H, CH$_3$, CH$_3$CH$_2$ or cyclopropyl.

In one embodiment, Ring A is phenyl, wherein Ring A is optionally substituted with d=1-3 occurrences of R$^8$ and wherein R$^8$ is halogen, CN, NH$_2$, NO$_2$, CF$_3$, C$_{1-4}$ aliphatic, cyclopropyl, NH(C$_{1-4}$ aliphatic), N(C$_{1-4}$ aliphatic)$_2$, OH, O(C$_{1-4}$ aliphatic), —C(O)NH$_2$, —C(O)NH(C$_{1-4}$ aliphatic), —C(O)C$_{1-4}$ aliphatic, —C(O)H, —NHC(O)C$_{1-4}$ aliphatic, —NHC(O)H, —C(O)OH, —C(O)O(C$_{1-4}$ aliphatic), —NHC (O)OH, —NHC(O)O(C$_{1-4}$ aliphatic), —OC$_{1-2}$ aliphatic, —OCF$_3$ or oxo, and wherein R$^8$ is optionally substituted with 1-3 occurrences of F, —OC$_{1-2}$ aliphatic, —OCF$_3$ or C$_{1-2}$ aliphatic. In another embodiment, Ring A is a phenyl ring, optionally substituted with d=1-2 occurrences of R$^8$, wherein R$^8$ is halogen, CN, methyl, ethyl, methoxy or ethoxy, and wherein R$^8$ is optionally substituted with 1-3 occurrences of F.

In another embodiment, the invention provides a compound of formula II:

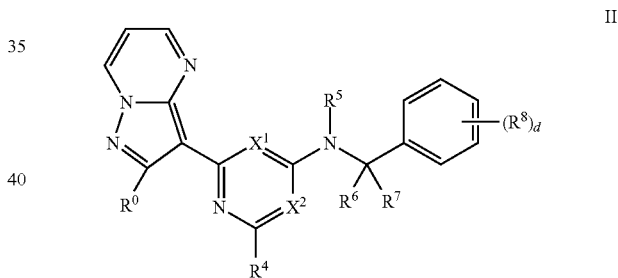

II or a pharmaceutically acceptable salt thereof, wherein R$^0$, R$^4$, R$^5$, R$^6$, R$^7$, R$^8$ and X$^1$ and X$^2$ are as defined above.

In one embodiment of formula II, R$^5$ is H, CH$_3$, CH$_3$CH$_2$, isopropyl or cyclopropyl. In another embodiment of formula II, R$^5$ is H.

In one embodiment of formula II, R$^6$ is independently selected from H, C$_{1-4}$ aliphatic, (C$_{1-4}$ aliphatic)C(O)NR$_2$, (C$_{1-4}$ aliphatic)C(O)NH$_2$, (C$_{1-4}$ aliphatic)C(O)NHR, (C$_{1-4}$ aliphatic)OR, (C$_{1-4}$ aliphatic)OH, (C$_{1-4}$ aliphatic)CO$_2$R or (C$_{1-4}$ aliphatic)NR$_2$. In another embodiment, R$^6$ is C$_{1-4}$ aliphatic, (C$_{1-4}$ aliphatic)C(O)NR$_2$, (C$_{1-4}$ aliphatic)C(O)NH$_2$, (C$_{1-4}$ aliphatic)C(O)NHR, (C$_{1-4}$ aliphatic)OR, (C$_{1-4}$ aliphatic)OH, and R$^6$ is optionally substituted with 1-3 occurrences of fluorine. In yet a further embodiment of formula II, R$^7$ is H.

In another embodiment of formula II, R$^6$ and R$^7$, together with the atom to which R$^6$ and R$^7$ are attached, form a 3-5-membered carbocyclic ring, wherein said ring is optionally substituted with 1-4 J$^Z$ or R$^6$ and R$^7$ form a carbonyl group. In yet a further embodiment, R$^6$ and R$^7$, together with the atom to which R$^6$ and R$^7$ are attached, form a 3-5-membered carbocyclic ring.

In yet another embodiment, the invention provides a compound of formula III:

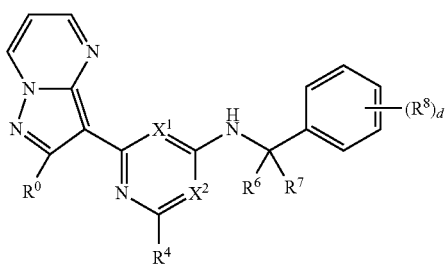

III

In one embodiment of formula III, $X^2$ is N or $CR^{10}$, wherein $R^{10}$ is H, halogen or a $C_{1-4}$ aliphatic group and $R^{10}$ is optionally substituted with 1-3 occurrences of OH, SH, halogen, $CF_3$, $NO_2$, C(O)OH, C(O)H, $CONH_2$, NHC(O)OH or CN.

In a further embodiment of formula III, $X^2$ is CH, N or CF.

In another embodiment of formula II, $R^6$ and $R^8$, together with the atoms to which each of $R^6$ and $R^8$ are bound, along with intervening atoms, form a 3-8 membered carbocyclic ring, a 5-8 membered heterocyclic ring, or a 5-6 membered aryl or heteroaryl ring, wherein said ring is optionally substituted with 1-4 occurrences of $J^Z$.

In another embodiment the invention also provides a compound of formula IV,

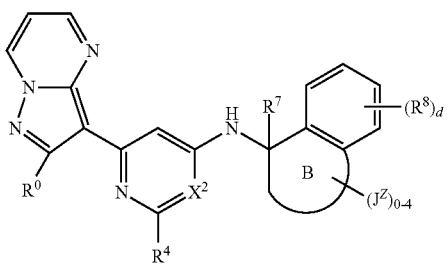

IV wherein Ring B is a 5-8 membered carbocyclic ring, a 5-8 membered heterocyclic ring, or a 5-6 membered aryl or heteroaryl ring and $R^0$, $R^4$, $R^7$, $R^8$ and $X^2$ are as described herein. In a further embodiment of formula IV, Ring B is a 5 or 6 membered carbocyclic or heterocyclic ring optionally substituted with 1-4 occurrences of $J^Z$.

In another embodiment of formula II, $R^5$ and $R^8$, together with the atoms to which each of $R^5$ and $R^8$ are bound, along with intervening atoms, form a 5-8-membered heterocyclic ring, or a 5-6 membered heteroaryl wherein said ring is optionally substituted with 1-4 $J^Z$.

In another embodiment, the invention also provides a compound of formula V,

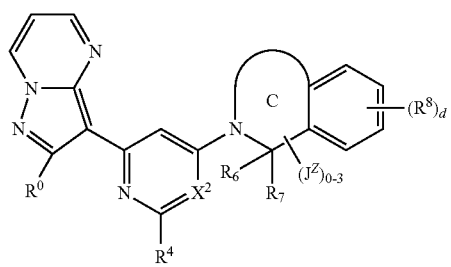

V wherein Ring C is a 5-8 membered heterocyclic ring optionally substituted with 1-3 occurrences of $J^Z$ and wherein $R^0$, $R^4$, $R^6$, $R^7$, $R^8$ and $X^2$ are as described above; or wherein ring C is a 5 membered heteroaryl ring. In yet a further embodiment of formula V, Ring C is an unsubstituted 5- or 6-membered heterocyclic ring.

In another embodiment, $R^6$ and $R^5$, together with the atoms to which each of $R^6$ and $R^5$ are attached, along with intervening atoms, form a 5-8 membered heterocyclic ring, or a 5 membered heteroaryl ring, wherein said ring is optionally substituted with 1-4 occurrences of $J^Z$.

In another embodiment, the invention also provides a compound of formula VI:

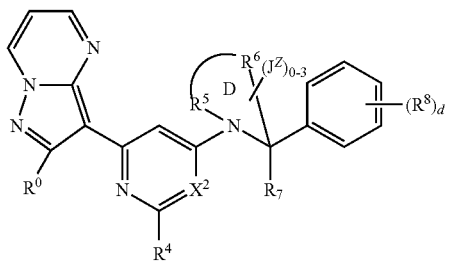

VI wherein ring D is a 3-8 membered heterocyclyl optionally substituted with 1-3 occurrences of $J^Z$.

In another embodiment, the invention provides a compound of any one of formulae I, II, III, IV, V or VI, wherein $R^0$ is $NH_2$.

In another embodiment, the invention provides a compound of any one of formulae I, II, III, IV, V or VI, wherein $X^1$ is CH and $X^2$ is N.

In another embodiment of formula VI, Ring D is a 5 or 6 membered heterocyclic ring or a 5 membered heteroaryl, optionally substituted with 1-3 occurrences of $J^Z$. In yet a further embodiment of formula VI, Ring D is an unsubstituted 5 or 6 membered heterocyclic ring.

In another embodiment, the invention provides a compound of formulae I, II, III, IV, V or VI wherein said compound inhibits a JAK2 kinase with a lower K, (i.e., is more potent) than said compound inhibits one or more kinases selected from JAK3, Aurora-2, Src, and CDK2. In another embodiment, the invention provides a compound of Table I:

TABLE I

TABLE I-continued
2
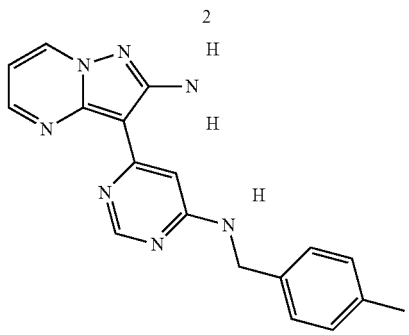
3
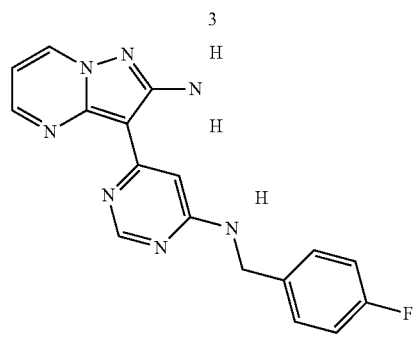
4
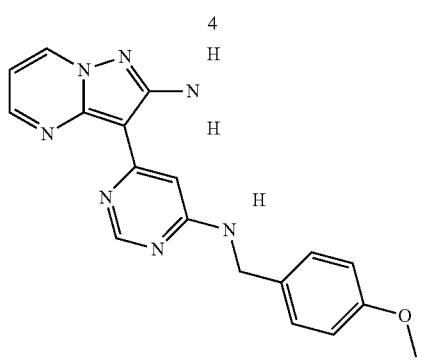
5
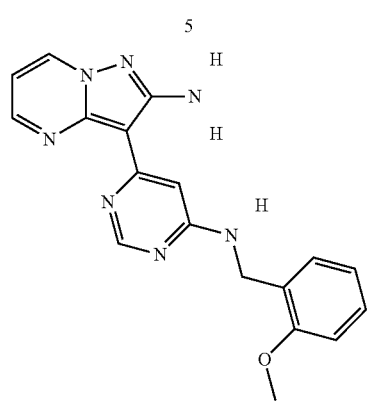
TABLE I-continued
6
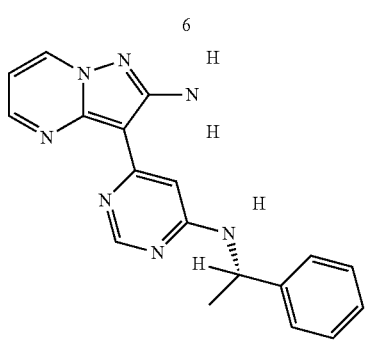
7
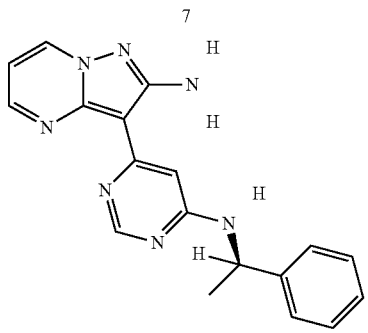
8
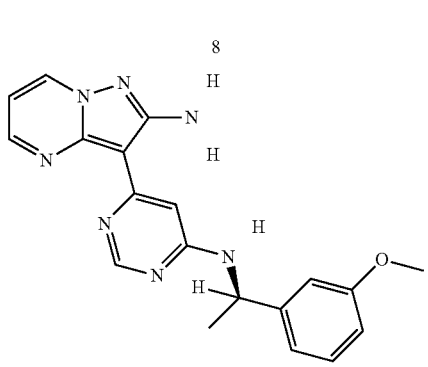
9
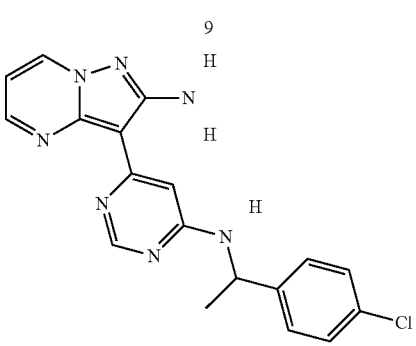

TABLE I-continued
10
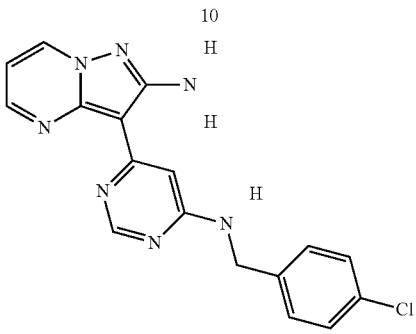
11
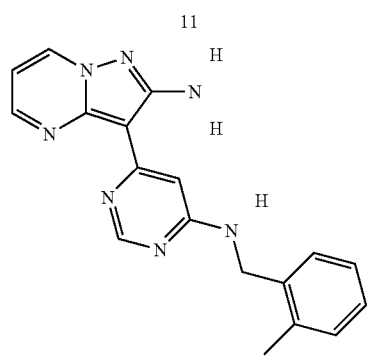
12
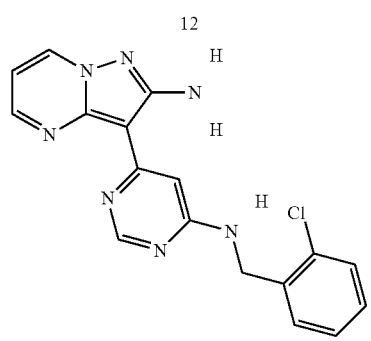
13
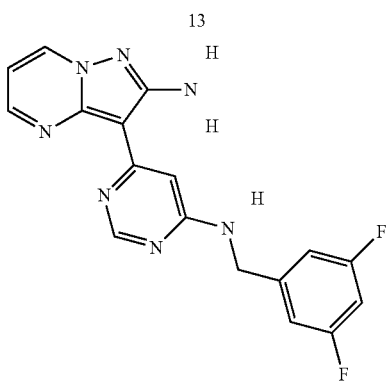
TABLE I-continued
14
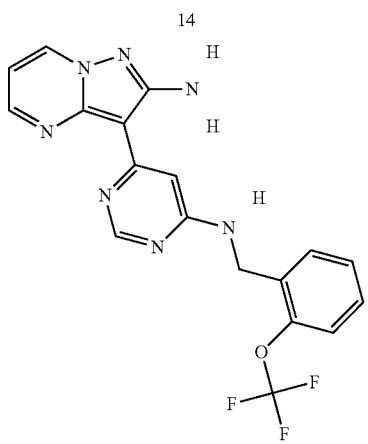
15
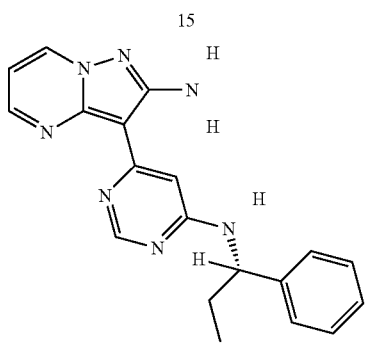
16
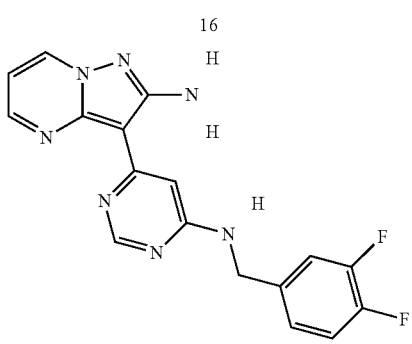
17
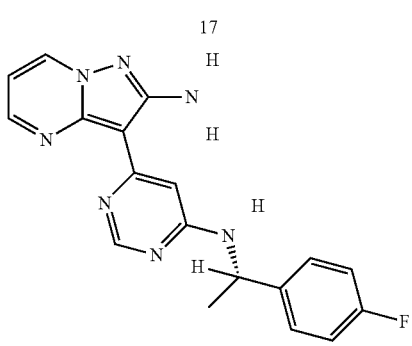

TABLE I-continued
18
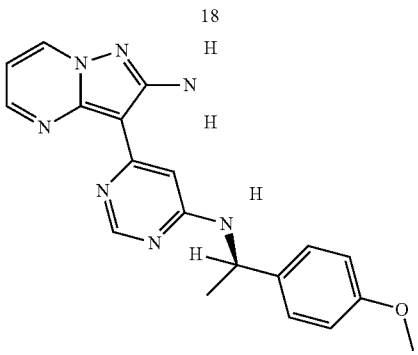
22
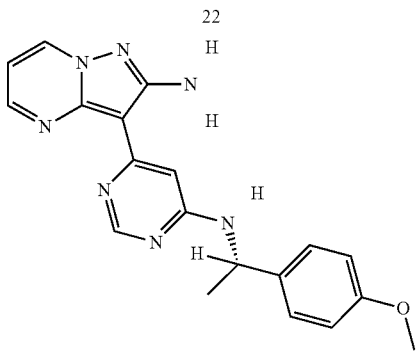
19
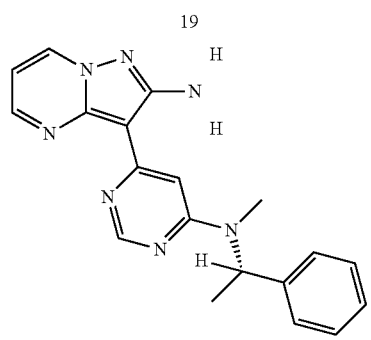
23
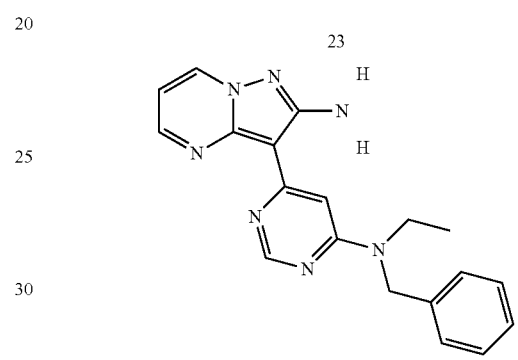
20
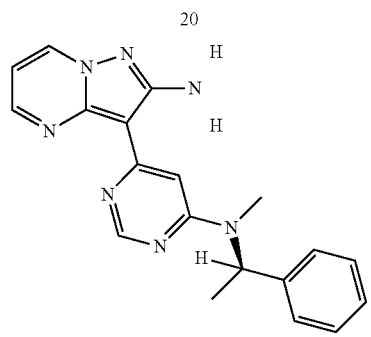
24
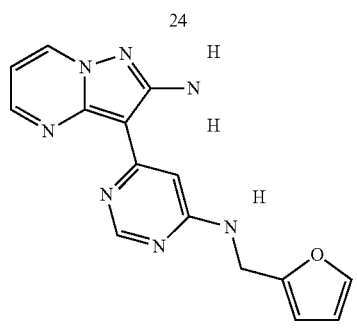
21
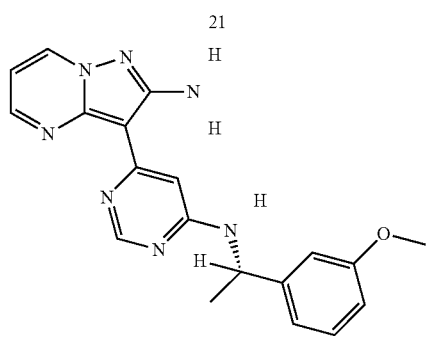
25
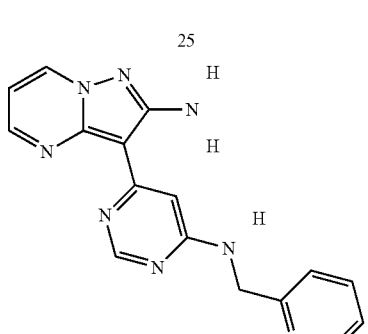

TABLE I-continued
26
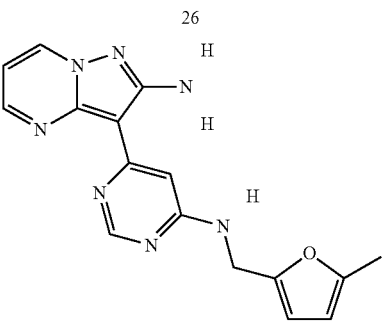
27
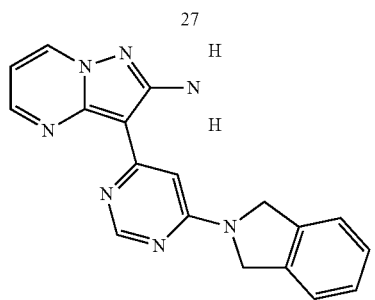
28
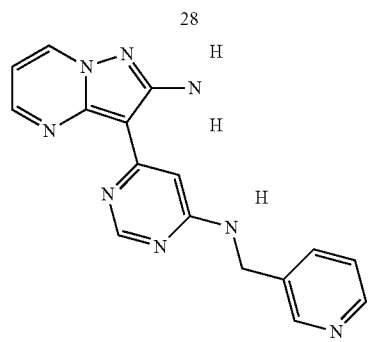
29
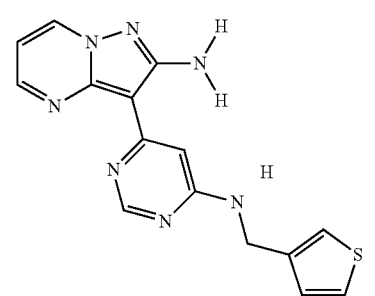
30
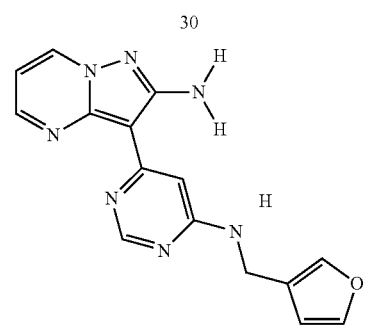
TABLE I-continued
31
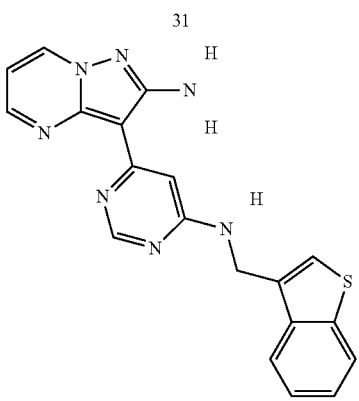
32
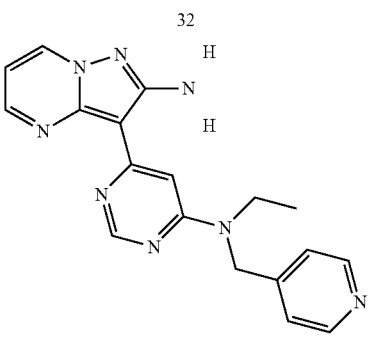
33
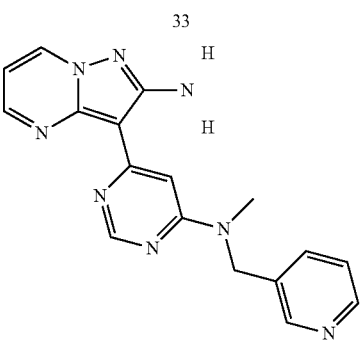
34
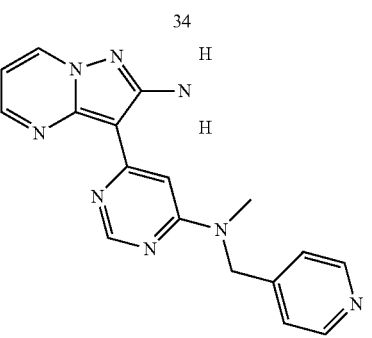

TABLE I-continued
35
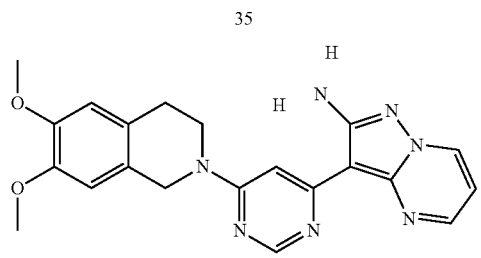
36
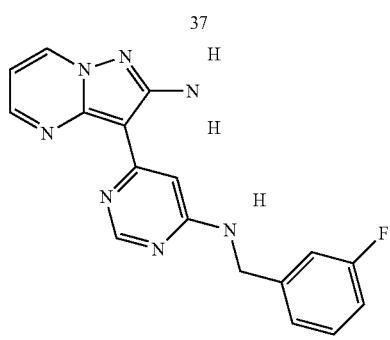
37
38
39
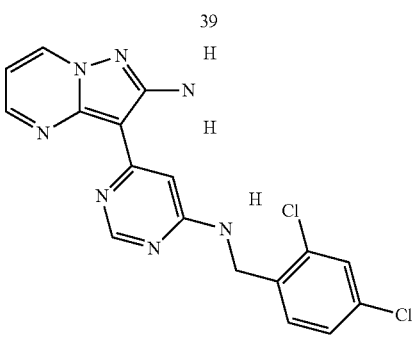
40
41
42
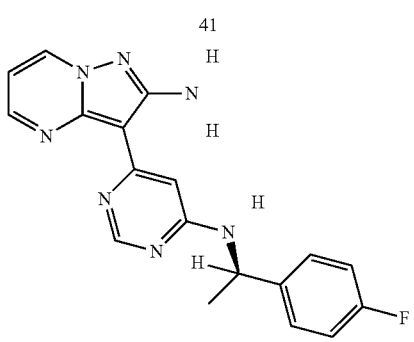

TABLE I-continued
43
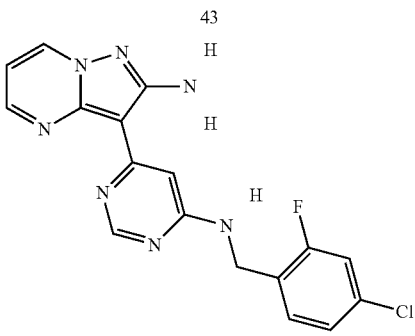
44
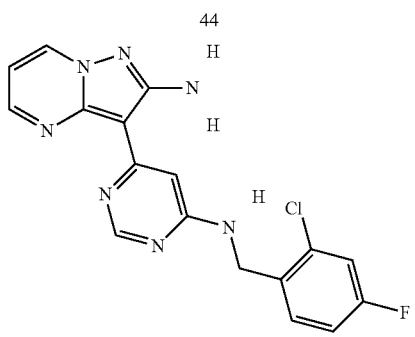
45
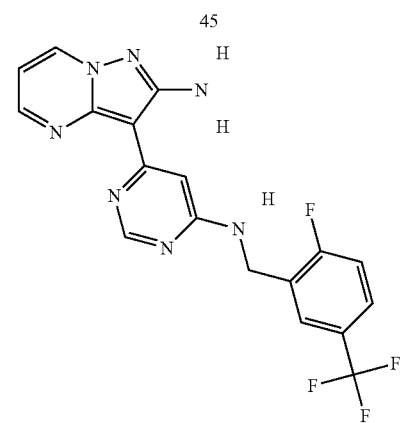
46
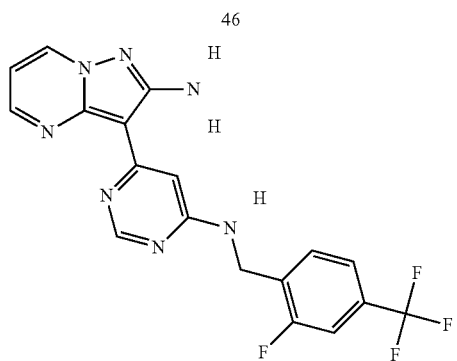
TABLE I-continued
47
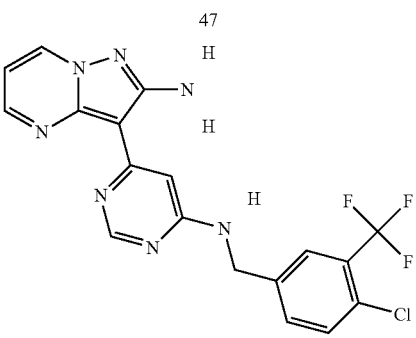
48
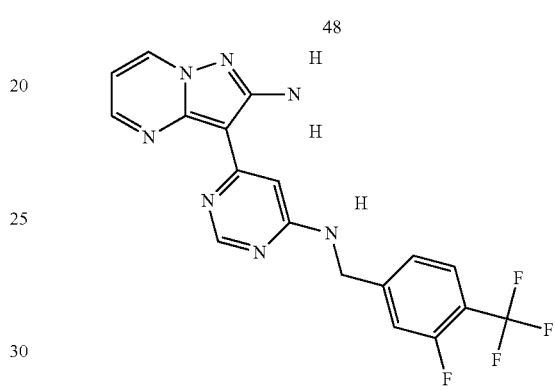
49
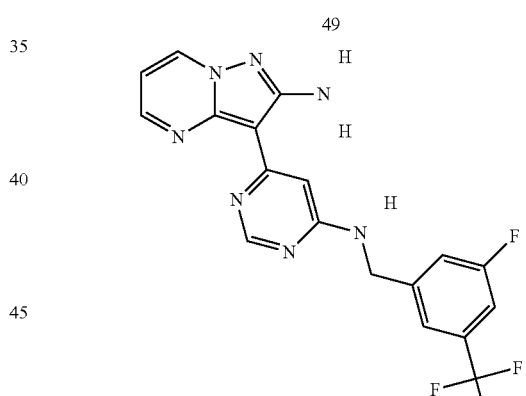
50
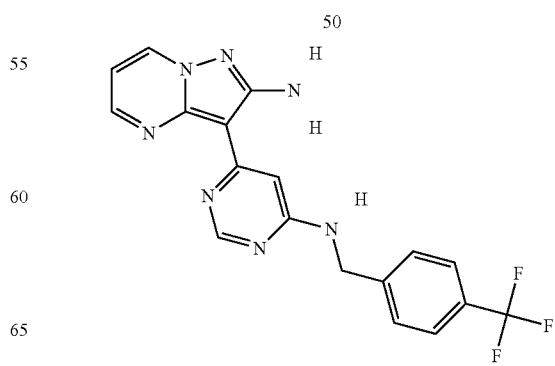

TABLE I-continued
51
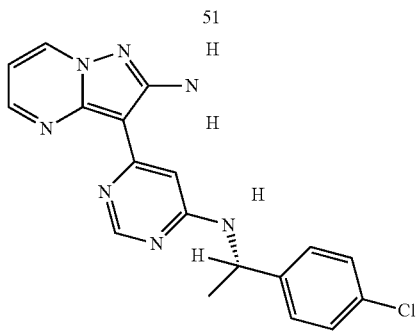
52
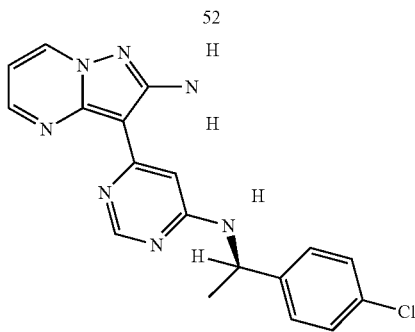
53
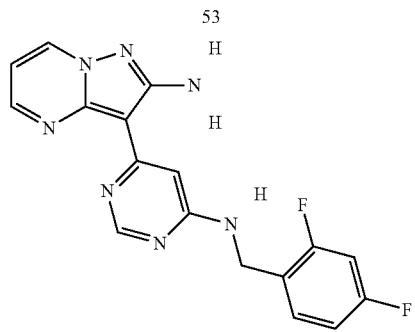
54
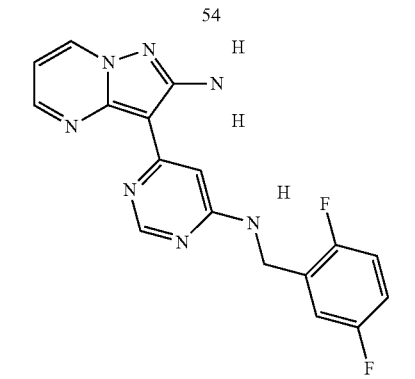
55
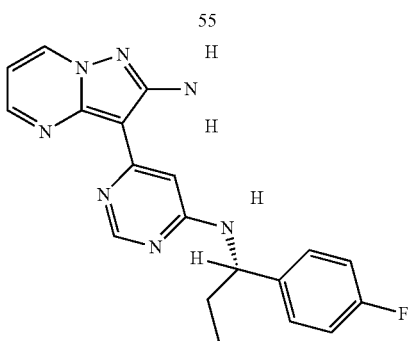
56
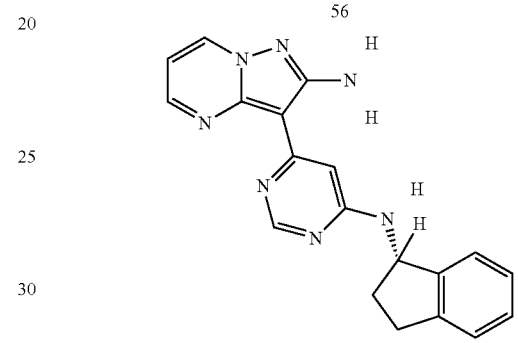
57
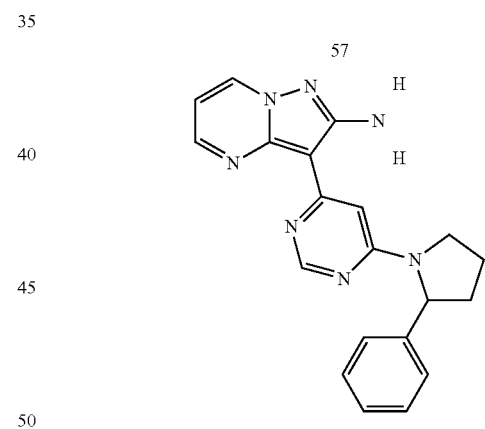
58
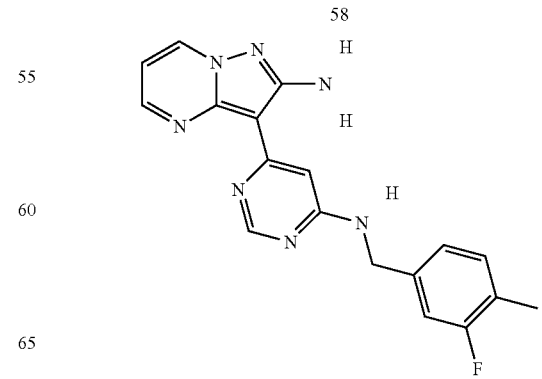

TABLE I-continued
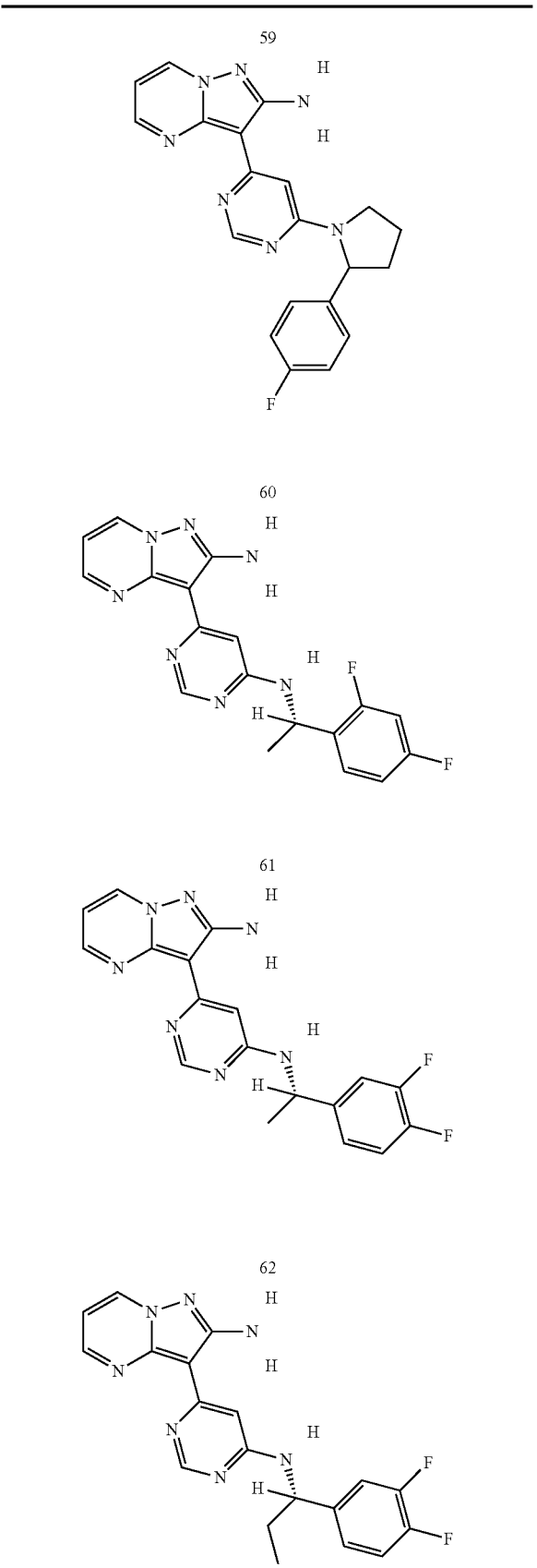
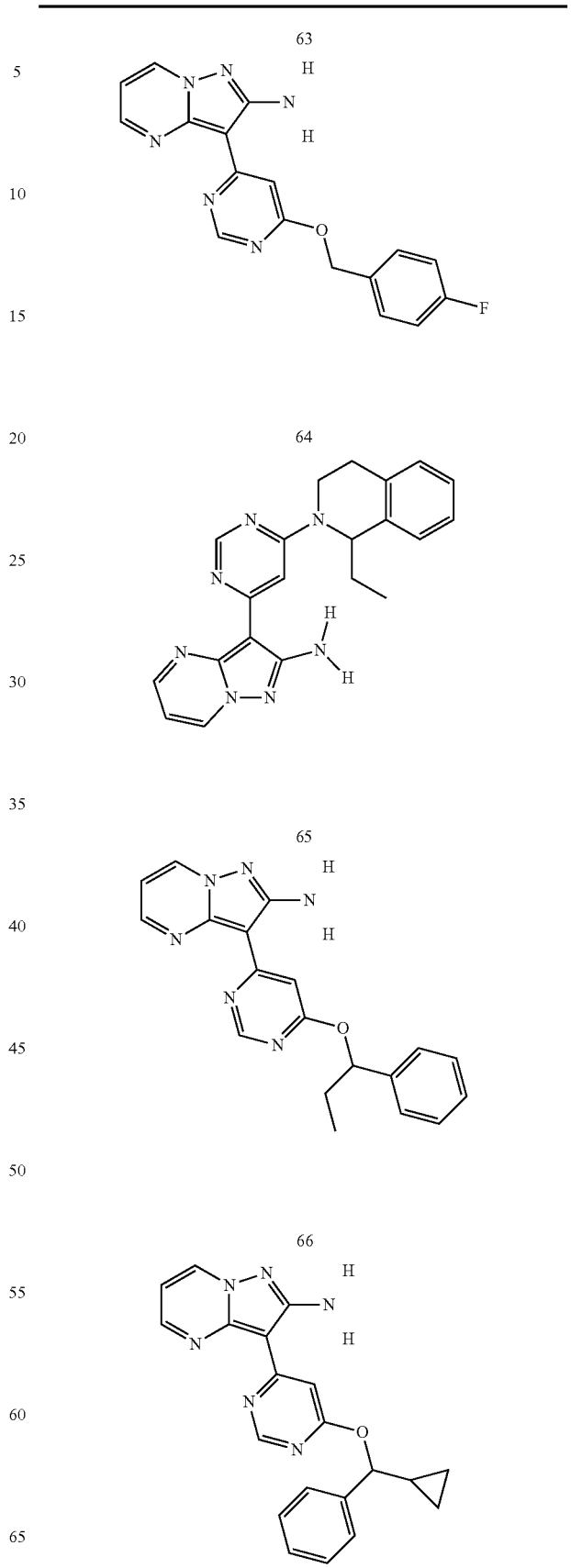

TABLE I-continued
67
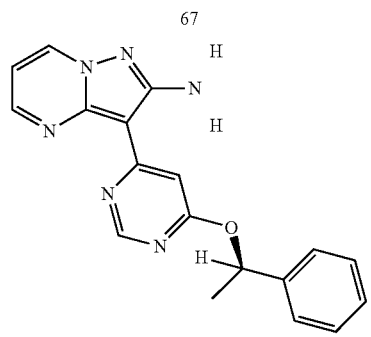
68
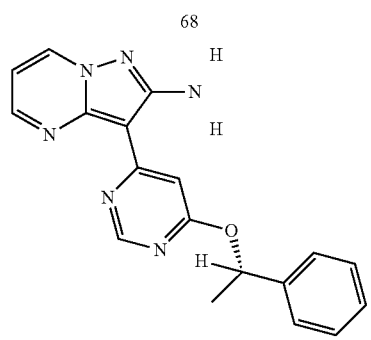
69
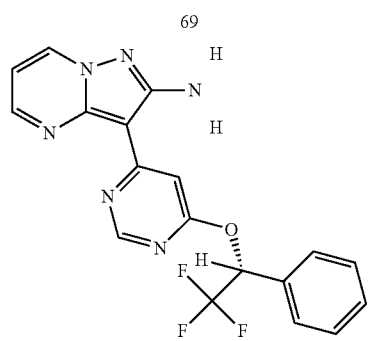
70
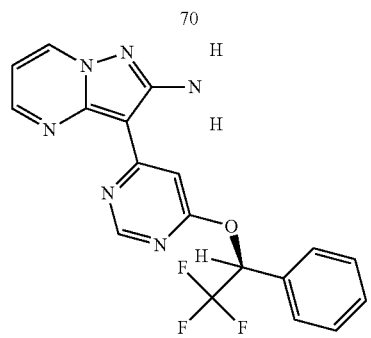
TABLE I-continued
71
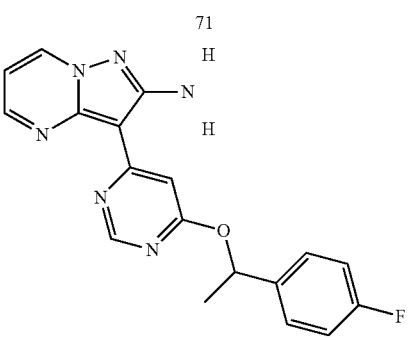
72
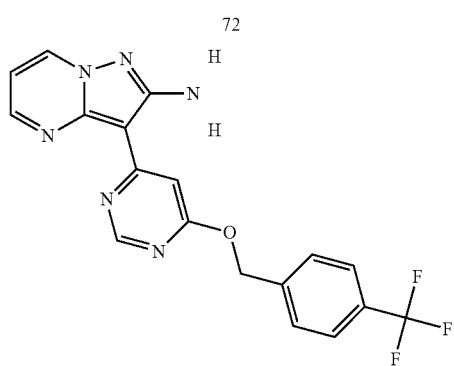
73
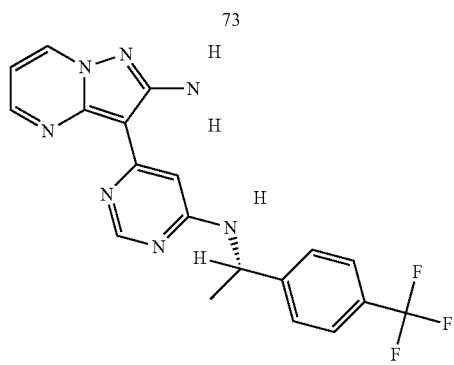
74
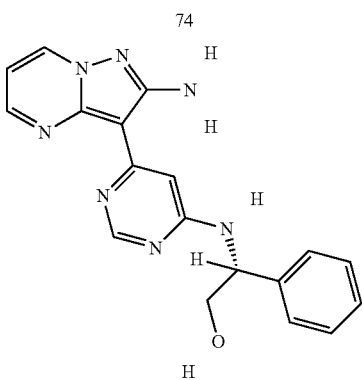

TABLE I-continued
75
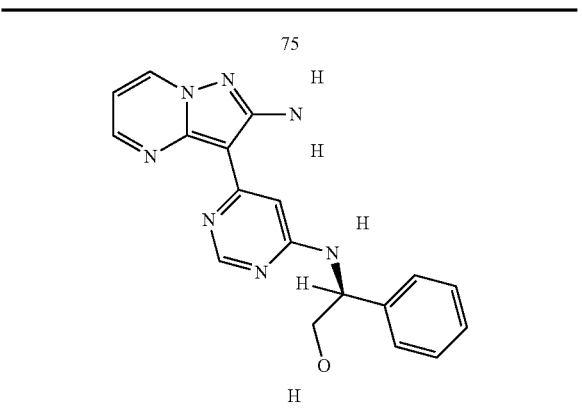
76
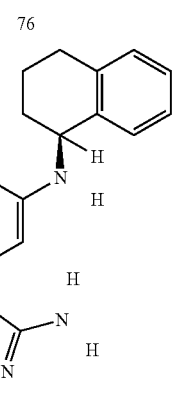
77
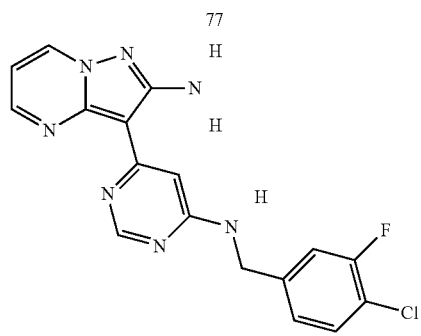
78
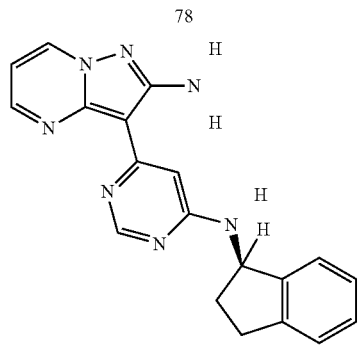
TABLE I-continued
79
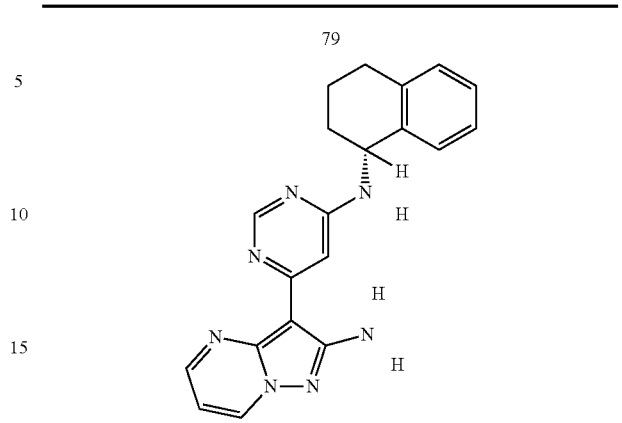
80
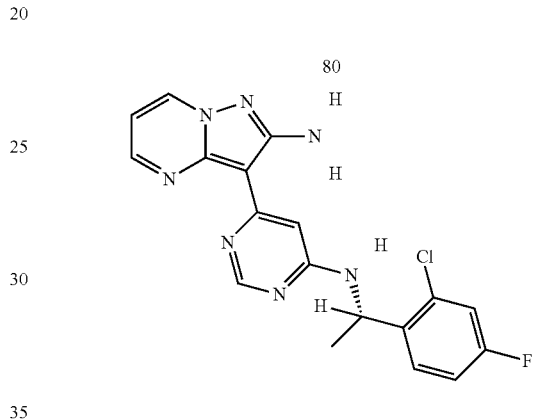
81
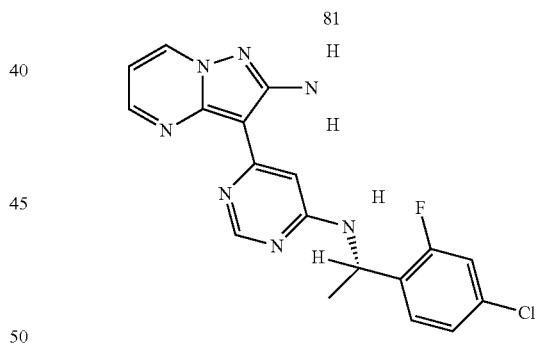
82
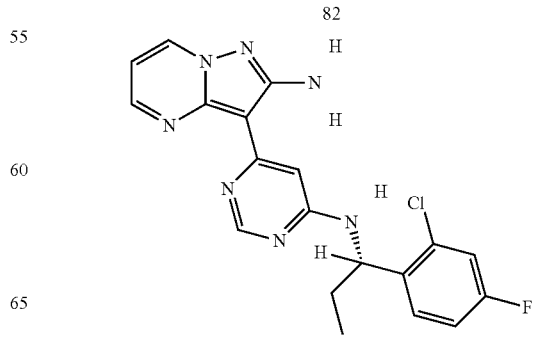

TABLE I-continued
83
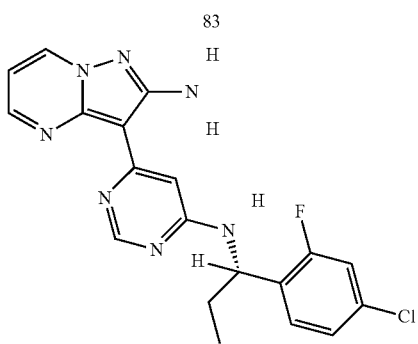
84
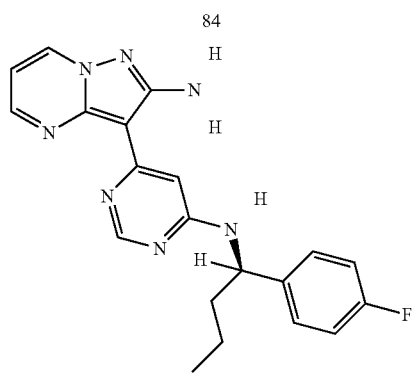
85
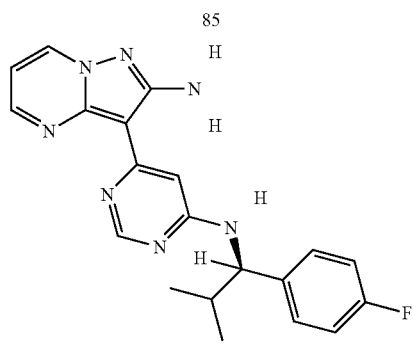
86
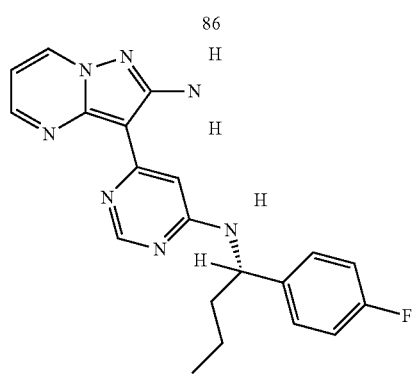
TABLE I-continued
87
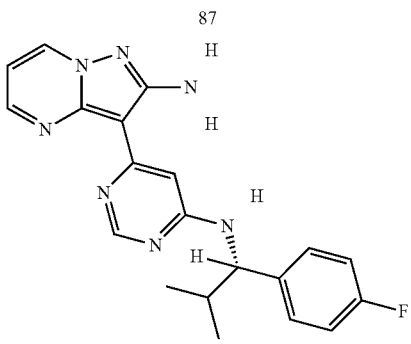
88
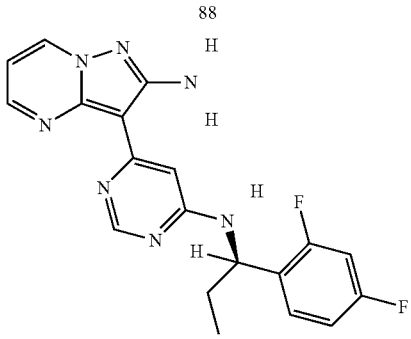
89
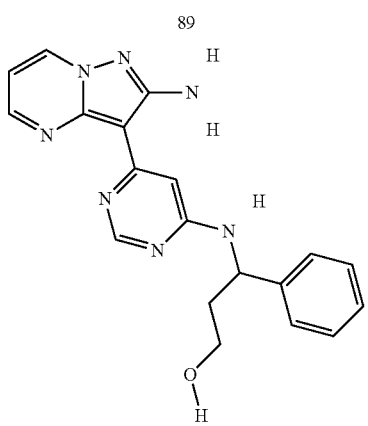
90
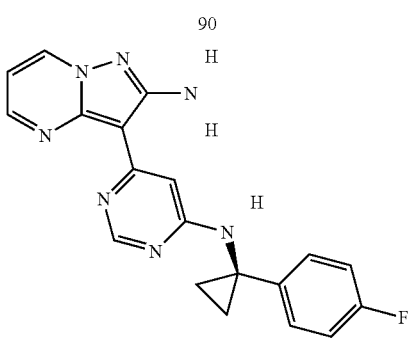

TABLE I-continued
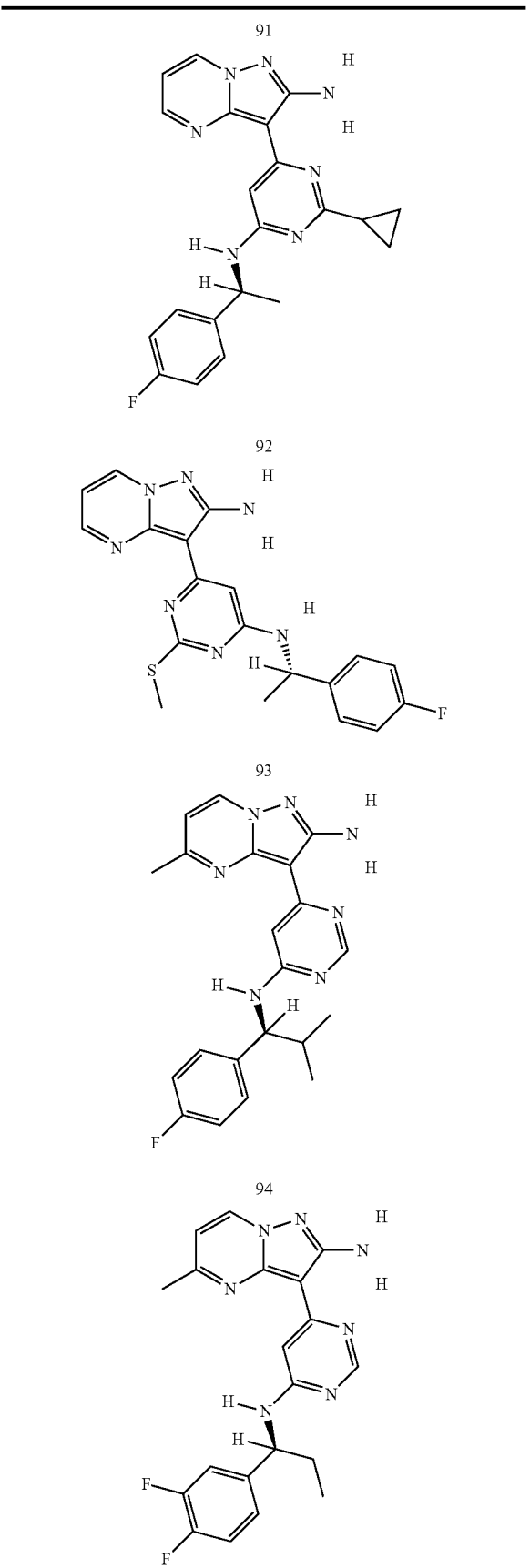
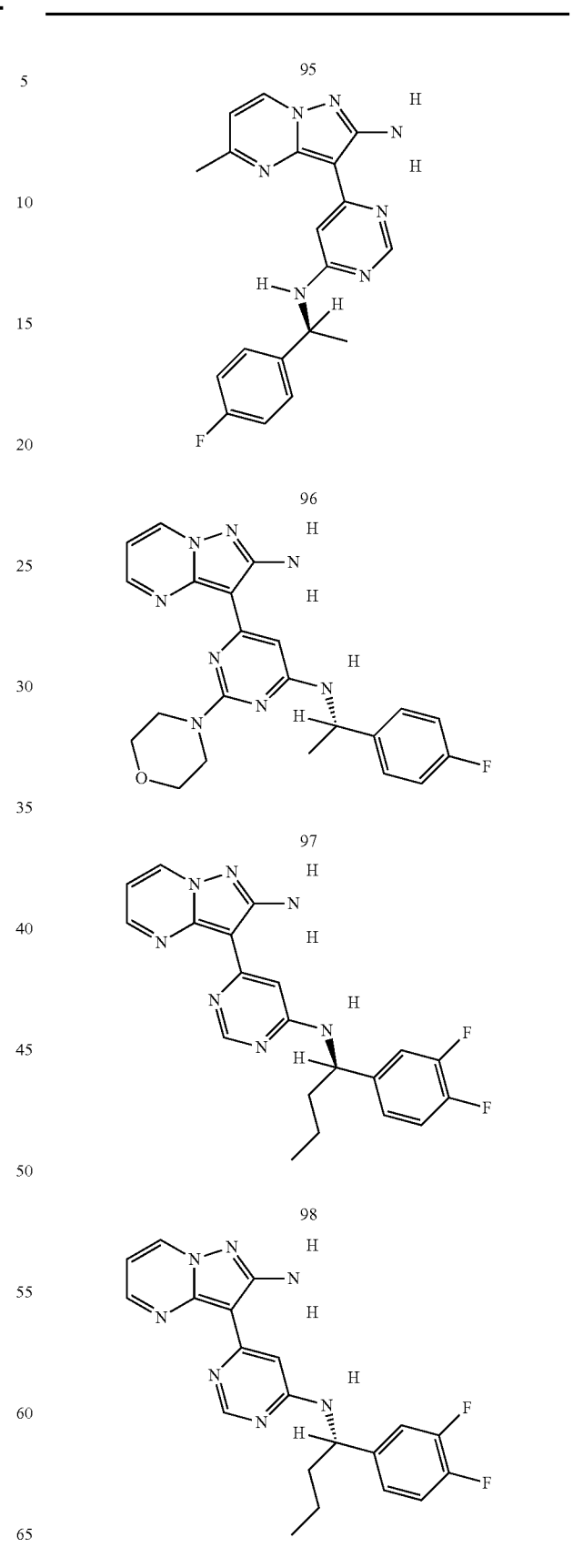

TABLE I-continued
99
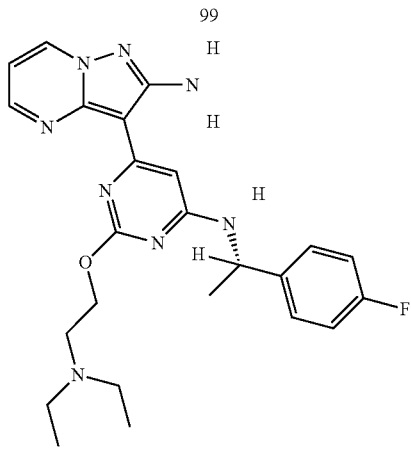
100
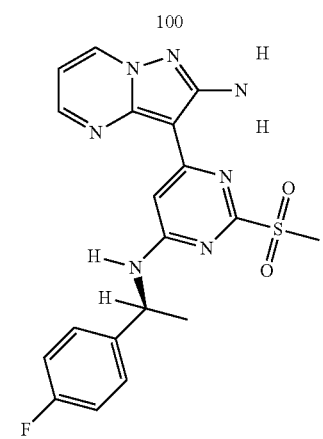
101
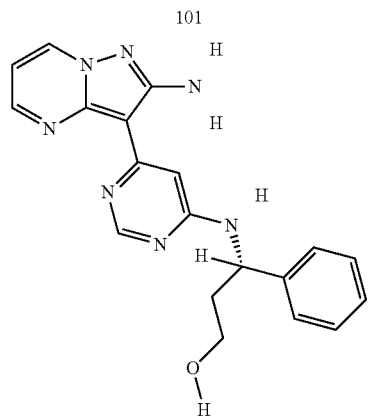
TABLE I-continued
102
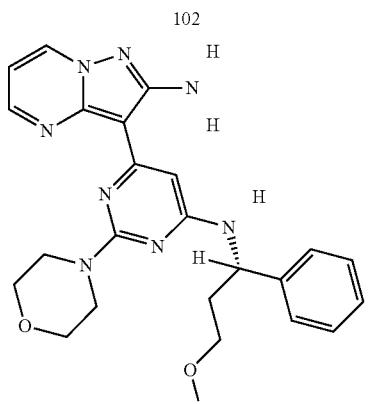
103
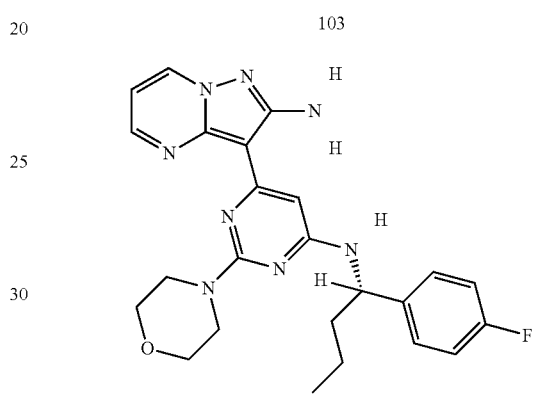
104
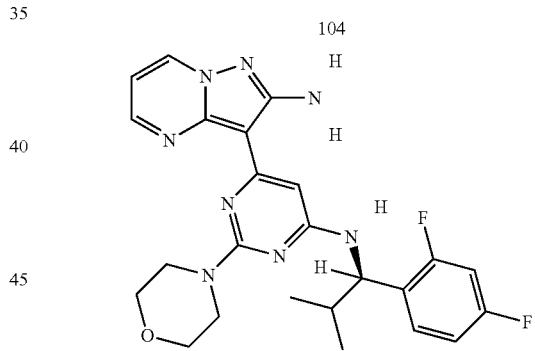
105
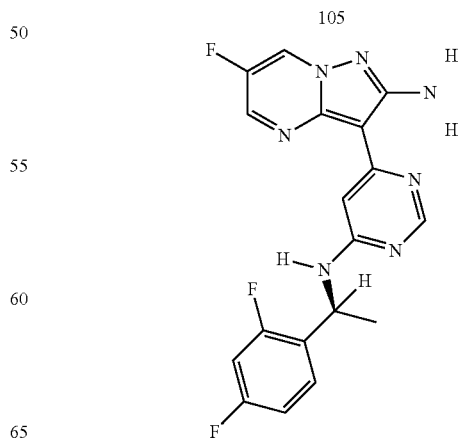

TABLE I-continued
106
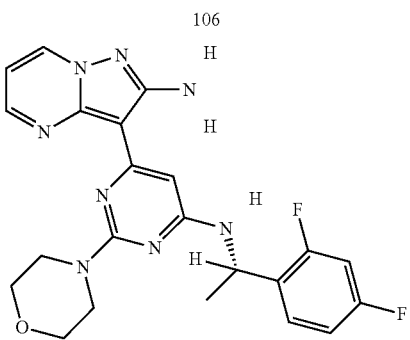
107
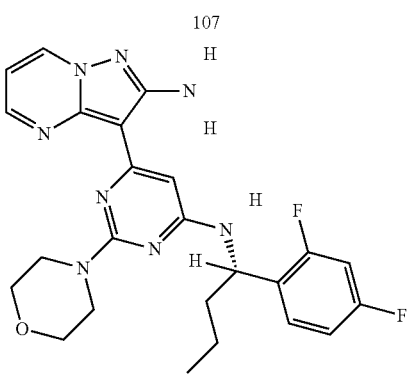
108
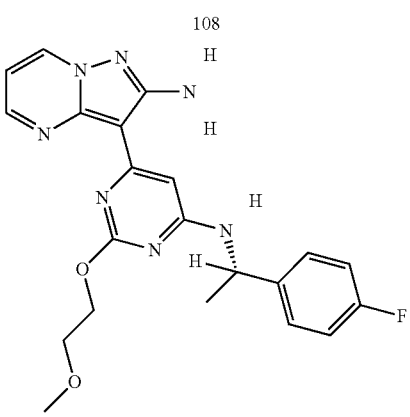
109
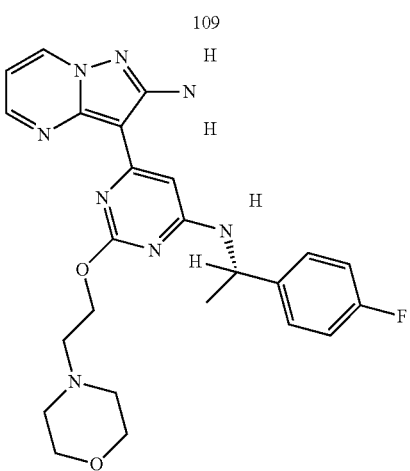
TABLE I-continued
110
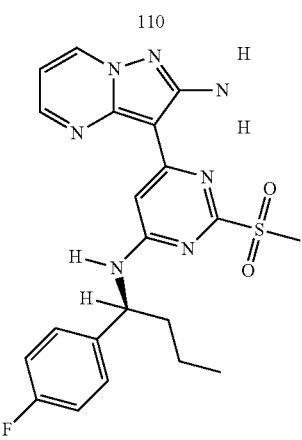
111
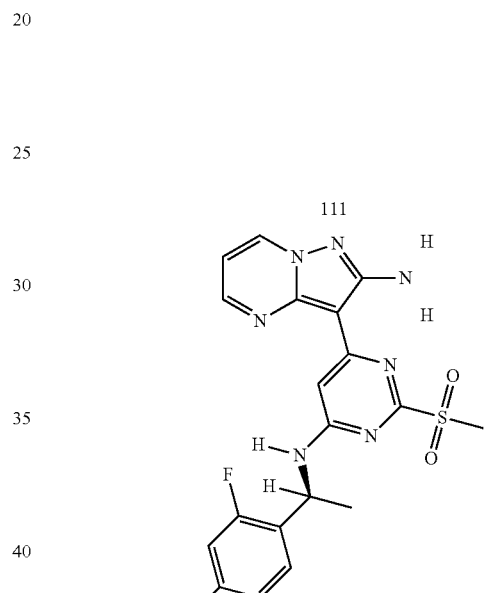
112
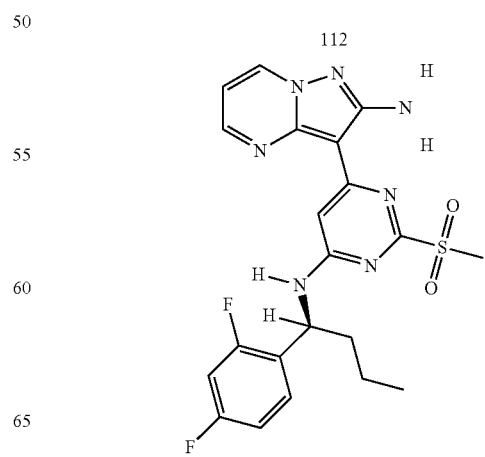

TABLE I-continued
113
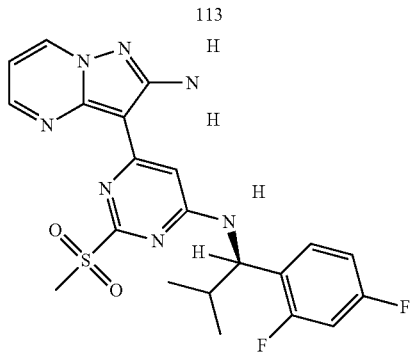
114
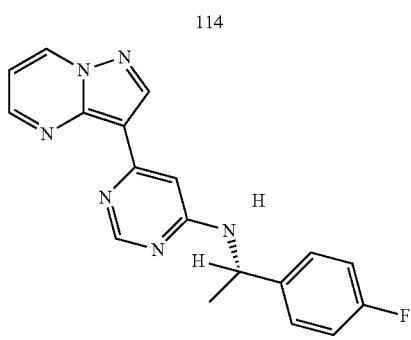
115
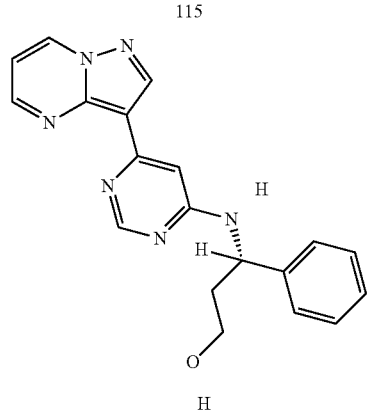
116
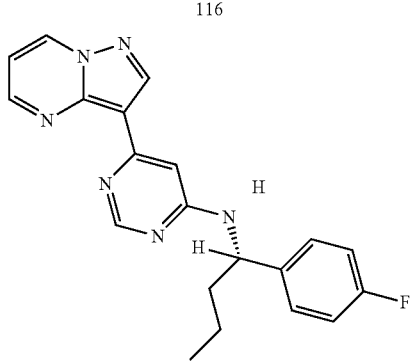
TABLE I-continued
117
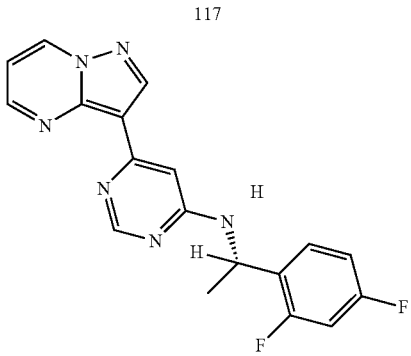
118
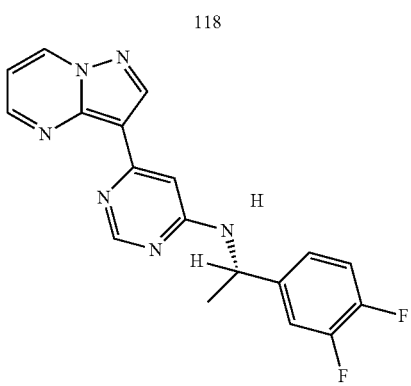
119
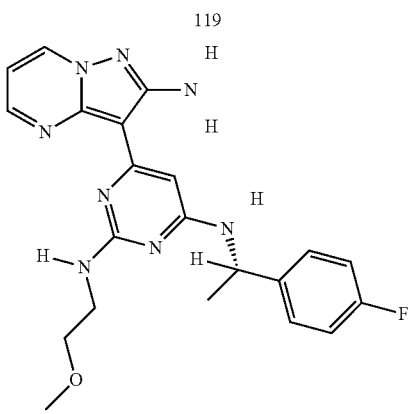
120
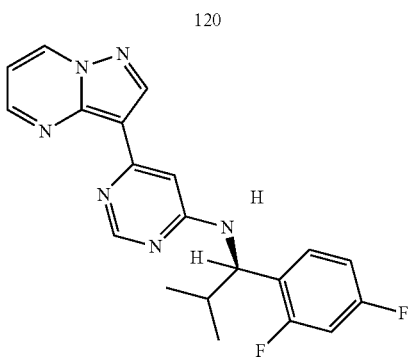

TABLE I-continued
121
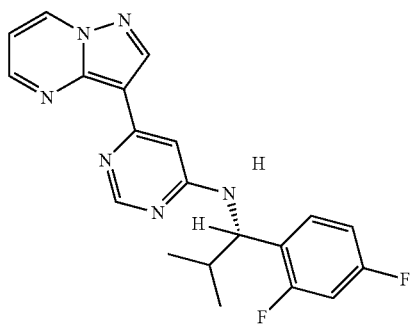
122
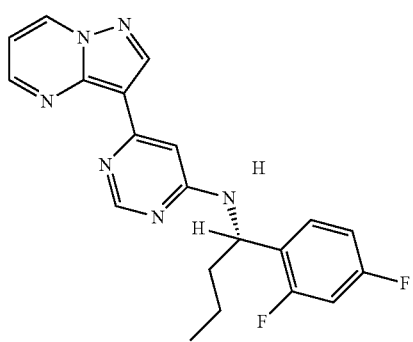
123
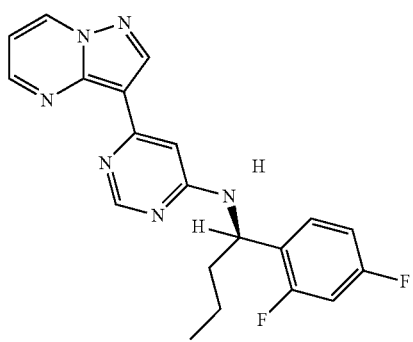
124
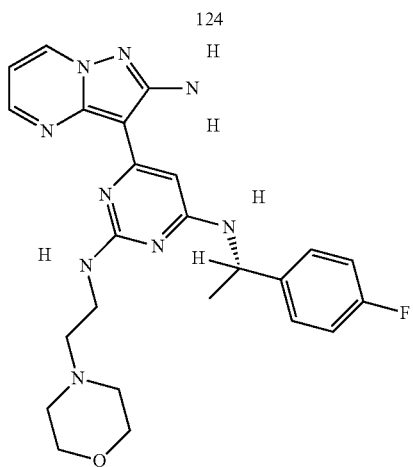
TABLE I-continued
125
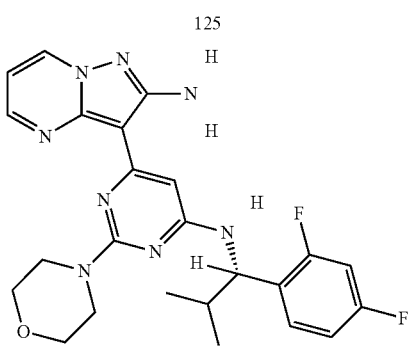
126
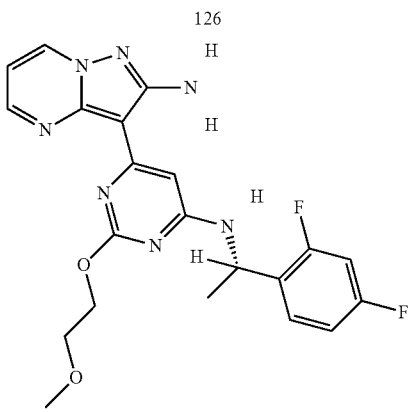
127
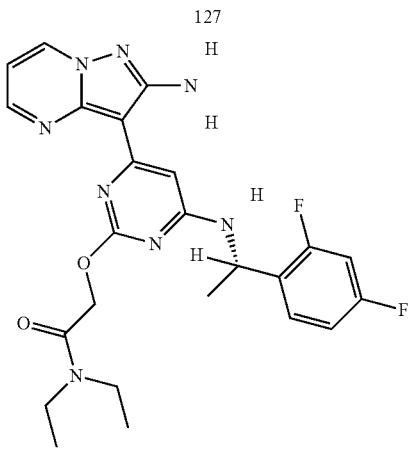

TABLE I-continued
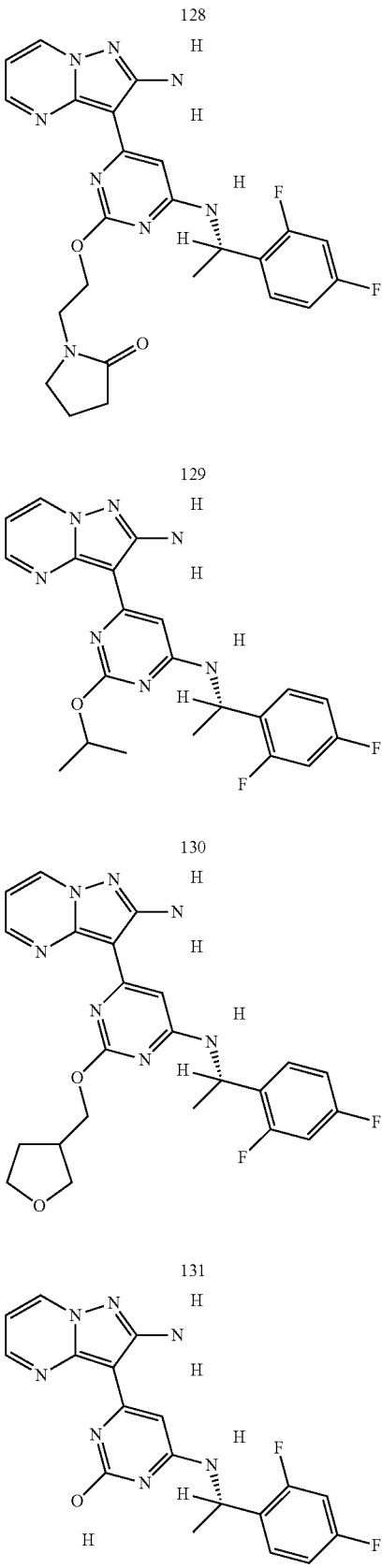
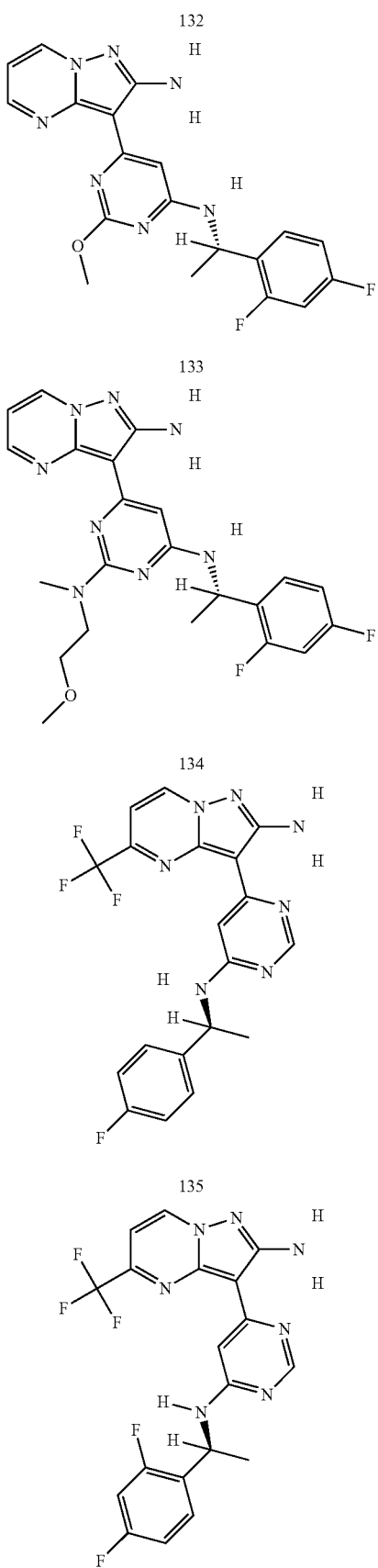

TABLE I-continued
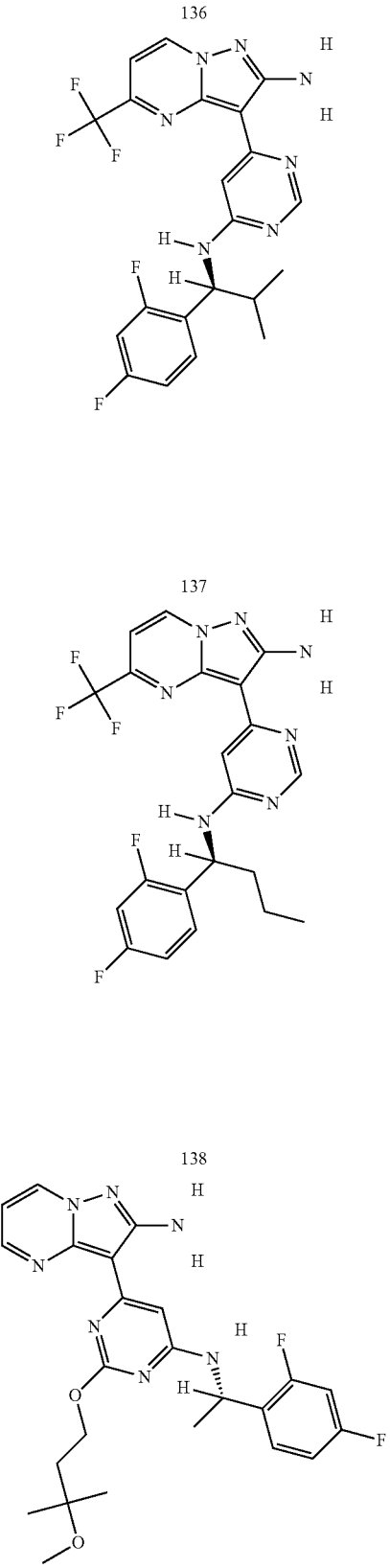
TABLE I-continued
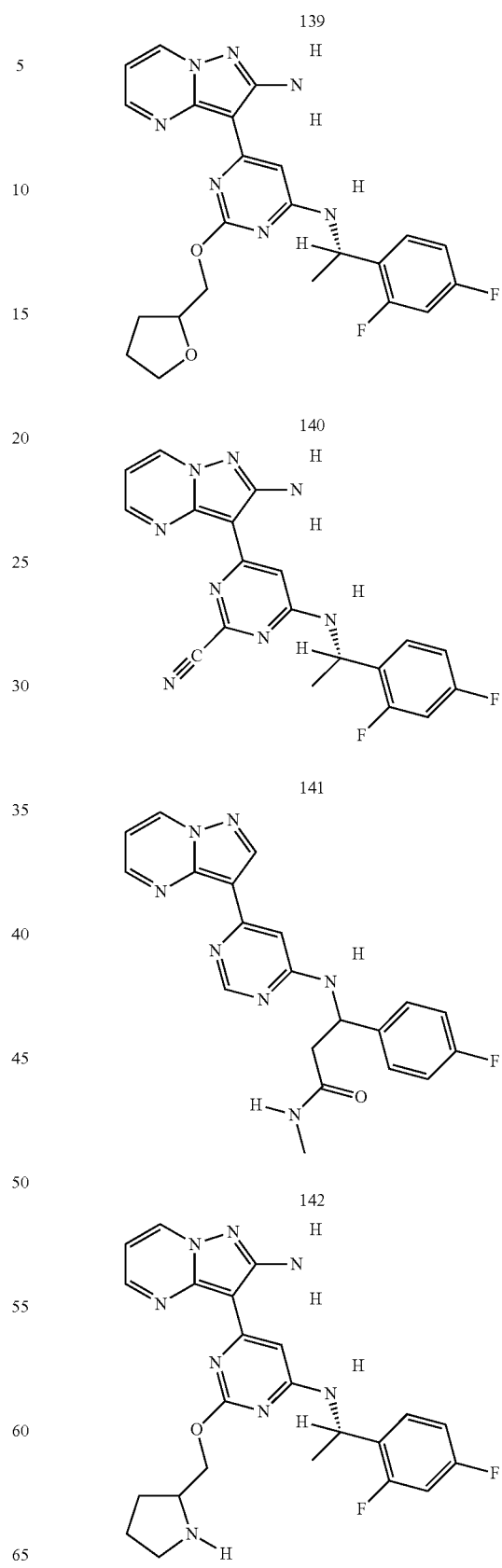

TABLE I-continued
143
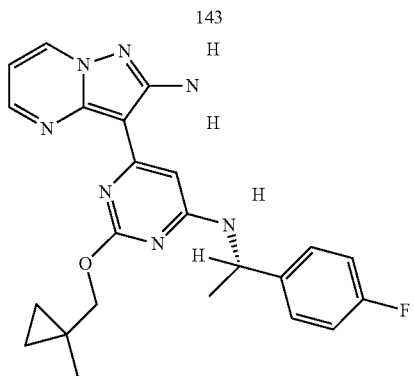
144
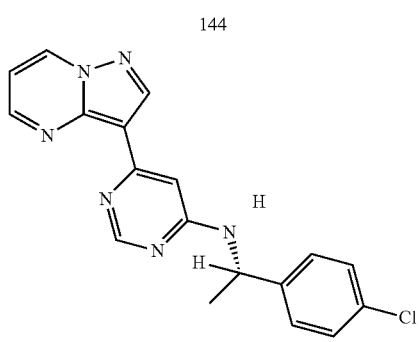
145
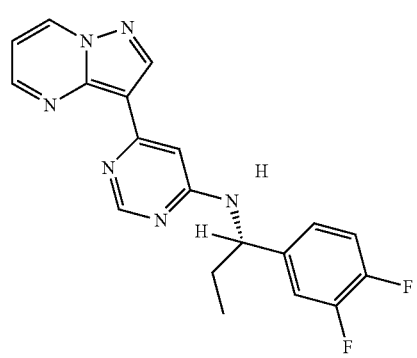
146
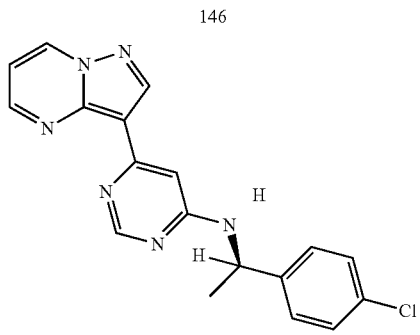
TABLE I-continued
147
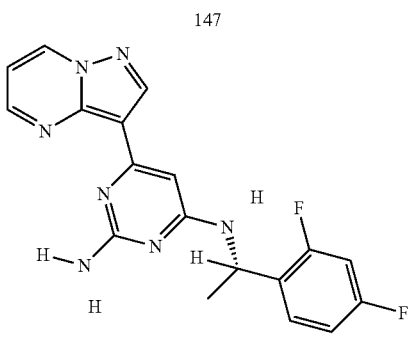
148
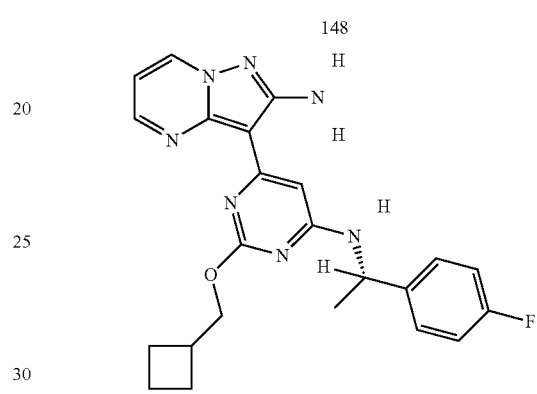
149
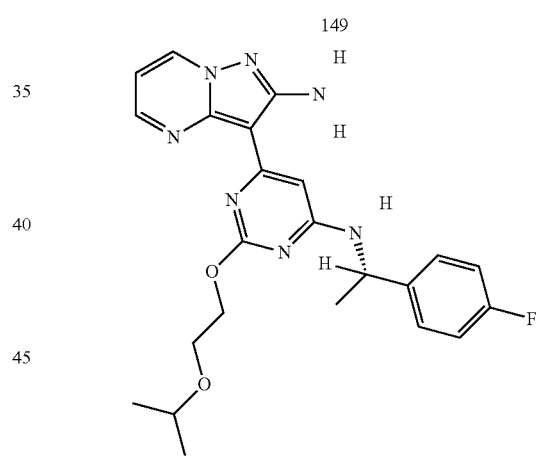
150
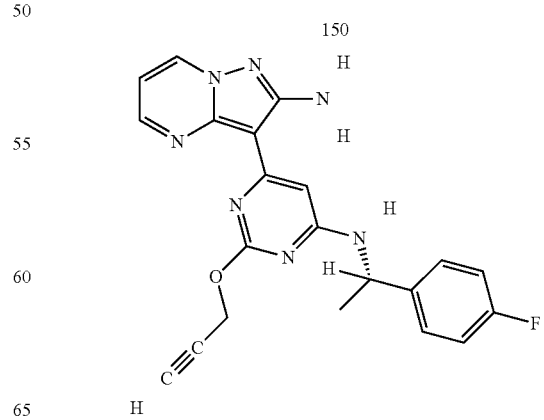

TABLE I-continued
151
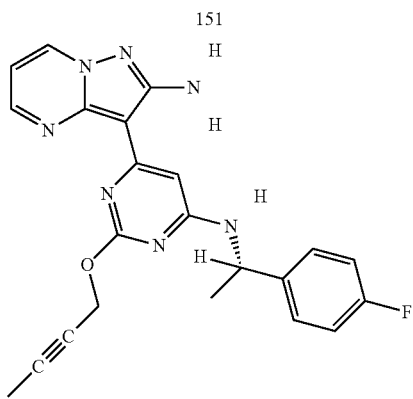
152
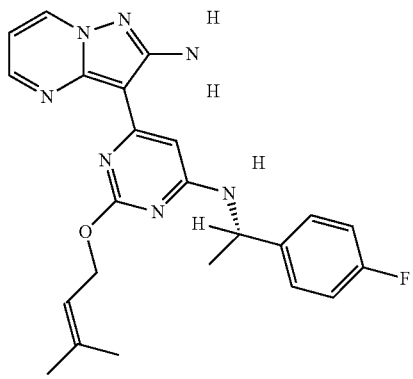
153
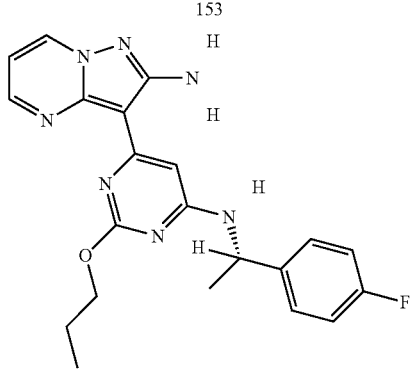
154
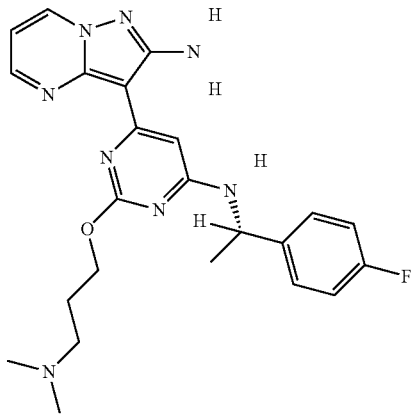
TABLE I-continued
155
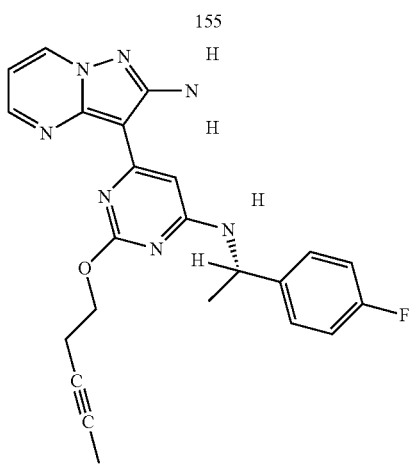
156
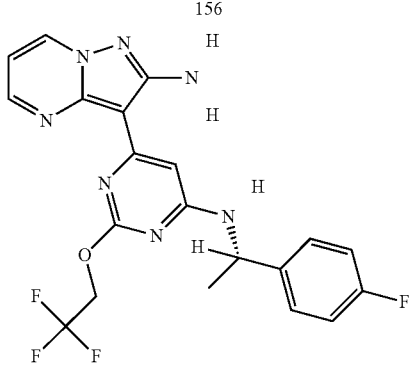
157
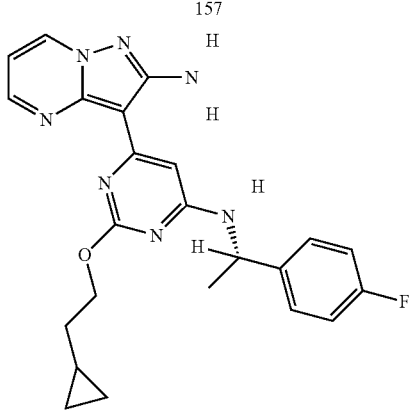

TABLE I-continued
158
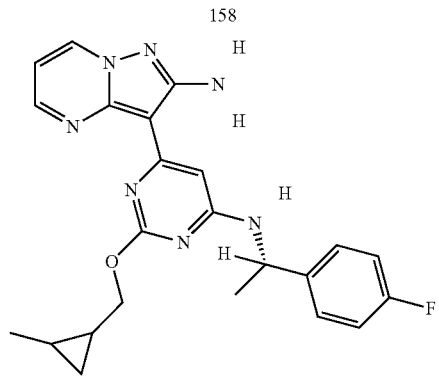
159
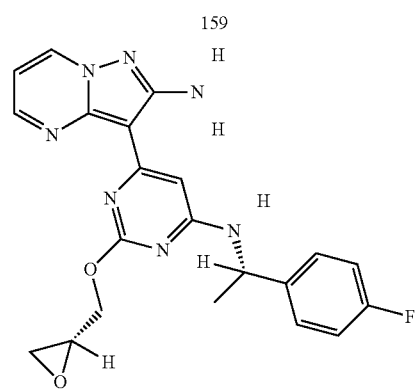
160
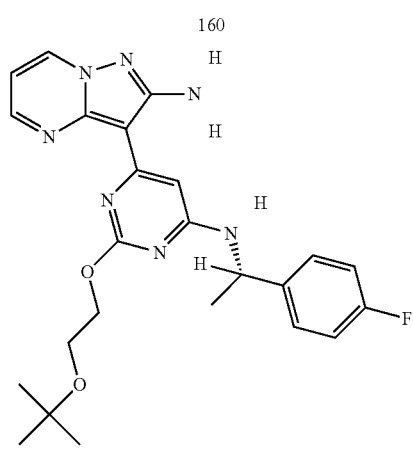
161
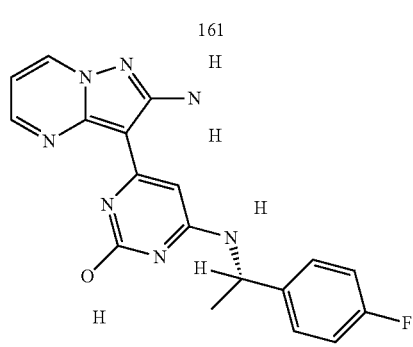
162
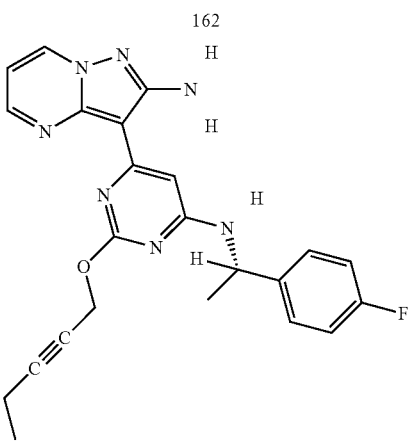
163
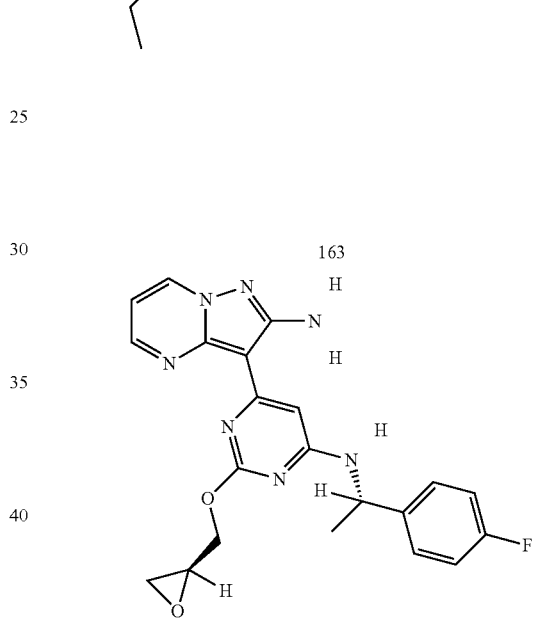
164
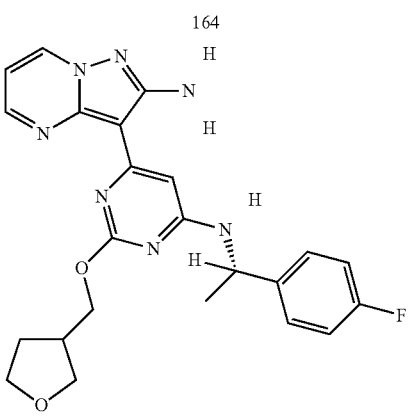

TABLE I-continued 165, 166, 167, 168, 169, 170

TABLE I-continued
171
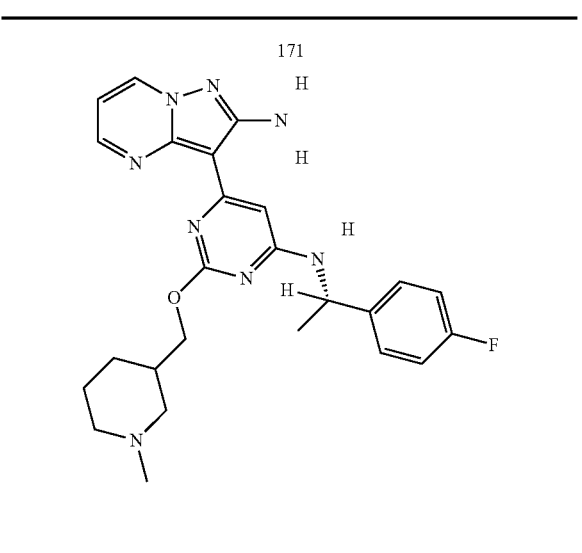
174
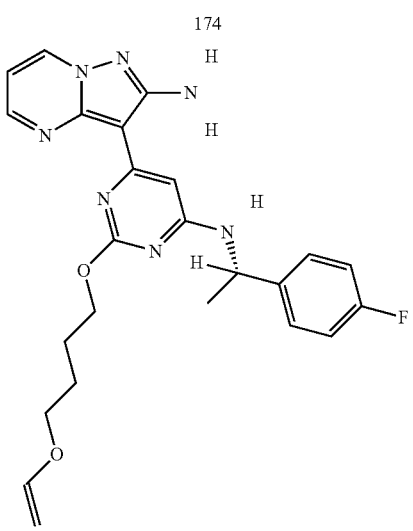
172
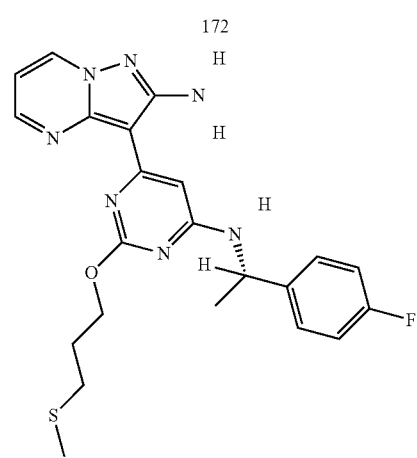
175
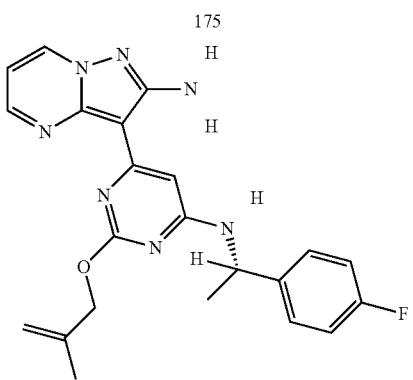
173
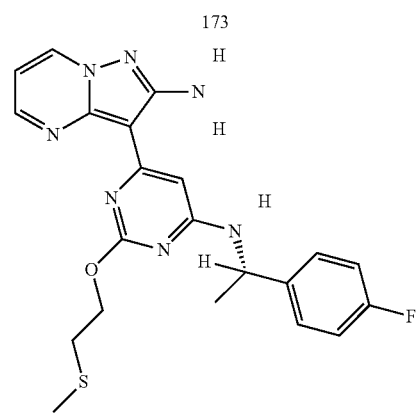
176
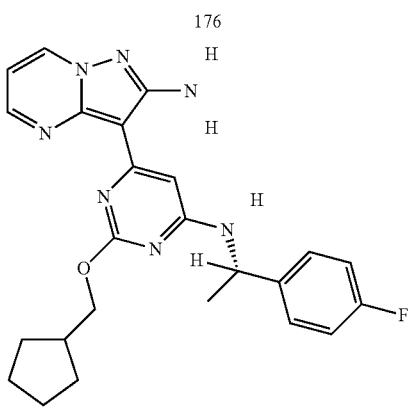

TABLE I-continued
177
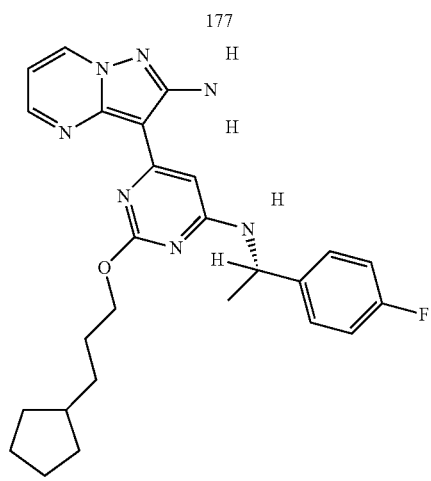
178
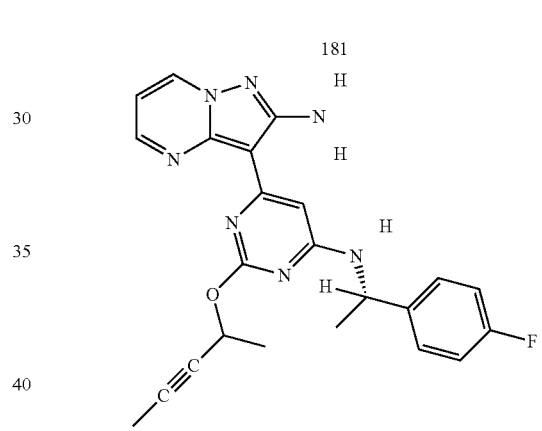
179
180
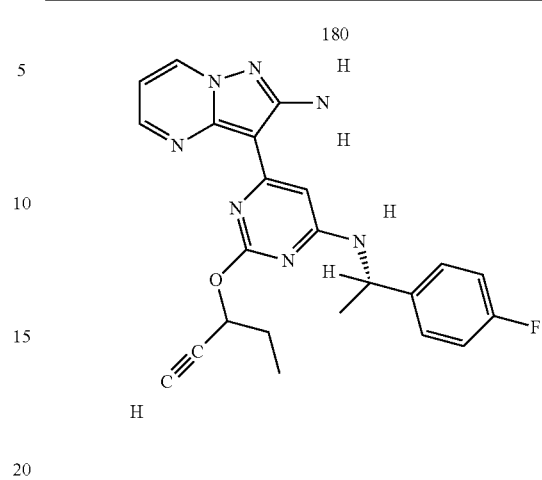
181
182
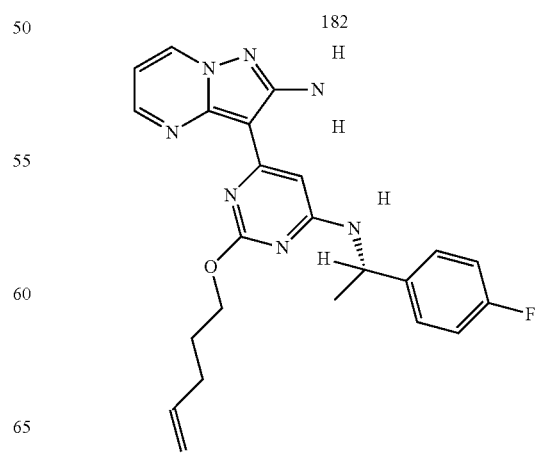

TABLE I-continued
183
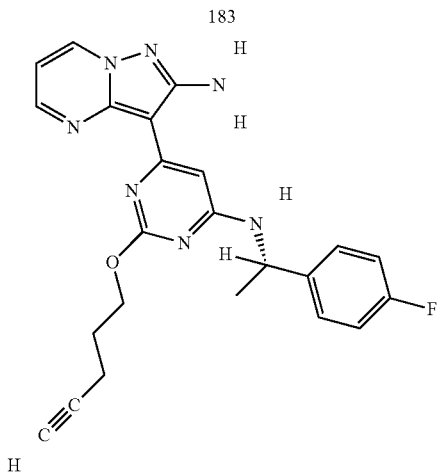
184
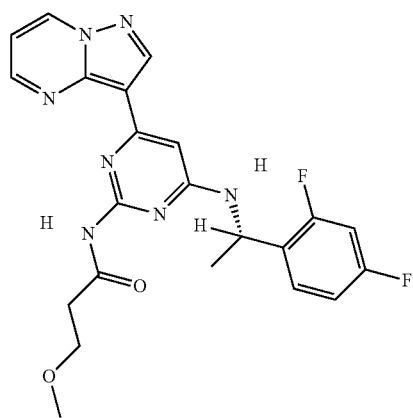
185
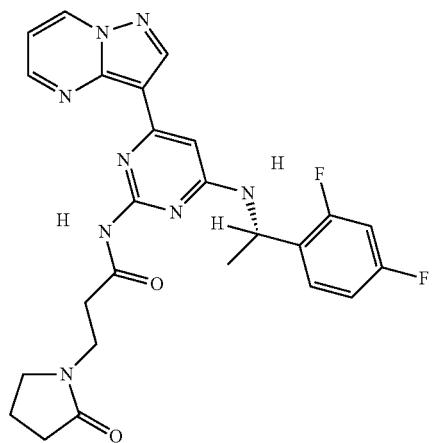
TABLE I-continued
186
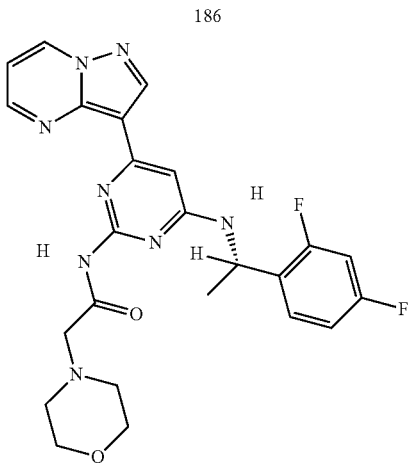
187
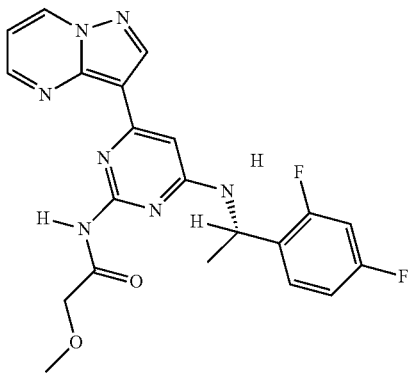
188
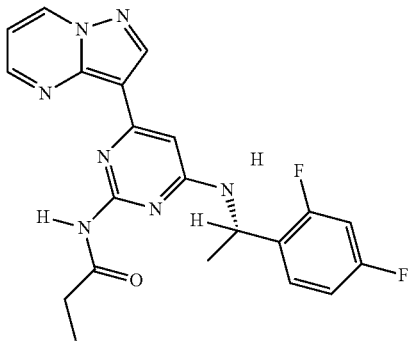

TABLE I-continued
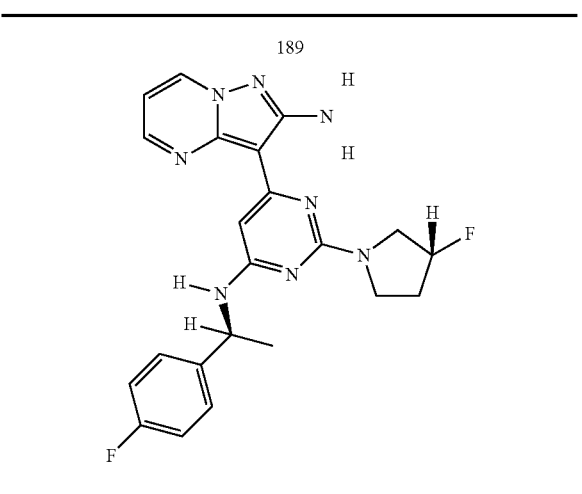
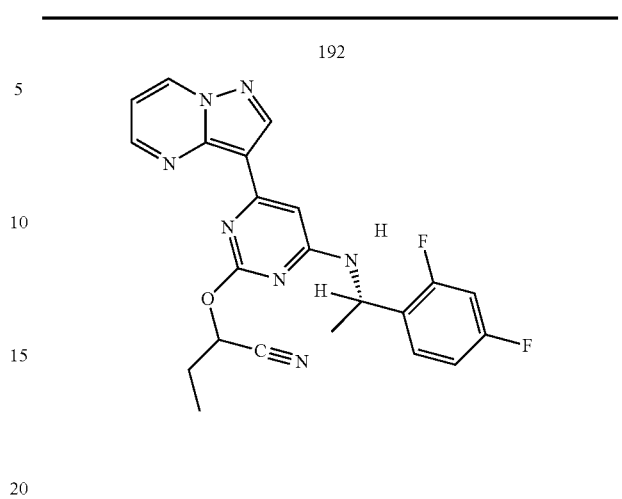

TABLE I-continued
195
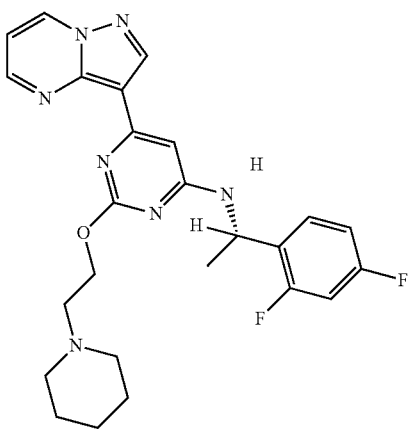
196
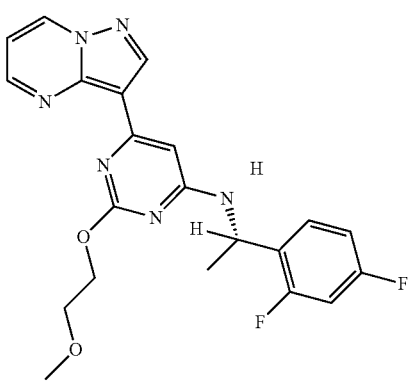
197
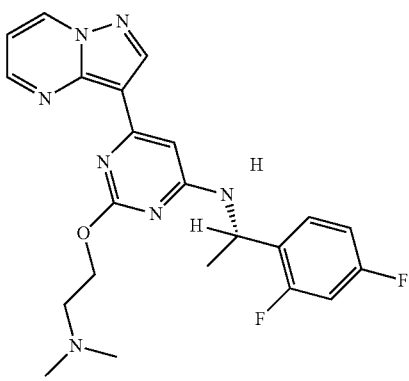
TABLE I-continued
198
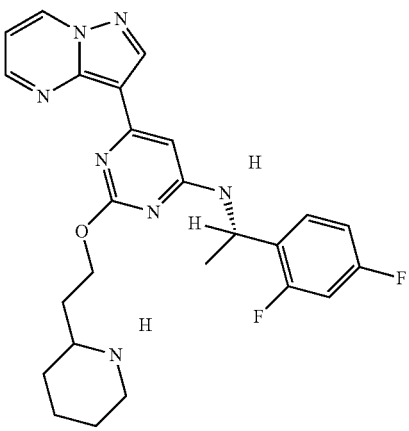
199
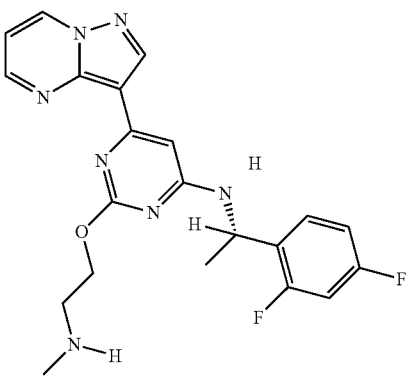
200
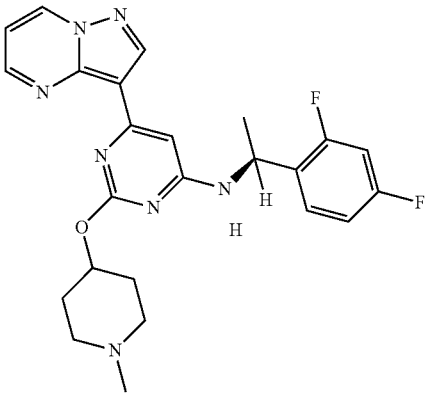

TABLE I-continued
201
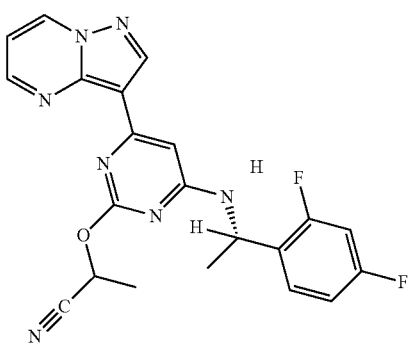
202
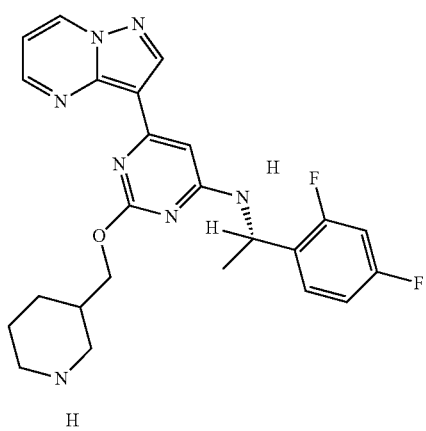
203
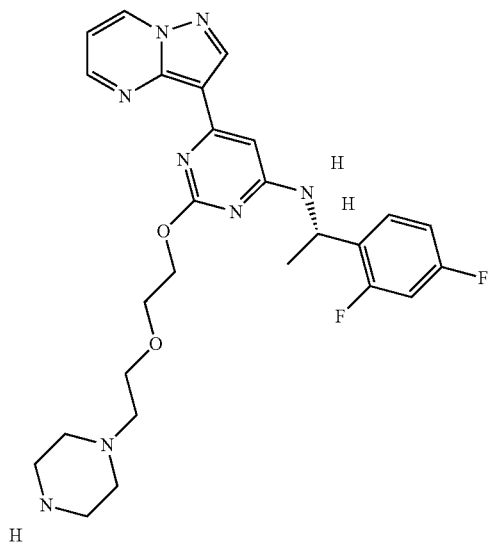
TABLE I-continued
204
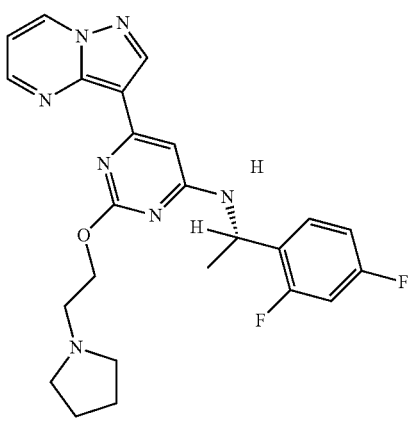
205
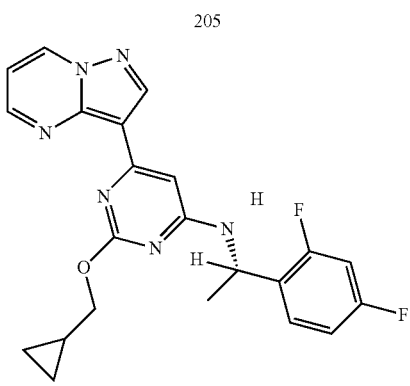
206
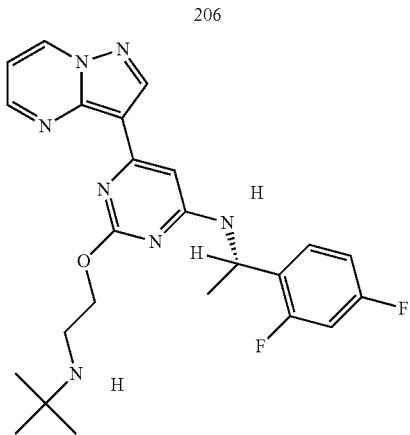

TABLE I-continued
207
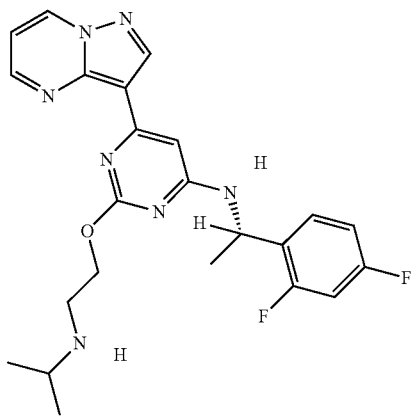
208
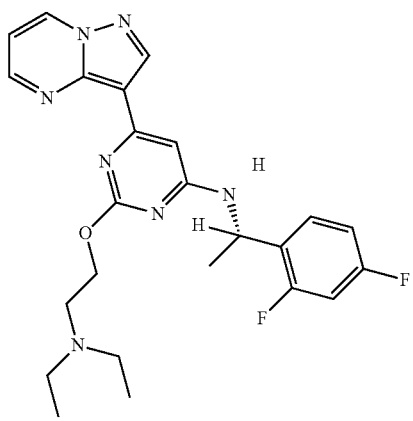
209
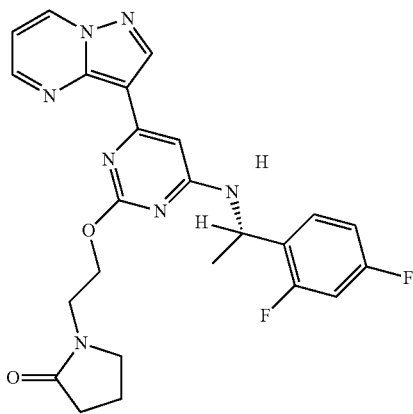
TABLE I-continued
210
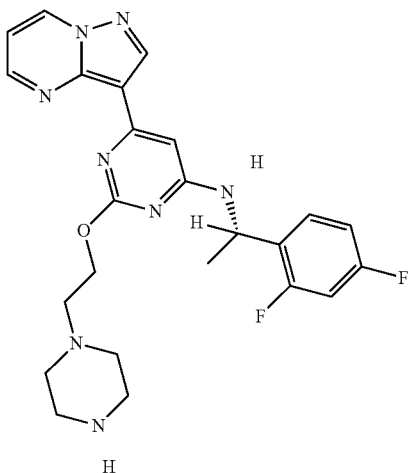
211
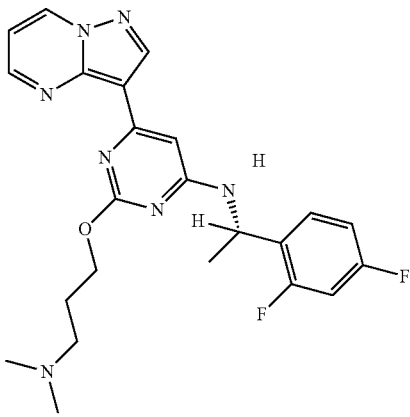
212
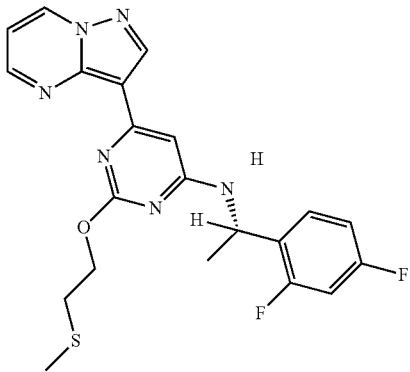

TABLE I-continued
213
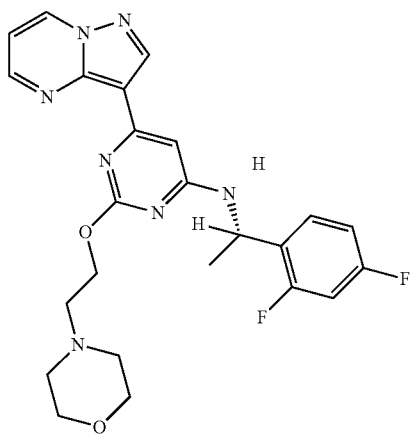
214
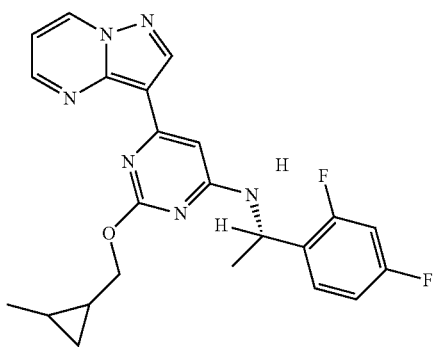
215
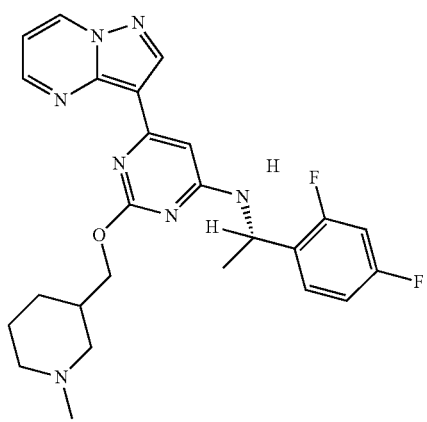
TABLE I-continued
216
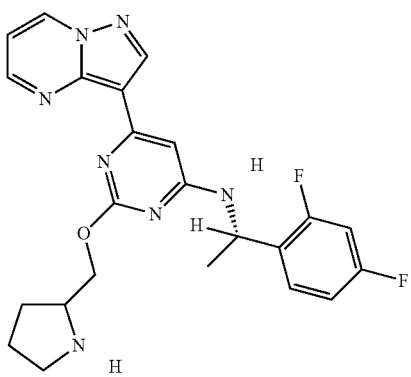
217
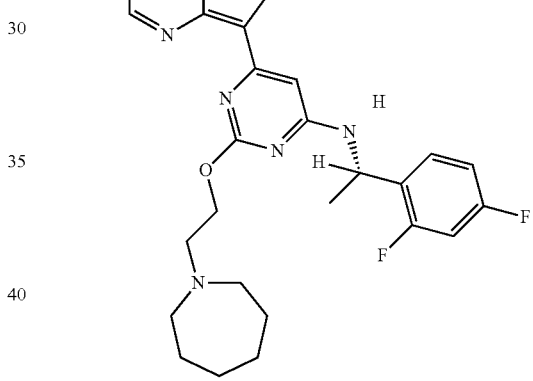
218
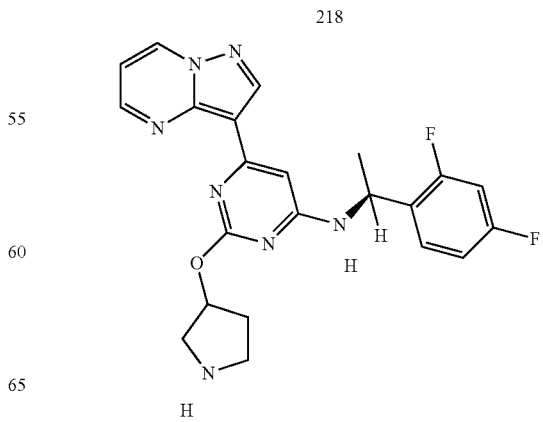

TABLE I-continued
219
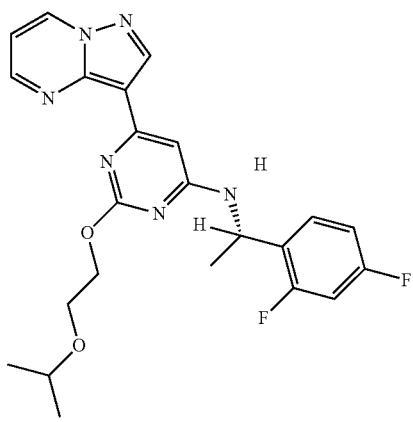
220
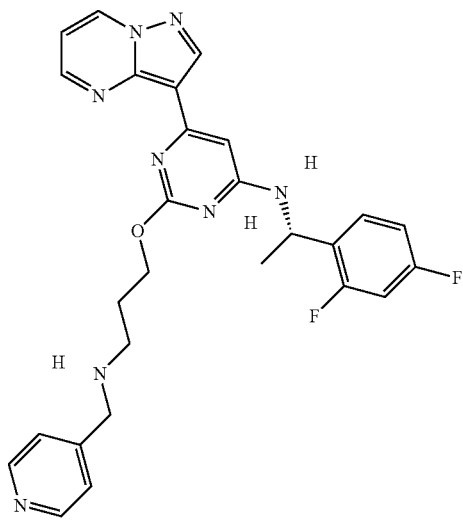
221
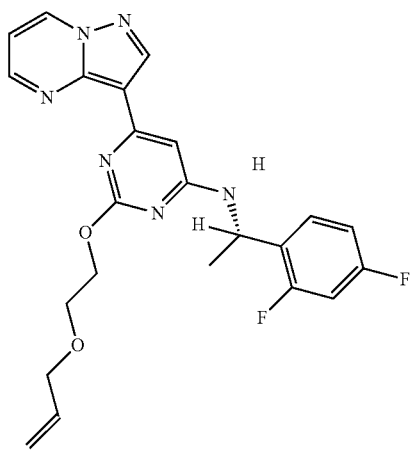
TABLE I-continued
222
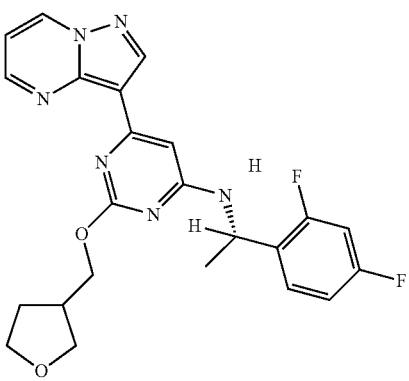
223
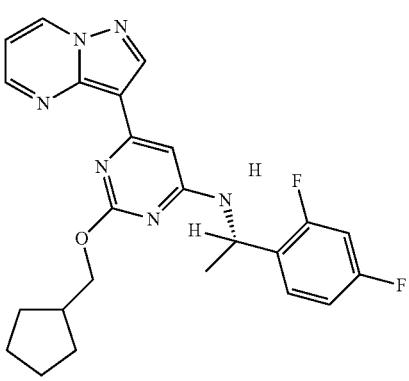
224
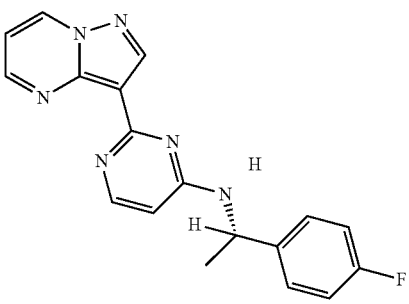
225
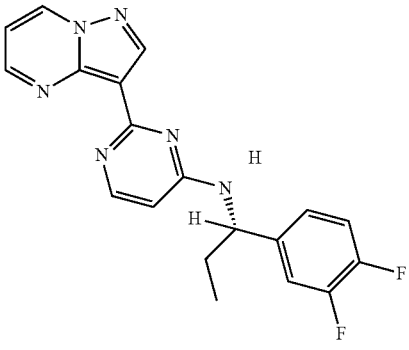

TABLE I-continued

| 226 | 230 |
|---|---|
| 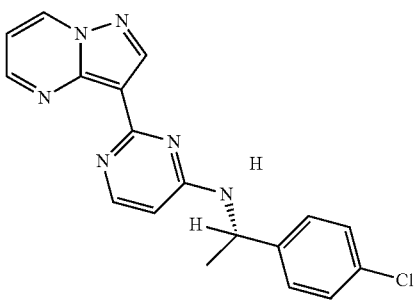 | 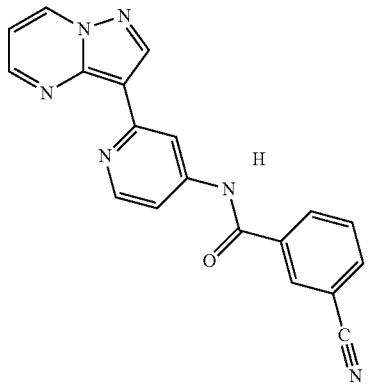 |
| 227 | 231 |
| 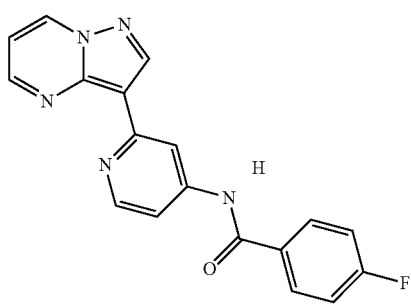 | 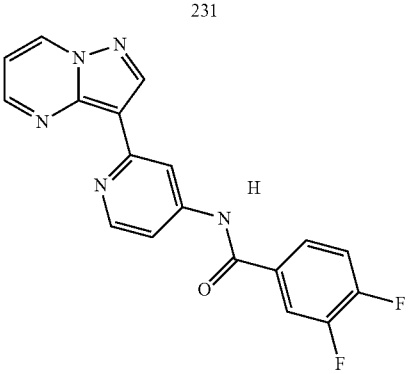 |
| 228 | |
| 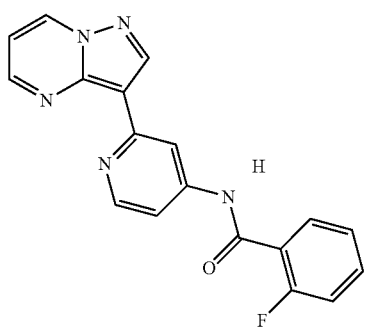 | |
| 229 | |
| 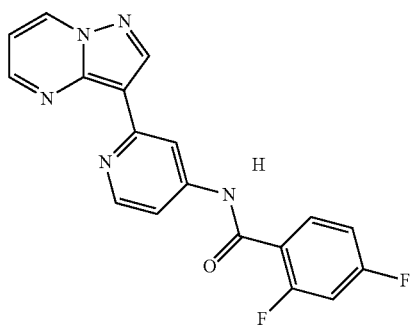 | |

Uses, Formulation and Administration

Pharmaceutically Acceptable Compositions

In another embodiment, the invention provides a pharmaceutical composition comprising a compound of formulae I, II, III, IV, V or VI.

In a further embodiment, the composition additionally comprises a therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating destructive bone disorders, an agent for treating liver disease, an agent for treating renal failure, an agent for treating anemia, an anti-viral agent, an antibiotic agent, an agent for treating blood disorders, an agent for treating diabetes, or an agent for treating immunodeficiency disorders.

According to another embodiment, the invention provides a composition comprising a compound of this invention or a pharmaceutically acceptable derivative thereof and a pharmaceutically acceptable carrier, adjuvant, or vehicle. The amount of compound in the compositions of this invention is such that it is effective to measurably inhibit a protein kinase, particularly JAK2, in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of the present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof. As used herein, the term "inhibitorily active metabolite or residue thereof" means that a metabolite or residue thereof is also an inhibitor of JAK2 kinase.

As used herein, the term "pharmaceutically acceptable salt" refers to those salts which are, within the scope of sound medical judgment, suitable for use in contact with the tissues of humans and lower animals without undue toxicity, irritation, allergic response and the like.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As described above, the pharmaceutically acceptable compositions of the present invention can additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The term "measurably inhibit", as used herein means a measurable change in kinase activity, particularly JAK2 kinase activity, between a sample comprising a compound of this invention and JAK2 kinase and an equivalent sample comprising JAK2 kinase in the absence of said compound.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated and the particular mode of administration. Preferably, the compositions should be formulated so that a dosage of between 0.01-100 mg/kg body weight/day of the inhibitor can be administered to a patient receiving these compositions.

Depending upon the particular condition, or disease, to be treated or prevented, additional therapeutic agents, which are normally administered to treat or prevent that condition, may also be present in the compositions of this invention. As used herein, additional therapeutic agents which are normally administered to treat or prevent a particular disease, or condition, are known as "appropriate for the disease, or condition, being treated".

For example, other chemotherapeutic or anti-proliferative agents may be combined with the compounds of this invention to treat myeloproliferative diseases and cancer. Examples of compounds used to treat myeloproliferative disorders and cancer. Examples of known chemotherapeutic and antiproliferative agents include, but are not limited to, imatinib mesylate ("Gleevec"), taxol, azacitidine, cytarabine ("ara-C"), hydroxyurea (also called "isohydroxycarbamide" or "Droxia"), bortezomid ("Velcade"), thalidomide, lenalidomide, etanercept, cytopenias, interferons, desatinib, imanitib, nilotinib, fludarabine phosphate, melphalan, 2-chlorodeoxyadenosine, fluorouracil, busulfan, topotecan, etoposide, cyclophosphamide, adriamycin, anthracyclines, dexamethasone, vincristine, prednisone.

Other examples of agents the inhibitors of this invention may also be combined with include, without limitation: anti-inflamatory agents such as corticosteroids, TNF blockers, IL-1 RA, azathioprine and sulfalazine; immunomodulatory and immunosuppressive agents such as cyclosporine, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole; agents for treating liver disease such as corticosteroids, cholestyramine, interferons, and antiviral agents; agents for treating blood disorders such as corticosteroids, anti-leukemic agents and growth factors; agents for treating cardiovascular disease such as anti-platelet aggregation agents (e.g. analgrelide) and anti-thrombosis agents (e.g. aspirin or heparin); antibiotic agents such as ofloxacin or rifampin; hormones such as granulocyte colony-stimulating factors; agents to treat bone disease such as pamidronate or zoledronic acid; agents for treating anemia such as erythropoietin; agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of the Compounds and Compositions

In one embodiment, the invention provides a method of selectively inhibiting JAK2 kinase activity in a patient, comprising administering to said patient a compound or composition of the invention.

In another embodiment, the invention comprises a method of treating or lessening the severity of a JAK2-mediated condition or disease in a patient. The term "JAK2-mediated disease", as used herein means any disease or other deleterious condition in which in particular JAK2 is known to play a role. In another embodiment the invention comprises a method of treating or lessening the severity of a myeloproliferative disorder, comprising administering to said patient a compound or composition of the invention or an acceptable pharmaceutical salt thereof.

Depending upon the particular condition, or disease, to be treated or prevented, additional therapeutic agents, which are normally administered to treat or prevent that condition, may also be present in the compositions of this invention. As used herein, additional therapeutic agents which are normally administered to treat or prevent a particular disease, or condition, are known as "appropriate for the disease, or condition, being treated".

In a further embodiment, the method comprises the additional step of administering to said patient an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating kidney failure, an agent for treating diabetes, an antibiotic, an agent for treating anemia, or an agent for treating immunodeficiency disorders, wherein said additional therapeutic agent is appropriate for the disease being treated and said additional therapeutic agent is administered together with said composition as a single dosage form or separately from said composition as part of a multiple dosage form.

For example other cancer or anti-proliferative agents may be combined with the compounds of this invention to treat cancer and proliferative diseases.

In a further embodiment treatment with a compound or composition of this invention can be combined with other therapies or treatments, including but not limited to: radiotherapy, phlebotomy, platelet aphaeresis, leukapheresis, plasmapheresis, intravenous nutrition, transfusions with red-blood cells or platelets, allogeneic or autologous bone-marrow transplant, autologous or allogeneic stem-cell transplantation, splenectomy, total body irradiation or dialysis.

In another embodiment, a compound or composition of this invention may be used to treat a myeloproliferative disorder. In one embodiment, the myeloproliferative disorder is polycythemia vera, essential thrombocythemia, or chronic idiopathic myelofibrosis. In another embodiment, the myeloproliferative disorder is myeloid metaplasia with myelofibrosis, chronic myeloid leukemia (CML), chronic myelomonocytic leukemia, chronic eosinophilic leukemia, hypereosinophilic syndrome, systematic mast cell disease, atypical CML or juvenile myelomonocytic leukemia.

In another embodiment, the invention provides a method of selectively inhibiting JAK2 kinase activity in a biological sample, comprising contacting said biological sample with a compound or composition of the invention.

The term "biological sample", as used herein, means an ex vivo sample, and includes, without limitation, cell cultures or extracts thereof; tissue or organ samples or extracts thereof, biopsied material obtained from a mammal or extracts thereof; and blood, saliva, urine, feces, semen, tears, or other body fluids or extracts thereof.

Inhibition of kinase activity, particularly JAK2 kinase activity, in a biological sample is useful for a variety of purposes that are known to one of skill in the art. Examples of such purposes include, but are not limited to, blood transfusion, organ transplantation, biological specimen storage, and biological assays.

In certain embodiments of the present invention an "effective amount" of the compound or pharmaceutically acceptable composition is that amount effective for treating or lessening the severity of one or more of the aforementioned disorders. The compounds and compositions, according to the method of the present invention, may be administered using any amount and any route of administration effective for treating or lessening the severity of the disorder or disease. The exact amount required will vary from subject to subject, depending on the species, age, and general condition of the subject, the severity of the infection, the particular agent, its mode of administration, and the like.

In certain embodiments of the present invention treatment with a compound or composition of this invention can be combined with an additional step involving applying an additional treatment, including but not limited to: radiotherapy, phlebotomy, platelet apheresis, leukapheresis, plasmapheresis, intravenous nutrition, transfusions with red-blood cells or platelets, allogeneic or autologous bone-marrow transplant, autologous or allogeneic stem-cell transplantation, splenectomy, total body irradiation or dialysis. These additional treatments can be administered to the patient prior to, sequentially or following administration of the compounds or compositions of this invention.

In an alternate embodiment, the methods of this invention comprise the additional step of separately administering to said patient an additional therapeutic agent or an additional treatment. When these additional therapeutic agents or treatments are administered separately they may be administered to the patient prior to, sequentially with or following administration of the compositions of this invention.

The compounds of this invention or pharmaceutical compositions thereof may also be used for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation.

These unwanted effects may be prevented or mitigated by pre-coating the device with a pharmaceutically acceptable composition comprising a compound of this invention.

Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Implantable devices coated with a compound of this invention are another embodiment of the present invention. The compounds may also be coated on implantable medical devices, such as beads, or co-formulated with a polymer or other molecule, to provide a "drug depot", thus permitting the drug to be released over a longer time period than administration of an aqueous solution of the drug.

Methodology for Synthesis and Characterization of Compounds

The compounds of this invention may be prepared in general by methods known to those skilled in the art for analogous compounds or by those methods depicted in the Examples below. See, e.g., the examples described in WO 2006/052913 A1, which are herein incorporated by reference in its entirety.

All references provided in the Examples are herein incorporated by reference. As used herein, all abbreviations, symbols and conventions are consistent with those used in the contemporary scientific literature. See, e.g., Janet S. Dodd, ed., *The ACS Style Guide: A Manual for Authors and Editors*, 2nd Ed., Washington, D.C.: American Chemical Society, 1997, herein incorporated by reference in its entirety.

General Analytical Methods.

As used herein the term RT (min) refers to the HPLC retention time, in minutes, associated with the compound. Unless otherwise indicated, the method employed to obtain the reported retention times is as follows:

Column: Ace 5 C8, 15 cm×4.6 mm id

Gradient: 0-100% acetonitrile/methanol 1:1 (20 mM Tris phosphate at pH 7.0). Flow rate: 1.5 ml/min. UV-vis detection.

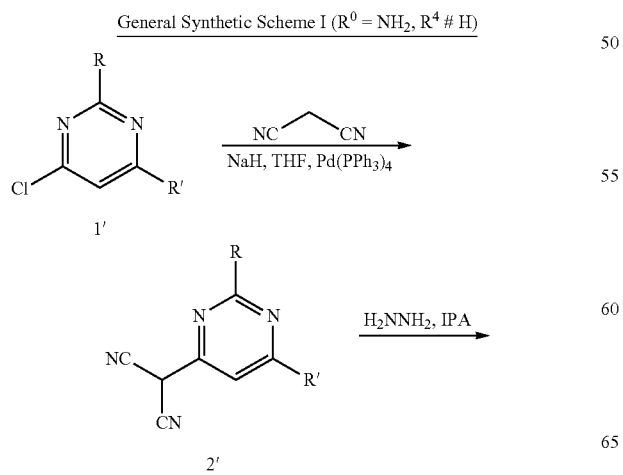

General Synthetic Scheme I ($R^0 = NH_2$, $R^4 \neq H$)

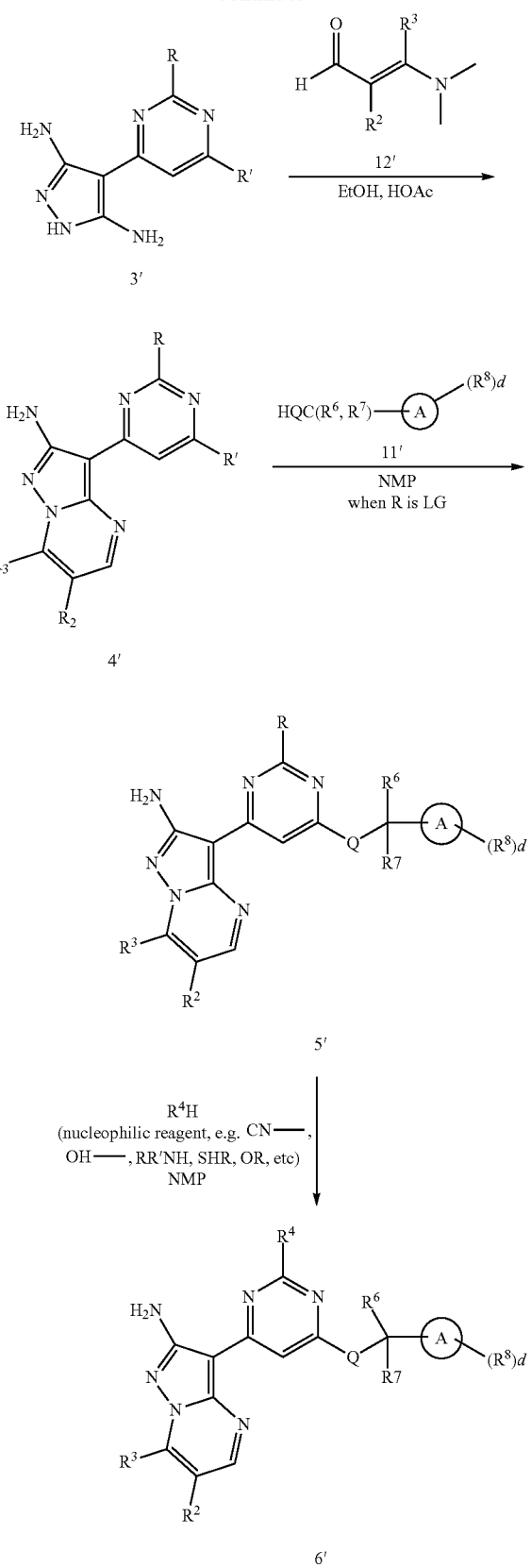

wherein, $R = R^4$, or a leaving group (LG) or a precursor therof and R' is a leaving group.

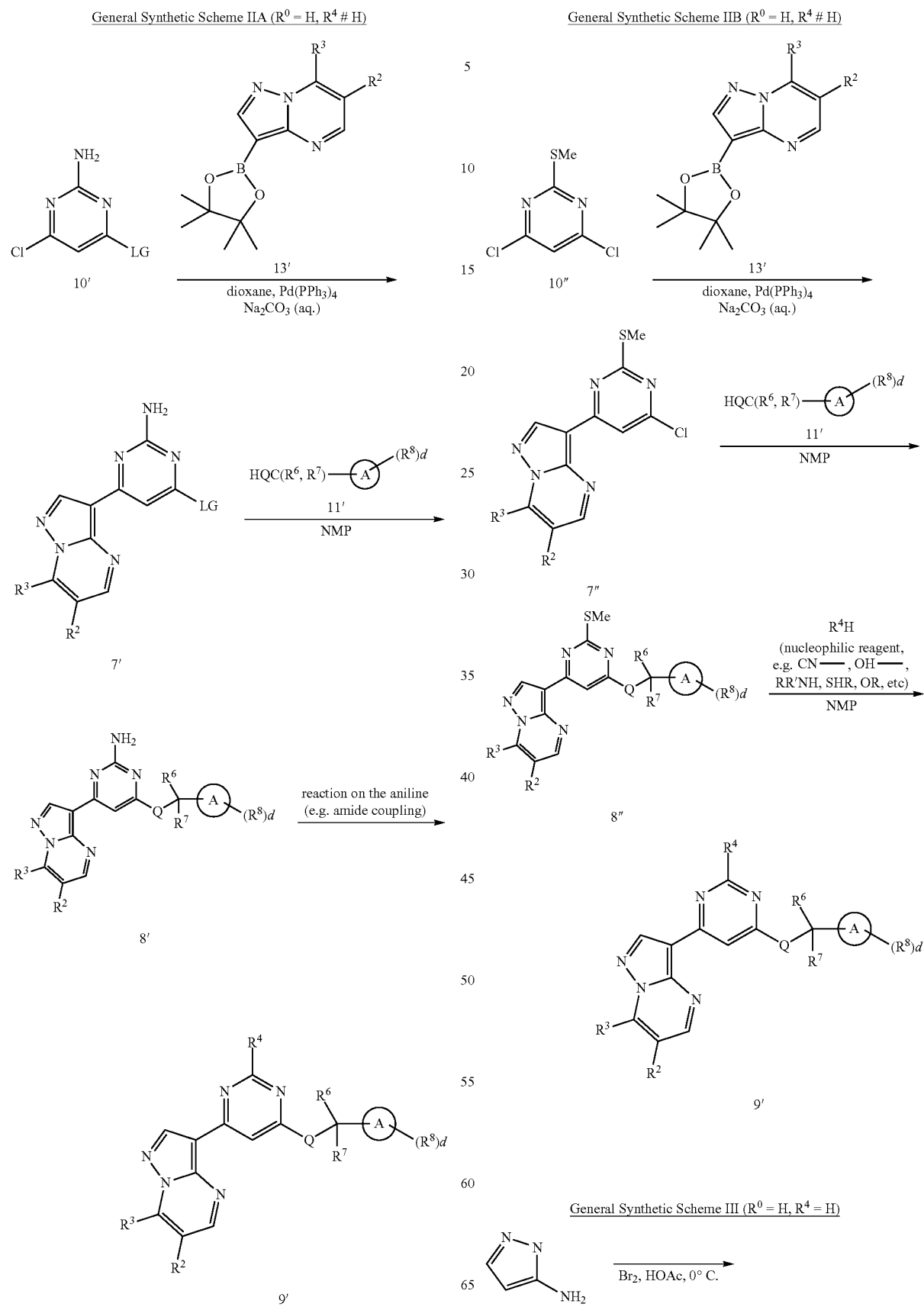

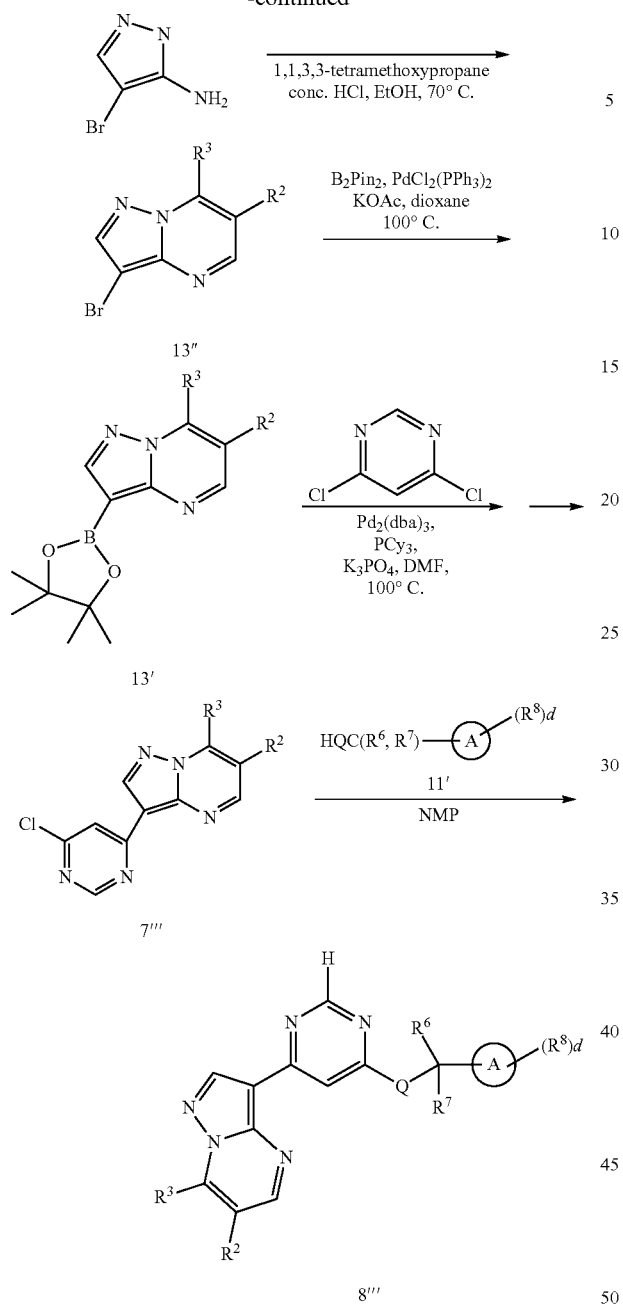

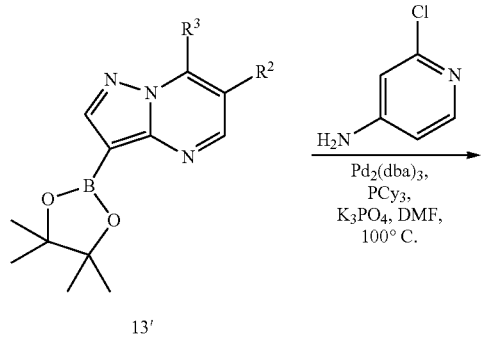

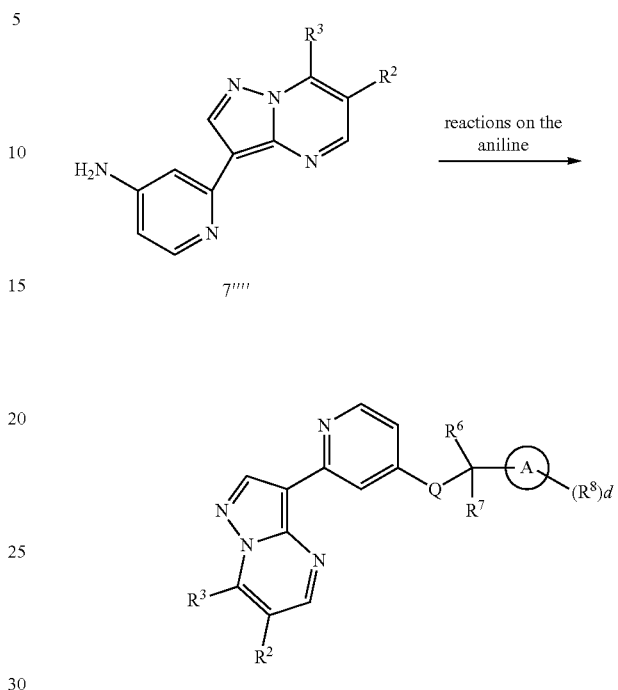

Compounds of the invention may be synthesized following the general approaches outlined above in Schemes I-IV. Starting with the appropriately 2-substituted 4,6-dichloropyrimidine or a pyrimidine in which one of the 2 chloro groups is replaced by another leaving group (LG, e.g. sulfonyl, halogen) palladium-mediated cross coupling can be effected with malononitrile or pinnacolborate ester 13' (Scheme I or Schemes II-III, respectively). Similarly, starting with a suitably substituted chloropyridine (Scheme IV) one can obtain compounds in which any combination of two instances of $X^1$, $X^2$ or $X^3$ are C. Alternatively, boronic acids, heteroarylstannanes or arylzincates derived from the corresponding aryl halides can be used in cross coupling reactions. Condensation of the substituted malononitrile 2' with hydrazine, followed by condensation with enaminone 12' leads to compound 4', precursor for all compounds in the $R^0$=$NH_2$ series. Alternatively, compounds 7', 7", 7' or 7", obtained as described in Scheme IIA, IIB, III and IV, respectively, can be used as the precursors for all compounds in the $R^0$=H series. Precursors 4' and 7', 7" or 7''' can additionally be substituted with a Q-linked group, with nucleophiles of general formula II' (Schemes I-III) to provide compounds of general formulae 5', 8', 8" and 8'''. In some cases, an additional step can lead to alternative $R^4$ groups, providing compounds of general formulae 6' or 9'.

In Schemes I and IIA, the term "leaving group" or "LG" is defined as in IUPAC Compendium of Chemical Terminology, Blackwell Scientific Publications, 1987 (ISBN-13: 978-

0632017652) which is herein incorporated by reference in its entirety, or as it is generally known to one skilled in the art.

EXAMPLES

Example 1

Preparation of 2,4-diamino 6-(2-aminopyrazolo[1,5-a]pyrimidin-3-yl)-pyrimidines of the invention Method A:

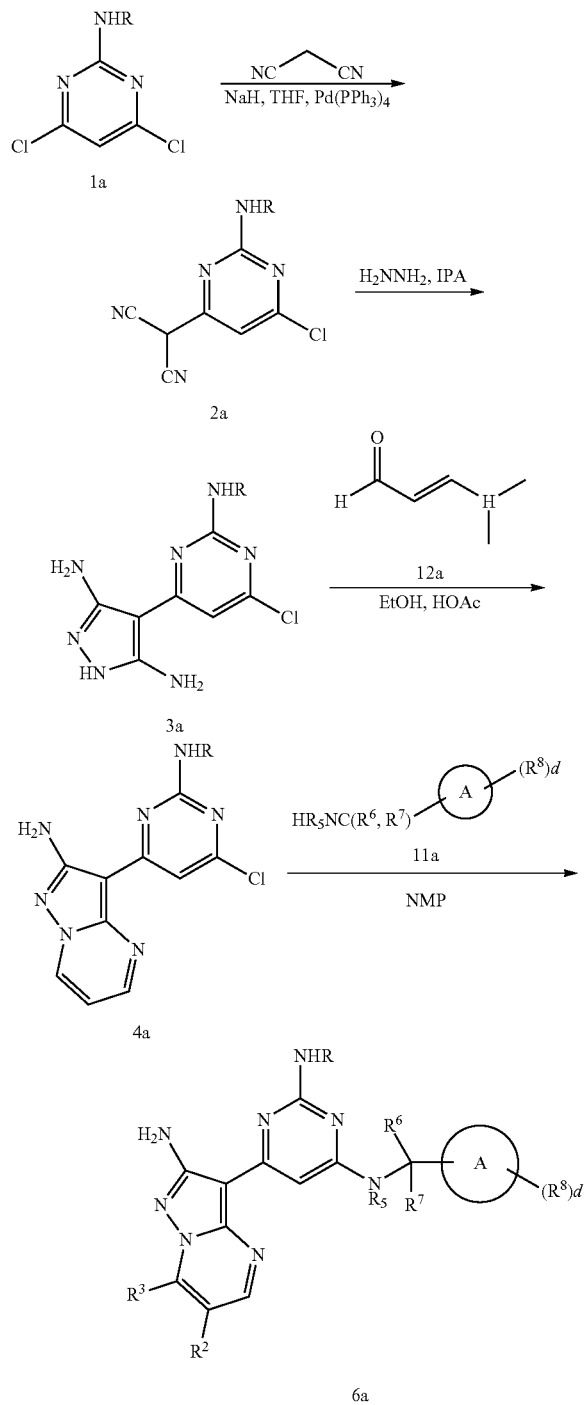

Synthesis of 2-(6-chloro-2-morpholinopyrimidin-4-yl)malononitrile (2aa)

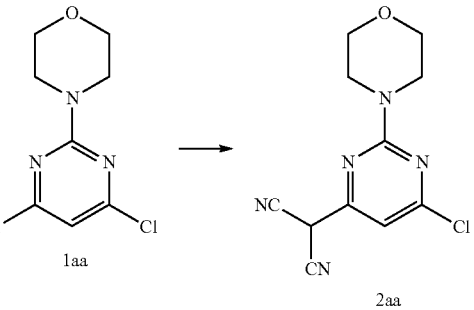

To a solution of malononitrile (277 mg, 4.2 mmol) in THF cooled to 0° C., sodium hydride (189 mg, 4.7 mmol) was added. When the evolution of gas ceased, 4,6-dichloro-2-morpholinopyrimidine (1aa) (500 mg, 2.1 mmol) was added to the reaction mixture, followed by $Pd(PPh_3)_4$. The resulting suspension was refluxed at 80° C. overnight. The mixture was treated with aq. 2M NaOH (10 mL) and stirred for 15 min. The organic layer was discharged and the aqueous was acidified with aq. 2M HCl and extracted with ethyl acetate, yielding 2-(6-chloro-2-morpholinopyrimidin-4-yl)malononitrile (2aa) (617 mg) after drying and solvent evaporation.

Synthesis of 4-(6-Chloro-2-morpholinopyrimin-4-yl)-1H-pyrazole-3,5-diamine (3aa)

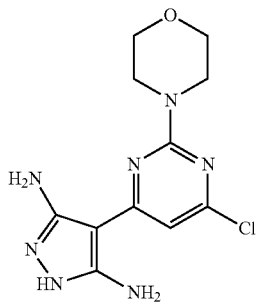

To a solution of 2aa (300 mg, 1.14 mmol) in iso-propanol (8 mL), hydrazine (0.02 mL) was added and the resulting mixture was exposed to microwave irradiation for 10 min at 140° C. The mixture was diluted in ethyl acetate, washed with water and dried over anhydrous sodium sulfate. 4-(6-Chloro-2-morpholinopyrimin-4-yl)-1H-pyrazole-3,5-diamine (3aa) was isolated as a solid and was used in the next step without further purification. LC/MS: 3.5 min, 296.4 (M+1), 294.3 (M−1).

Synthesis of 3-(6-chloro-2-morpholinopyrimidin-4-yl)pyrazolo[1,5-a]pyrimidin-2-amine (4aa)

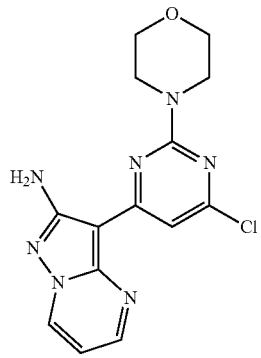

4aa

A solution of 3aa (349 mg, 1.2 mmol), 3-dimethylacrylaldedhyde (0.24 mL, 2.4 mmol) and acetic acid (144 mg, 2.4 mmol) in ethanol (4 mL) was exposed to microwave irradiation for 15 min at 160° C. A solid was formed and was isolated by filtration, yielding the title compound 4aa as a brown solid which was used in the next step without further purification. LC/MS: 2.9 min, 332.4 (M+1).

General Synthesis of 6aa.

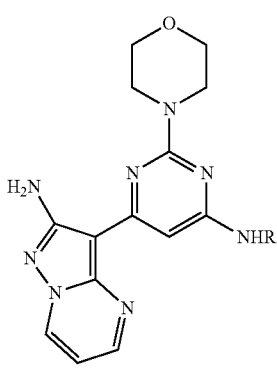

6aa

A solution of 4aa (40 mg, 0.12 mmol) in NMP (1 mL) and amine NH$_2$R (11a) (0.36 mmol) was exposed to microwave irradiation for 75 min at 230° C. The resulting mixture was then diluted with 1 mL of DMSO and purified by HPLC using ammonium formate 1% as a modifier. All amines were isolated after lyophilizing.

Method B:

Scheme VI

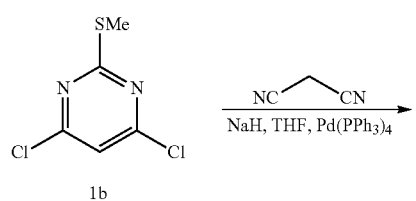

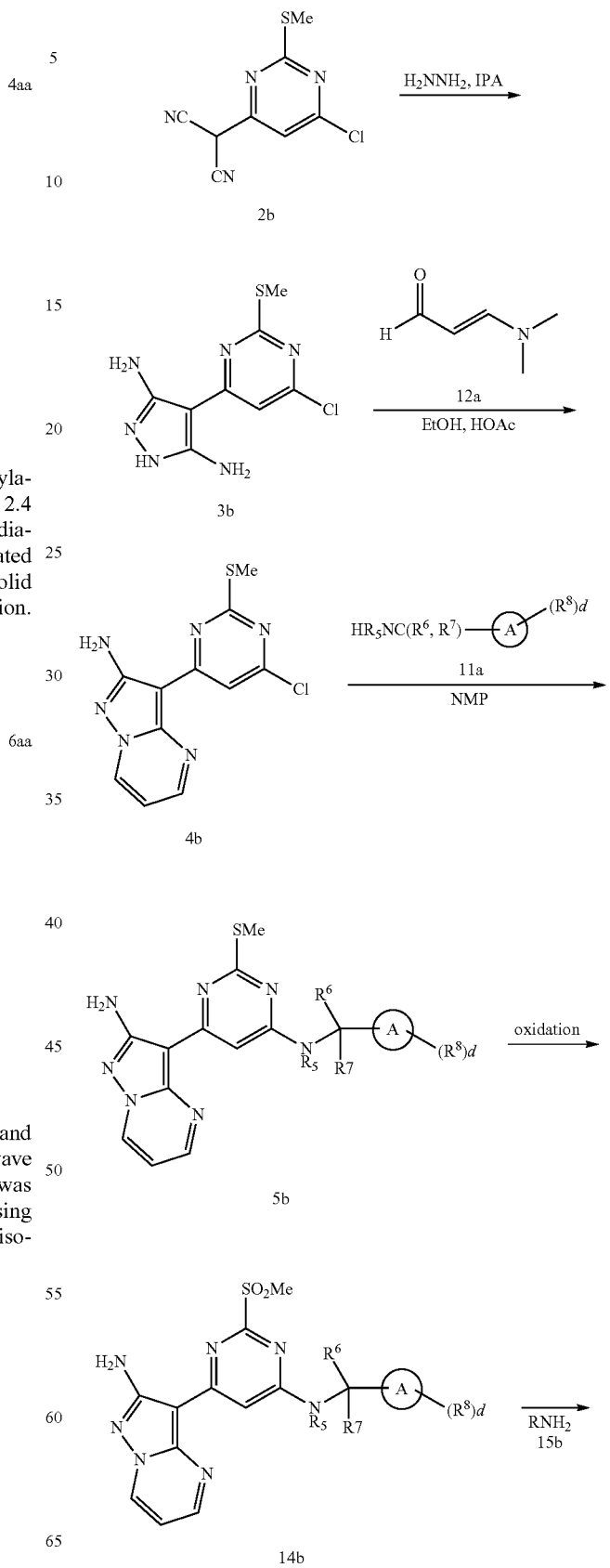

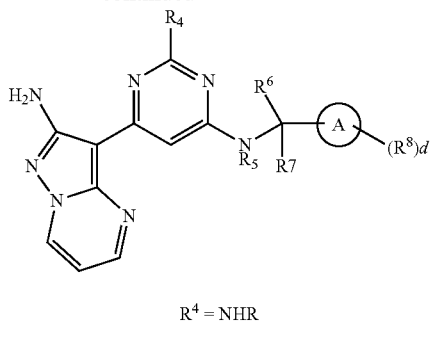

R⁴ = NHR

6b

Preparation of 2-(6-chloro-2-(methylthio)pyrimidin-4-yl)malononitrile 2b

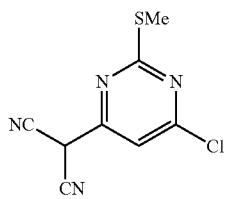

2-Methylthio-4,6-dichloropyrimidine (1b) (10 g, 51.27 mmoles) was suspended in 150 mL of dry THF along with malononitrile (3.72 g, 56.14 mmoles) and trans-dichloro-bis(triphenylphosphine)palladium (II) (2.0 g, 2.85 mmoles). The reaction mixture was purged with a stream of nitrogen gas for five minutes with rapid stirring before the cautious portion wise addition of sodium hydride (60% oil dispersion, 6.15 g, 154 mmoles). Note that the reaction is exothermic and THF starts to reflux upon addition of NaH. Nitrogen purging was continued throughout the addition. Upon completion of the sodium hydride addition, the nitrogen purge was ceased and the reaction mixture was placed into a pre-heated oil bath at ~70° C. The reaction mixture was heated under a blanket of nitrogen for 2 hours or until complete (color changes from a yellow to orange brown). The reaction was cooled and cautiously quenched with 30 mL of aq. 1N HCl solution and when gas formation ceased the majority of the solvent was removed under reduced pressure. The concentrated mixture was diluted with aq. 0.25 N HCl solution with stirring and the orange brown precipitate was collected via suction filtration, washed with water and vacuum-dried. The crude cake was transferred to a round bottomed flask containing acetonitrile (250 mL) and stirred vigorously for one hour. The precipitate was isolated via suction filtration, washed with acetonitrile and cautiously washed with DCM. The cake was then re-suspended in acetonitrile, warmed to ~60° C., allowed to cool while stirring, and re-isolated via suction filtration and vacuum-dried. 8.81 g of a pale yellow solid was obtained (77% yield).

LC/MS (M+1) 225, 227;

¹H NMR (300 MHz DMSO-d6): δ 6.23 (s, 1H), 2.4 (s, 3H).

Preparation of 4-(6-chloro-2-(methylthio)pyrimidin-4-yl)-1H-pyrazole-3,5-diamine 3b

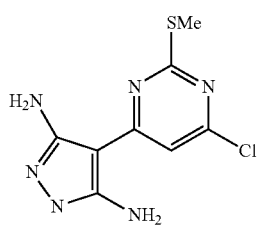

2-(6-Chloro-2-(methylthio)pyrimidin-4-yl)malononitrile (2b) (500 mg, 2.23 mmoles) was dissolved in 15 mL of diethylene glycol dimethyl ether along with of hydrazine [68.4 µL, 69.8 mg; 2.18 mmoles) and the reaction mixture sealed in a microwave vessel. The reaction was heated at 150° C. for 10 minutes (300 Watt) and then allowed to cool down. The solvent was removed under reduced pressure and the crude suspended in acetone, warmed to almost reflux and stirred. Then continued stirring while allowing to cool down to rt. The precipitate was isolated via suction filtration and washed with more acetone and air-dried. The product (3b) was obtained as a mustard colored powder (240 mg, 42% yield) and was used in the next step without further purification. LC/MS (M+1) 257, 259.

Preparation of 3-(6-chloro-2-(methylthio)pyrimidin-4-yl)-1,2-dihydropyrazolo[1,5-a]pyrimidin-2-amine 4b

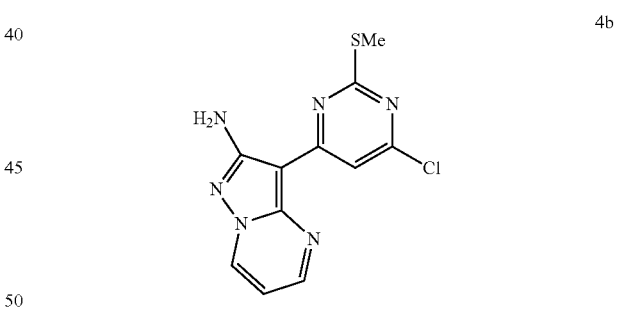

4-(6-Chloro-2-(methylthio)pyrimidin-4-yl)-1H-pyrazole-3,5-diamine (3b) (500 mg, 1.98 mmoles) was dissolved/suspended in 15 mL of diethylene glycol dimethyl ether and 1,3-tetramethoxypropane (325 µL, 320 mg, 2.0 mmoles) was added, followed by several drops of 11 M HCl, in a microwave vessel. The vessel was sealed and heated at 160° C. for 10 minutes in a microwave set at 300 Watt power. The reaction was cooled and the solvents were removed under reduced pressure. The residue was triturated in a 1:1 mixture of methanol and acetonitrile and suctioned-filtered to isolate the precipitate. The filtrate was reduced under vacuum to an oil and triturated with acetonitrile until powdered. The powder was isolated via suction filtration and air-dried. LC/MS (M+1): 293. The product was obtained and used directly in next step without further purification.

Preparation of (S)-3-(6-(1-(2,4-difluorophenyl)ethylamino)-2-(methylthio)pyrimidin-4-yl)pyrazolo[1,5-a]pyrimidin-2-amine 5bb

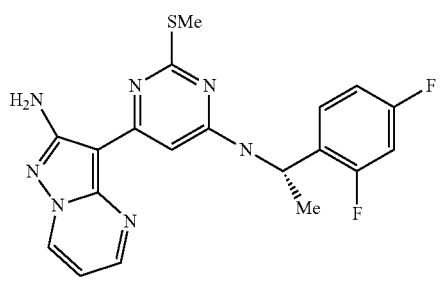

5bb 3-(6-Chloro-2-(methylthio)pyrimidin-4-yl)-1,2-dihydropyrazolo[1,5-a]pyrimidin-2-amine (4b) (500 mg, 1.70 mmoles) was dissolved in 5 mL of NMP along with (S)-1-(2,4 difluorophenyl)-ethylamine (988 mg, 5.0 mmoles, added as the free base). The reaction mixture was heated in the microwave three times at 220° C., for 15 minutes each. The reaction progress was monitored by LC/MS. Upon completion, the reaction was quenched by addition of 1N HCl to the vigorously stirred material until a thick oily material separated. This crude mixture was centrifuged and the thick oil separated. The oily mass was transferred to a round-bottomed flask and methanol was added. Solvents were removed under reduced pressure and the resulting solid was suspended in acetonitrile, warmed to 50° C. and vigorously stirred. Then it was cooled and the resulting precipitate was suction-filtered. The filtrate was reduced to an oil under reduced pressure and then re-dissolved in a minimum amount of methanol and purified via HPLC on C18 silica with acetonitrile/water/TFA as the eluent. After lyophilizing the desired fractions a beige solid was obtained (136 mg, 19.4% yield).

LC/MS (M+1): 414.

Preparation of (S)-3-(6-(1-(2,4-difluorophenyl)ethylamino)-2-(methylsulfonyl)pyrimidin-4-yl)pyrazolo[1,5-a]pyrimidin-2-amine 14b

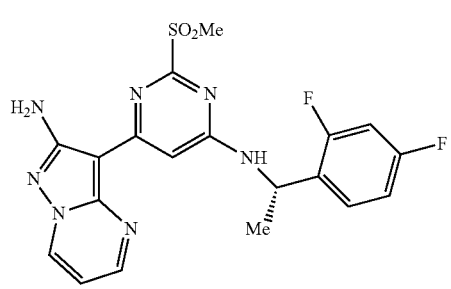

14b (S)-3-(6-(1-(2,4-Difluorophenyl)ethylamino)-2-(methylthio)pyrimidin-4-yl)pyrazolo[1,5-c]pyrimidin-2-amine (136 mg, 0.329 mmoles) was stirred with 75% meta-per benzoic acid (166 mg, 0.723 mmoles) in 5 mL of DMF for 45 minutes at rt. The reaction was deemed to be complete by LC/MS and was worked up as follows. The solvent was removed under reduced pressure and the residue was partitioned between sat $Na_2CO_3$ solution and EtOAc. The organic phase was again extracted with base, then water and finally brine, and dried with $Na_2SO_4$. The solvents were removed under vacuum. The crude sulfone was obtained (127 mg, 86.4%) and it was used directly in the next step without further purification. LC/MS (M+1): 446.

General Synthesis of 6b.

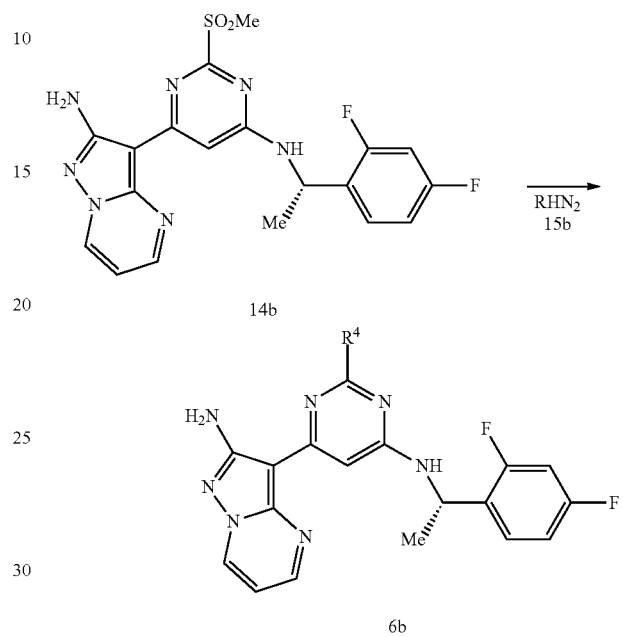

$R^4$ = NHR

A solution of methylsulfone 14b (0.06 mmol) and desired amine (15b, excess) in NMP (1 mL) was exposed to microwave irradiation for 30 min at 220° C. The resulting mixture was then diluted with 1 mL of DMSO and purified by HPLC using ammonium formate 0.1% as a modifier. All amines were isolated pure after lyophilizing.

Method C:

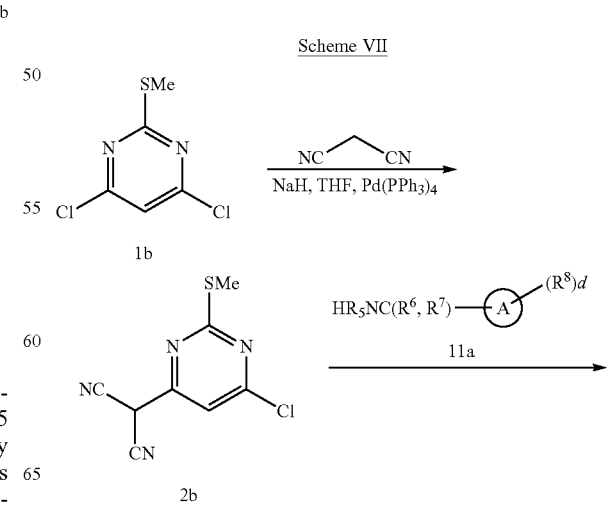

Scheme VII

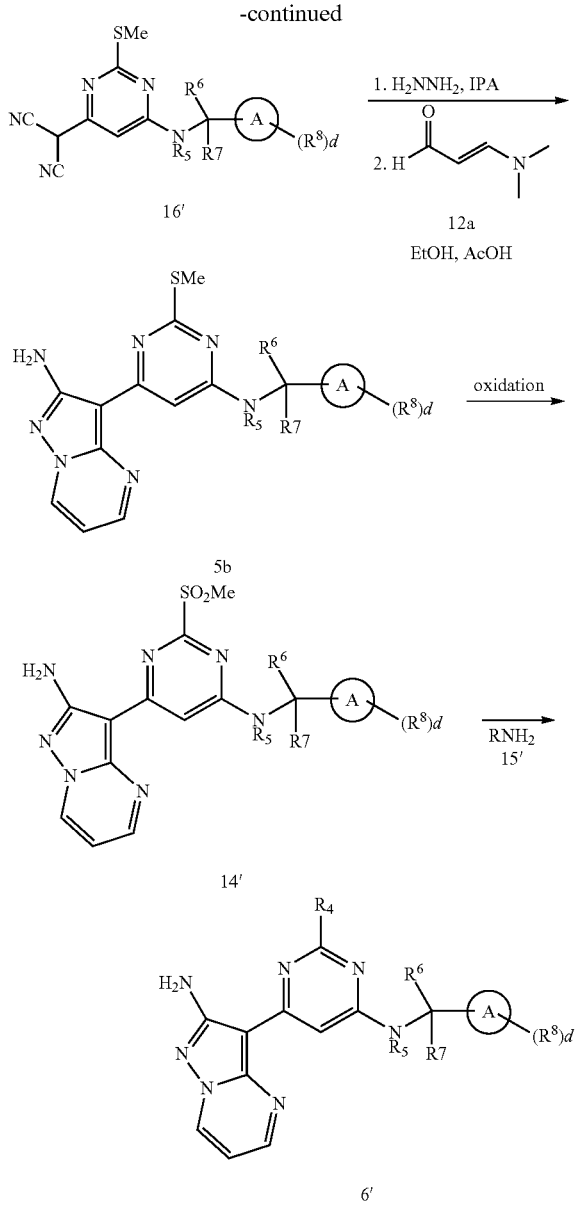

Synthesis of (S)-2-(6-(1-(4-fluorophenyl)ethy-lamino)-2-(methylthio)pyrimidin-4-yl)malononitrile (16c)

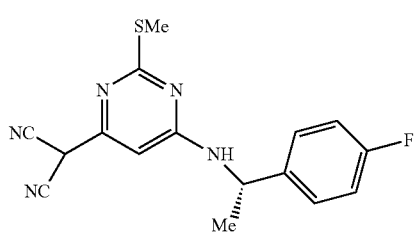

2-(6-Chloro-2-(methylthio)pyrimidin-4-yl)malononitrile (2b, 500 mg, 2.2 mmol) was suspended in acetonitrile (10 mL). S-(−)-1-(4-Fluorophenyl)ethyl amine (370 mg, 2.66 mmol) was added and the reaction mixture was heated at 160° C. with microwave irradiation. After 20 min., the reaction mixture was allowed to cool to rt. All volatiles were removed at reduced pressure and the residue was suspended in $CH_2Cl_2$. The crude material was pre-absorbed onto silica gel and purified by chromatography on a combi-flash system (0-20% MeOH/$CH_2Cl_2$) to yield 110 mg (15%) of the title compound.

LC/MS (M+1): 328.4.

Preparation of (S)-3-(6-(1-(4-fluorophenyl)ethy-lamino)-2-(methylthio)pyrimidin-4-yl)pyrazolo[1,5-a]pyrimidin-2-amine (5bc)

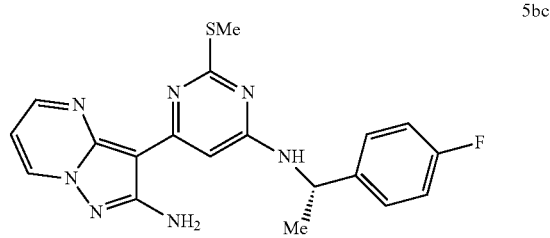

(1(S)-2-(6-(1-(4-Fluorophenyl)ethylamino)-2-(methylthio)pyrimidin-4-yl)malononitrile (16c, 110 mg, 0.33 mmol) was suspended in IPA (6.0 mL). Hydrazine was then added (11.0 mg, 0.34 mmol). The reaction mixture was heated at 160° C. with microwave irradiation. After 10 minutes, the reaction mixture was allowed to cool to rt. LC/MS showed the presence of product (LC/MS (M+1): 360.5). In the same pot, glacial acetic acid (130 mg) was added, followed by N,N-dimethyl acrolein (130 mg, 1.3 mmol). The reaction mixture was heated at 160° C. with microwave irradiation for 10 minutes. The mixture was then allowed to cool down to rt. All volatiles were removed at reduced pressure and the crude residue was purified on a combi-flash system (0-100% Hexane/EtOAc). Yield: 55 mg (45%) of the title compound.

$^1$H NMR (300 MHz, $CDCl_3$): δ 8.30 (dd, 2H), 7.32 (dd, 2H), 6.94 (t, 2H), 6.63 (dd, 1H), 6.10 (br s, 2H), 5.10 (br d, 1H), 4.93 (m, 1H), 2.42 (s, 3H), 1.50 (d, 3H).

Example 2

Preparation of 4-substituted 6-(2-aminopyrazolo[1,5-a]pyrimidin-3-yl)-pyrimidines of the invention (with R4=H at position 2 of the pyrimidine ring)

Method A.

Scheme VIII

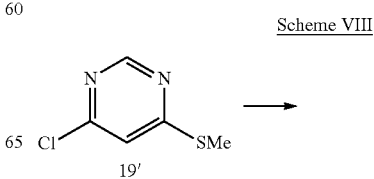

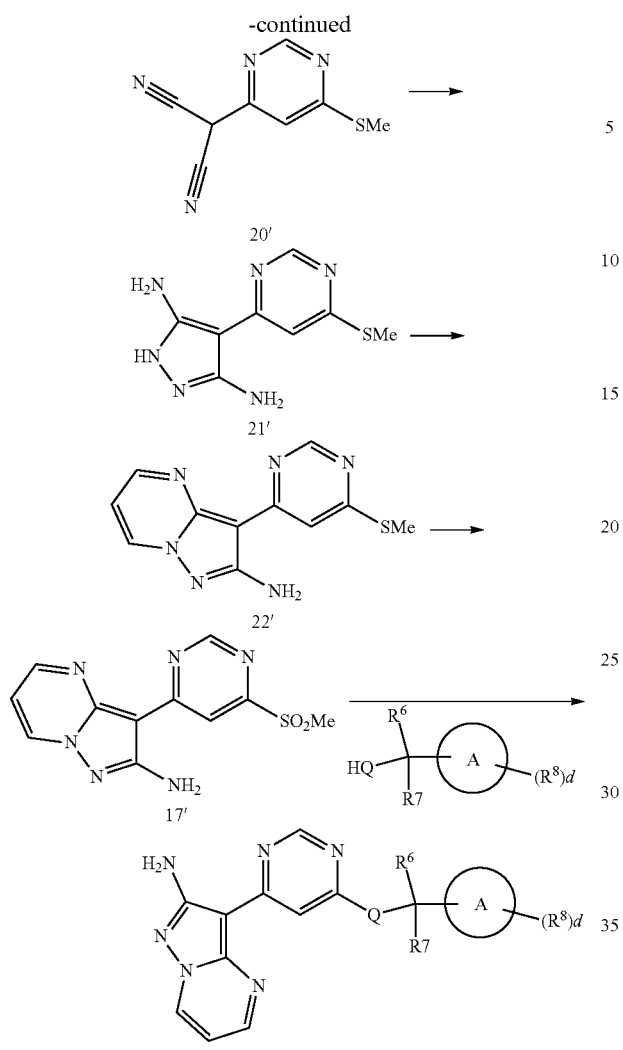

Preparation of 4-chloro-6-thiomethylpyrimidine (19')

Sodium thiomethoxide (28.2 g, 0.403 mol) was suspended in 350 mL of THF and stirred at ambient temperature under a blanket of nitrogen gas while 4,6-dichloropyrimidine (50 g, 0.33 mol) was added. After the addition was completed, the reaction was stirred and heated at 60° C. for 4 hours. The solvent was removed under reduced pressure and the residue was dissolved into 500 mL of 0.25N sodium hydroxide and extracted 3 times with ethyl acetate. The organics were combined and backwashed with water, brine, and 1:1 brine/1N HCl. The combined organic layer was dried (Na$_2$SO$_4$ anh.) and the solvent was removed under reduced pressure. The crude material was re-crystallized from hot petroleum ether to afford ~24 g of material.
LC/MS (M+1): 161.

Preparation of 4-(1,1-dicyanomethyl)-6-thiomethylpyrimidine (20')

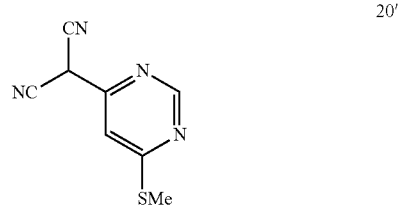

4-Chloro-6-thiomethylpyrimidine (19', 15 g, 99.5 mmol) was heated in 60 mL of DMSO and 12 mL of water with malononitrile (8.0 g; 121 mmol) and KOH (6.0 g; 107 mmol) at 100° C. for 2 hours under a nitrogen blanket. The crude reaction mixture was cooled and poured, with stirring, into 10 volumes of water containing 10 mL of glacial acetic acid and stirred for 30 minutes. The crude dark yellow ppt was isolated via suction filtration and washed with water. The crude material was slurried in acetonitrile, heated to boiling, allowed to cool and the product re-isolated via suction filtration. The material was washed with more acetonitrile, ethyl ether and finally petroleum ether, and air dried. The yield was 7.7 g of a mustard yellow powder (43%).
LC/MS (M+1): 191.

Preparation of 4-(3,5-diaminopyrazol-3-yl)-6-thiomethylpyrimidine (21')

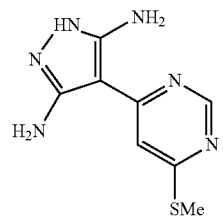

4-(1,1-Dicyanomethyl)-6-thiomethylpyrimidine (20', 24.4 g; 128.3 mmol) was refluxed in 250 mL of 2-propanol, under a nitrogen blanket, with hydrazine hydrate (7.0 mL, 7.19 g; 140 mmol) for 72 hours. The reaction was cooled and the ppt was isolated via suction filtration, washed with more cold 2-propanol and finally with MTBE and air dried. The yield was 25.6 g of a beige solid (82%).
LC/MS (M+1): 223.

Preparation of 3-(6-(methylthio)pyrimidin-4-yl)-1,3a-dihydropyrazolo[1,5-a]pyrimidin-2-amine (22')

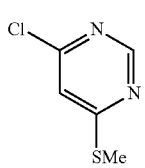

4-(3,5-Diaminopyrazolo-3-yl)-6-thiomethylpyrimidine (21', 21 g, 94.5 mmol) was heated in 250 mL of 2-propanol with N,N-dimethylacrolein (15.3 mL, 15 4 g, 154 mmol) and 10 mL of glacial acetic acid at 85° C. for 8 hours. A gentle stream of nitrogen gas was swept over the top of the flask to aid in the removal of the dimethylamine generated. The reaction was cooled and the dark ppt was isolated via suction filtration. The ppt was then washed with 2-propanol and acetonitrile. The crude material was re-crystallized from glacial acetic acid to furnish 11.2 g of material (1$^{st}$ crop) and 7.2 g (2$^{nd}$ crop) (75%)

LC/MS (M+1): 259.
$^1$H NMR (300 MHz, d$_6$-DMSO): δ 8.9 (dd, 1H), 8.85 (s, 1H), 8.58 (m, 1H), 8.32 (s, 1H), 7.03 (m, 2H), 7.00 (m, 1H), 2.57 (s, 3H).

Preparation of 3-(6-(methylsulfinyl)pyrimidin-4-yl)-1,3a-dihydropyrazolo[1,5-a]pyrimidin-2-amine (17')

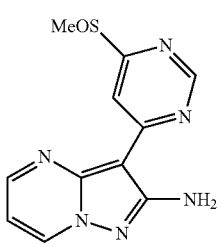

17'

3-(6-(Methylthio)pyrimidin-4-yl)-1,3a-dihydropyrazolo[1,5-a]pyrimidin-2-amine (22', 7.2 g, 27.9 mmol) was suspended/dissolved in 70 mL of DMF and stirred at 0° C. while mCPBA (8.0 g, 34.8 mmol) in 20 mL of DMF was added drop wise over 30 minutes. After addition, the reaction was stirred for an additional hour at ambient temperature. The ppt was isolated via suction filtration, and washed with acetonitrile, and finally ethyl ether and air dried. Isolated 5.1 g of solid (66.7% yield)

LC/MS (M+1): 275.
$^1$H NMR (300 MHz, d$_6$-DMSO): δ 9.20 (d, 1H), 8.95 (m, 2H), 8.67 (m, 1H), 7.23 (s, 2H), 7.13 (m, 1H), 2.89 (s, 3H).

Synthesis of 3-(6-4-fluorobenzyloxy)pyrimidin-4-yl) pyrazolo[1,5-a]pyrimidin-2-amine (18a)

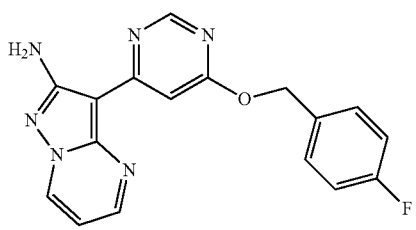

18a

4-Fluorobenzyl alcohol (37.9 mg, 0.3 mmol) was dissolved in 1.0 ml of THF under N$_2$. Sodium Hydride (12.0 mg, 0.3 mmol) was then added. The reaction mixture was allowed to stir at rt for 10 minutes. Solid 3-(6(methylsulfonyl)pyrimidin-4-yl)pyrazolo[1,5-a]pyrimidin-2-amine (17') (29.3 mg, 0.10 mmol) was then added and the mixture was allowed to stir at rt for an additional 2 hours. The reaction was quenched with water. The product crashed out of solution and was collected by filtration. The crude residue was dissolved in acetonitrile and partitioned with hexane. The flask was shaken and the resulting layers were separated (hexane pipetted off). The acetonitrile layer was evaporated to dryness to yield 8.7 mg (26%) of the title compound.

$^1$H NMR (300 MHz, CDCl$_3$): δ 8.71 (s, H), 8.43 (m, 2H), 8.00 (s, H), 7.46 (t, 2H), 7.07 (t, 2H), 6.75 (t, H), 6.23 (s, br, 2H), 5.43 (s, 2H).

LC/MS (M+1): 337.5.
Method B.

Scheme X.

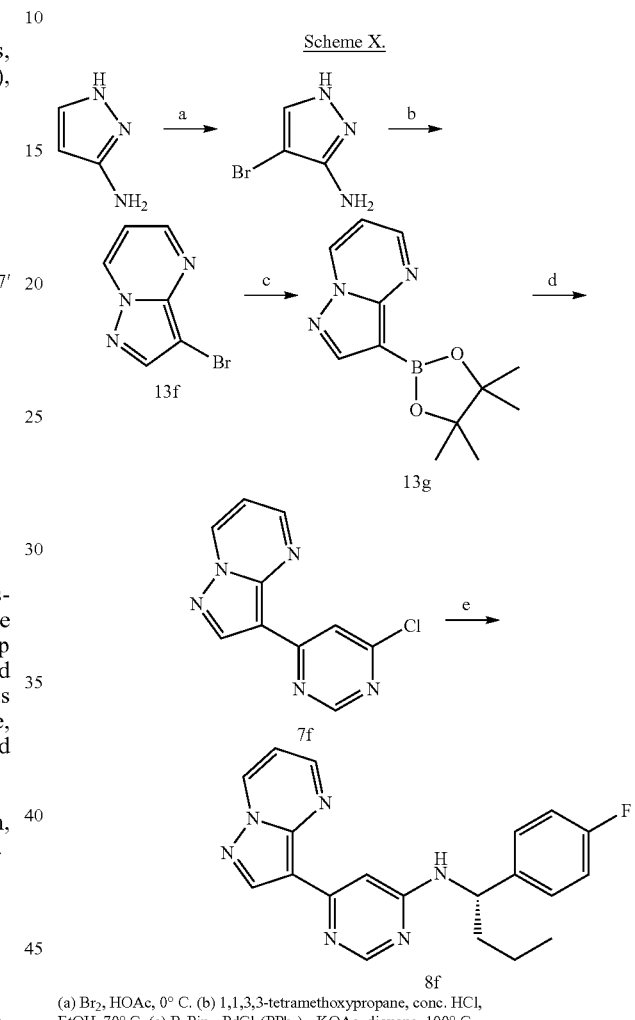

(a) Br$_2$, HOAc, 0° C. (b) 1,1,3,3-tetramethoxypropane, conc. HCl, EtOH, 70° C. (c) B$_2$Pin$_2$, PdCl$_2$(PPh$_3$)$_2$, KOAc, dioxane, 100° C.
(d) 4,6-dichloropyrimidine, Pd$_2$(dba)$_3$, PCy$_3$, K$_3$PO$_4$, DMF, 100° C.
(e) (S)-1-(4-fluorophenyl)butan-1-amine, NMP, 240° C.

Synthesis of 4-bromo-1H-pyrazol-3-amine

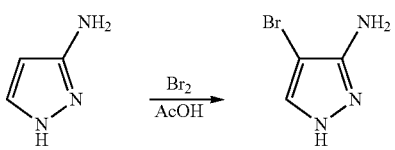

At 0-5° C., a solution of 3-amino pyrazole (120 mmol) in AcOH (22 mL) was slowly added a solution of Br$_2$ in AcOH (22 mL) over a period of 2 h. The reaction was complete immediately after the addition of Br$_2$ solution (120 mmol). To the reaction mixture was added CCl$_4$ (8 mL), stirred for 30 min at rt. The precipitated solid was filtered and washed with additional CCl₄ (8 mL). The solid so obtained was dissolved in water (40 mL), adjusted to pH ~7.5 (using aq. NaHCO₃ solution) and the precipitated solid was filtered and washed with water (8 mL). The combined filtrates were also adjusted to pH ~8 (aq. Na₂CO₃ solution), extracted with EtOAc (800 mL), washed with brine solution (200 mL), dried (Na₂SO₄), filtered and evaporated to obtain the desired compound as a yellow solid. The crude compound was stirred with CCl₄ (20 mL), filtered and washed with acetone (5 mL) and CCl₄ (8 mL), and dried under vacuum. The product was obtained as a pale yellow solid (17.2 g, 88% yield). TLC system: DCM/MeOH (9:1). R$_f$ value: 0.5. (M+H): 162.3.

Synthesis of 3-bromopyrazolo[1,5-a]pyrimidine (13f)

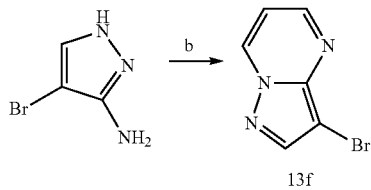

A solution of the amino-bromo-pyrazole obtained above, dissolved in EtOH (230 mL) was treated with conc. HCl (13.6 mL) followed by tetra-methoxypropane (31 mL) at rt. The resulting turbid solution was heated to 71° C. for 2 h, during this time, the reaction mixture turned into a suspension and a solid started separating out. The reaction mixture was cooled to rt, the precipitated solid was collected by filtration, washed with EtOH (min vol.) and dried to obtain the desired compound. The crude compound (C) was used as such for the next step without further purification (26.8 g, 74.1%). (M+H): 198.0.

Preparation of 3-(4,4,5,5-tetramethyl-1,3,2-dioxaborolan-2-yl)pyrazolo[1,5-a]pyrimidine (13g)

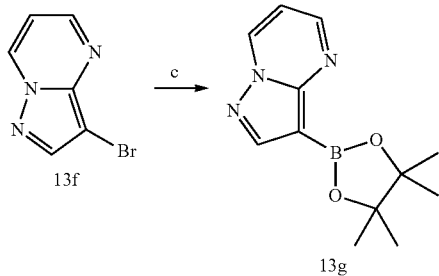

To a stirred solution of compound 13f (27.8 mmol) in 1,4-dioxane (120 mL) was added B₂Pin₂ (126 mmol) and KOAc (101 mmol) at rt. The resulting mixture was purged with Ar for 45 min, PdCl₂(PPh₃)₂ (1.5 mmol) was added and the mixture again purged with Ar for 30 min. The resulting mixture was heated to 100° C. for 15 h. The reaction mixture was concentrated to obtain a viscous mass, which was charged over a fluorosil plug, washed with pentane, followed by 60% EtOAc/Pet ether. The relevant fractions were concentrated to obtain a crude compound 13g as a pale yellow solid. The crude compound 13g was stirred with pentane (25 mL) at −40° C. for 30 min, filtered, washed with cold pentane (5 mL) and dried under vacuum to obtain sufficiently pure compound (3.5 g, 51.4%). TLC system: Ethyl acetate: Petroleum ether (2:3) R$_f$ value: 0.4. (M+H): 246.3.

Synthesis of 3-(6-chloropyrimidin-4-yl)pyrazolo[1,5-a]pyrimidin (7f)

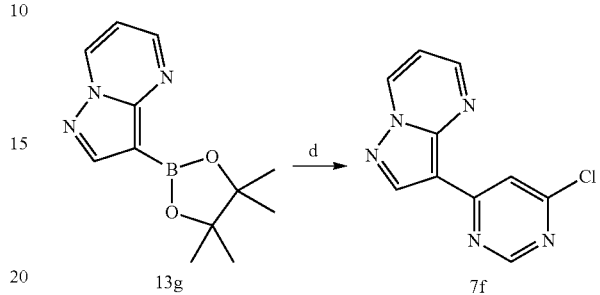

To a stirred solution of compound 13g (14.3 mmol) in DMF (90 mL), was added 4,6-dichloropyrimidine (14.3 mmol), K₃PO₄, (42.7 mmol) and PCy₃ (1.4 mmol) at rt. The mixture was purged with Ar for 45 min, Pd₂(dba)₃ (0.70 mmol) added and again the mixture purged with Ar for 30 min and heated to 100° C. for 1 h. The reaction was cooled to rt, EtOAc (800 mL) added, and the mixture filtered through Celite®. The combined filtrate was washed with water (3×200 mL), 2N aq. HCl solution (400 mL), sat. aq. NaHCO₃ and brine solution (200 mL). The organic layer was dried (Na₂SO₄), filtered and concentrated to give a crude compound as a brown residue. The crude compound 7f was purified by column chromatography (100-200 mesh silica gel, 0-70% EtOAc/Petroleum ether). The product was obtained as a solid (350 mg, 10.6%). TLC system: EtOAc: Pet ether (7:3). R$_f$ value: 0.56. mp: 260-270° C.

Preparation of (S)—N-(1-(4-fluorophenyl)butyl)-6-(pyrazolo[1,5-a]pyrimidin-3-yl)pyrimidin-4-amine (8f)

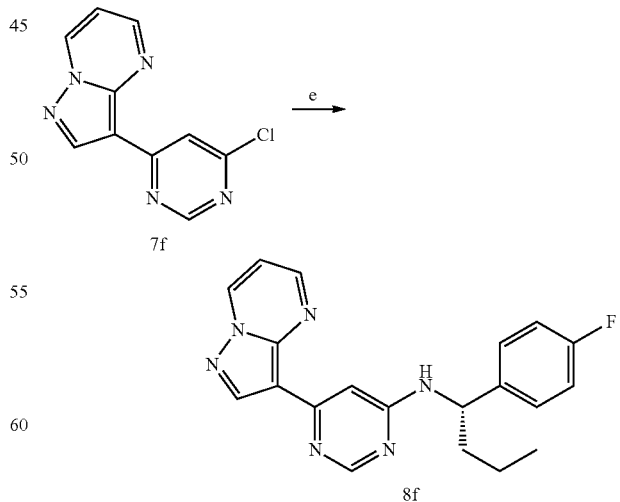

A stirred solution of 7f (0.1 mmol) and (S)-1-(4-fluorophenyl)butan-1-amine (2.1 mmol) in NMP (1 mL) was heated in a sealed tube to 240° C. (in a Microwave reactor) for 15 min.

The solution was then diluted with DMSO (1 mL) and the crude product was purified by preparative HPLC. R$_t$: 2.9 min. (M+H): 363.3.

$^1$H NMR (300 MHz, DMSO-δ$_6$): 9.40 (s, H), 8.93 (s, 2H), 8.70 (s, H), 7.77 (s, H), 7.42 (m, 3H), 7.18 (m, 2H), 5.27 (s, br, H), 1.85 (m, 2H), 1.35 (m, 2H), 0.91 (m, 3H).
Method C.

Scheme XI.

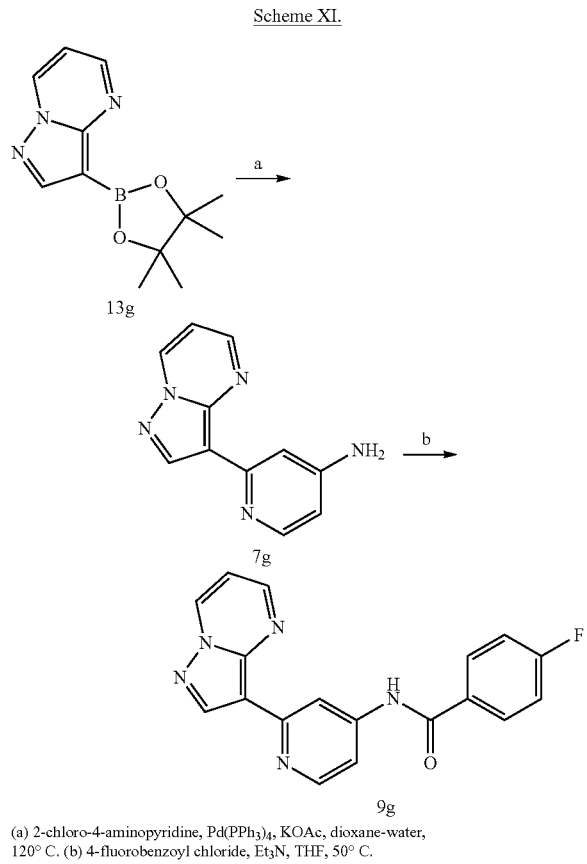

(a) 2-chloro-4-aminopyridine, Pd(PPh$_3$)$_4$, KOAc, dioxane-water, 120° C. (b) 4-fluorobenzoyl chloride, Et$_3$N, THF, 50° C.

Preparation of 2-(pyrazolo[1,5-a]pyrimidin-3-yl)pyridin-4-amine (7g)

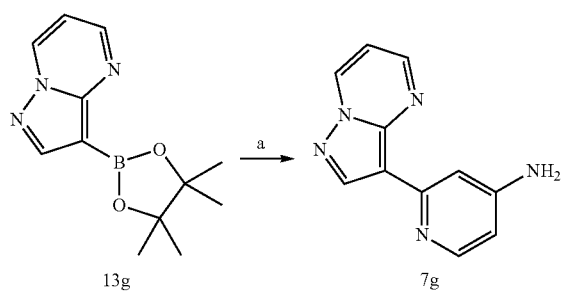

A suspension of 10 ml 1,4-dioxane and 8 ml 4N KOAc (5.9 g) with 3-(4,4,5,5-tetramethyl-1,3,2-dioxaborolan-2-yl) pyrazolo[1,5-a]pyrimidine (13 g, 3.68 g) and 2-chloro-4-aminopyridine (3.68 g) was purged with nitrogen for 30 min. Then, to the suspension was added Pd(PPh$_3$)$_4$ (867 mg) and the reaction mixture was heated at 120° C. in microwave for 20 min. Upon cooling, the precipitated solid was filtered and used without further purification (1.0 g, 31% yield).

4-fluoro-N-(2-(pyrazolo[1,5-a]pyrimidin-3-yl)pyridin-4-yl)benzamide (9g):

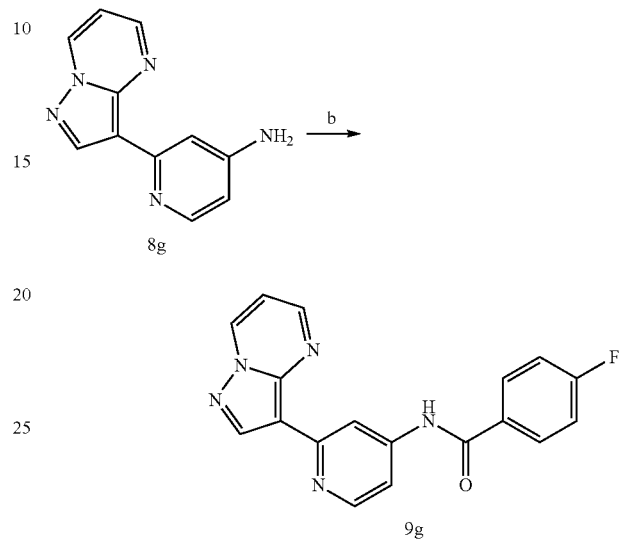

To a THF suspension of 2-(pyrazolo[1,5-a]pyrimidin-3-yl) pyridin-4-amine (8g) was added Et$_3$N and 4-fluorobenzoyl chloride. The reaction mixture was stirred at 50° C. for 2 hours until LS/MS indicated the desired product was the major peak. After aqueous work up, the residue was dissolved in 1 ml of DMSO and purified by preparative HPLC. The product was obtained as a solid (10 mg).

RT: 2.34 min (M+H): 334.2

$^1$H NMR (300, DMSO-δ$_6$): 11.24 (s, H), 9.36 (dd, H), 9.09 (s, H), 8.97 (s, H), 8.90-8.89 (m, H), 8.62 (d, H), 8.14 (dd, H), 7.96 (d, H), 7.44 (t, H), 7.34 (dd, H) ppm.

Example 3

Compounds of the Invention Wherein R$^4$ in not Hydrogen

Scheme XII.

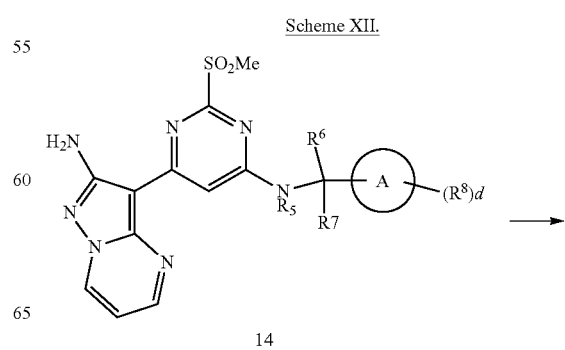

Preparation of (S)-4-(2-aminopyrazolo[1,5-a]pyrimidin-3-yl)-6-(1-(2,4-difluorophenyl)ethylamino)pyrimidin-2-ol (6d)

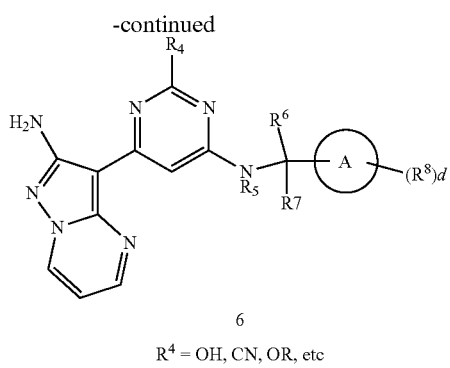

6
R⁴ = OH, CN, OR, etc

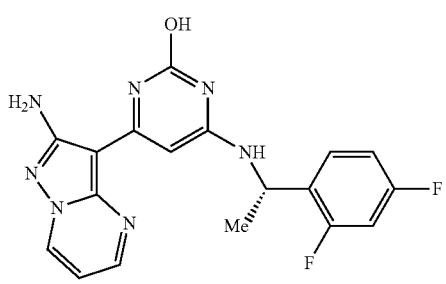

6d

Crude (S)-3-(6-(1-(2,4-difluorophenyl)ethylamino)-2-(methylsulfonyl)pyrimidin-4-yl)pyrazolo[1,5-c]pyrimidin-2-amine (14a, prepared as indicated in scheme VII) (25 mg, 0.056 mmoles) was dissolved in 1 mL of DMF and 1 mL of 2N NaOH solution was added. The reaction was stirred at 80° C. for 8 hours in a sealed flask. The reaction was made acidic with conc. HCl (11M). It was then cooled and the DMF removed under reduced pressure. The crude material was purified via HPLC on C18 silica using acetonitrile/water/TFA as the eluent. The product was obtained as a pale yellow material in the form of its TFA salt (6.4 mg, 22.8%).

LC/MS (M+1): 384.
¹H NMR (300 MHz, CH₃CN-d₃): δ 11.25 (m, H), 8.66 (d, 1H), 8.59 (d, 1H), 7.53 (m, 2H), 7.11 (m, 1H), 7.00 (m, 2H), 5.81 (s, 1H), 5.23 (m, 2H), 1.66 (d, 3H).

Preparation of (S)-4-(2-aminopyrazolo[1,5-a]pyrimidin-3-yl)-6-(1-(2,4-difluorophenyl)ethylamino)pyrimidine-2-carbonitrile (6e)

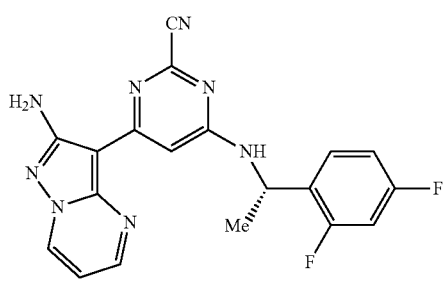

6e (S)-3-(6-(1-(2,4-Difluorophenyl)ethylamino)-2-(methylsulfonyl)pyrimidin-4-yl)pyrazolo[1,5-a]pyrimidin-2-amine (14a) (25 mg, 0.056 mmoles) was dissolved in 1 mL of DMSO and the mixture stirred with of potassium cyanide (14 mg, 0.22 mmoles] at 80° C. for 3 hours. The crude product was purified via HPLC C18 silica with acetonitrile/water/TFA as the eluent. The product was obtained as a light yellow powder, in the form of its TFA salt (4.5 mg 16.4%).

LC/MS (M+1): 393.

Example 4

Preparation of 2,4-disubstituted 6-(pyrazolo[1,5-a]pyrimidin-3-yl)-pyrimidines of the invention Method A.

Scheme XII.

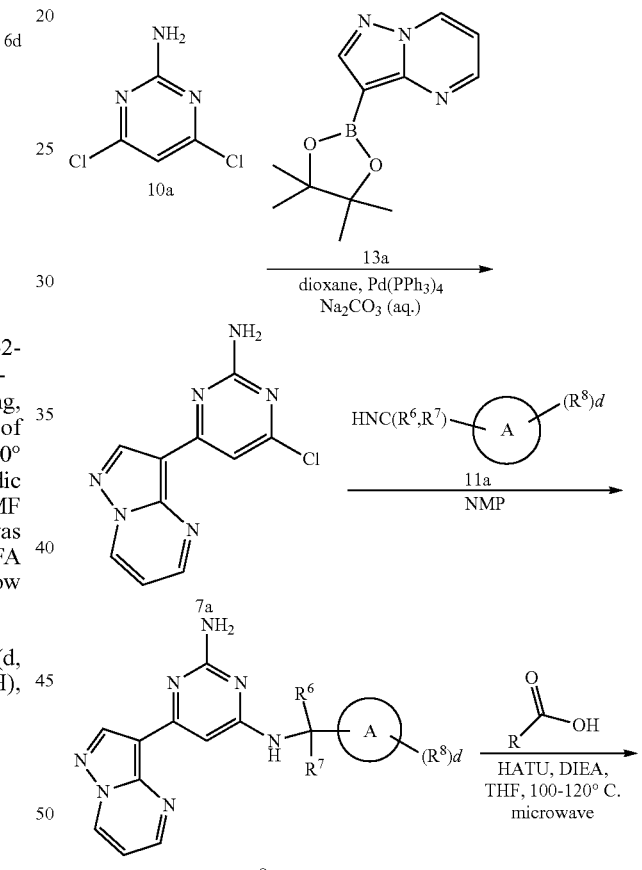

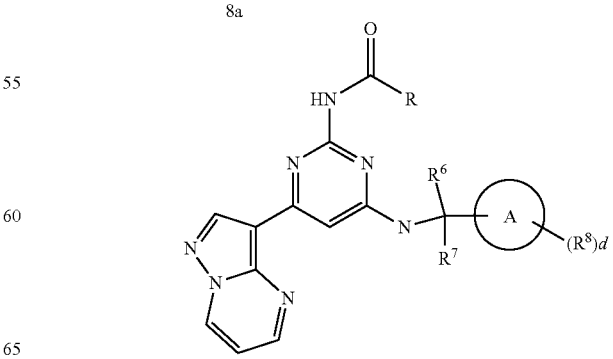

9a

Preparation of 4-chloro-6-(pyrazolo[1,5-a]pyrimidin-3-yl)pyrimidin-2-amine (7a)

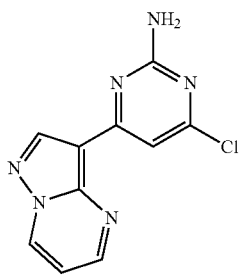

A mixture of 10a (0.5 g, 2.0 mmol), 13a (1.3 g, 7.9 mmol), Pd(PPh3)4 in dioxane (15 mL) and saturated Na$_2$CO$_3$ (2 mL) was heated at 120° C. under microwave irradiation for 10 min. The mixture was diluted with water, filtered and the solid was washed with a small amount of DCM to provide 7a (250 mg, 1.0 mmol, 50% yield) as an off white solid.

Preparation of (S)—N-4-(1-(2,4-difluorophenyl)ethyl)-6-(pyrazolo[1,5-a]pyrimidin-3-yl)-pyrimidine-2,4-diamine (8aa)

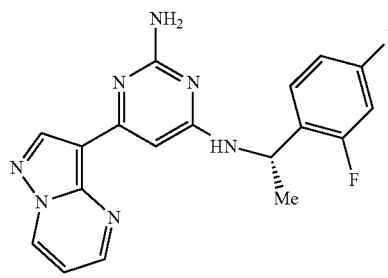

The HCl salt of (S)-1-(2,4-difluorophenyl)-ethylamine was treated with aq Na$_2$CO$_3$. Repeated extraction with DCM followed by concentration provided the freebase, which was transferred directly in NMP (6 mL) for use in this reaction. To this solution was added 7a (240 mg) and the resulting solution was heated in a sealed vial at 220° C. for 15 min with microwave irradiation. The reaction mixture was diluted with EtOAc and was repeatedly washed with water and brine. The organic layer was dried, filtered and concentrated. Flash chromatography (SiO$_2$, 0-20% MeOH/DCM gradient) provided 8aa as a pale yellow solid (275 mg, 0.75 mmol, 75% yield).

Preparation of (S)—N-(4-(1-(2,4-difluorophenyl)ethylamino)-6-(pyrazolo[1,5-a]pyrimidin-3-yl)pyrimidin-2-yl)-3-(2-oxopyrrolidin-1-yl)propanamide (9aa)

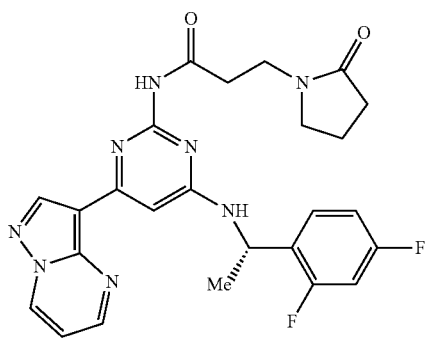

A mixture of 8aa (25 mg, 0.068 mmol), acid 3-(2-oxopyrrolidin-1-yl)propanoic acid (32 mg, 0.20 mmol), HATU (78 mg, 0.20 mmol), and DIEA (59 μL, 0.334 mmol) in THF (1 mL) and DMF (0.1 mL) were heated at 120° C. for 20 min with microwave irradiation. The solution was concentrated. Preparative HPLC provided the target compound 9aa (10 mg). LC-MS: rt 1.9 min; (M+1): 507.4.

Method B.

Scheme XIII.

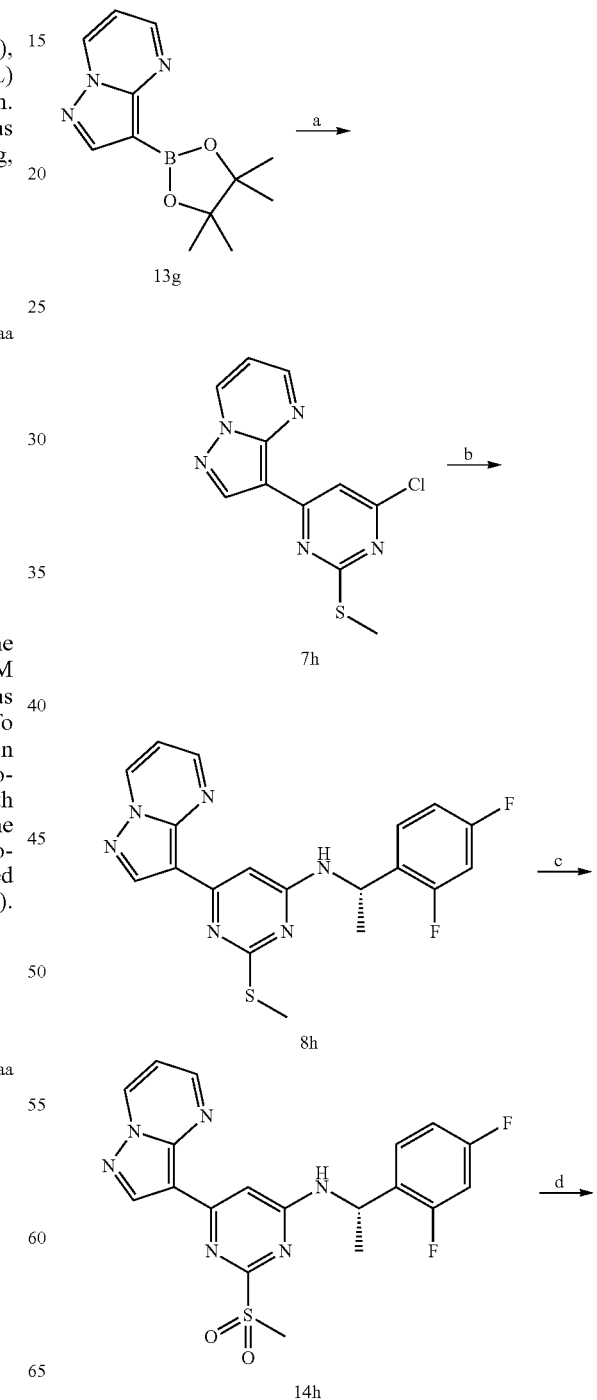

continued

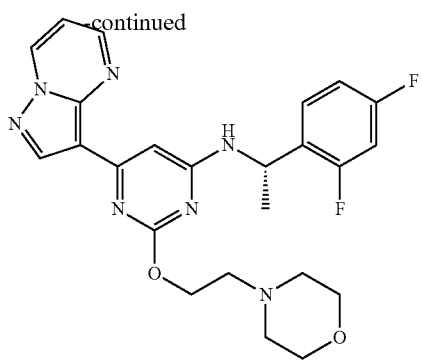

6h (a) 2-thiomethyl-4,6-dichloropyrimidine, Pd$_2$(dba)$_3$, PCy$_3$, K$_3$PO$_4$, DMF, 100° C. (b) (S)-1-(2,4-difluoro-phenyl)ethanamine, NMP, 220° C. (c) mCPBA, DMF (d) 2-morpholino-ethanol, NaH, THF Preparation of Compound 7h Compound 7h was prepared from intermediate 13g and 4,6-dichloro-2-(methylthio)pyrimidine by the previously described Suzuki coupling method (1.30 g)

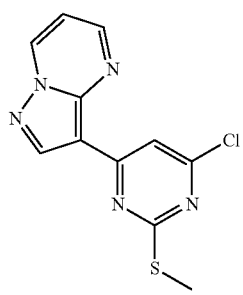

7h

Preparation of (S)—N-(1-(2,4-difluorophenyl)ethyl)-2-(methylthio)-6-(pyrazolo[1,5-a]pyrimidin-3-yl)pyrimidin-4-amine (8h)

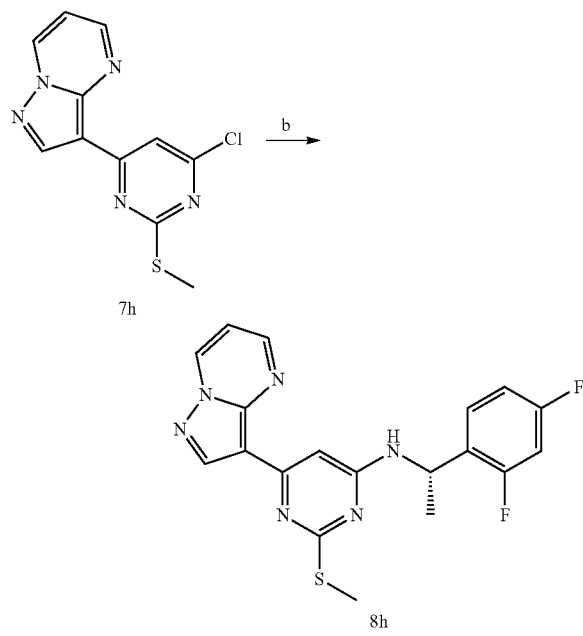

A 7 ml NMP solution of 3-(6-chloro-2-(methylthio)pyrimidin-4-yl)pyrazolo[1,5-a]pyrimidine (7h, 1.30 g) and (S)-1-(2,4-difluoro-phenyl)ethanamine (1.47 g) was heated in a microwave reactor at 220° C. for 20 min. LC/MS indicated the major peak was the desired product. The reaction mixture was partitioned between ethyl acetate and sat. NH$_4$OAc. The organic phase was dried with MgSO$_4$, filtered and the solvent was removed under reduced pressure. The product was purified by chromatography (SiO2, EtOAc-Hex, 1:1) (1.09 g, 58.6% yield).

Synthesis of (S)—N-(1-(2,4-difluorophenyl)ethyl)-2-(methylsulfonyl)-6-(pyrazolo[1,5-a]pyrimidin-3-yl)pyrimidin-4-amine (14h)

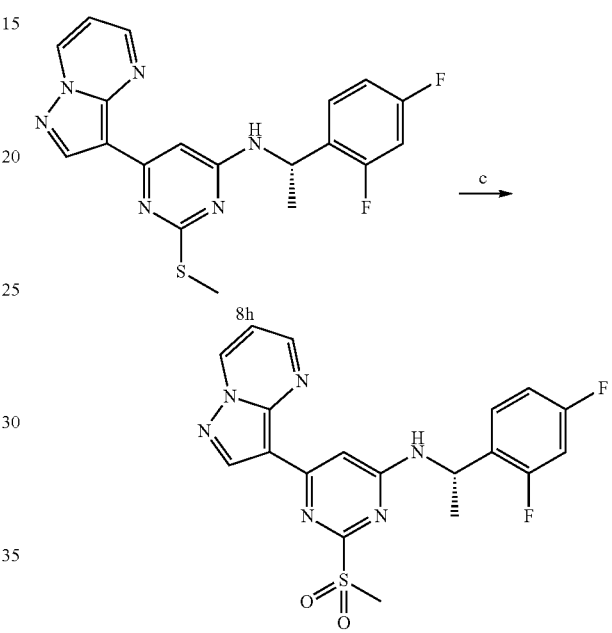

14h

To a 30 ml DMF solution of (S)—N-(1-(2,4-difluorophenyl)ethyl)-2-(methylthio)-6-(pyrazolo[1,5-a]pyrimidin-3-yl)pyrimidin-4-amine (8h) was added 3-chloroperoxybenzoic acid at rt. The reaction mixture was stirred at rt for 2 hours, when LC/MS indicated the absence of SM and the conversion to product (95%). To the reaction mixture was added ethyl acetate and brine and the organic phase was washed with Sat. NaHCO$_3$ and brine. The organic layer was then dried with MgSO$_4$, filtered and the solvent was removed under reduced pressure to provide the desired crude product (1.12 g), which was used in the next step without further purification.

S)—N-(1-(2,4-difluorophenyl)ethyl)-2-(2-morpholinoethoxy)-6-(pyrazolo[1,5-a]pyrimidin-3-yl)pyrimidin-4-amine (6h

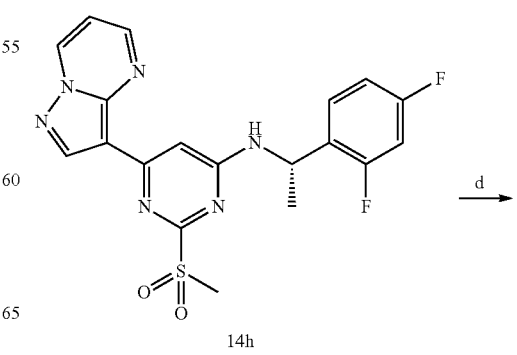

14h

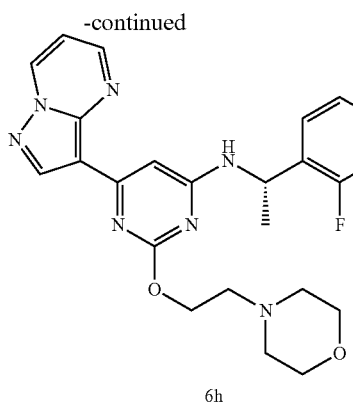

6h

To a THF solution of 2-morpholino-ethanol (32 mg) was added NaH (10 mg, 60% in oil) at rt, until all $H_2$ gas stopped releasing. Then, to it was added sulfone K (21.5 mg). The reaction solution was stirred at rt for 2 hours, until LC/MS indicated the major peak was the desired product. To the reaction mixture was added ethyl acetate and brine. The product was extracted into the organic solvent, and the organic solvent was removed. The residue was dissolved in ~1 ml DMSO and purified by preparative HPLC to provide the target compound (12.3 mg, 52% yield). RT: 2.68 min. (M+H): 480.5.

TABLE 2

Analytical data for the compounds of the invention.

| Compound # | LCMS M + 1 | LCM SRT (min) | NMR |
|---|---|---|---|
| 1 | 318.2 | 2.3 | (300 MHz, DMSO) 8.95 (d, 1H), 8.65 (br s, 1H), 8.52 (s, 1H), 7.55 (m, 1H), 7.45 (m, 4H), 7.23 (m, 1H), 7.00 (t, 1H), 4.55 (s, 2H) |
| 2 | 332.2 | 2.5 | |
| 3 | 336.2 | 2.4 | |
| 4 | 348.2 | 2.3 | (300 MHz, CDCl3) 10.83 (br s, 1H), 8.53 (dd, 2H), 8.33 (s, 1H), 7.95 (s, 1H), 7.42 (d, 2H), 7.88 (m, 4H), 4.55 (d, 2H), 3.77 (s, 3H) |
| 5 | 348.2 | 2.4 | |
| 6 | 332.2 | 2.5 | |
| 7 | 332.2 | 2.5 | |
| 8 | 362.2 | 2.5 | |
| 9 | 366.1 | 2.7 | (300 MHz, CDCl3) 10.65 (br s, 1H), 8.52 (d, 2H), 8.45 (s, 1H), 7.82 (s, 1H), 7.42 (d, 2H), 7.33 (d, 2H), 6.93 (dd, 1H), 4.73 (br s, 1H), 1.70 (d, 3H) |
| 10 | 352.1 | 2 | |
| 11 | 332.2 | 1.9 | |
| 12 | 352.2 | 1.9 | |
| 13 | 353.1 | 1.9 | |
| 14 | 402.1 | 2.1 | (300 MHz, DMSO) 8.85 (dd, 1H), 8.45 (d, 1H), 8.40 (s, 1H), 7.94 (br s, 1H), 7.65 (br s, 1H), 7.44 (m, 1H), 7.37 (m, 3H), 6.99 (d, 1H), 6.93 (dd, 1H), 4.62 (d, 2H) |
| 15 | 346.2 | 2 | (300 MHz, dmso) 8.83 (dd, 1H), 8.48 (d, 1H), 8.33 (s, 1H), 7.85 (br s, 1H), 7.60 (br s, 1H), 7.38 (m, 2H), 7.30 (dd, 2H), 7.18 (t, 1H), 6.98 (m, 1H), 6.92 (m, 1H), 5.02 (br s, 1), 1.76 (m, 2H), 0.90 (t, 3H) |
| 16 | 354.1 | 1.9 | (300 MHz, dmso) 8.85 (dd, 1H), 8.47 (dd, 1H), 8.41 (s, 1H), 7.96 (br s, 1H), 7.61 (s, 1H), 7.37 (m, 2H), 7.19 (br s, 1H), 6.99 (m, 1H), 6.93 (dd, 1H), 4.52 (d, 2H), |
| 17 | 350.2 | 1.9 | (300 MHz, dmso) 8.55 (d, 1H), 8.46 (d, 1H), 8.36 (s, 1H), 8.17 (br s, 1H), 7.50 (br s, 1H), 7.45 (m, 3H), 7.12 (m, 3H), 6.93 (d, 1H), 5.17 (br s, 1H), 1.42 (d, 3H) |
| 18 | 362.2 | 1.9 | |
| 19 | 346.3 | 2 | |
| 20 | 346.3 | 2 | |
| 21 | 362.2 | 1.9 | |
| 22 | 362.2 | 1.9 | |
| 23 | 346.3 | 2 | |
| 24 | 308.2 | 2.1 | |
| 25 | 319.2 | 1.8 | 300 MHz, DMSO-d6 - 8.92 (d, H), 8.61 (d, 2H), 8.56-8.47 (m, 2H), 7.97 (m, H), 7.53 (d, H), 7.45 (m, H), 7.02 T, H), 2.54 (s, 2H). |
| 26 | 322.2 | 2.3 | |
| 27 | 330.2 | 2.8 | |
| 28 | 319.2 | 1.7 | |
| 29 | 324.2 | 2 | 300 MHz, DMSO-d6 - 8.89 (m, H), 8.72 (m, H), 8.61 (m, H), 8.49 (m, 2H), 8.09 (d, H), 7.65 (m, H), 6.98 (m, H), 4.67 (m, 2H). |
| 30 | 308.1 | 1.6 | |
| 31 | 374.1 | 2 | |
| 32 | 347.2 | 1.3 | |
| 33 | 333.2 | 1 | |
| 34 | 333.2 | 1 | |
| 35 | 404.1 | 2.6 | |
| 36 | 401.9 | 2.6 | 300 MHz, DMSO-d6 - 8.91 (m, H), 8.53 (m, 2H), 7.68-7.35 (m, 2H), 7.01 (m, 2H), 4.50 (m, 2H). |
| 37 | 336.5 | 1.81 | (300 MHz, DMSO), 8.91 (d, 1H), 8.52 (br s, 2H), 7.49 (m, 1H), 7.38 (m, 1H), 7.19 (m, 2H), 7.08 (t, 1H), 7.01 (dd, 1H), 4.65 (d, 2H) |
| 38 | 386.5 | 2.04 | |
| 39 | 386.4 | 2.17 | (300 MHz, dmso) 8.90 (d, 1H), 8.49 (m, 2H), 7.64 & 7.57 (m, 2H), 7.41 (m, 2H), 6.99 (m, 1H), 4.62 (d, 2H) |

TABLE 2-continued

Analytical data for the compounds of the invention.

| Compound # | LCMS M + 1 | LCMSRT (min) | NMR |
|---|---|---|---|
| 40 | 386.4 | 2.12 | |
| 41 | 350.5 | 1.85 | |
| 42 | 344.1 | 1.9 | |
| 43 | 370.5 | 2.04 | |
| 44 | 370.5 | 2 | (300 MHz, dmso) 8.90 (d, 1H), 8.51 (br s 2H), 8.6-8.4 (br m, 1H), 7.65-7.35 (m, 4H), 7.21 (m, 1H), 6.99 (dd, 1H), 4.62 (d, 2H) |
| 45 | 404.5 | 2.13 | |
| 46 | 404.5 | 2.17 | (300 MHz, dmso) 8.90 (d, 1H), 8.51 (br s, 3H), 7.72-7.46 (m, 4H), 7.00 (dd, 1H), 4.70 (d, 2H) |
| 47 | 420.5 | 2.26 | |
| 48 | 404.5 | 2.19 | (300 MHz, dmso) 8.91 (d, 1H), 8.56 (m, 1H), 8.51 (br s 2H), 7.77 (dd, 2H), 7.58-7.34 (m, 3H), 7.00 (dd, 1H), 7.70 (d, 2H) |
| 49 | 404.5 | 2.19 | |
| 50 | 386.5 | 2.08 | |
| 51 | 366.5 | 2 | |
| 52 | 366.5 | 2.04 | |
| 53 | 354.5 | 1.9 | 300 MHz, DMSO-d6- 8.91 (d, H), 8.54 (m, 2H), 7.59-7.40 (m, 2H), 7.32-7.19 (m, H), 7.13-6.95 (m, 2H), 4.60 (m, 2H). |
| 54 | 354.5 | 1.9 | 300 MHz, DMSO-d6- 8.92 (d, H), 8.54 (m, 2H), 7.51 (s, br, H), 7.34-7.10 (m, 3H), 7.01 (m, H), 4.64 (m, 2H). |
| 55 | 364.5 | 2 | (300 MHz, CDCl3) 8.41 (s, 1H), 8.32 (m, 1H), 8.31 (s, 1H), 7.44 (s, 1H), 7.30 (m, 2H), 6.94 (dd, 2H), 6.64 (dd, 1H), 6.18 (br s, 2H), 5.44 (br s, 1H), 4.61 (br s, 1H), 1.83 (m, 2H), 0.91 (t, 3H) |
| 56 | 344.1 | 1.9 | (300 MHz, CDCl3) 8.66 (s, 1H), 8.46 (2m, 2H), 7.81 (br s, 1H), 7.41 (d, 1H), 7.31 (m, 2H), 7.25 (m, 1H), 6.77 (dd, 1H), 6.29 (br s, 2H), 5.53 (m, 1H), 3.38-3.16 (m, 1H0, 3.15-2.93 (m, 1H), 2.64 (m, 1H), 2.15 (m, 1H) |
| 57 | 358.1 | 1.9 | |
| 58 | 350.2 | 1.9 | 300 MHz, DMSO-d6- 8.92 (d, H), 8.52 (s, 2H), 7.48 (s, br, H), 7.30-6.96 (m, 5H), 4.57 (s, br, 2H), 2.19 (s, 3H). |
| 59 | 376.1 | 1.9 | |
| 60 | 368 | 2.1 | 300 MHz, CDCl3-d1: 8.45(s, 1H), 8.39(m, 1H), 7.53(s, 1H), 7.35 (m, 1H), 6.82(m, 2H), 6.7(m, 1H), 6.2(m, 2H), 5.45(m ex, 1H), 5.2 (m, 1H), 1.6(d, 3H) |
| 61 | 368 | 2.1 | 300 MHz, DMSO-d6: 8.94(d, 1H), 8.75(m, 1H), 8.53(m, 2H), 7.45 (m, 3H), 7.25(m, 1H), 7.05(m, 1H), 5.2(m, 1H), 1.5(d, 3H), |
| 62 | 382 | 2.24 | 300 MHz, CDCl3-d: 8.48(d, 1H), 8.38(m, 2H), 7.5 (s, 1H), 7.14 (m, 2H), 6.72(m, 1H), 6.2(m, 2H), 4.62(m, 1H), 1.93(m, 2H), 1.0(t, 3H) |
| 63 | 337.5 | 3.3 | 300 MHz, CDCl3-8.71 (s, H), 8.43 (m, 2H), 8.00 (s, H), 7.46 (t, 2H), 7.07 (t, 2H), 6.75 (t, H), 6.23 (s, br, 2H), 5.43 (s, 2H). |
| 64 | 372.2 | 3.4 | |
| 65 | 347.5 | 3.6 | H NMR (300 MHz, CDCl3) 8.61 (s, H), 8.48-8.41 (m, 2H), 7.96 (d, J = 0.9 Hz, H), 7.46-7.43 (m, 2H), 7.35-7.22 (m, 4H), 6.75 (dd, J = 4.3, 6.7 Hz, H), 6.08-6.01 (m, H), 2.17-1.88 (m, 3H), 0.98 (t, J = 7.3 Hz, 3H). |
| 66 | 359.5 | 2.7 | |
| 67 | 333.5 | 3.3 | H NMR (300 MHz, CDCl3) 8.64-8.62 (m, H), 8.46-8.40 (m, 2H), 7.96 (d, J = 1.1 Hz, H), 7.49-7.46 (m, 2H), 7.37-7.23 (m, 3H), 6.73 (dd, J = 2.3, 4.4 Hz, H), 6.29 (q, J = 6.5 Hz, H), 1.70-1.61 (m, 3H). |
| 68 | 333.5 | 3.3 | |
| 69 | 387.5 | 3.6 | H NMR (300 MHz, CDCl3) 8.58 (d, J = 12.1 Hz, H), 8.49-8.40 (m, 2H), 8.11 (s, H), 7.61 (t, J = 3.6 Hz, 2H), 7.41-7.32 (m, 3H), 6.78-6.69 (m, 2H). |
| 70 | 387.5 | 3.6 | |
| 71 | 351.5 | 3.4 | H NMR (300 MHz, CDCl3) 8.63-8.62 (m, H), 8.46-8.40 (m, 2H), 7.96-7.94 (m, H), 7.48-7.41 (m, 2H), 7.06-6.99 (m, 2H), 6.75 (dd, J = 4.4, 6.7 Hz, H), 6.28 (q, J = 6.5 Hz, 3H), 1.67 (t, J = 6.6 Hz, 3H). |
| 72 | 387.5 | 3.6 | |
| 73 | 400 | 2.2 | 300 MHz; CDCl3-d: 10.7(br m, 1H), 8.42(d, 2H), 8.34(d, 1H), 7.71 (d, 1H), 7.60(m, 4H), 6.90(m, 1H), 4.80(m, 1H) 1.76(d, 3H) |
| 74 | 348 | 1.6 | 300 MHz; CDCl3-d: 10.78(br m, 1H), 8.43(d, 2H), 8.31(d, 1H), 7.71 (s, 1H), 7.48(m, 2H), 7.37(m, 2H), 7.27(m, 2H), 6.88(m, 1H), 4.75(m, 1H) 4.0(m, 2H) |
| 75 | 348 | 1.6 | 300 MHz; CDCl3-d: 10.73(br m, 1H), 8.45(d, 2H), 8.31(s, 1H), 7.70 (s, 1H), 7.48(m, 2H), 7.37(m, 2H), 7.27(m, 2H), 6.88(m, 1H), 4.75(m, 1H) 4.0(m, 2H) |
| 76 | 358.2 | 2.05 | |
| 77 | 370.1 | 2.01 | |
| 78 | 344.2 | 1.97 | |
| 79 | 358.1 | 2.04 | |
| 80 | 384 | 2.1 | 300 MHz; CDCl3-d: 8.47(s, 1H), 8.36(d, 2H), 7.45(m, 2H), 7.31(m, 1H), 7.24(m, 2H), 6.96(m, 2H), 6.7(m, 1H), 5.7(m, 1H), 5.3(m, 1H), 1.56(sets of d, 3H: 1H) |
| 81 | 384 | 2.1 | 300 MHz; DMSO-d6: 8.82(dd, 1H), 8.45(dd, 1H), 8.35(s, 1H), 7.97(m, 1H), 7.61(m, 1H), 7.4(m, 2H), 7.26(m, 1H), 6.95(m, 3H), 5.36(m, 1H), 1.44(d, 3H) |
| 82 | 398 | 2.3 | 300 MHz; DMSO-d6: 8.82(dd, 1H), 8.5(dd, 1H), 8.33(s, 1H), 7.97(m, 1H), 7.5(m, 3H), 7.21(m, 1H), 6.98(m, 3H), 5.37(m, 1H), 1.73(m, 2H), 0.93 (t, 3H) |
| 83 | 398 | 2.3 | 300 MHz; DMSO-d6: 8.85(dd, 1H), 8.48(dd, 1H), 7.92(m, 1H), 7.62(m, 1H), 7.4(m, 2H), 7.26(m, 1H), 6.98m, 3H), 5.27(m, 1H), 1.77(m, 2H), 0.92(t, 3H) |

TABLE 2-continued

Analytical data for the compounds of the invention.

| Compound # | LCMS M + 1 | LCM SRT (min) | NMR |
|---|---|---|---|
| 84 | 378 | 2.1 | 300 MHz; DMSO-d6: 8.83(d, 1H), 8.46(m, 1H), 8.41(s, 2H), 7.36(m, 3H), 7.08(dd, 2H), 6.90(dd, 1H), 5.1(m, 1H), 1.72(m, 1H), 1.67(m, 1h), 0.83(t, 3H) |
| 85 | 378 | 2.1 | 300 MHz; DMSO-d6: 8.90(d, 1H), 8.51(m, 1H), 8.41(s, 2H), 7.36(m, 3H), 7.15(dd, 2H), 7.01(dd, 1H), 4.91(m, 1H), 2.09(m, 1H), 1.1(m, 3H), 0.75(t, 3H) |
| 86 | 378 | 2.1 | 300 MHz; DMSO-d6: 8.86(d, 1H), 8.46(m, 1H), 8.41(s, 2H), 7.36(m, 3H), 7.08(dd, 2H), 6.90(dd, 1H), 5.1(m, 1H), 1.72(m, 1H), 1.67(m, 1h), 0.83(t, 3H) |
| 87 | 378 | 2.1 | 300 MHz; DMSO-d6: 8.90(d, 1H), 8.51(m, 1H), 8.41(s, 2H), 7.36(m, 3H), 7.15(dd, 2H), 7.01(dd, 1H), 4.91(m, 1H), 2.09(m, 1H), 1.1(m, 3H), 0.75(t, 3H) |
| 88 | 382 | 2.3 | 300 MHz; CDCl3-d: 8.48(s, 1H), 8.39(dd, 2H), 7.54(s, 1H), 7.33(m, 1H), 6.78(m, 2H), 6.68(m, 1H), 6.22(br s, 2H), 5.29(m. 1H), 5.0(m, 1H), 1.98(m, 2H), 1.00(t, 3H) |
| 89 | 362 | 1.8 | 300 MHz; CDCl3-d: 8.5(s, 1H), 8.38(m, 2H), 7.56(d, 1H), 7.37(m, 3H), 7.25(m, 1H), 6.71(dd, 1H), 6.24(br s, 2H), 5.22(m, 1H), 3.74(m, 2H), 2.17(m, 1H), 2.03(m, 1H) |
| 90 | 362.3 | 1.91 | CDCl3: 8.45(s, !H), 8.36-8.28(m, 2H), 7.78(s, 1H), 7.28-7.24(m, 2H), 6.9(dd, 2H), 6.65(dd, 1H), 6.18(s, 2H), 1.35(m, 2H), 1.31(m, 2H) |
| 91 | 390.3 | 2.1 | (free base, DMSO) 8.81(dd, 1H), 8.45 (dd, 1H), 7.70 (br d, 1H), 7.44-7.35 (m, 3H), 7.12 (t, 2H), 7.00 (br s, 2H), 6.88 (dd, 1H), 5.05 (brs , 1H), 1.90 (m, 1H), 1.42 (d, 3H), 0.98-0.65 (m, 4H) |
| 92 | 396.4 | 3.1 | (CDCl3, 300 MHz) 8.30 (dd, 2H), 7.32 (dd, 2H), 6.94 (t, 2H), 6.63 (dd, 1H), 6.10 (br s, 2H), 5.10 (br d, 1H), 4.93 (m, 1H), 2.42 (s, 3H), 1.50 (d, 3H) |
| 93 | 392.4 | 3.07 | H NMR (300 MHz, CDCl3) 8.46 (d, J = 1.1 Hz, 1H), 8.25 (d, J = 6.9 Hz, 1H), 7.49 (d, J = 0.9 Hz, 1H), 7.40-7.34 (m, 2H), 7.06-6.98 (m, 2H), 6.59 (d, J = 6.9 Hz, 1H), 6.20 (s, 2H), 5.62 (s, 1H), 4.50 (s, 1H), 2.64 (d, J = 6.3 Hz, 3H), 2.12 (td, J = 13.5, 6.7 Hz, 1H), 0.96 (d, J = 6.8 Hz, 3H), 0.89 (d, J = 6.3 Hz, 3H) |
| 94 | 396.3 | 2.99 | H NMR (300 MHz, CDCl3) 8.49 (d, J = 1.1 Hz, 1H), 8.26 (d, J = 6.9 Hz, 1H), 7.49 (d, J = 1.1 Hz, 1H), 7.27-7.23 (m, 1H), 7.20-7.11 (m, 2H), 6.60 (d, J = 6.9 Hz, 1H), 6.21 (s, 2H), 5.40 (s, 1H), 4.63 (d, J = 5.3 Hz, 1H), 2.64 (d, J = 2.4 Hz, 3H), 2.01-1.76 (m, 2H), 1.03 (t, J = 7.4 Hz, 3H) |
| 95 | 364.4 | 2.75 | H NMR (300 MHz, CDCl3) 8.49 (d, J = 1.0 Hz, 1H), 8.25 (d, J = 6.9 Hz, 1H), 7.53 (d, J = 1.0 Hz, 1H), 7.46-7.40 (m, 2H), 7.07-6.99 (m, 2H), 6.59 (d, J = 6.9 Hz, 1H), 6.20 (s, 2H), 5.47 (d, J = 2.3 Hz, 1H), 4.96-4.92 (m, 1H), 2.62 (d, J = 6.1 Hz, 3H), 1.62 (d, J = 6.8 Hz, 3H) |
| 96 | 435.5 | 2 | |
| 97 | 396.5 | 2.4 | 300 MHz; CDCl3-d: 8.47(d, 1H), 8.41(s, 1H), 8.38(m, 1H), 7.49(d, 1H), 7.25(m, 1H), 7.14(m, 2H), 6.74(m, 1H), 6.23(br m, 2H), 5.37(m, 1h), 4.7 (m, 1H), 1.86(m, 2H), 1.40(m, 2H), 0.94(t, 3H) |
| 98 | 396.5 | 2.4 | |
| 99 | 465.6 | 1.8 | (300 MHz, CDCl3) 8.37 (m, 2H), 7.38 (dd, 2H), 7.25 (s, 1H), 7.01 (t, 2H), 6.70 (dd, 1H), 6.14 (br s, 2H), 5.27 (m, 1H), 5.03 (br m, 1H), 4.45 (dd, 2H), 2.99 (dd, 2H), 2.74 (dd, 4H), 1.56 (d, 3H), 1.13 (t, 6H) |
| 100 | 428.4 | 2.85 | (300 MHz, CDCl3) 8.39(m, 2H), 7.57 (s, 1H), 7.36 (dd, 2H), 7.02 (t, 2H), 6.77 (dd, 1H), 6.13 (br s, 2H), 5.58 (br s, 1H), 4.94 (m, 1H), 3.15 (s, 3H), 1.60 (d, 3H) |
| 101 | 362.5 | 1.6 | H NMR (300 MHz, CDCl3) 8.45 (d, J = 1.0 Hz, 1H), 8.35-8.29 (m, 2H), 7.49 (d, J = 1.2 Hz, 1H), 7.36-7.27 (m, 5H), 6.64 (dd, J = 4.4, 6.7 Hz, 1H), 6.17 (bs, 2H), 5.21 (bs, 1H), 3.68 (dd, J = 3.5, 7.4 Hz, 2H), 2.15-2.07 (m, 1H), 1.97-1.93 (m, 1H) |
| 102 | 447.4 | 2.3 | |
| 103 | 463.5 | 3.3 | H NMR (300 MHz, CDCl3) 8.43 (d, J = 5.8 Hz, 2H), 7.41-7.36 (m, 2H), 7.17 (bs, 1H), 7.04-6.93 (t, 2H), 6.80-6.76 (bt, 1H), 4.78 (bs, 1H), 3.81-3.73 (m, 8H), 1.95-1.74 (m, 2H), 1.53-1.28 (m, 2H), 0.97 (t, J = 7.3 Hz, 3H) |
| 104 | 481.3 | 3.4 | H NMR (300 MHz, CDCl3) 8.47 (d, J = 5.5 Hz, 2H), 7.52-7.47 (m, 1H), 7.36 (s, 1H), 6.93-6.75 (m, 3H), 3.86-3.79 (m, 8H), 2.26 (q, J = 7.3 Hz, 1H), 1.16 (d, J = 6.6 Hz, 3H), 0.88 (d, J = 6.7 Hz, 3H) (dilute NMR) |
| 105 | 386.3 | 2.9 | H NMR (300 MHz, CDCl3) 8.41 (d, J = 2.6 Hz, 2H), 8.38 (dd, J = 2.7, 3.9 Hz, 1H), 7.50 (d, J = 0.9 Hz, 1H), 7.37 (dd, J = 6.5, 8.3 Hz, 1H), 6.85-6.77 (m, 2H), 6.16 (s, 1H), 5.17-5.12 (m, 1H), 1.61 (d, J = 6.8 Hz, 3H) |
| 106 | 453.3 | 3 | H NMR (300 MHz, CDCl3) 8.42 (dd, J = 1.8, 3.1 Hz, 1H), 8.40 (s, 1H), 7.42-7.34 (m, 1H), 7.11 (bs, 1H), 6.93-6.72 (m, 3H), 5.30 (bt, 1H), 3.83-3.63 (m, 8H), 1.58 (d, J = 6.8 Hz, 3H) |
| 107 | 481.3 | 3.4 | H NMR (300 MHz, CDCl3) 8.39 (d, 2H), 7.33 (m, 1H), 7.13 (bs, 1H), 6.89-6.71 (m, 3H), 5.13 (bs, 1H), 3.76-3.67 (m, 8H), 1.89-1.72 (m, 2H), 1.51-1.23 (m, 2H), 0.94 (t, J = 7.3 Hz, 3H) |
| 108 | 424.5 | 2.3 | (CDCl3, 300 MHz) 8.37 (m, 2H), 7.37 (dd, 2H), 7.23 (s, 1H), 7.00 (t, 2H), 6.68 (dd, 1H), 6.13 (br s, 2H), 5.15 (m, 1H), 5.04 (m, 1H), 4.42 (t, 2H), 3.72 (t, 2H), 3.41 (s, 3H), 1.55 (d, 3H) |
| 109 | 478.2 | 1.8 | (CDCl3, 300 MHz) 8.47 (m, 2H), 7.36 (dd, 2H), 7.23 (s, 1H), 7.00 (t, 2H), 6.70 (dd, 2H), 6.12 (m, 2H), 5.70 (m, 1H), 5.01 (m, 1H), 4.42 (t, 2H), 3.73 (t, 4H), 2.81 (t, 2H), 2.60 (t, 4H), 1.54 (d, 3H) |
| 110 | 456.3 | 3.2 | (300 Mhz, CDCl3) 8.40 (m, 2H), 7.57 (s, 1H), 7.34 (m, 2H), 7.01 (t, 2H), 6.76 (dd, 1H), 6.12 (br s, 2H), 1.83 (m, 2H), 1.38 (m, 2H), 0.95 (t, 3H) |
| 111 | 446 | 2.9 | 300 MHz-CDCl3-d: 8.42(m, 2H), 7.60(br m, 1H), 7.33(m, 1H) 66.80m, 3H), 5.65(m, 1H), 5.23(m, 1H), 3.62(dofm, 1H), 3.1 (s, 3H), 1.62(d, 3H) |

TABLE 2-continued

Analytical data for the compounds of the invention.

| Compound # | LCMS M + 1 | LCM SRT (min) | NMR |
|---|---|---|---|
| 112 | 474 | 3.3 | |
| 113 | 474.2 | 3.2 | |
| 114 | 335.1 | 2.5 | |
| 115 | 347.1 | 1.9 | 300 MHz, DMSO-d6 9.38 (s, H), 8.93 (s, 2H), 8.71 (s, H), 7.55-7.20 (m, 7H), 5.43 (s, br, H), 3.47 (m, 2H), 2.02(m, 2H). |
| 116 | 363.3 | 2.9 | 300 MHz, DMSO-d6 9.40(s, H), 8.93 (s, 2H), 8.70 (s, H), 7.77 (s, H), 7.42 (m, 3H), 7.18(m, 2H), 5.27(s, br, H), 1.85 (m, 2H), 1.35 (m, 2H), 0.91 (m, 3H). |
| 117 | 353.1 | 2.6 | |
| 118 | 353.1 | 2.6 | |
| 119 | 423.5 | 2.3 | |
| 120 | 381.2 | 2.1 | |
| 121 | 381.1 | 2.1 | |
| 122 | 381.2 | 2.2 | (300 MHz, DMSO-d6) 9.29 (dd, J = 1.6, 7.0 Hz, 1H), 8.81 (dd, J = 1.7, 4.1 Hz, 2H), 8.47 (s, 2H), 7.70 (s, 1H), 7.51-7.43 (m, 1H), 7.29-7.16 (m, 1H), 7.09-7.04 (m, 1H), 1.83 (d, J = 7.7 Hz, 2H), 1.73-1.63 (m, 1H), 1.45-1.25 (m, 2H) and 0.88 (s, 3H) ppm. |
| 123 | 381.1 | 2.2 | (300.0 MHz, DMSO) d 9.30 (d, J = 7.0 Hz, 1H), 8.81 (s, 2H), 8.49 (s, 2H), 7.70 (s, 1H), 7.52-7.44 (m, 1H), 7.28 (s, 1H), 7.09-7.04 (m, 1H), 1.83 (s, 2H), 1.71 (s, 1H), 1.41-1.33 (m, 2H) and 0.93-0.89 (m, 3H) ppm |
| 124 | 478.4 | 2.8 | |
| 125 | 481.5 | 2.26 | (CDCl3, 300 MHz) 8.39 (m, 2H), 7.04 (s, 1H), 6.78-6.64 (m, 3H), 6.09 (s, 2H), 5.07 (m, 1H), 4.93 (m, 1H), 3.74 (m, 4H), 3.64 (m, 4H0, 2.08 (m, 1H), 1.05 (d, 3H), 0.88 (d, 3H) |
| 126 | 442.5 | 2.5 | 300 MHz, CDCl3-d: 8.4(d, 2H), 7.3(m, 1H), 6.80(t, 2H), 6.73 (m, 1H), 6.11(m, 1h), 5.3(m. 1H), 4.44(m, 2H), 3.73(m, 2H), 3.41(s, 3H), 1.59(d, 3H) |
| 127 | 497.5 | 2.6 | (CDCl3, 300 MHz) 8.34 (m, 2H), 7.33 (m 1H), 7.30 s, 1H), 6.78 t, 2H), 6.68 (dd, 1H), 6.12 (br s, 2H), 5.44 (, m, 1H), 5.24 (m, 1H), 4.90 (dd, 2H), 3.50-3.25 (m, 4H), 1.54 (d, 3H), 1.18-1.02 (two t, 6H) |
| 128 | 495.6 | 2.33 | |
| 129 | 426 | 2.5 | |
| 130 | 468 | 2.3 | |
| 131 | 384 | 2 | 300 MHz, CH3 CN-d3: 11.25(m, 1H), 8.67(d, 1H), 8.6(d, 1H), 7 7.57(m, 2H), 7.11(M, 1H), 6.98(m, 2H), 5.809(s, 1H), 5.23(br m, 2H), 1.60(d, 3H) |
| 132 | 398.5 | 2.3 | |
| 133 | 455.5 | 2.5 | |
| 134 | 418.4 | 2.38 | |
| 135 | 436.5 | 2.42 | |
| 136 | 464.2 | 2.68 | |
| 137 | 464.6 | 2.71 | |
| 138 | 484 | 2.6 | |
| 139 | 467 | 2.4 | |
| 140 | 393 | 3.2 | |
| 141 | 392.5 | 1.56 | |
| 142 | 467 | 2 | |
| 143 | 434.5 | 2.6 | (300 MHz, CDCl3) 8.37 (m, 2H), 7.38 (m, 2H), 7.22 (m, H), 7.00 (t, 2H), 6.70 (m, H), 6.14 (s, br, 2H), 5.21 (s, br, H), 5.00 (s, br, H), 4.17 (m, 2H), 1.63-1.43 (m, 5H), 1.25 (m, 2H), 0.97 (t, H), 0.56 (s, br, H), 0.41 (s, br, H). |
| 144 | 351.4 | 1.91 | |
| 145 | 367.5 | 1.95 | |
| 146 | 351.4 | 1.91 | |
| 147 | 368.5 | 1.85 | (CDCl3, 300 MHz) 8.74 (s, 1H), 8.69 (dd, 1H), 8.56 (dd, 1H), 7.33 (m, 1H), 6.95 (br s, 1H), 6.87 (dd, 1H), 6.83-6.74 (complex m, 2H), 5, 23 (m, 1H), 5.15 (m, 1H), 4.78 (br s, 2H), 1.54 (d, 3H) |
| 148 | 434.6 | 2.5 | (300.0 MHz, CDCl3) 8.43 (dd, J = 1.8, 4.2 Hz, 2H), 7.41 (dd, J = 5.4, 8.6 Hz, 3H), 7.26 (s, CDCl3), 7.05-6.98 (m, 2H), 6.83-6.79 (m, 1H), 4.36-4.27 (m, 2H), 2.83-2.78 (m, 1H), 2.36-2.31 (m, 2H), 2.16-1.83 (m, 5H) and 1.64-1.48 (m, 3H) |
| 149 | 452.3 | 2.3 | |
| 150 | 404.4 | 2.3 | (300.0 MHz, CDCl3) d 8.42 (dd, J = 1.8, 2.8 Hz, 2H), 7.51-7.32 (m, 3H), 7.05-6.99 (m, 2H), 6.78 (t, J = 5.6 Hz, 1H), 4.95 (d, J = 2.4 Hz, 2H), 2.48 (dd, J = 2.3, 17.5 Hz, 1H), 2.23 (s, 1H) and 1.63-1.53 (m, 3H) |
| 151 | 418.3 | 2.3 | (300.0 MHz, CDCl3) d 8.42-8.38 (m, 2H), 7.40 (dd, J = 5.4, 8.6 Hz, 3H), 7.04-6.97 (m, 2H), 6.74 (dd, J = 4.6, 6.4 Hz, 1H), 4.90 (t, J = 2.2 Hz, 2H), 1.88-1.84 (m, 3H), 1.74 (s, 1H) and 1.60 (d, J = 6.8 Hz, 3H) |
| 152 | 434.5 | 2.5 | |
| 153 | 408.4 | 2.3 | |
| 154 | 451 | 1.6 | |
| 155 | 431.9 | 2.3 | (300.0 MHz, CDCl3) d 8.45-8.43 (m, 2H), 7.44-7.34 (m, 3H), 7.04 (s, 2H), 6.85-6.81 (m, 1H), 4.43 (t, J = 7.4 Hz, 2H), 2.61 (s, 1H), 1.80 (t, J = 2.5 Hz, 2H) and 1.64 (d, J = 6.9 Hz, 6H) |
| 156 | 448.2 | 2.8 | |
| 157 | 434.3 | 2.5 | |
| 158 | 433.9 | 2.5 | |
| 159 | 422.5 | 1.8 | |
| 160 | 466.3 | 2.4 | |

TABLE 2-continued

Analytical data for the compounds of the invention.

| Compound # | LCMS M + 1 | LCM SRT (min) | NMR |
|---|---|---|---|
| 161 | 366.4 | 1.7 | (300.0 MHz, CDCl3) d 8.49 (d, J = 6.8 Hz, 2H), 7.46-7.41 (m, 3H), 7.10-7.00 (m, 2H), 6.93 (d, J = 11.3 Hz, 1H), 2.61 (s, 1H) and 1.74-1.68 (m, 3H) |
| 162 | 432.4 | 2.5 | (300.0 MHz, CDCl3) d 8.41 (d, J = 5.6 Hz, 2H), 7.41 (dd, J = 5.3, 8.7 Hz, 3H), 7.01 (dd, J = 2.1, 15.3 Hz, 2H), 6.77 (t, J = 5.6 Hz, 1H), 4.93 (t, J = 2.0 Hz, 2H), 2.61 (s, 1H), 2.26-2.18 (m, 3H), 1.62 (d, J = 6.8 Hz, 2H) and 1.13 (q, J = 7.5 Hz, 3H) |
| 163 | 422.2 | 1.9 | |
| 164 | 450.4 | 2.1 | |
| 165 | 434.4 | 2.5 | |
| 166 | 420.4 | 2.3 | |
| 167 | 450.6 | 2.7 | |
| 168 | 480.4 | 2.2 | |
| 169 | 406.4 | 2.3 | |
| 170 | 420.4 | 2.4 | |
| 171 | 477.6 | 1.7 | |
| 172 | 454.4 | 2.3 | |
| 173 | 440.4 | 2.3 | |
| 174 | 464.4 | 2.5 | |
| 175 | 420.5 | 2.4 | |
| 176 | 448.4 | 2.6 | |
| 177 | 476.5 | 2.9 | |
| 178 | 466.4 | 2.3 | |
| 179 | 446.4 | 2.5 | |
| 180 | 432.4 | 2.4 | |
| 181 | 432.4 | 2.4 | |
| 182 | 434.5 | 2.5 | |
| 183 | 432.4 | 2.3 | |
| 184 | 454.4 | 2 | |
| 185 | 507.4 | 1.9 | (DMSO, 300 MHz) 9.73 (s, 1H), 9.25 (d, 1H), 8.76 (dd, 1H), 8.65 (s, 1H), 8.10 (m, 1H), 7.51 (dd, 1H), 7.37 (br s, 1H), 7.25-7.15 (m, 2H), 7.04 (ddd, 1H), 5.44 (m, 1H), 3.46 (m, 2H), 3.33 (t, 2H), 2.86 (m, 2H), 2.18 (t, 2H), 1.45 (d, 3H) |
| 186 | 495.3 | 1.6 | |
| 187 | 440.3 | 1.97 | (DMSO, 300 MHz) 9.57 (s, 1H), 9.27 (dd, 1H), 8.78 (dd, 1H), 8.67 (s, 1H), 8.16 (br s, 1H), 7.48 (dd, 1H), 7.37 (br s, 1H), 7.25-7.15 (m, 2H), 7.04 (ddd, 1H), 5.42 (m, 1H), 4.37 (d, 1H), 4.18 (d, 1H), 3.30 (burried s, 3H), 1.47 (d, 3H) |
| 188 | 424.4 | 2.05 | |
| 189 | 437.5 | 3.1 | |
| 190 | 462.5 | 2.8 | |
| 191 | 437.5 | 3.1 | |
| 192 | 436.5 | 3.12 | |
| 193 | 468.5 | 2.6 | |
| 194 | 469.4 | 3.2 | |
| 195 | 480.5 | 2.68 | |
| 196 | 427.4 | 2.86 | |
| 197 | 440.4 | 2.53 | |
| 198 | 480.4 | 2.68 | |
| 199 | 426.5 | 2.48 | |
| 200 | 466.4 | 2.6 | |
| 201 | 422.3 | 3.01 | |
| 202 | 466.4 | 2.56 | |
| 203 | 525.4 | 2.53 | |
| 204 | 466.4 | 2.64 | |
| 205 | 423.4 | 3.27 | |
| 206 | 468.4 | 2.64 | |
| 207 | 454.4 | 2.56 | |
| 208 | 468.5 | 2.6 | |
| 209 | 480.4 | 2.56 | |
| 210 | 481.4 | 2.12 | |
| 211 | 454.4 | 1.56 | |
| 212 | 443.3 | 2.22 | |
| 213 | 482.4 | 1.56 | |
| 214 | 437.4 | 2.4 | |
| 215 | 480.4 | 2.49 | |
| 216 | 452 | 1.6 | |
| 217 | 494.4 | 1.71 | |
| 218 | 438.4 | 1.56 | |
| 219 | 455.4 | 2.23 | |
| 220 | 517.4 | 1.49 | |
| 221 | 453.3 | 2.19 | |
| 222 | 453.3 | 2.04 | |
| 223 | 451.4 | 2.53 | |
| 224 | 335 | 2.13 | |
| 225 | 367 | 2.3 | |
| 226 | 351 | 2.26 | |

TABLE 2-continued

Analytical data for the compounds of the invention.

| Compound # | LCMS M + 1 | LCMS RT (min) | NMR |
|---|---|---|---|
| 227 | 334.2 | 2.34 | 1H NMR (300, DMSO-d6) 11.24 (s, H), 9.36 (dd, J = 1.5, 7.0 Hz, H), 9.09 (s, H), 8.97 (s, H), 8.90-8.89 (m, H), 8.62 (d, J = 6.5 Hz, H), 8.14 (dd, J = 5.4, 8.9 Hz, H), 7.96 (d, J = 4.8 Hz, H), 7.44 (t, J = 8.9 Hz, H), 7.34 (dd, J = 4.2, 7.0 Hz, H), 2.50 (qn, J = 1.8 Hz, DMSO-d6), ppm |
| 228 | 334.2 | 2.3 | |
| 229 | 352.3 | 2.41 | 1HNMR (300, DMSO-d6) 11.40 (s, H), 9.37 (s, H), 9.34 (dd, J = 1.6, 7.0 Hz, H), 8.96 (s, H), 8.87 (dd, J = 1.7, 4.1 Hz, H), 8.61 (d, J = 6.3 Hz, H), 7.90 (s, H), 7.85 (dd, J = 6.5, 8.4 Hz, H), 7.54-7.46 (m, H), 7.34-7.27 (m, H), 2.50 (qn, J = 1.8 Hz, DMSO-d6), ppm |
| 230 | 341.2 | 2.29 | 1H NMR (300, DMSO-d6) 11.32 (s, H), 9.35 (dd, J = 1.6, 7.0 Hz, H), 9.06 (s, H), 8.97 (s, H), 8.89 (dd, J = 1.5, 4.2 Hz, H), 8.63 (d, J = 6.4 Hz, H), 8.51 (s, H), 8.34-8.29 (m, H), 8.15 (d, J = 7.8 Hz, H), 7.95 (d, J = 6.6 Hz, H), 7.82 (t, J = 7.9 Hz, H), 7.35-7.31 (m, H), 6.57 (s, H), 2.50 (qn, J = 1.8 Hz, DMSO-d6), ppm |
| 231 | 352.3 | 2.51 | 1H NMR (300, DMSO-d6) 11.23 (s, H), 9.35 (dd, J = 1.6, 7.0 Hz, H), 9.06 (s, H), 8.96 (s, H), 8.89 (dd, J = 1.6, 4.1 Hz, H), 8.62 (d, J = 6.2 Hz, H), 8.19-8.11 (m, H), 7.97-7.93 (m, H), 7.71 (dd, J = 8.2, 10.6 Hz, H), 7.65 (s, H), 7.33 (dd, J = 4.2, 7.0 Hz, H), 2.50 (qn, J = 1.8 Hz, DMSO-d6), ppm |

Example 6

JAK3 Inhibition Assay

Compounds were screened for their ability to inhibit JAK3 using the assay shown below. Reactions were carried out in a kinase buffer containing 100 mM HEPES (pH 7.4), 1 mM DTT, 10 mM $MgCl_2$, 25 mM NaCl, and 0.01% BSA. Substrate concentrations in the assay were 5 µM ATP (200 uCi/µmole ATP) and 1 µM poly(Glu)$_4$Tyr. Reactions were carried out at 25° C. and 1 nM JAK3.

To each well of a 96 well polycarbonate plate was added 1.5 µl of a candidate JAK3 inhibitor along with 50 µl of kinase buffer containing 2 µM poly(Glu)$_4$Tyr and 10 µM ATP. This was then mixed and 50 µl of kinase buffer containing 2 nM JAK3 enzyme was added to start the reaction. After 20 minutes at room temperature (25° C.), the reaction was stopped with 50 µl of 20% trichloroacetic acid (TCA) that also contained 0.4 mM ATP. The entire contents of each well were then transferred to a 96 well glass fiber filter plate using a TomTek Cell Harvester. After washing, 60 µl of scintillation fluid was added and $^{33}$P incorporation detected on a Perkin Elmer TopCount.

Example 5

JAK2 Inhibition Assay

The assays were as described below in Example 6 except that JAK-2 enzyme was used, the final poly(Glu)$_4$Tyr concentration was 15 µM, and final ATP concentration was 12 µM.

Tables 3I, 3II and 3III depict enzyme inhibition data ($K_i$) for certain exemplary compounds. Compound numbers in Tables 3I, 3II and 3III correspond to those compounds depicted in Table 1. In Tables 3I, 3II and 3III, "A" represents a $K_i$ of less than 0.01 µM, "B" represents a $K_i$ of between 0.01 and ≤0.1 µM, "C" represents a $K_i$ of between 0.1 and 0.5 "D" represents a Ki of higher than 0.5 µM and less than 5.0 µM, "E" represents a $K_i$ of >5.0 µM.

TABLE 3I

| compound # | JAK2 Ki uM | JAK3 Ki uM |
|---|---|---|
| 1 | A | B |
| 2 | B | C |
| 3 | A | B |
| 4 | B | C |
| 5 | A | B |
| 6 | A | B |
| 7 | B | C |
| 8 | B | C |
| 9 | A | B |
| 10 | A | B |
| 11 | A | B |
| 12 | A | B |
| 13 | A | B |
| 14 | A | B |
| 15 | A | A |
| 16 | A | B |
| 17 | A | A |
| 18 | B | C |
| 19 | B | C |
| 20 | B | C |
| 21 | B | C |
| 22 | C | C |
| 23 | B | C |
| 24 | B | B |
| 25 | B | C |
| 26 | B | C |
| 27 | B | C |
| 28 | B | B |
| 29 | B | C |
| 30 | A | B |
| 31 | B | C |
| 32 | C | D |
| 33 | B | B |
| 34 | B | C |
| 35 | C | C |
| 36 | A | B |
| 37 | A | B |
| 38 | B | C |
| 39 | A | B |
| 40 | B | B |
| 41 | A | B |
| 42 | B | C |
| 43 | B | B |
| 44 | A | B |
| 45 | B | C |
| 46 | A | B |
| 47 | B | C |
| 48 | A | C |

TABLE 3I-continued

| compound # | JAK2 Ki uM | JAK3 Ki uM |
|---|---|---|
| 49 | B | C |
| 50 | A | C |
| 51 | A | B |
| 52 | A | B |
| 53 | A | B |
| 54 | A | B |
| 55 | A | A |
| 56 | B | C |
| 57 | A | B |
| 58 | B | C |
| 59 | A | B |
| 60 | A | A |
| 61 | A | B |
| 62 | A | B |
| 63 | A | C |
| 64 | A | C |
| 65 | A | B |
| 66 | D | E |
| 67 | B | C |
| 68 | A | B |
| 69 | B | C |
| 70 | C | D |
| 71 | A | B |
| 72 | C | E |

TABLE 3II

| compound # | JAK2 Ki uM | JAK3 Ki uM |
|---|---|---|
| 73 | C | D |
| 74 | A | B |
| 75 | B | C |
| 76 | B | C |
| 77 | A | B |
| 78 | B | C |
| 79 | B | C |
| 80 | A | B |
| 81 | A | B |
| 82 | A | B |
| 83 | A | C |
| 84 | B | C |
| 85 | B | C |
| 86 | A | A |
| 87 | A | B |
| 88 | A | B |
| 89 | A | B |
| 90 | A | B |
| 91 | A | B |
| 92 | A | B |
| 93 | A | B |
| 94 | A | B |
| 95 | A | B |
| 96 | A | B |
| 97 | B | C |
| 98 | A | B |
| 99 | A | B |
| 100 | A | A |
| 101 | A | B |
| 102 | B | C |
| 103 | B | C |
| 104 | C | D |
| 105 | A | B |
| 106 | A | B |
| 107 | B | C |
| 108 | A | B |
| 109 | A | B |
| 110 | A | B |
| 111 | A | A |
| 112 | A | B |
| 113 | C | D |
| 114 | A | B |
| 115 | B | B |
| 116 | A | B |
| 117 | A | B |
| 118 | A | B |

TABLE 3II-continued

| compound # | JAK2 Ki uM | JAK3 Ki uM |
|---|---|---|
| 119 | A | B |
| 120 | B | C |
| 121 | A | B |
| 122 | A | B |
| 123 | B | C |
| 124 | A | B |
| 125 | B | C |
| 126 | A | A |
| 127 | B | C |
| 128 | A | B |
| 129 | B | C |
| 130 | A | B |
| 131 | A | B |
| 132 | A | A |
| 133 | B | C |
| 134 | B | B |
| 135 | B | C |
| 136 | B | C |
| 137 | C | C |
| 138 | A | B |
| 139 | A | B |
| 140 | A | A |
| 141 | A | B |
| 142 | B | C |
| 143 | B | C |
| 144 | A | C |

TABLE 3III

| compound # | JAK2 Ki uM | JAK3 Ki uM |
|---|---|---|
| 145 | A | B |
| 146 | B | D |
| 147 | A | B |
| 148 | B | C |
| 149 | A | B |
| 150 | A | B |
| 151 | B | C |
| 152 | B | B |
| 153 | A | B |
| 154 | A | B |
| 155 | A | C |
| 156 | A | C |
| 157 | B | C |
| 158 | B | C |
| 159 | A | C |
| 160 | B | C |
| 161 | A | B |
| 162 | B | C |
| 163 | B | D |
| 164 | A | B |
| 165 | B | C |
| 166 | A | B |
| 167 | B | D |
| 168 | A | B |
| 169 | A | B |
| 170 | A | B |
| 171 | B | B |
| 172 | A | B |
| 173 | A | B |
| 174 | B | C |
| 175 | A | C |
| 176 | B | C |
| 177 | C | D |
| 178 | A | B |
| 179 | B | D |
| 180 | A | C |
| 181 | B | C |
| 182 | B | C |
| 183 | A | B |
| 184 | A | C |
| 185 | A | C |
| 186 | A | C |
| 187 | A | B |
| 188 | A | C |

TABLE 3III-continued

| compound # | JAK2 Ki uM | JAK3 Ki uM |
|---|---|---|
| 189 | A | C |
| 190 | A | B |
| 191 | B | C |
| 192 | A | B |
| 193 | A | C |
| 194 | B | C |
| 195 | A | B |
| 196 | A | B |
| 197 | A | B |
| 198 | A | B |
| 199 | A | B |
| 200 | A | C |
| 201 | A | B |
| 202 | A | B |
| 203 | B | C |
| 204 | A | B |
| 205 | A | C |
| 206 | A | B |
| 207 | A | B |
| 208 | A | B |
| 209 | A | B |
| 210 | A | B |
| 211 | A | B |
| 212 | A | B |
| 213 | A | B |
| 214 | A | C |
| 215 | A | B |
| 216 | A | C |
| 217 | A | B |
| 218 | B | C |
| 219 | A | B |
| 220 | A | B |
| 221 | A | B |
| 222 | A | B |
| 223 | B | C |
| 224 | B | C |
| 225 | B | D |
| 226 | C | D |
| 227 | C | D |
| 228 | C | D |
| 229 | C | D |
| 230 | C | D |
| 231 | C | D |

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments which have been represented by way of example.

The invention claimed is:

1. A compound selected from the group consisting of:

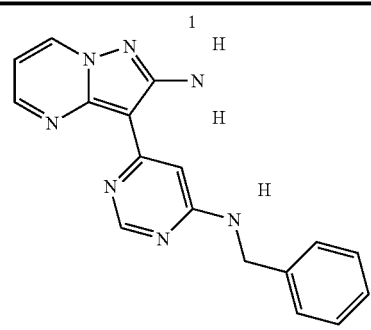

1

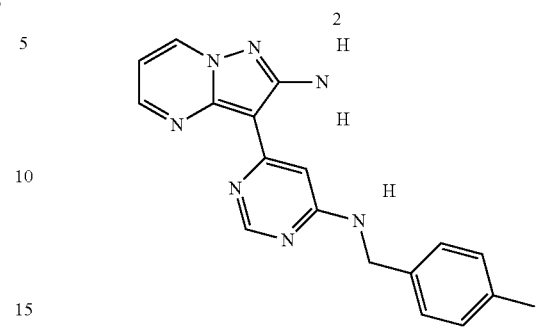

2

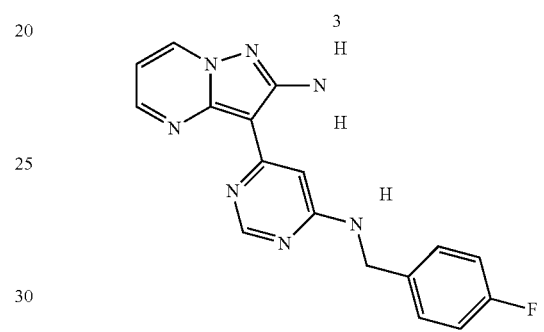

3

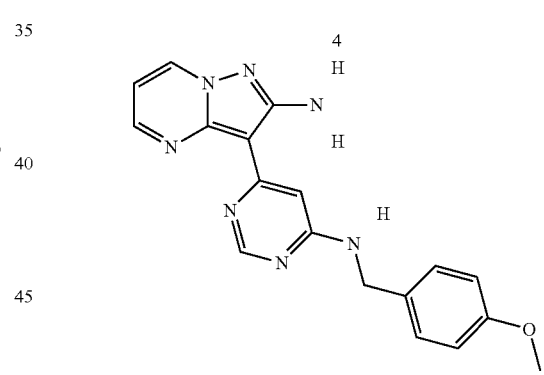

4

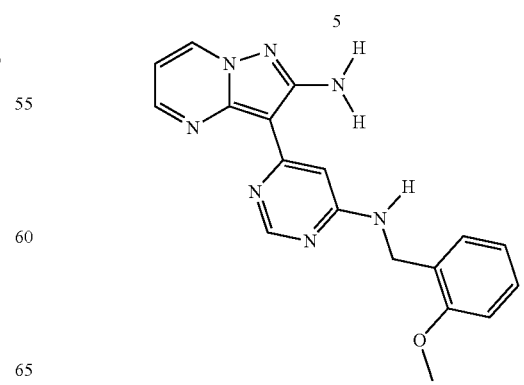

5

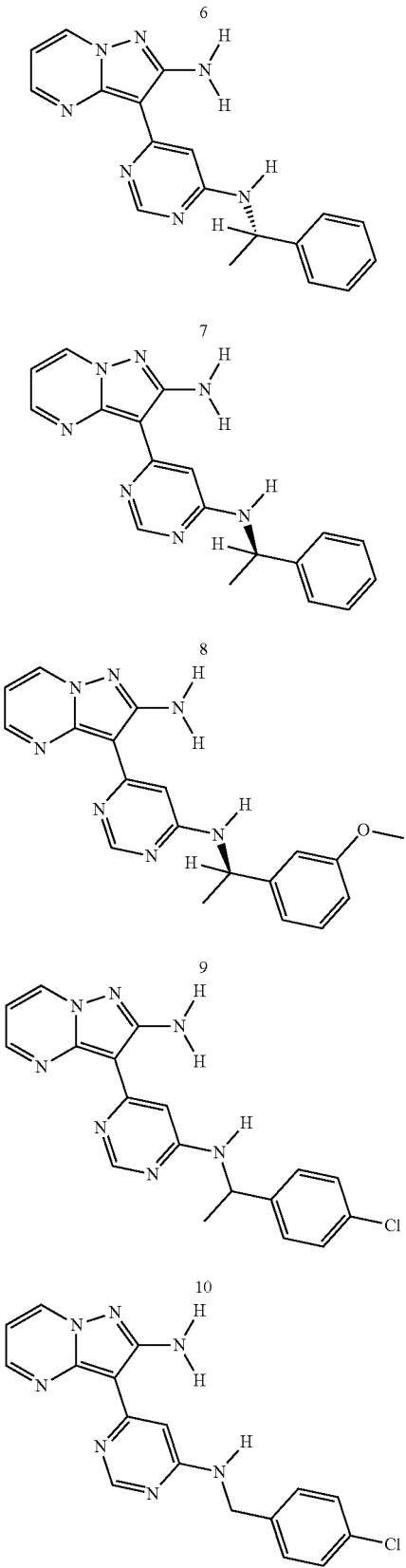
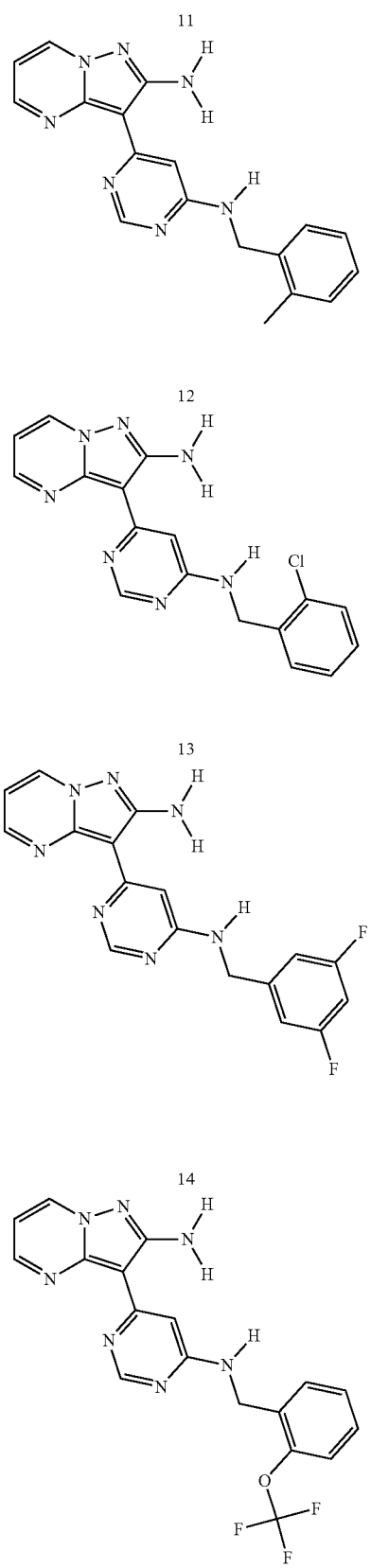

| 135 -continued | 136 -continued |
|---|---|
| 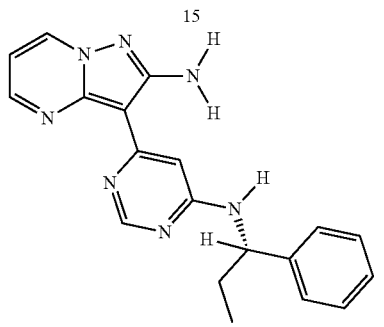 15 | 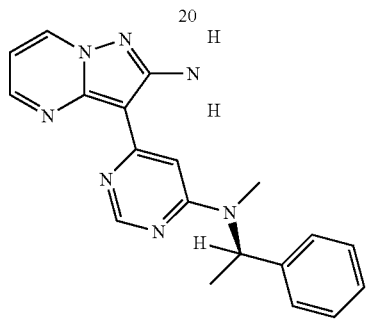 20 |
| 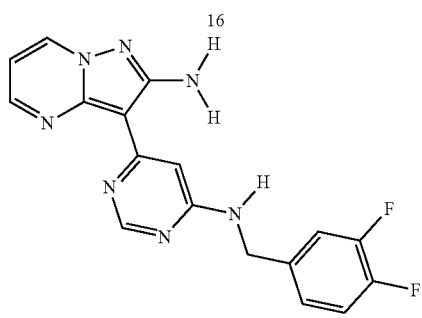 16 | 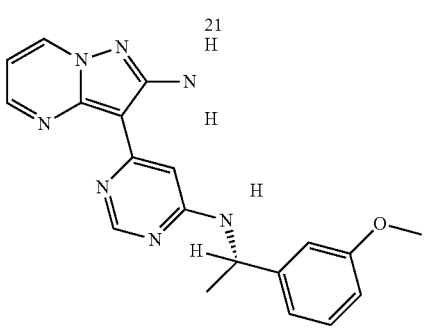 21 |
| 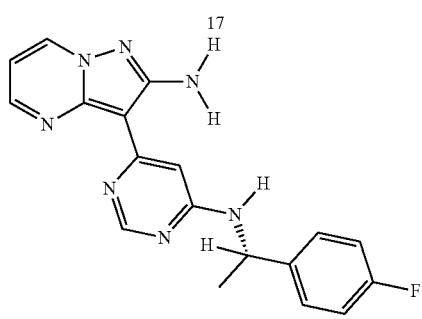 17 | 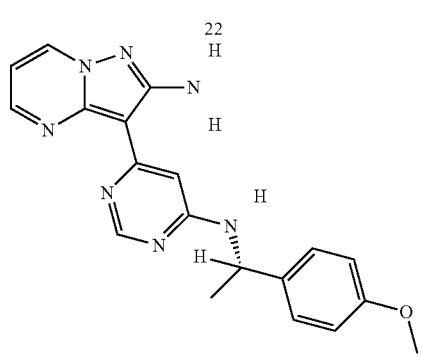 22 |
| 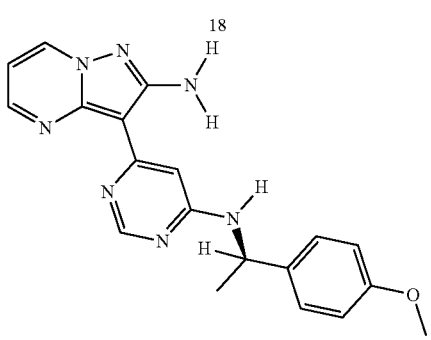 18 | 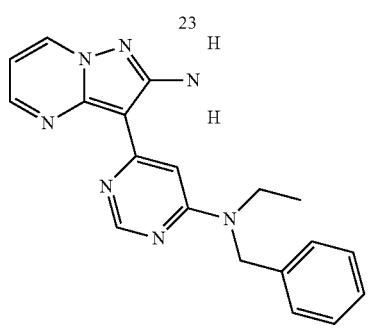 23 |
| 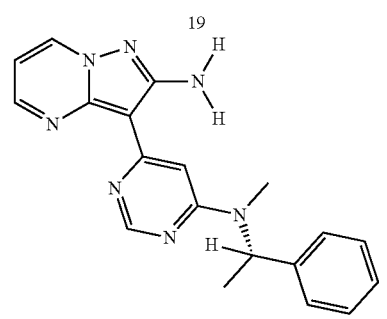 19 | 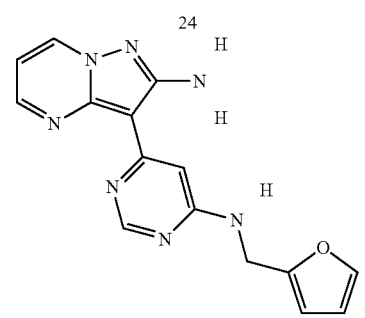 24 |

| 25 | 30 |
|---|---|
| 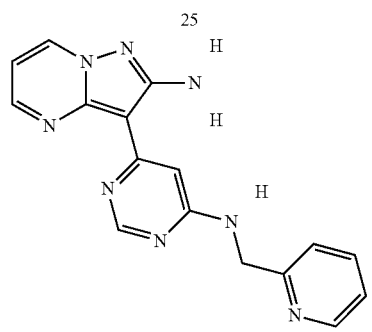 | 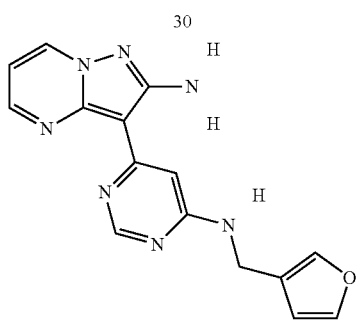 |
| 26 | 31 |
| 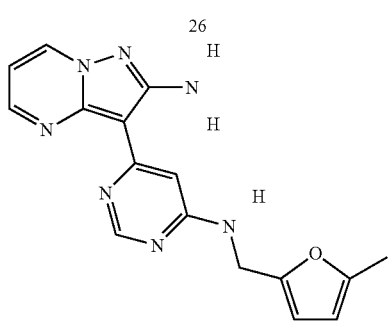 | 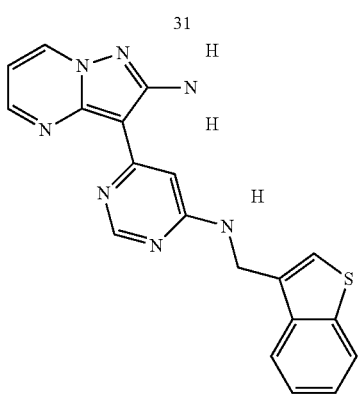 |
| 27 | 32 |
| 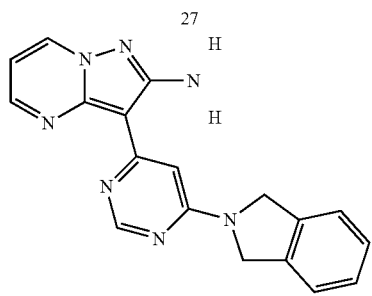 | 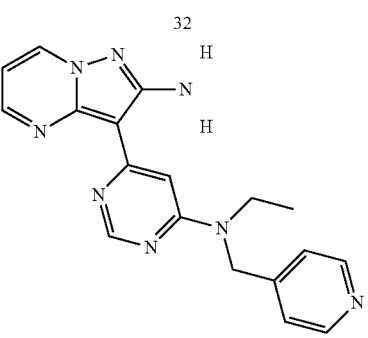 |
| 28 | 33 |
| 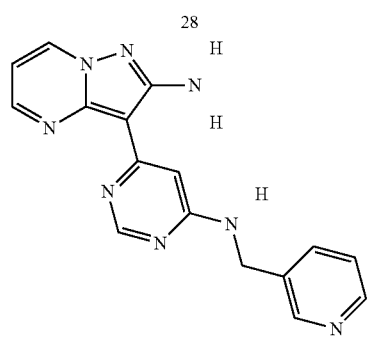 | 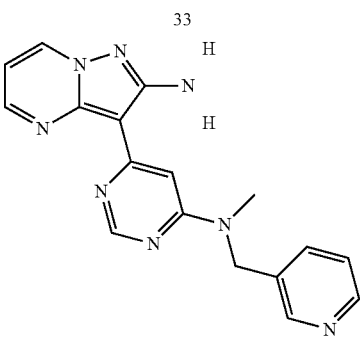 |
| 29 | |
| 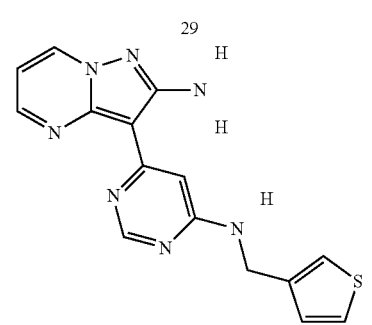 | |

34 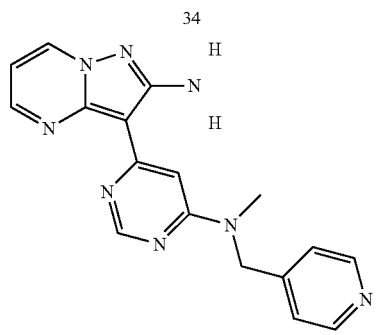
35 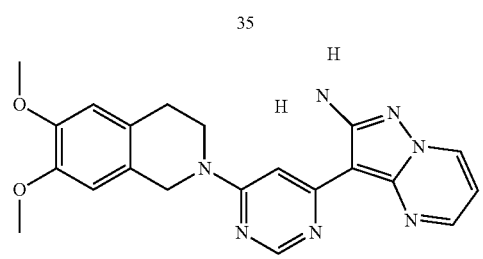
36 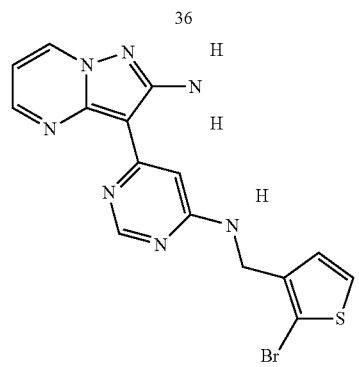
37 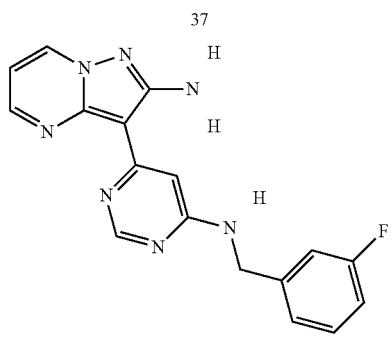
38 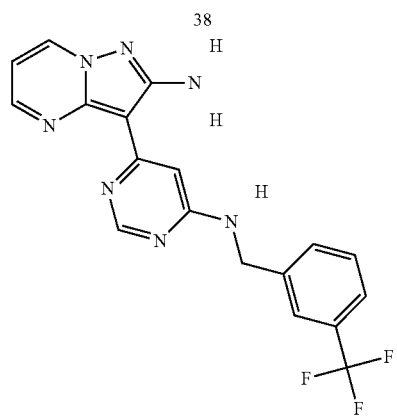
41 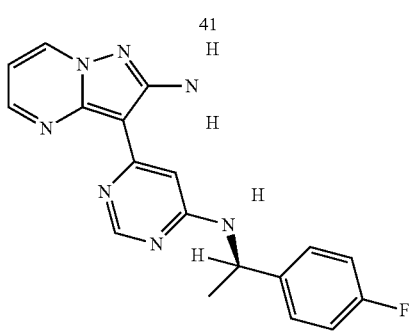
42 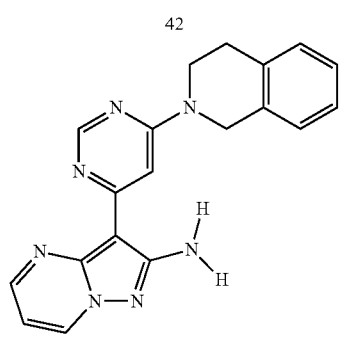
43 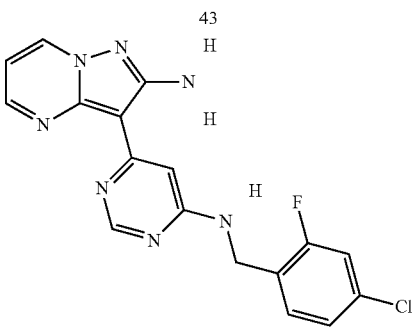

44
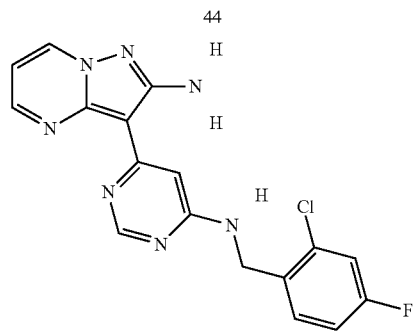
45
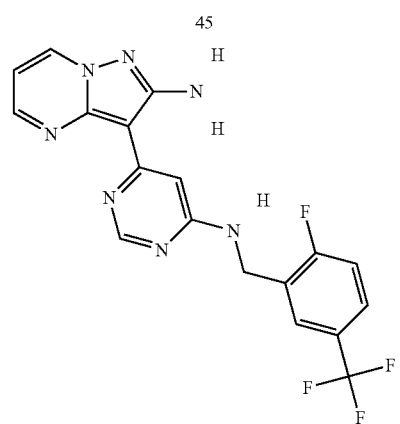
46
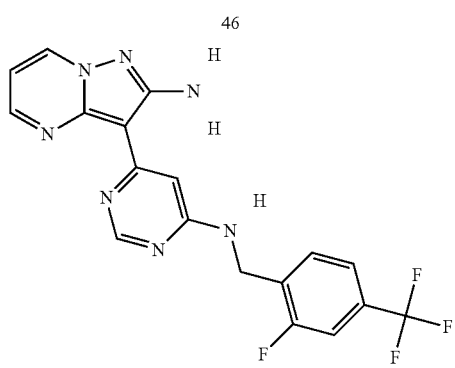
47
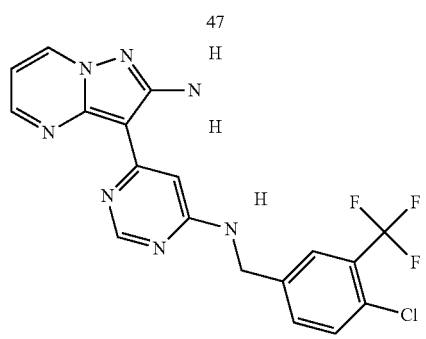
48
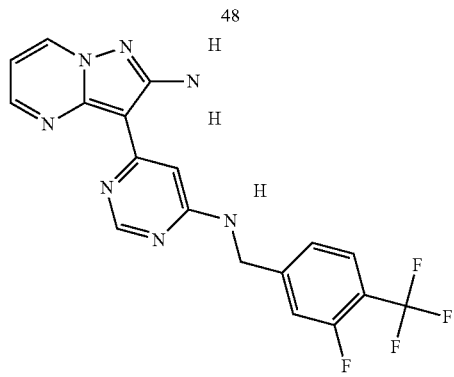
49
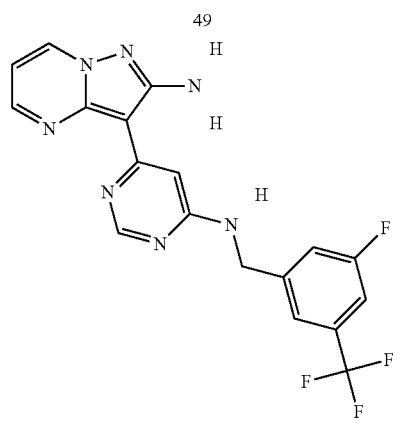
50
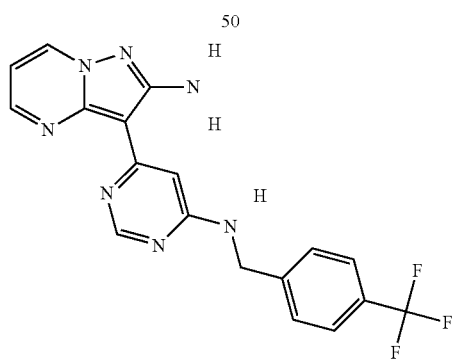
51
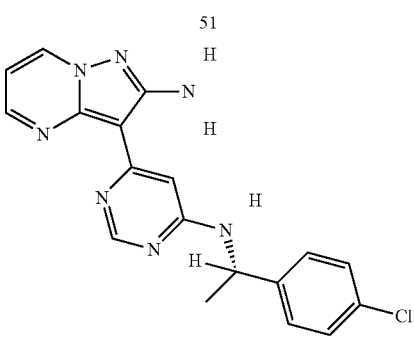

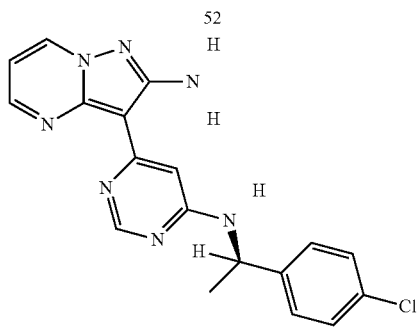
52
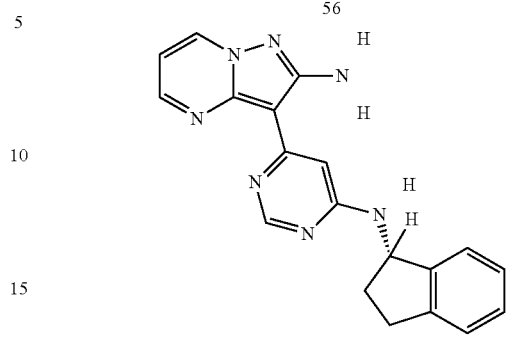
56
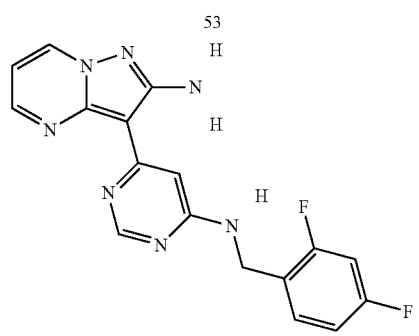
53
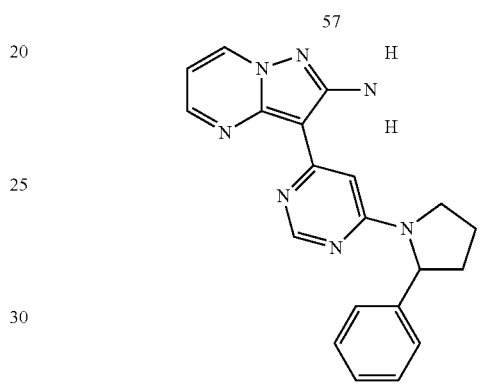
57
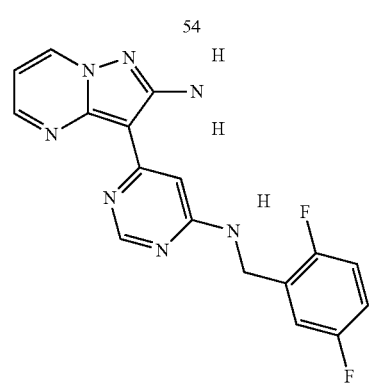
54
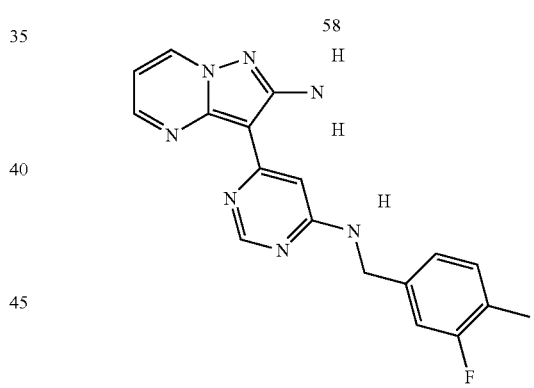
58
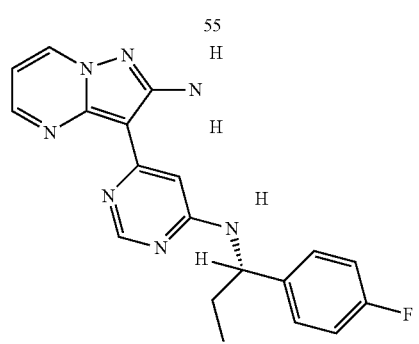
55
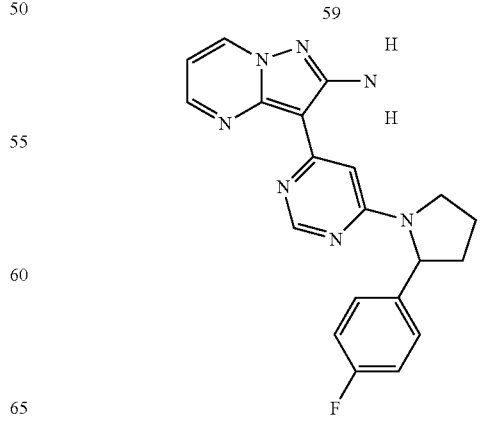
59

60 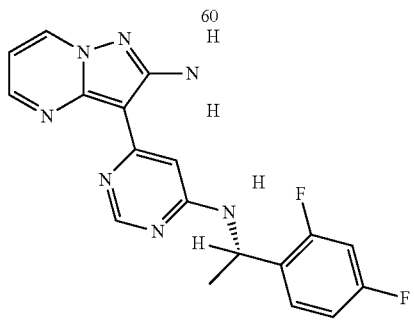
61 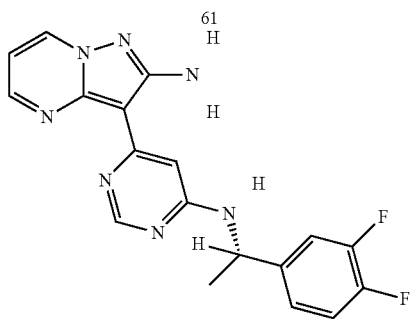
62 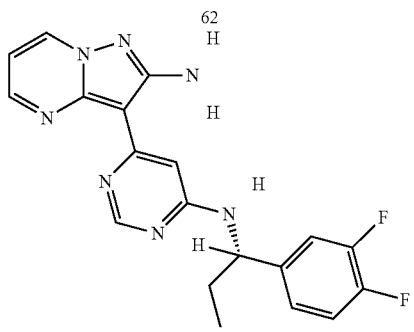
63 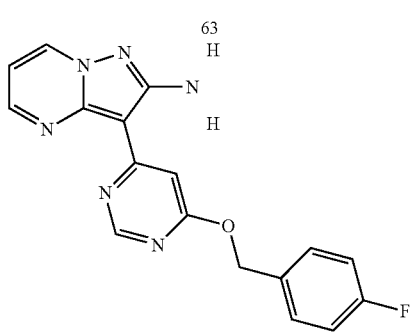
64 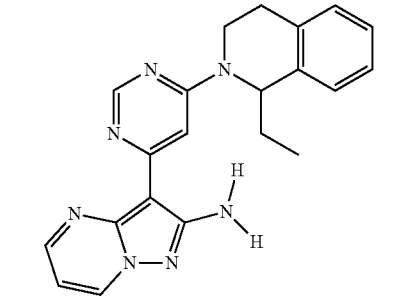
65 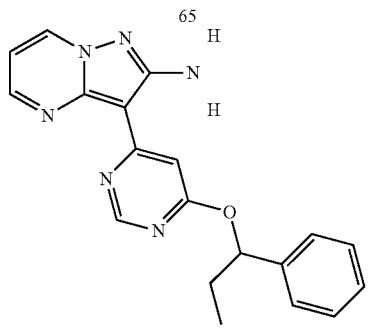
66 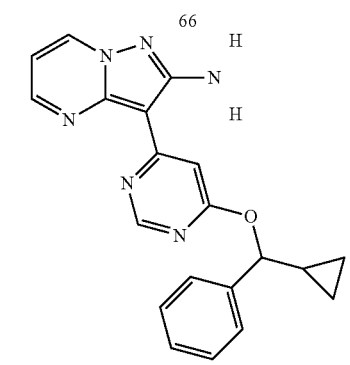
67 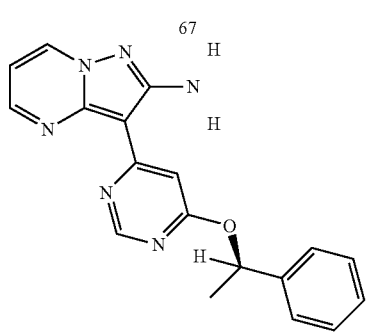
68 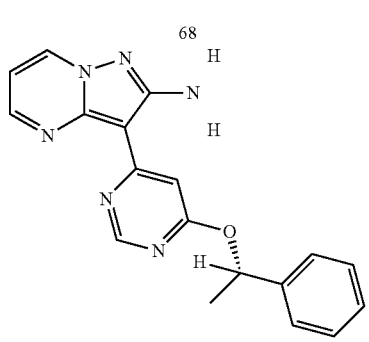

-continued
69
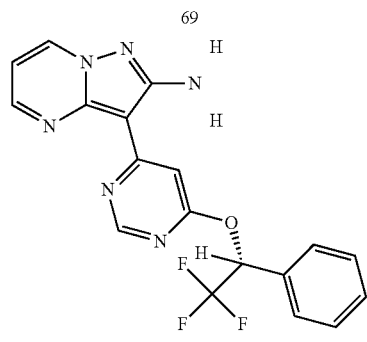
70
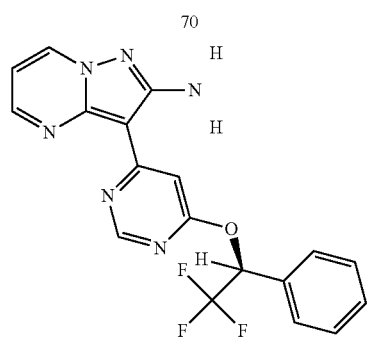
71
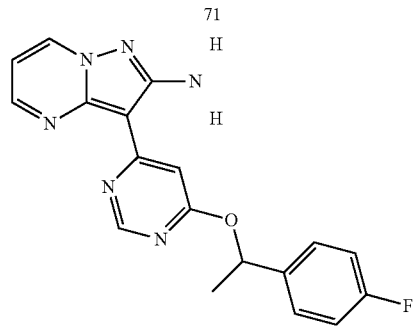
72
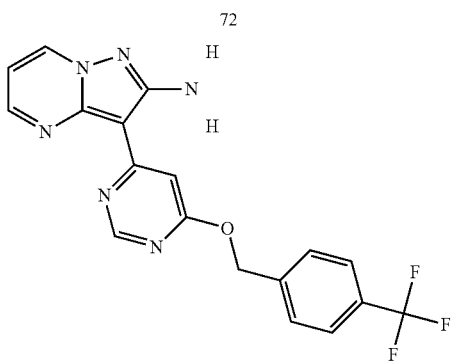
-continued
73
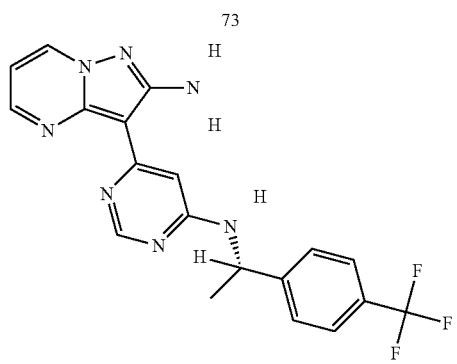
74
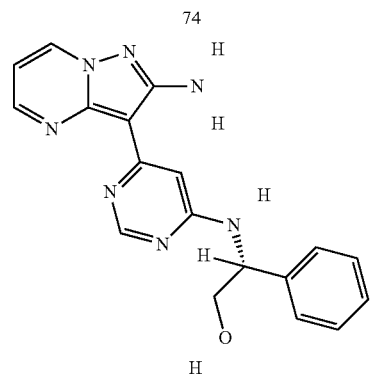
75
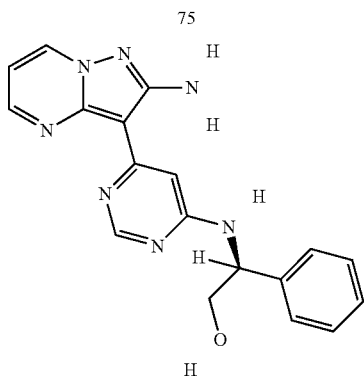
76
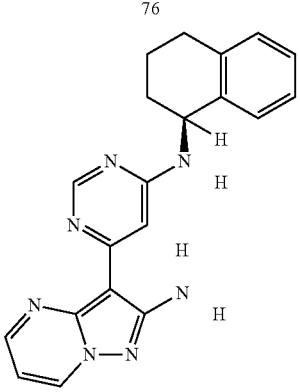

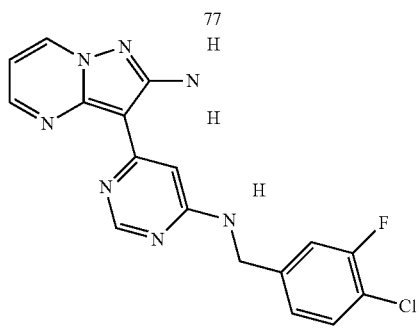
77
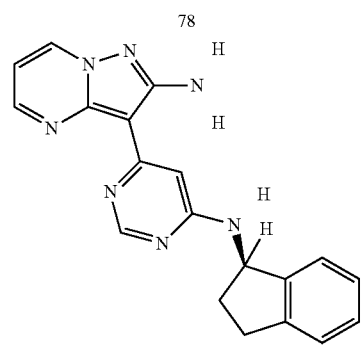
78
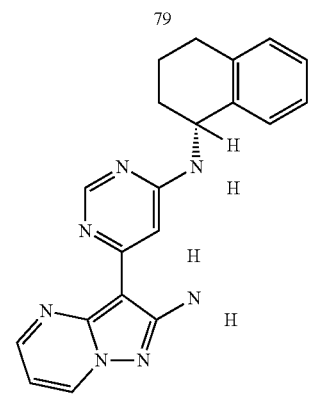
79
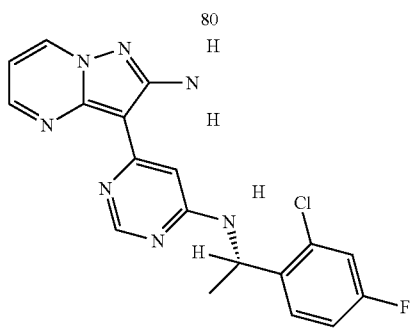
80
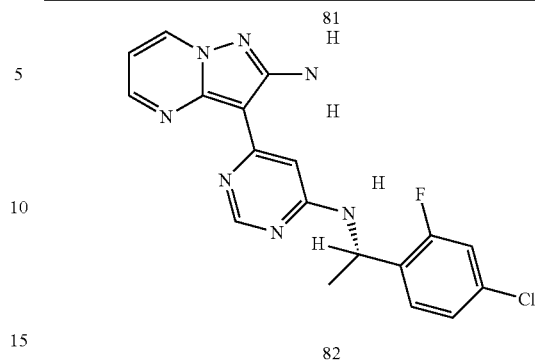
81
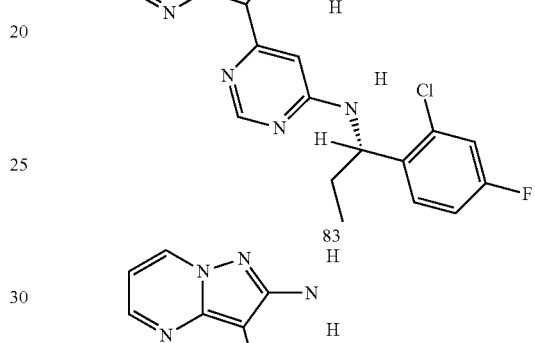
82
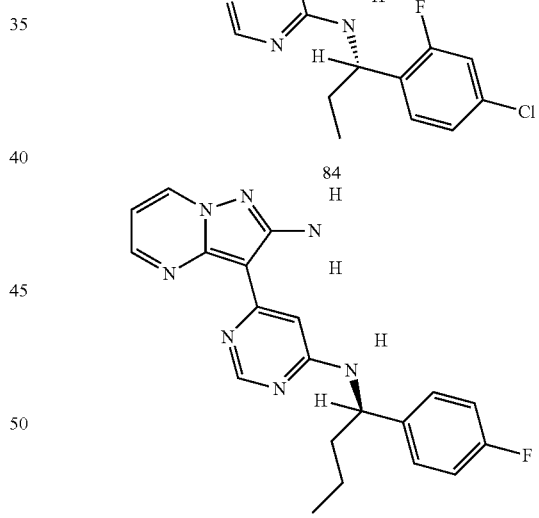
83
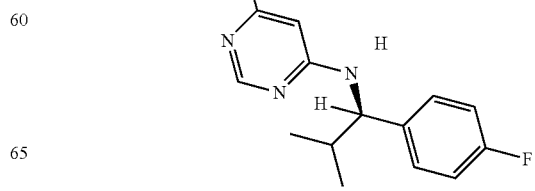
84
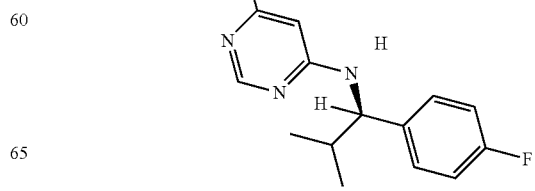
85

| 86 | 90 |
|---|---|
| 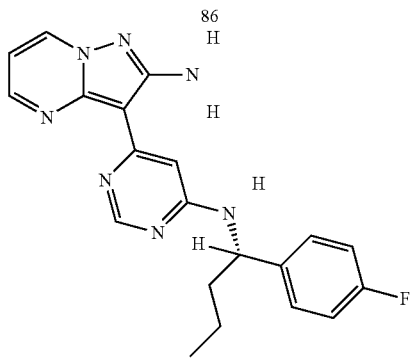 | 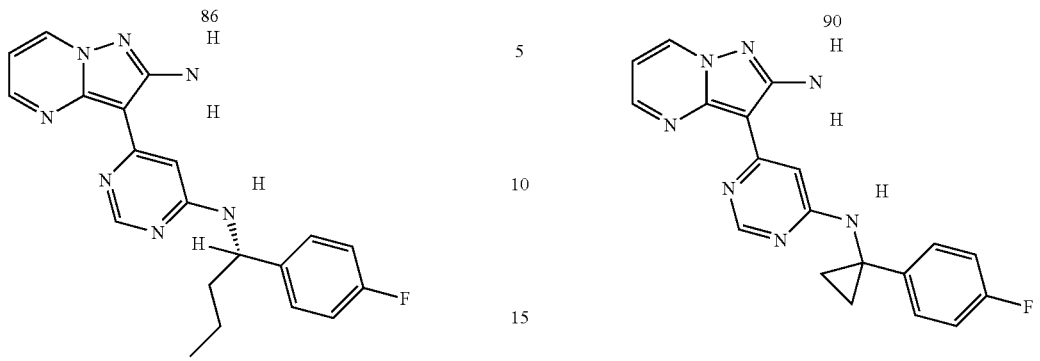 |
| 87 | 91 |
| 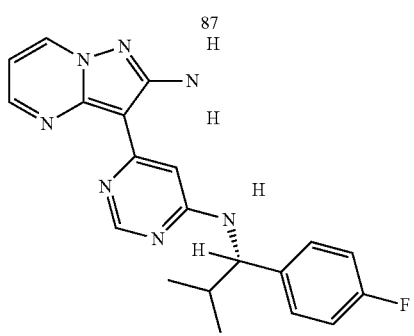 | 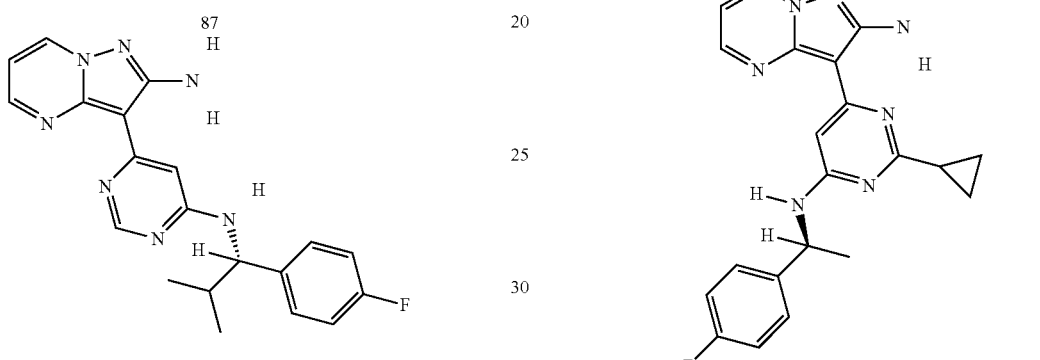 |
| 88 | 92 |
| 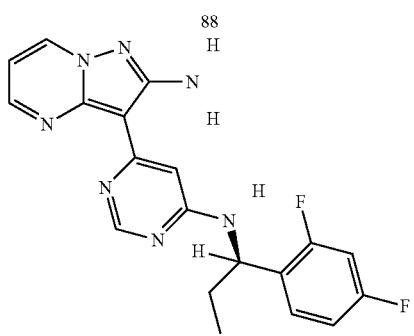 | 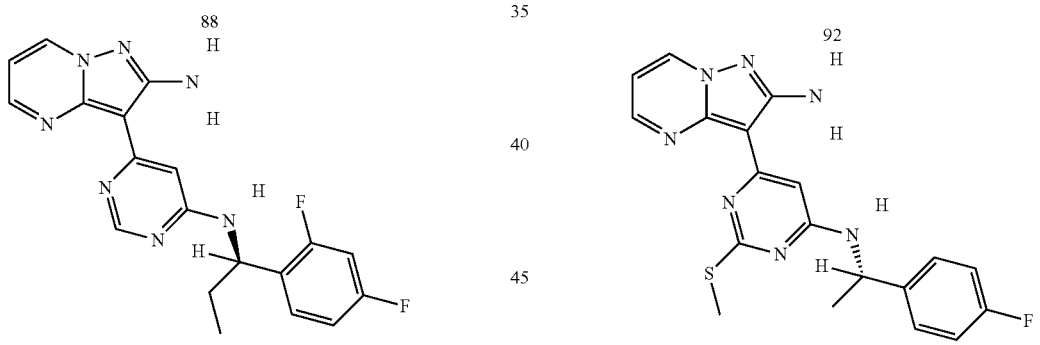 |
| 89 | 93 |
| 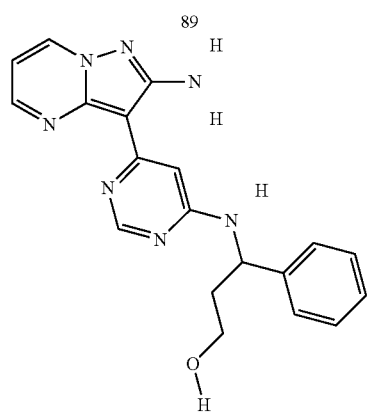 | 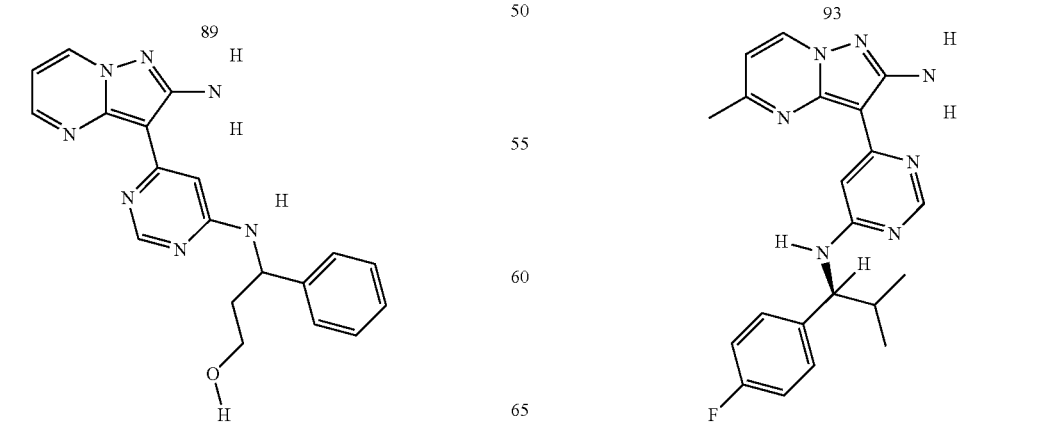 |

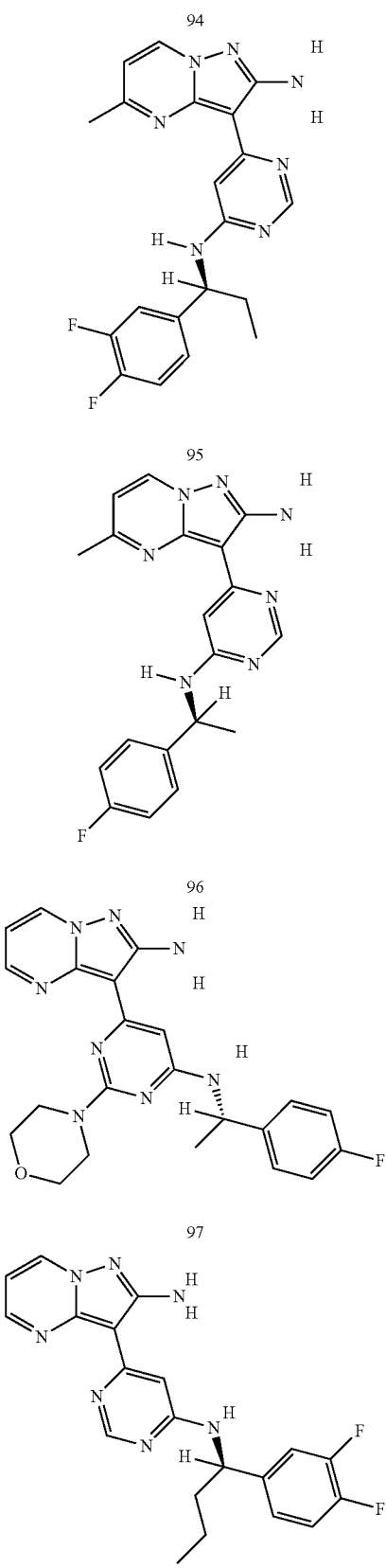
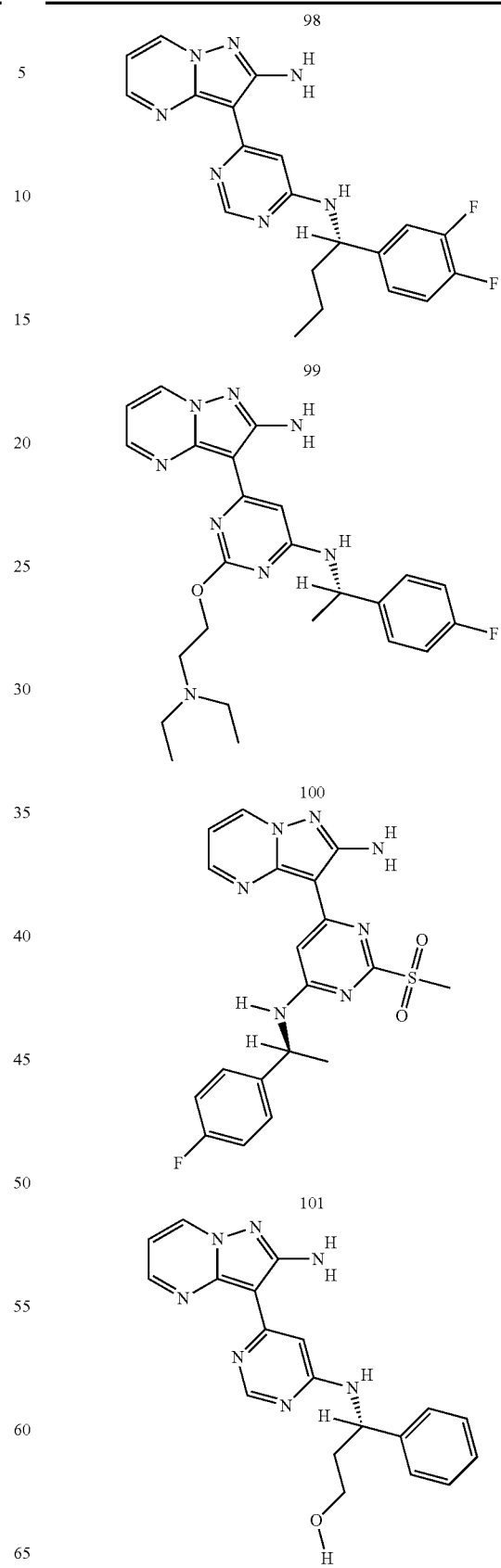

155
-continued
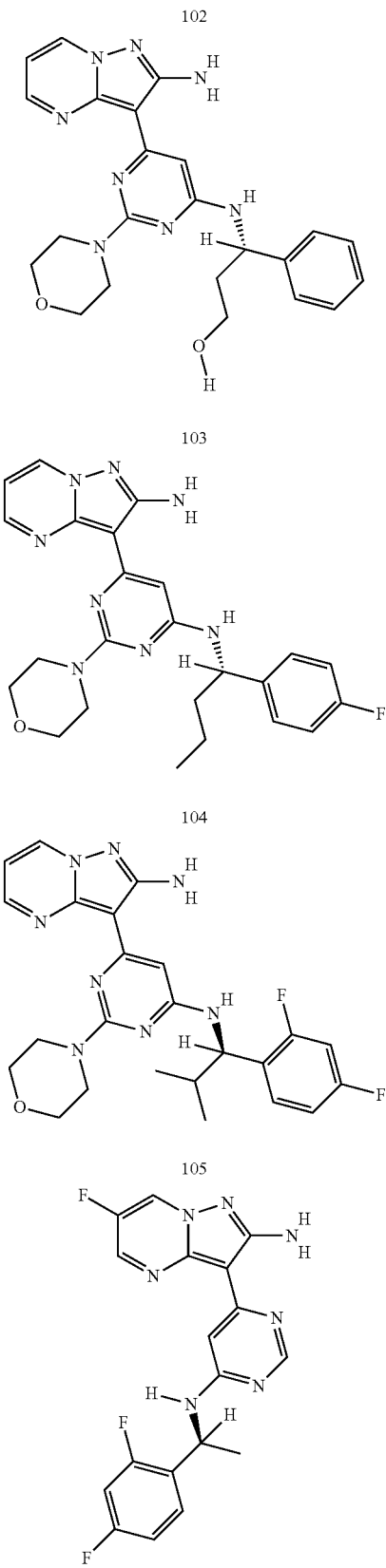
156
-continued
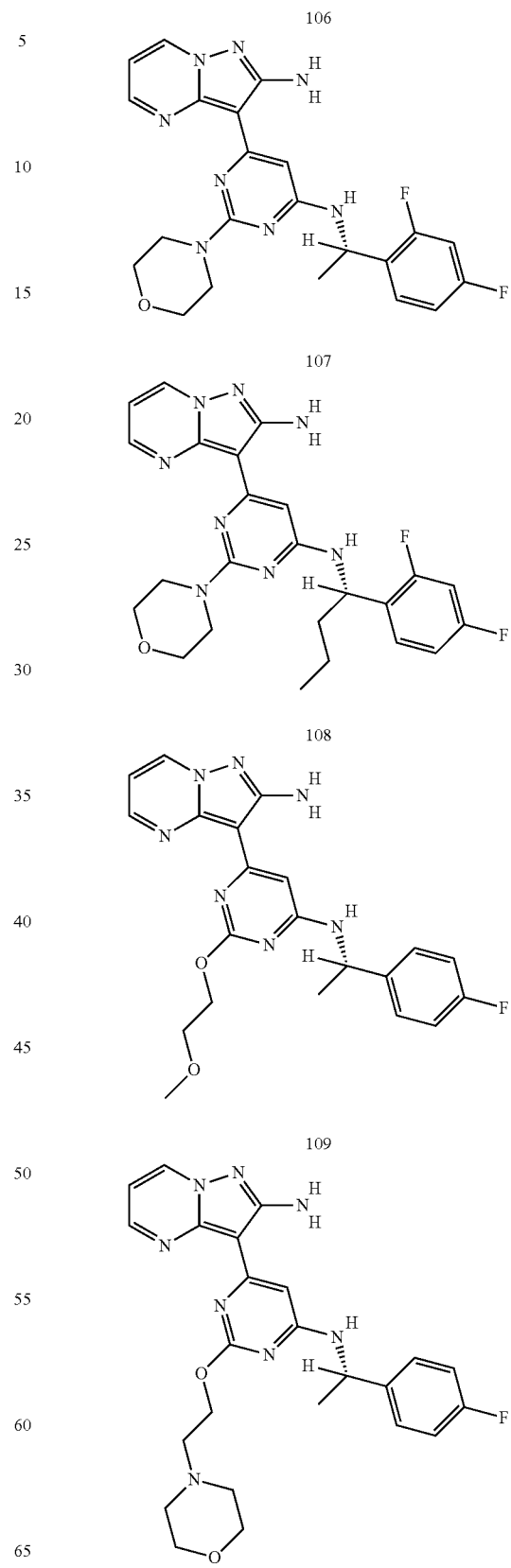

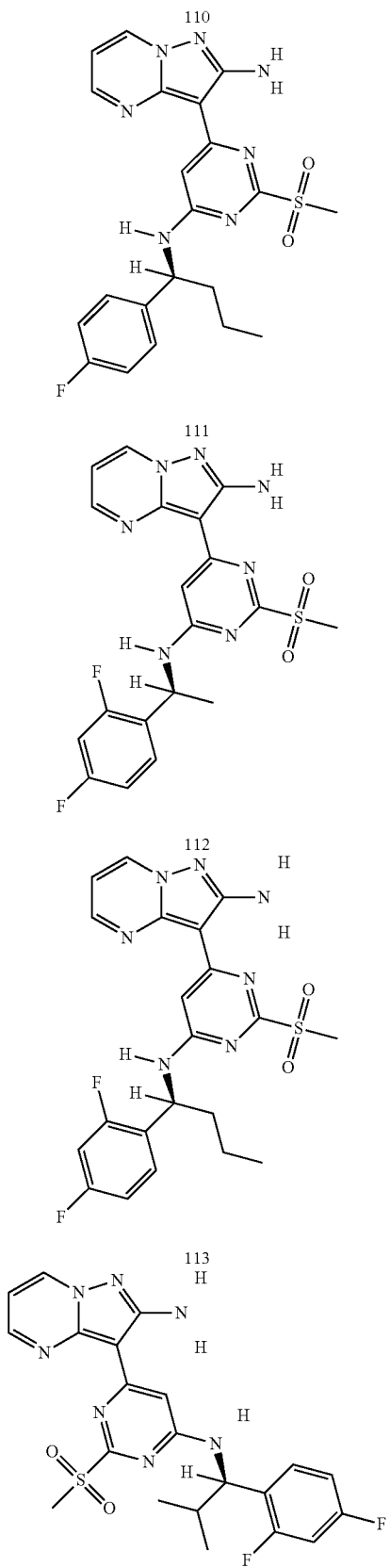
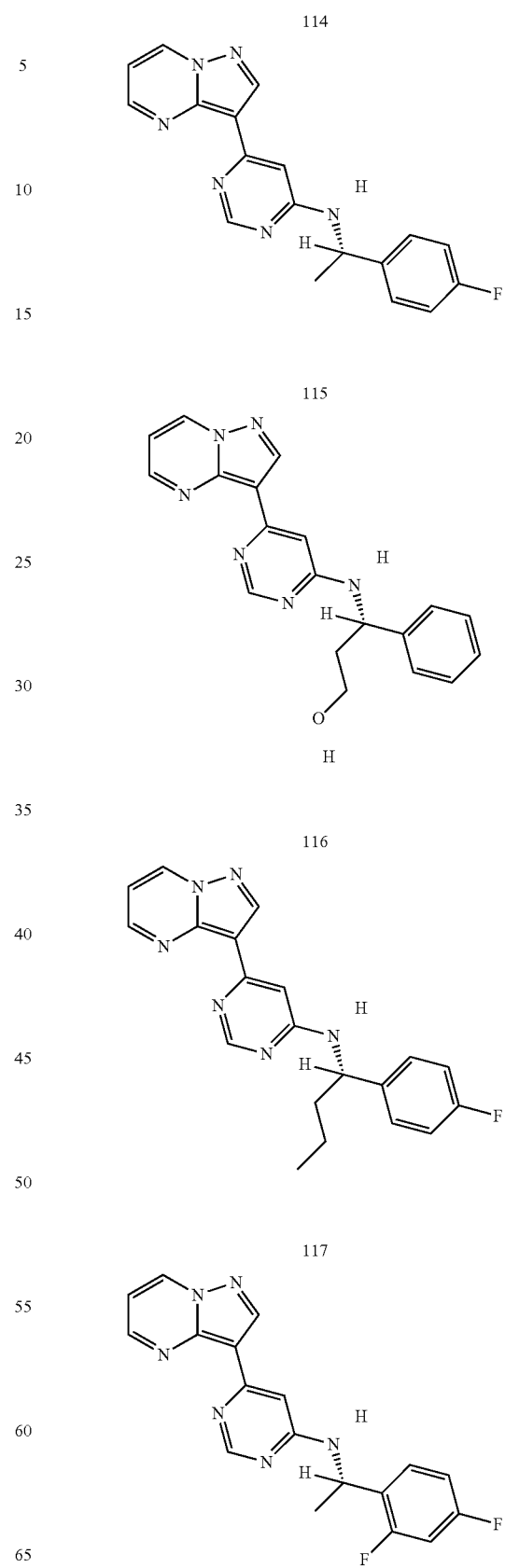

118
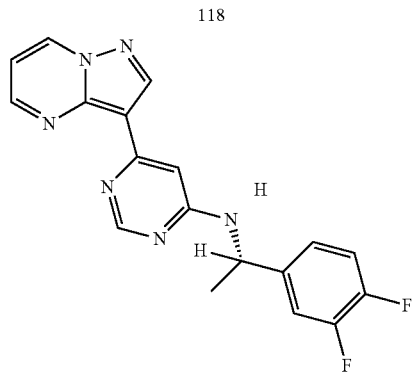
119
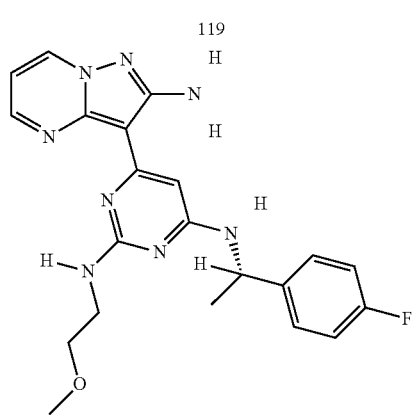
120
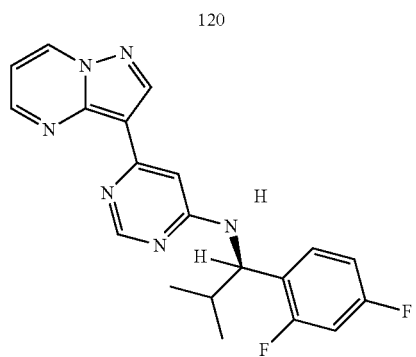
121
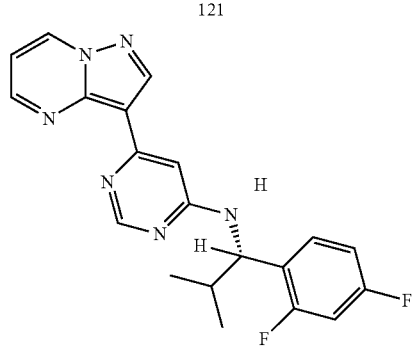
122
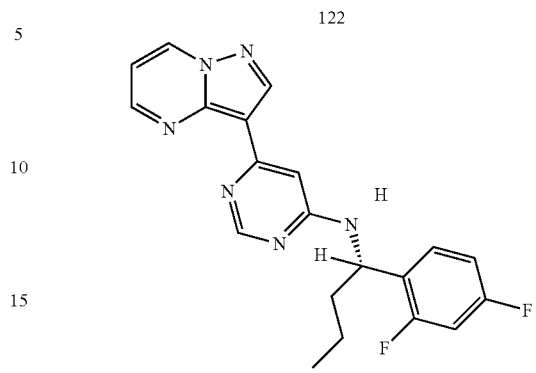
123
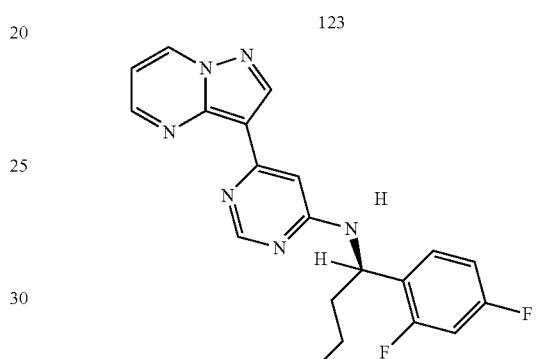
124
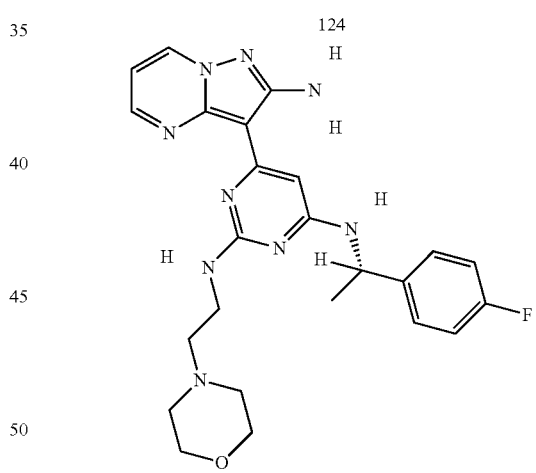
125
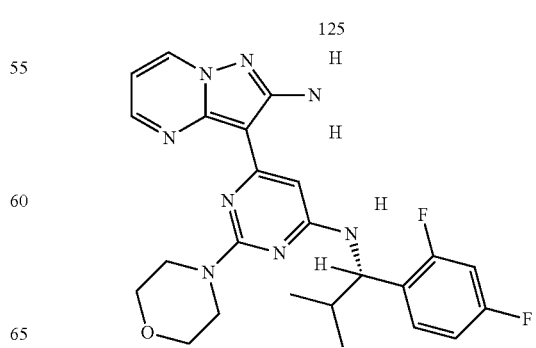

-continued
126
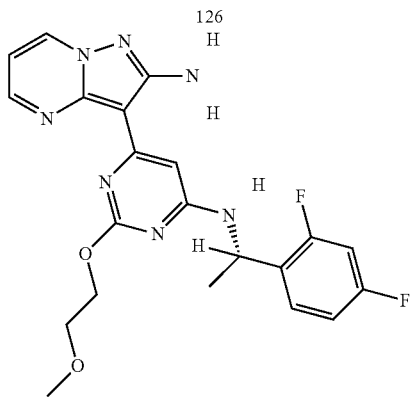
127
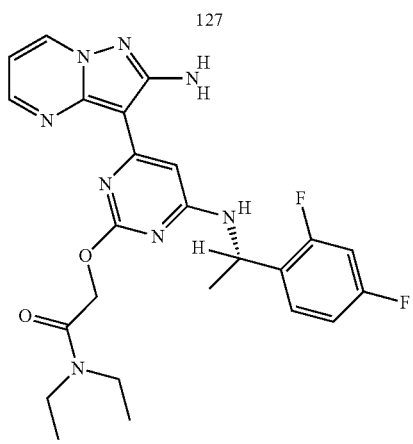
128
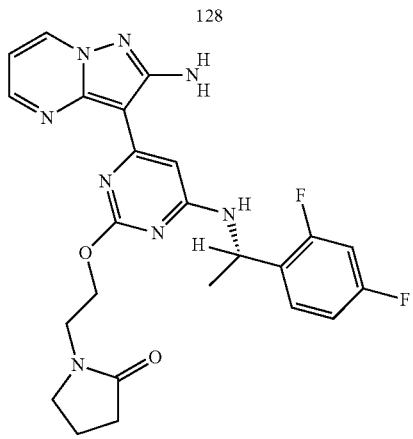
129
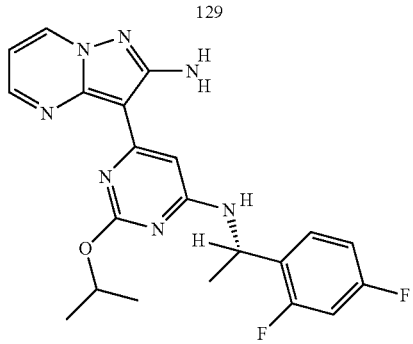
-continued
130
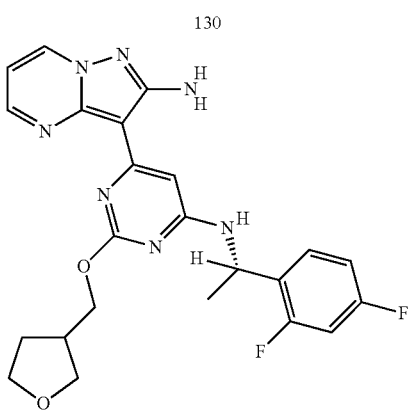
131
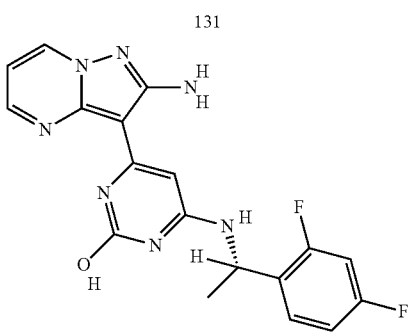
132
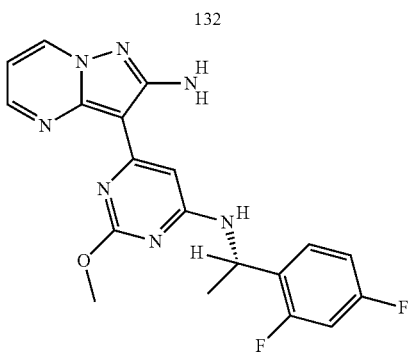
133
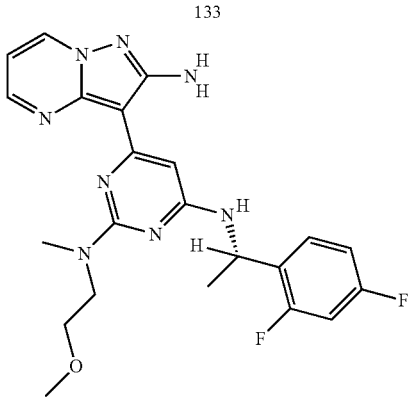

163
-continued
134
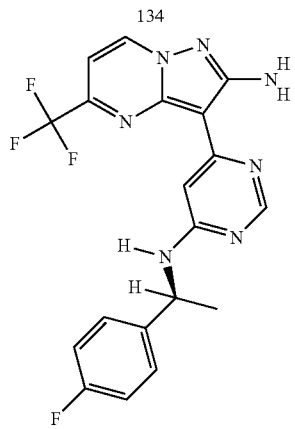
135
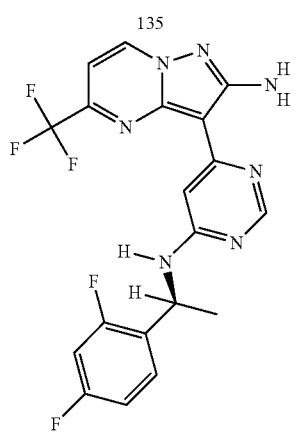
136
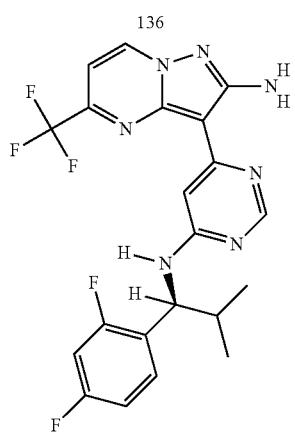
164
-continued
137
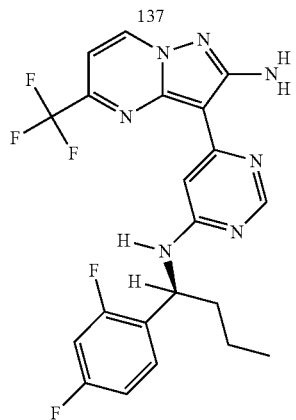
138
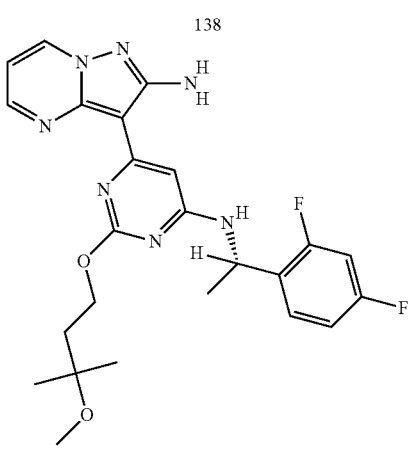
139
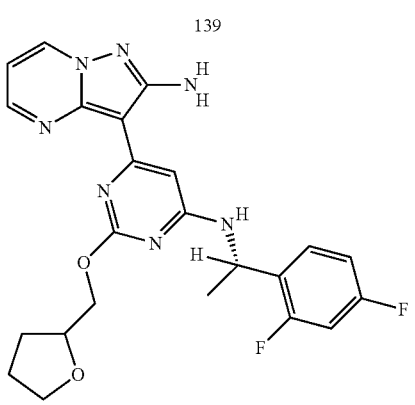
140
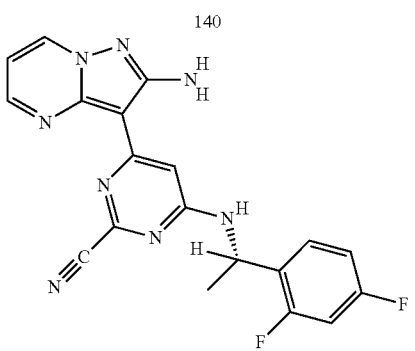

141
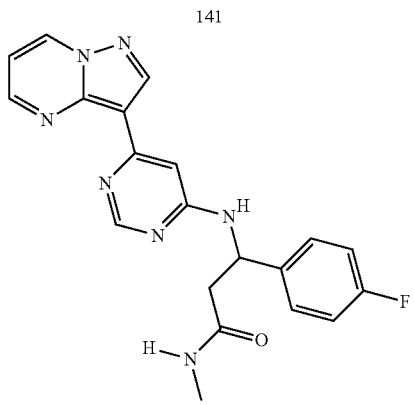
142
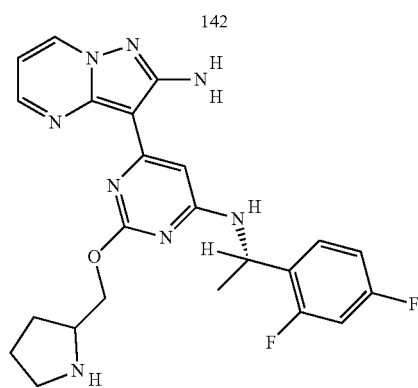
143
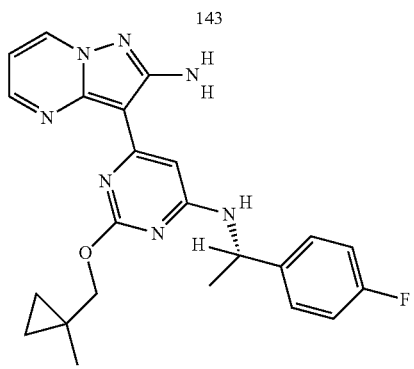
144
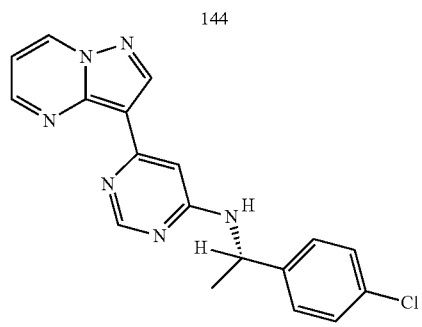
145
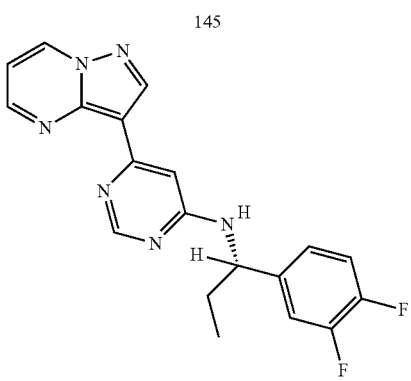
146
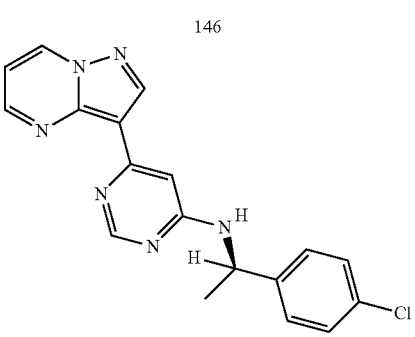
147
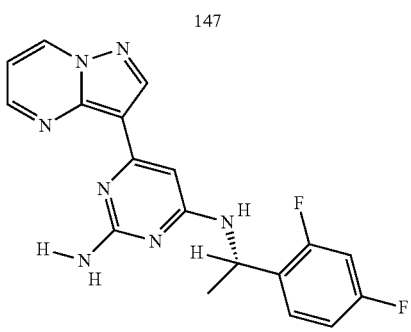
148
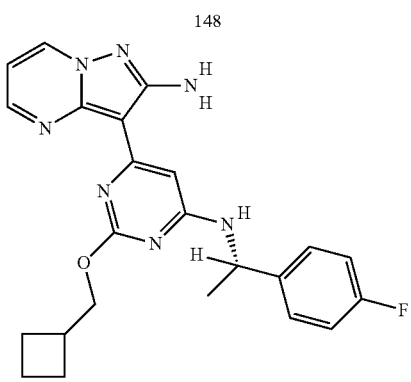

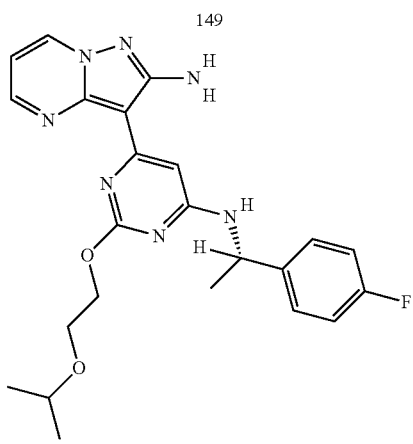
149
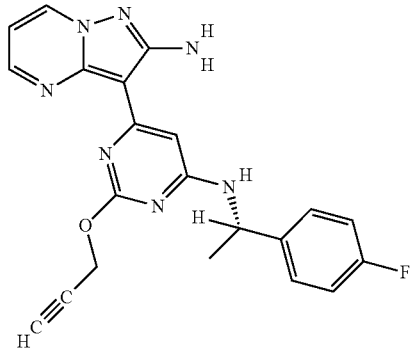
150
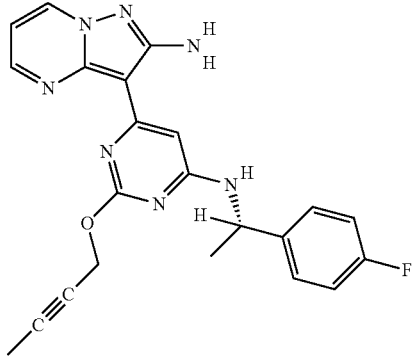
151
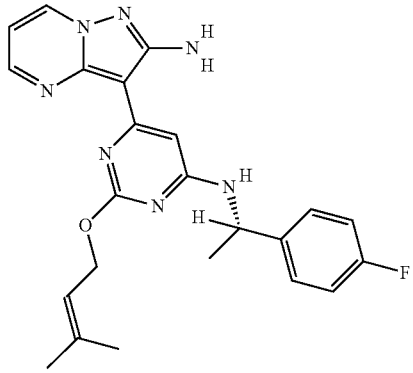
152
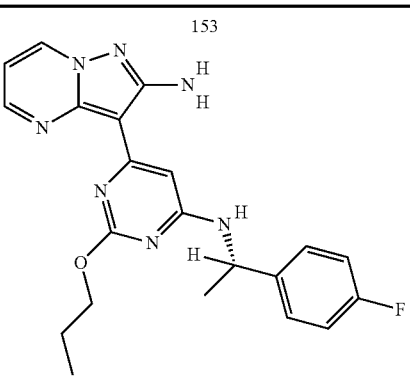
153
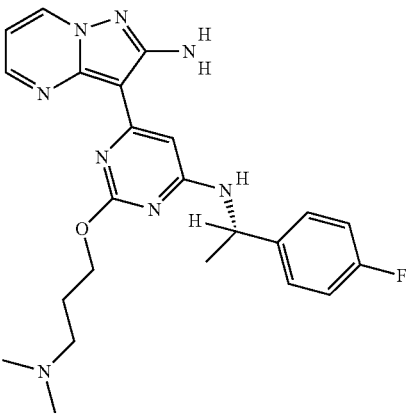
154
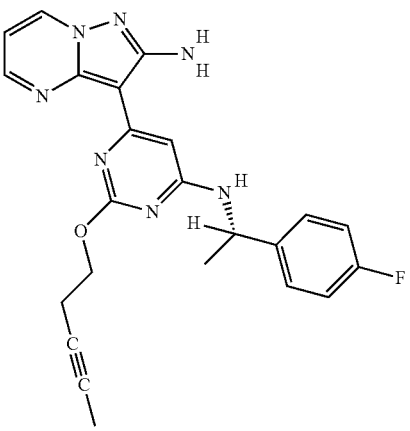
155
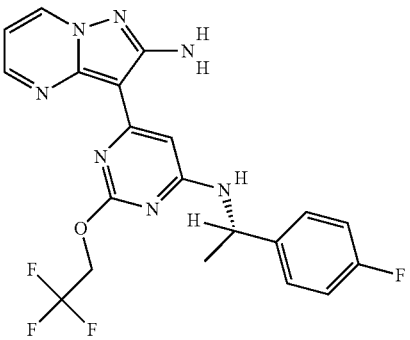
156

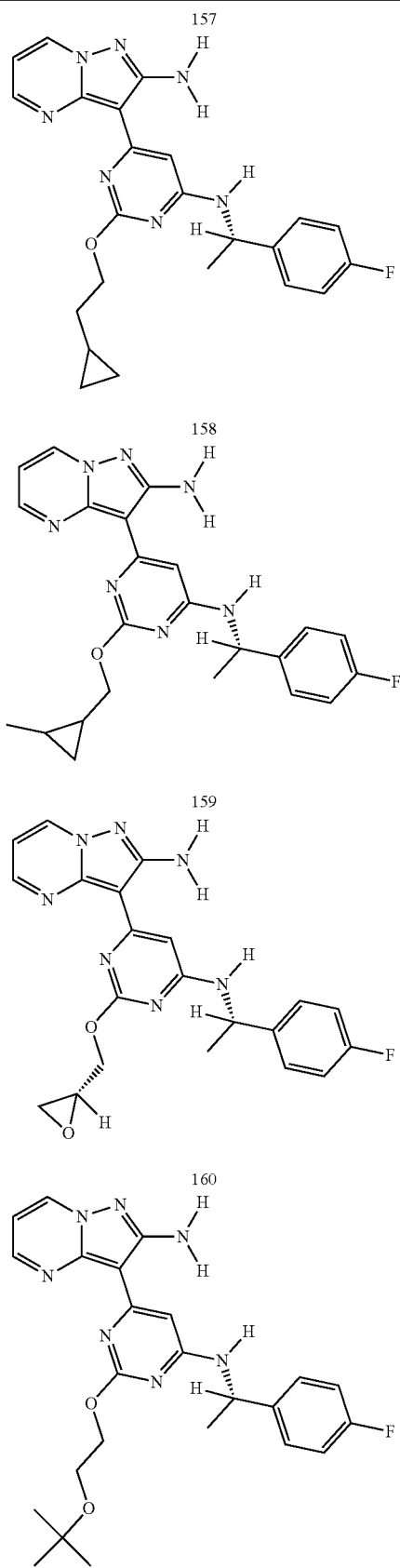
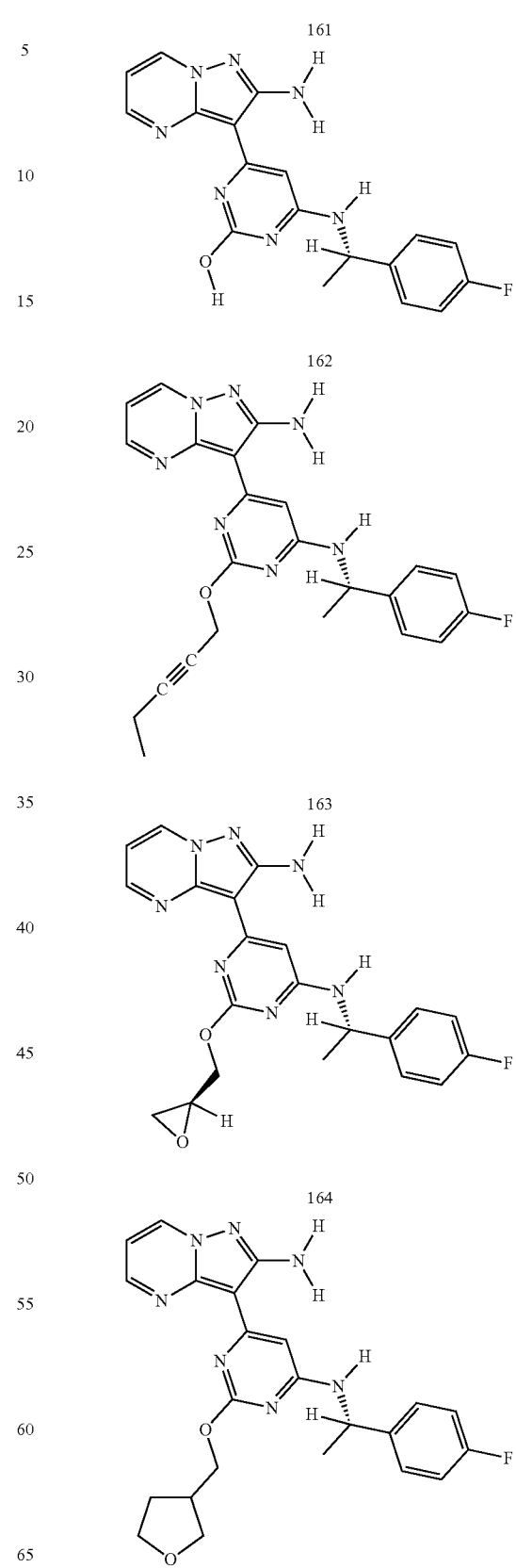

-continued
165
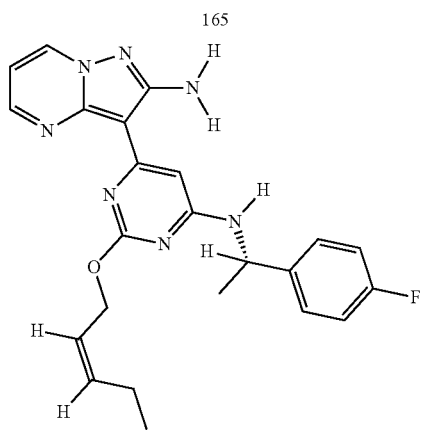
168
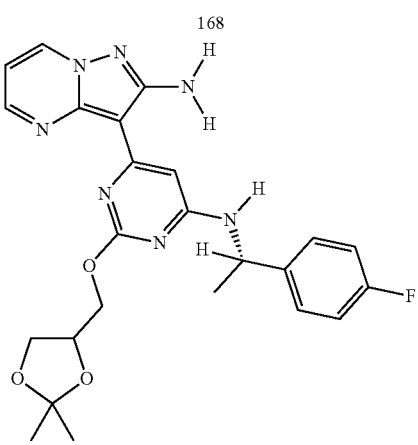
166
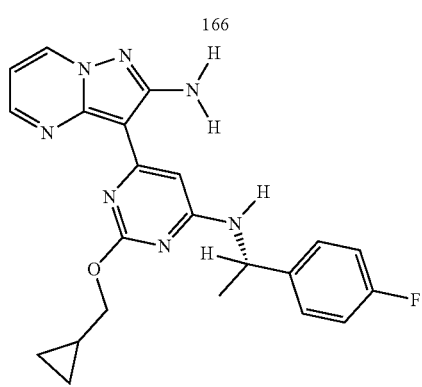
169
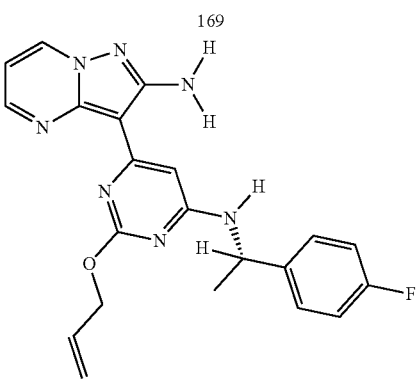
167
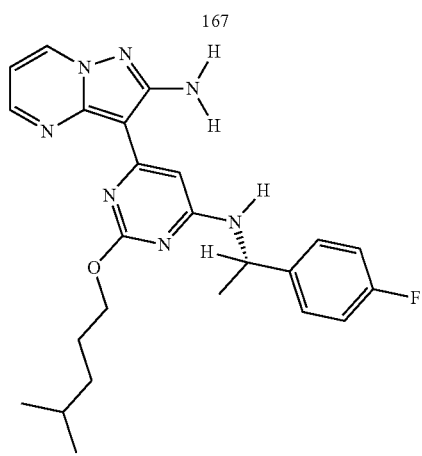
170
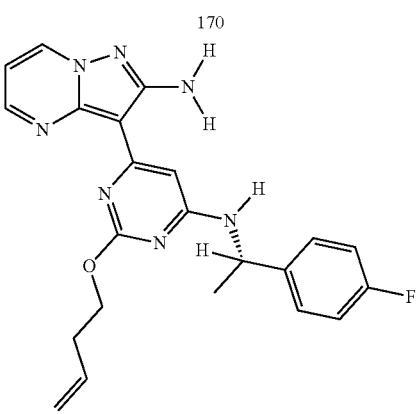

171
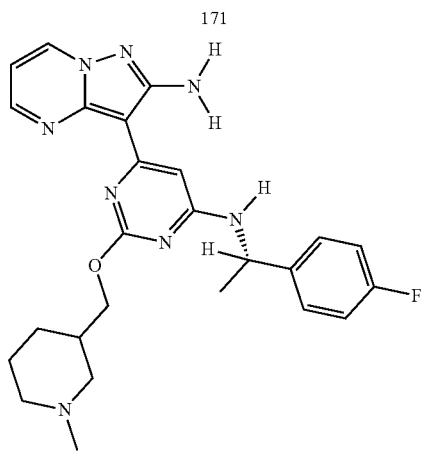
174
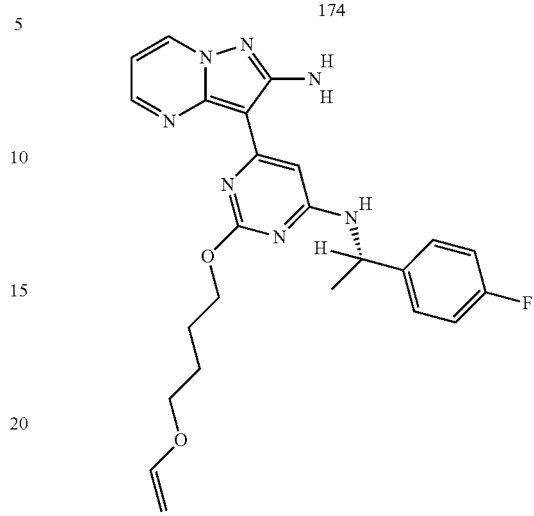
172
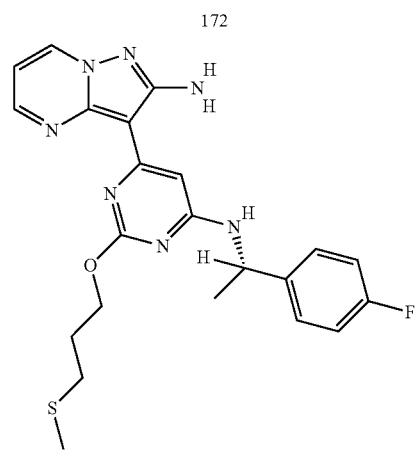
175
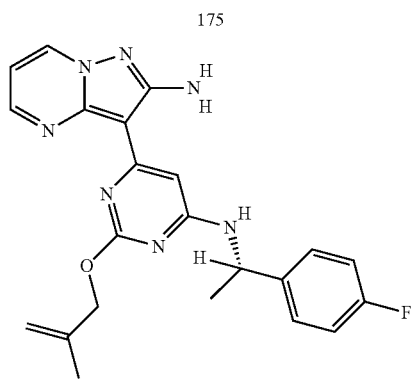
173
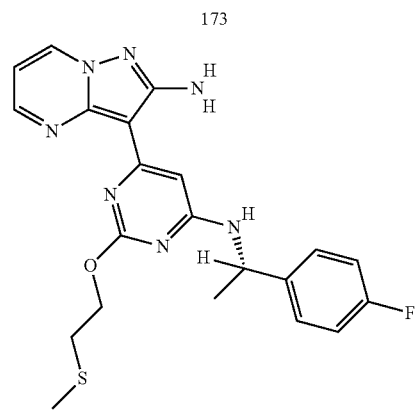
176
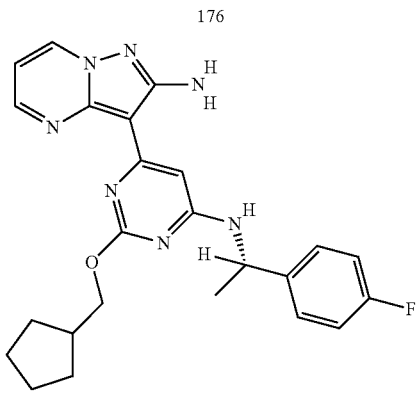

175 -continued
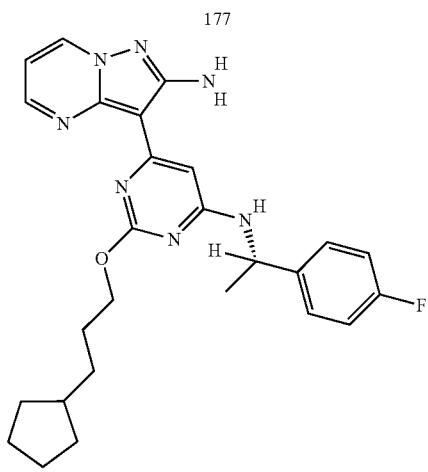
177
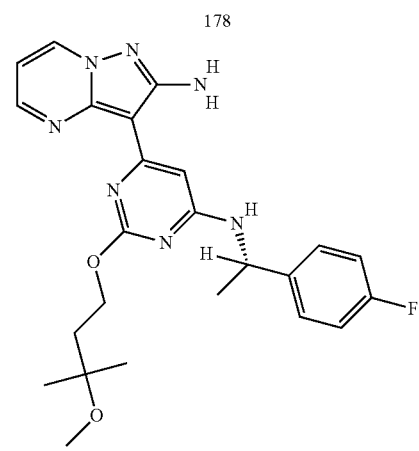
178
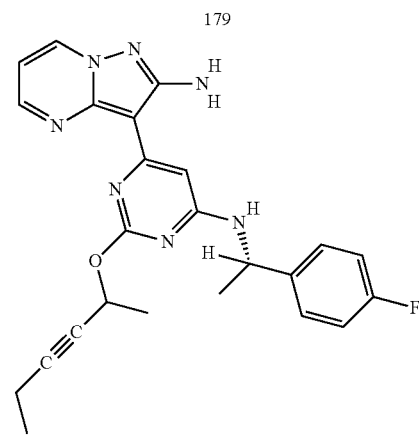
179
176 -continued
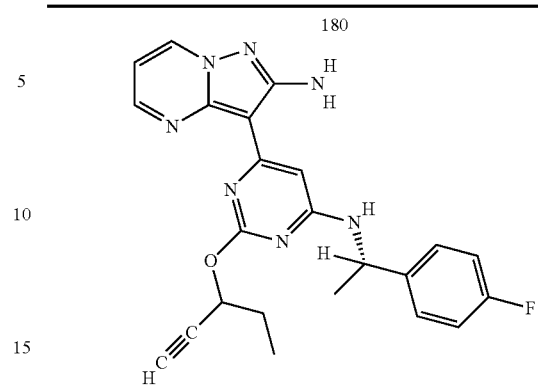
180
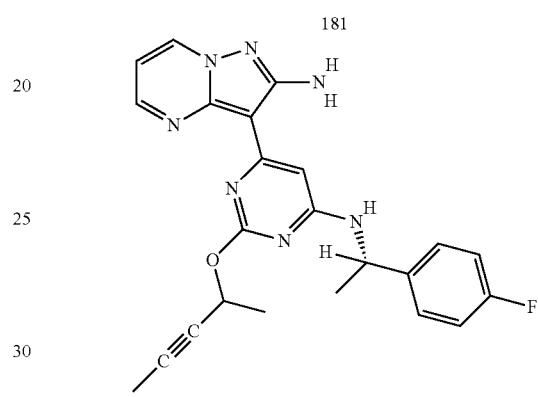
181
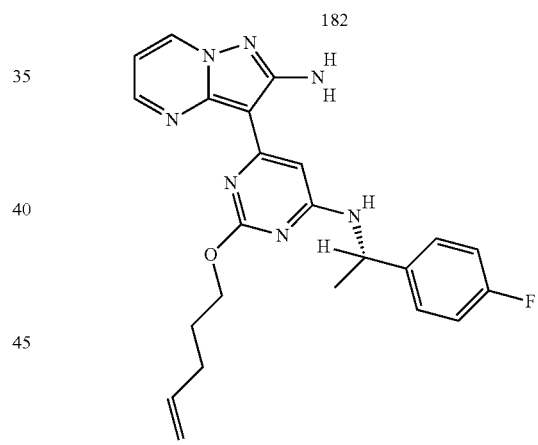
182
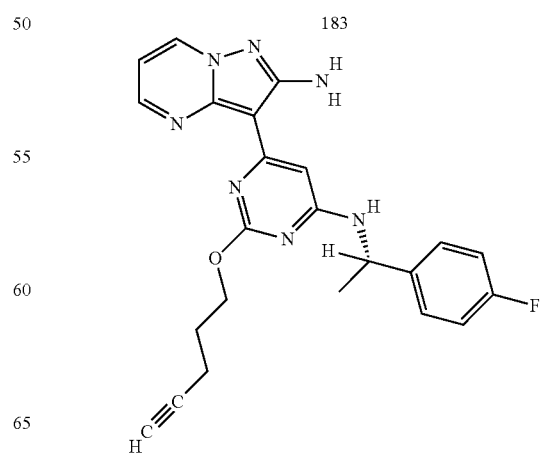
183

-continued
184
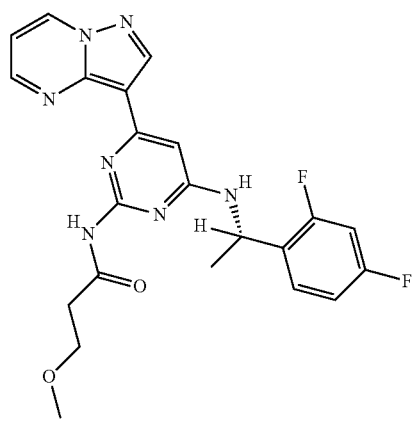
185
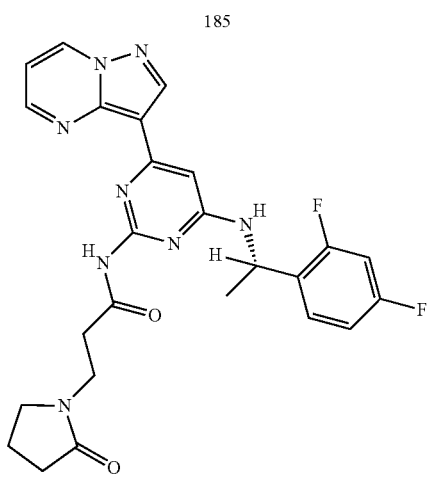
186
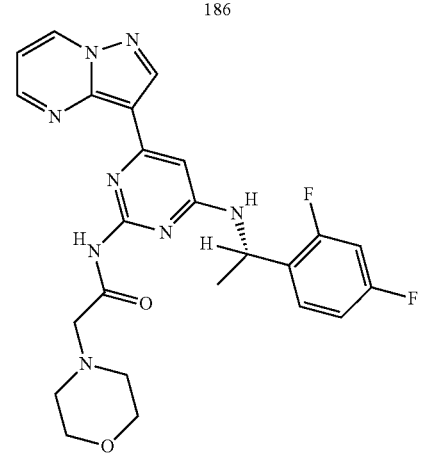
-continued
187
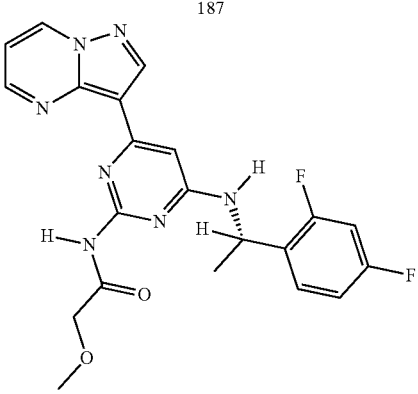
188
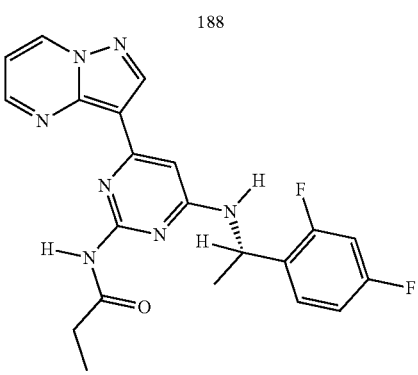
189
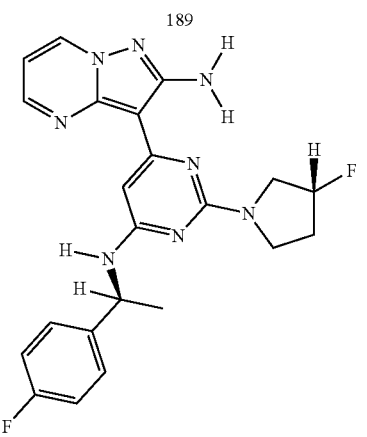
190
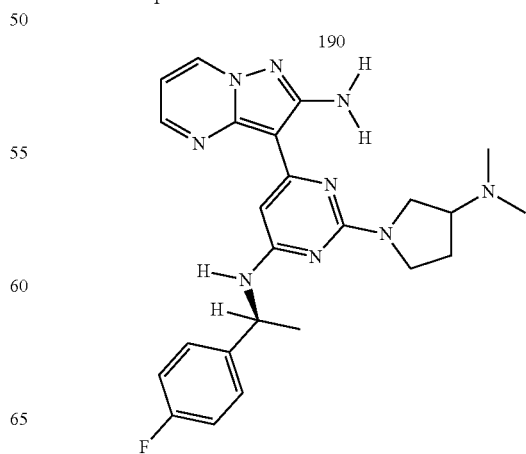

| 191 | 194 |
|---|---|
| 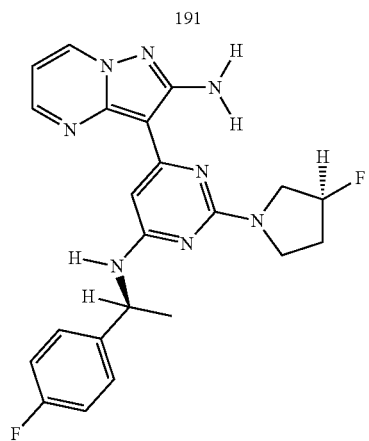 | 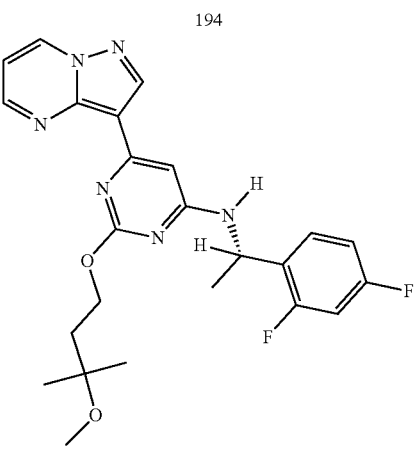 |
| 192 | 195 |
| 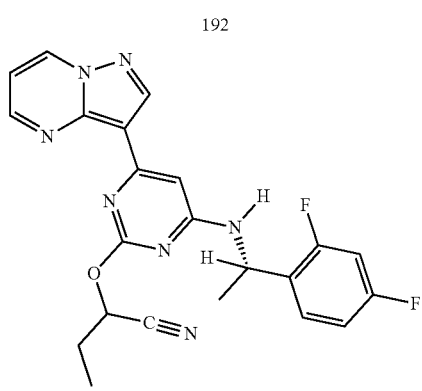 | 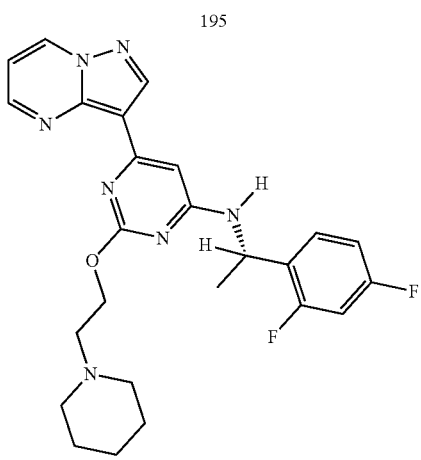 |
| 193 | 196 |
| 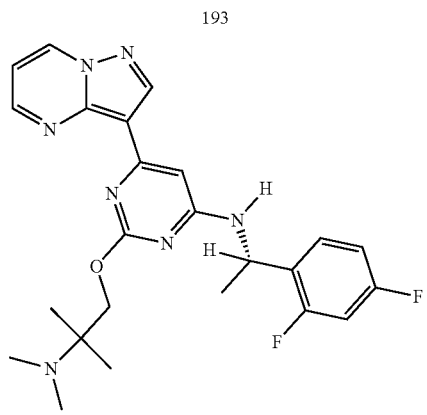 | 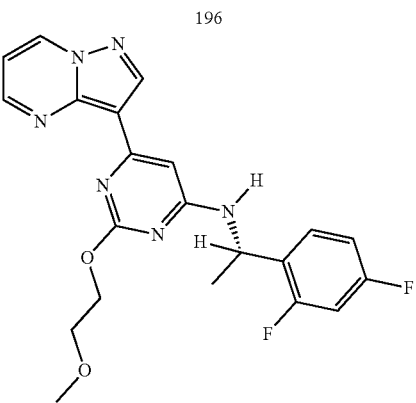 |

181
-continued
197
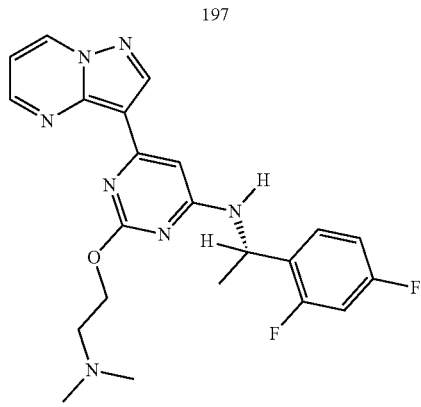
198
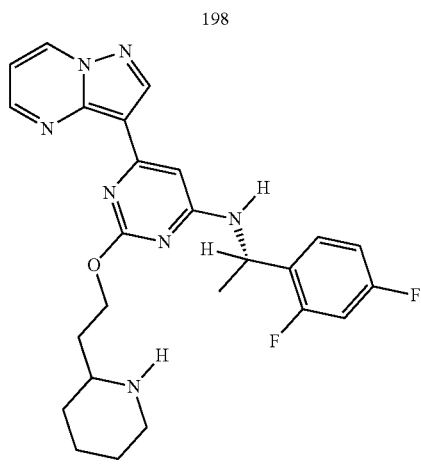
199
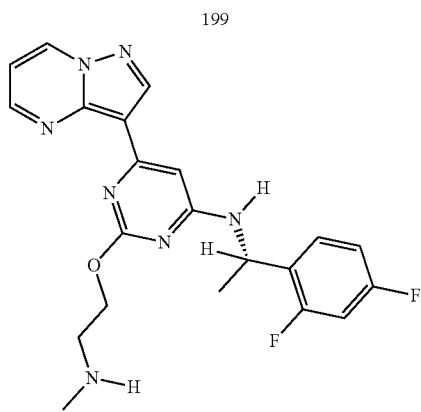
182
-continued
200
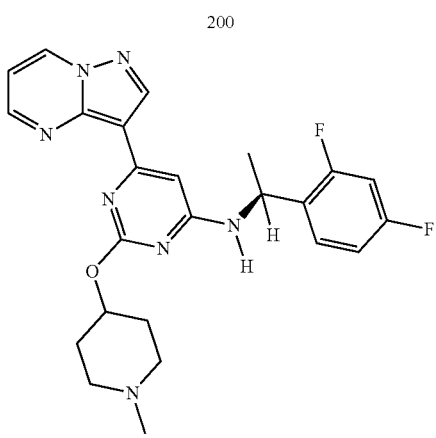
201
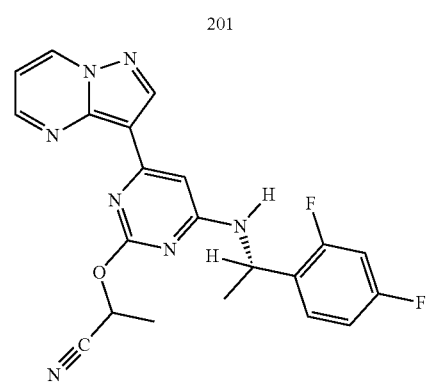
202
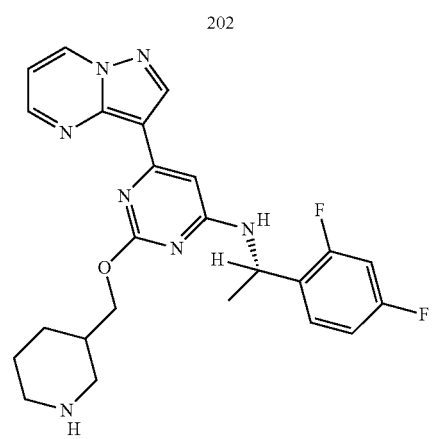

-continued
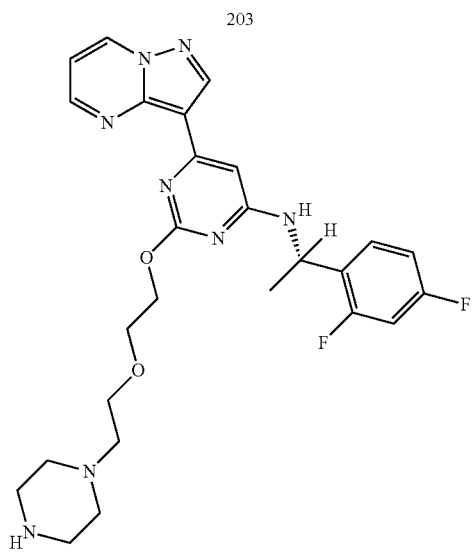
203
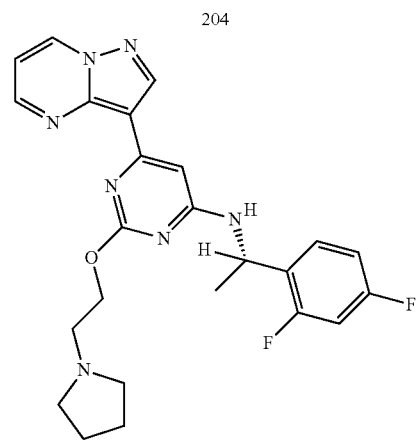
204
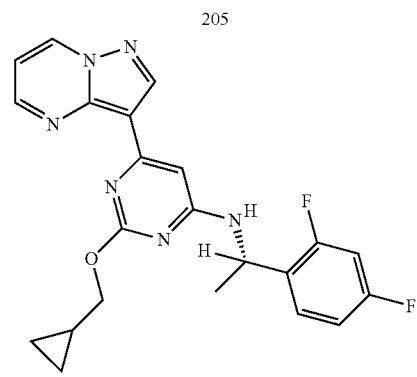
205
-continued
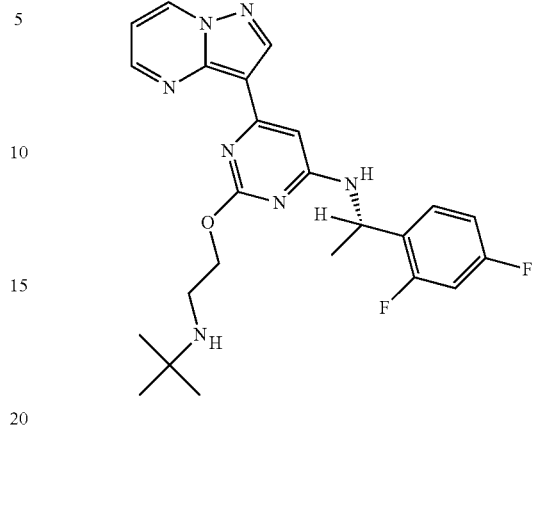
206
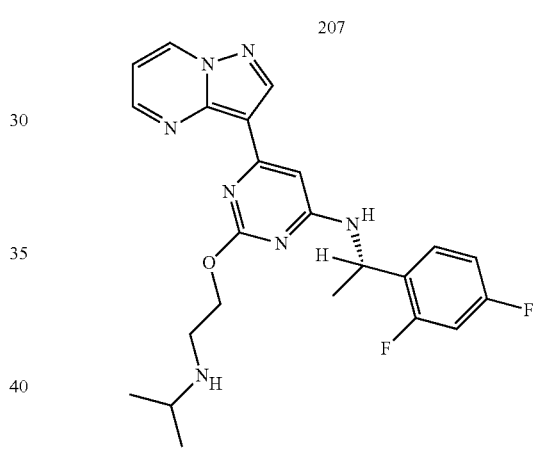
207
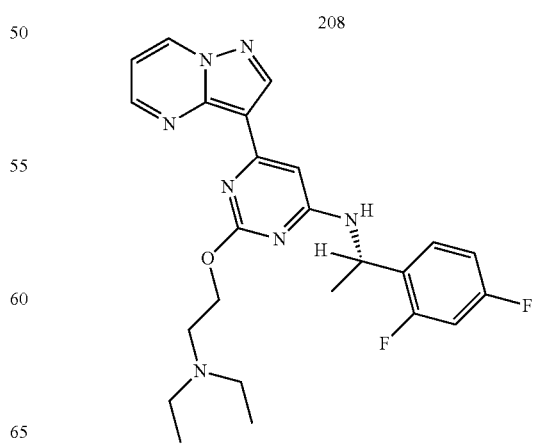
208

209
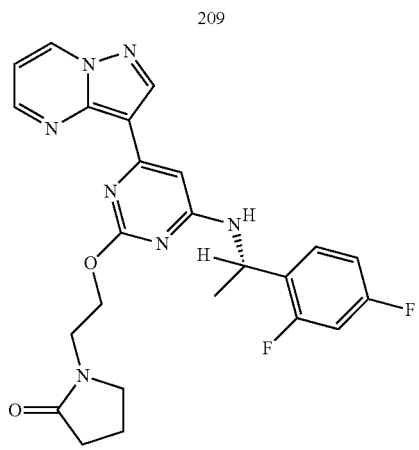
210
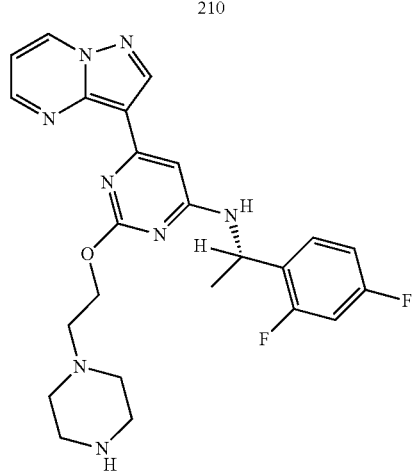
211
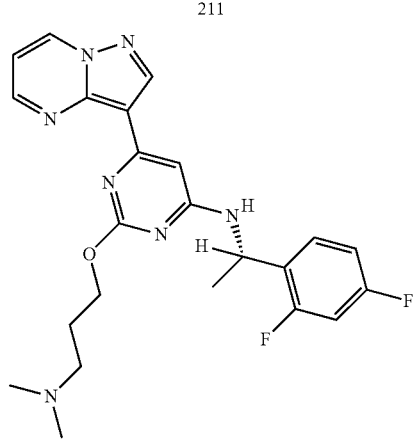
212
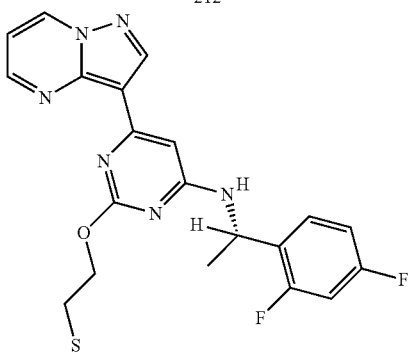
213
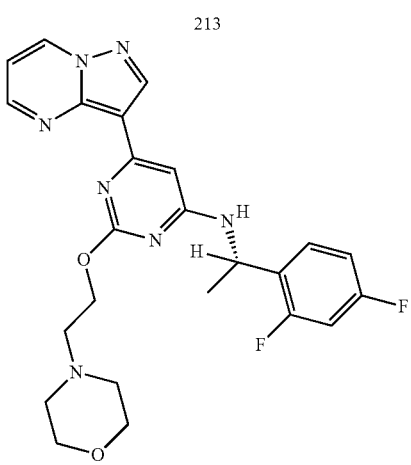
214
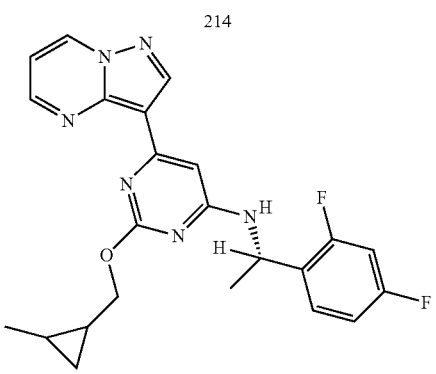
215
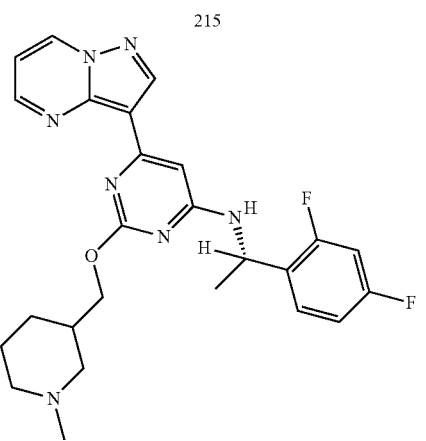

216
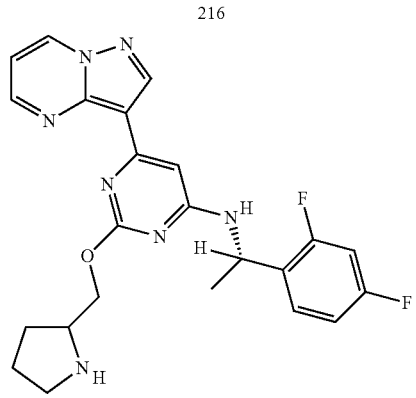
219
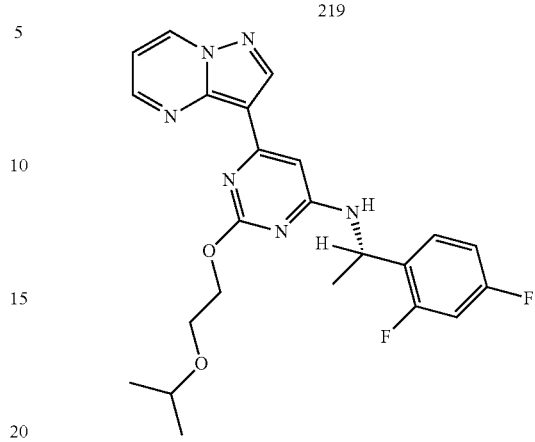
217
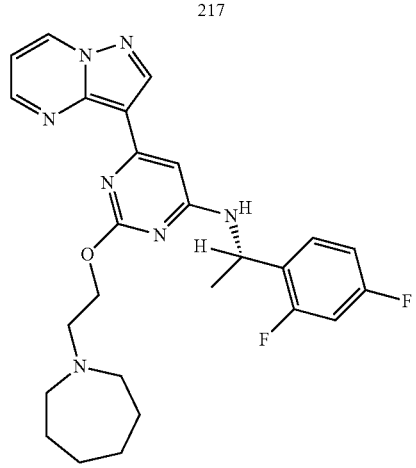
220
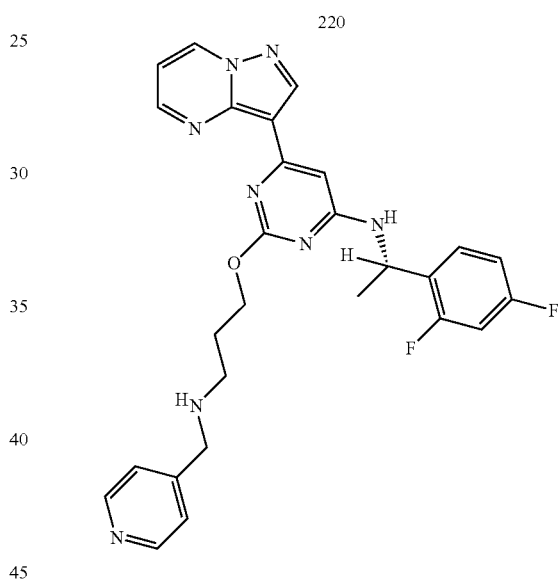
218
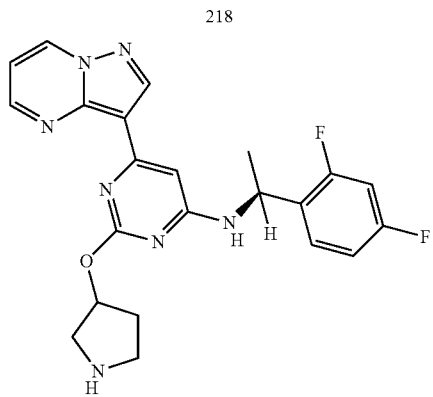
221
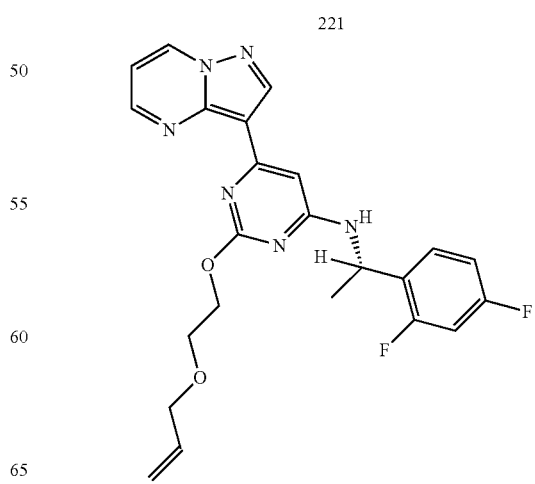

-continued
222
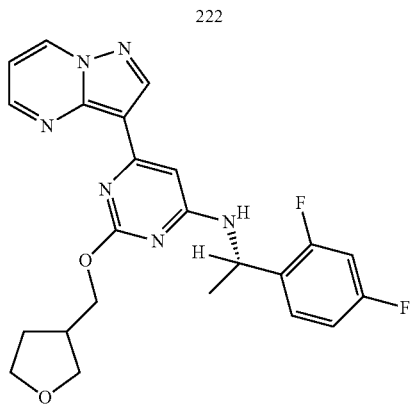
223
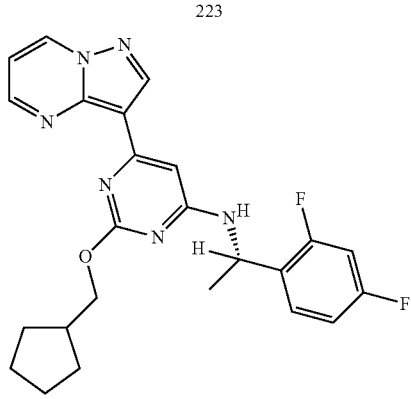
224
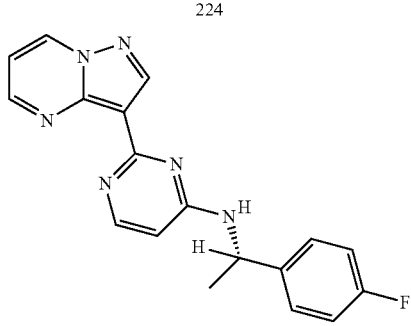
225
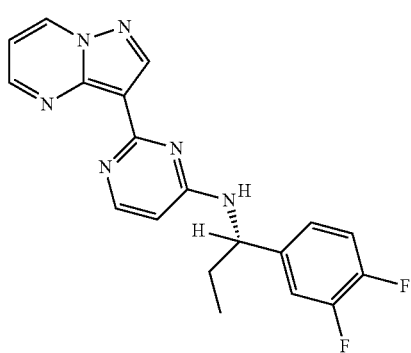
-continued
226
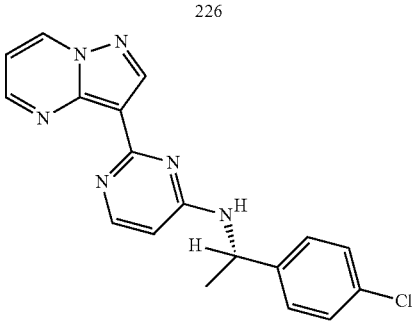
227
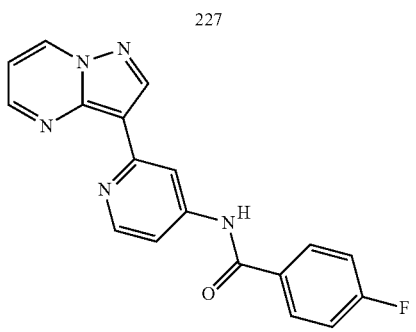
228
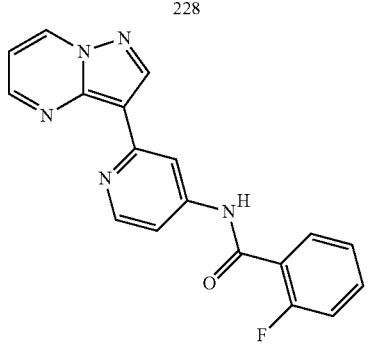
229
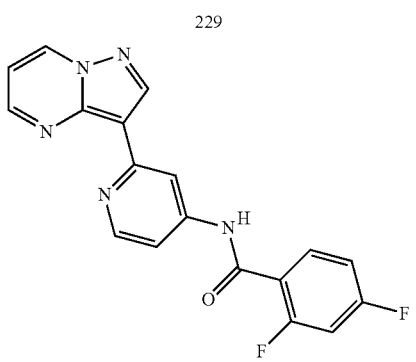

230
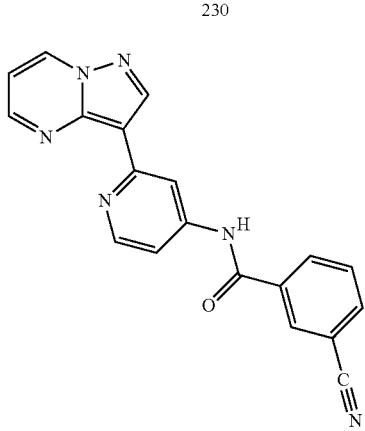
and
231
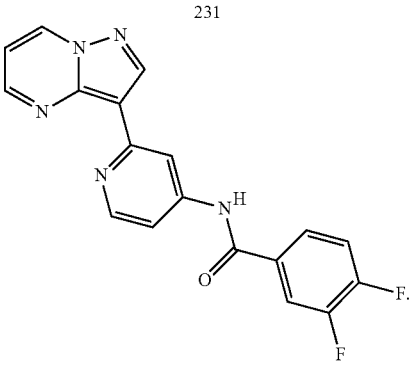
2. A pharmaceutical composition comprising a compound according to claim 1, or a pharmaceutically acceptable salt thereof, and a pharmaceutically acceptable carrier, adjuvant, or vehicle.
* * * * *